US012747240B2

(12) United States Patent
Alen et al.

(10) Patent No.: US 12,747,240 B2
(45) Date of Patent: Sep. 29, 2026

(54) SUBSTITUTED [1,2,4]TRIAZOLO[4,3-a]QUINOXALINES, DOSAGE FORMS CONTAINING THEM, AND METHODS OF USING THEM TO TREAT OR PREVENT PAIN AND/OR INFLAMMATION

(71) Applicant: GRUENENTHAL GMBH, Aachen (DE)

(72) Inventors: Jo Alen, Averbode (BE); Florian Jakob, Aachen (DE); Sebastian Krueger, Aachen (DE); Daniela Friebe, Duesseldorf (DE); Stephanie Hennen, Aachen (DE)

(73) Assignee: GRUENENTHAL GMBH (DE)

( * ) Notice: Subject to any disclaimer, the term of this patent is extended or adjusted under 35 U.S.C. 154(b) by 976 days.

(21) Appl. No.: 17/866,670

(22) Filed: Jul. 18, 2022

(65) Prior Publication Data

US 2022/0396578 A1 Dec. 15, 2022

Related U.S. Application Data

(63) Continuation of application No. PCT/EP2021/050840, filed on Jan. 15, 2021.

(30) Foreign Application Priority Data

Jan. 17, 2020 (EP) .................................... 20152465

(51) Int. Cl.

| | |
|---|---|
| ***A61K 31/4985*** | (2006.01) |
| ***C07D 487/04*** | (2006.01) |
| ***C07D 491/147*** | (2006.01) |
| ***C07D 519/00*** | (2006.01) |

(52) U.S. Cl.

CPC ....... *C07D 487/04* (2013.01); *C07D 491/147* (2013.01); *C07D 519/00* (2013.01)

(58) Field of Classification Search

CPC .......................... A61K 31/4985; C07D 487/04

USPC .......................................... 514/250; 544/346

See application file for complete search history.

(56) References Cited

U.S. PATENT DOCUMENTS

| | | | |
|---|---|---|---|
| 2013/0303537 A1 | 11/2013 | Matsuda et al. | |
| 2019/0359577 A1 | 11/2019 | Kawashima et al. | |
| 2021/0139488 A1 | 5/2021 | Jakob et al. | |
| 2024/0327416 A1 | 10/2024 | Jakob et al. | |

FOREIGN PATENT DOCUMENTS

| | | | |
|---|---|---|---|
| EP | 1 995 242 | A1 | 11/2008 |
| EP | 3 342 768 | A1 | 7/2018 |
| WO | 2009/035067 | A1 | 3/2009 |
| WO | 2017/034006 | A1 | 3/2017 |
| WO | 2020/016452 | A1 | 1/2020 |
| WO | 2020/016453 | A1 | 1/2020 |

OTHER PUBLICATIONS

Buttgereit F. et al., “Polymyalgia Rheumatica and Giant Cell Arteritis a Systematic Review”, JAMA. 2016;315(22):2442-2458).

Buttgereit F. et al., “Novel Glucocorticoids: Where are we now and where do we want to go?”, Clin. Exp. Rheumatol. 2015, vol. 33, pp. S29-S33.

De Bosscher K. et al., “Activation of the Glucocorticoid Receptor in Acute Inflammation: The SEDIGRAM Concept”, Trends Pharmacol. Sci. Jan. 2016;37(1):4-16.

Hapgood J.P. et al., “Glucocorticoid-independent Modulation of GR activity: Implications for Immunotherapy”, Pharmacol. Ther. Sep. 2016; 165: 93-113.

Hartmann K. et al., “Molecular Actions of Glucocorticoids in Cartilage and Bone During Health, Disease, and Steroid Therapy”, Physiol. Rev. vol. 96, No. 2, pp. 409-447, 2016.

Liu D. et al., “A Practical guide to the monitoring and management of the complications of systemic corticosteriod therapy”, Allergy Asthma Clin. Immunol. Aug. 15, 2013;9(1):30, pp. 1-25.

“Science of Synthesis: Compounds with One Saturated Carbon-Heteroatom Bond”, vol. 35, Houben-Weyl, 2007 (Schaumann E., vol. Ed.).

*Primary Examiner* — Douglas M Willis

(74) *Attorney, Agent, or Firm* — Finnegan, Henderson, Farabow, Garrett & Dunner, LLP

(57) ABSTRACT

The present invention relates to compounds according to general formula (I)

(I)

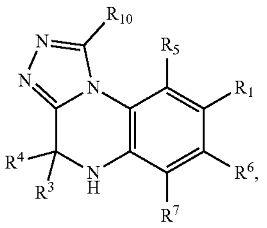

which act as modulators of the glucocorticoid receptor and can be used in the treatment and/or prophylaxis of disorders which are at least partially mediated by the glucocorticoid receptor.

20 Claims, No Drawings

SUBSTITUTED [1,2,4]TRIAZOLO[4,3-a]QUINOXALINES, DOSAGE FORMS CONTAINING THEM, AND METHODS OF USING THEM TO TREAT OR PREVENT PAIN AND/OR INFLAMMATION

This application is a continuation of International Patent Application No. PCT/EP2021/050840, filed Jan. 15, 2021, which claims priority of European Patent Application No. EP 20152465.9, filed Jan. 17, 2020, the entire contents of which patent applications are hereby incorporated herein by reference.

The present invention relates to compounds according to general formula (I)

(I)

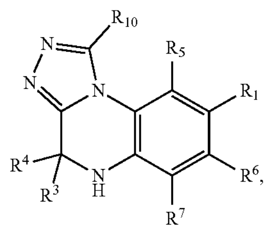

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. el al, Clin Exp Rheumatol. 2015 July-August; 33 (4 Suppl 92):S29-33; Hartmann K. et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et al., *JAMA*. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known from WO 2009/035067 and WO 2017/034006.

It was an object of the present invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter of the patent claims.

It was surprisingly found that the compounds according to the present invention are highly potent modulators of the glucocorticoid receptor.

The present invention relates to a compound according to general formula (I), (I)

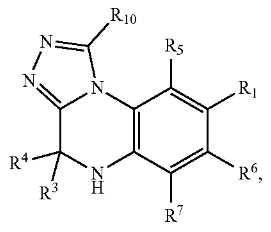

wherein $R^1$ represents C(=O)—N(H)—$C_{1-6}$-alkylene-aryl; $C_{3-10}$-cycloalkyl; 3 to 7 membered heterocycloalkyl; aryl; or 5 to 10-membered heteroaryl; wherein $C_{3-10}$-cycloalkyl, 3 to 7 membered heterocycloalkyl, aryl and 5 to 10-membered heteroaryl can optionally be bridged via $C_{1-6}$-alkylene;

$R^3$ and $R^4$ represent H or $C_{1-10}$-alkyl;

$R^5$ represents F; Cl; Br; I; $C_{1-10}$-alkyl; O—$C_{1-10}$-alkyl; or $C_{3-10}$-cycloalkyl;

$R^6$ represents H; F; Cl; Br; I; $C_{1-10}$-alkyl; O—$C_{1-10}$-alkyl; or $C_{3-10}$-cycloalkyl;

$R^7$ represents H; F; Cl; Br; I; OH; $C_{1-10}$-alkyl; S—$C_{1-10}$-alkyl; or $C_{3-10}$-cycloalkyl;

or $R^6$ and $R^7$, together with the carbon atoms they are attached to, form $C_{3-10}$-cycloalkyl or 3 to 7 membered heterocycloalkyl;

$R^{10}$ represents $C_{1-10}$-alkyl; or $C_{3-10}$-cycloalkyl;

wherein if $R^7$ represents H, F or Cl and $R^1$ represents indolyl or indazolyl, the indolyl or indazolyl is bound via its 5-membered ring to the superordinate general structure;

wherein $C_{1-6}$-alkyl, $C_{1-10}$-alkyl, and $C_{1-6}$-alkylene in each case independently from one another is linear or branched, saturated or unsaturated;

wherein $C_{1-6}$-alkyl, $C_{1-10}$-alkyl, $C_{1-6}$-alkylene, $C_{3-10}$-cycloalkyl and 3 to 7 membered heterocycloalkyl in each case independently from one another are unsubstituted or mono- or polysubstituted with one or more substituents selected from F; Cl; Br; I; CN; $C_{1-6}$-alkyl; $CF_3$; $CF_2H$; $CFH_2$; $CF_2Cl$; $CFCl_2$; C(O)—$C_{1-6}$-alkyl; C(O)—OH; C(O)—$OC_{1-6}$-alkyl; C(O)—$NH_2$; C(O)—N(H)($C_{1-6}$-alkyl); C(O)—N($C_{1-6}$-alkyl)$_2$; OH; ═O; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—S(O)$_2$—$NH_2$; O—S(O)$_2$—N(H)($C_{1-6}$-alkyl); O—S(O)$_2$—N($C_{1-6}$-alkyl)$_2$; $NH_2$; N(H)($C_{1-6}$-alkyl); N($C_{1-6}$-alkyl)$_2$; N(H)—C(O)—$C_{1-6}$-alkyl; N(H)—C(O)—O—$C_{1-6}$-alkyl; N(H)—C(O)—$NH_2$; N(H)—C(O)—N(H)($C_{1-6}$-alkyl); N(H)—C(O)—N($C_{1-6}$-alkyl)$_2$; N($C_{1-6}$-alkyl)-C(O)—$C_{1-6}$-alkyl; N($C_{1-6}$-alkyl)-C(O)—O—$C_{1-6}$-alkyl; N($C_{1-6}$-alkyl)-C(O)—$NH_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$OH; N(H)—S(O)$_2$—$C_{1-6}$-alkyl; N(H)—S(O)$_2$—O—$C_{1-6}$-alkyl; N(H)—S(O)$_2$—$NH_2$; N(H)—S(O)$_2$—N(H)($C_{1-6}$-alkyl); N(H)—S(O)$_2$N($C_{1-6}$-alkyl)$_2$; N($C_{1-6}$-alkyl)-S(O)$_2$—OH; N($C_{1-6}$-alkyl)-S(O)$_2$—$C_{1-6}$-alkyl; N($C_{1-6}$-alkyl)-S(O)$_2$—O—$C_{1-6}$-alkyl; N($C_{1-6}$-alkyl)-S(O)$_2$—$NH_2$; N($C_{1-6}$-alkyl)-S(O)$_2$—N(H)($C_{1-6}$-alkyl); N($C_{1-6}$-alkyl)-S(O)$_2$—N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; 3 to 7-membered heterocycloalkyl; phenyl; 5 or 6-membered heteroaryl; O—$C_{3-6}$-cycloalkyl; O-(3 to 7-membered heterocycloalkyl); O-phenyl; O-(5 or 6-membered heteroaryl); C(O)—$C_{3-6}$-cycloalkyl; C(O)-(3 to 7-membered heterocycloalkyl); C(O)-phenyl; C(O)-(5 or 6-membered heteroaryl); S(O)$_2$—($C_{3-6}$-cycloalkyl); S(O)$_2$-(3 to 7-membered heterocycloalkyl); S(O)$_2$-phenyl or S(O)$_2$-(5 or 6-membered heteroaryl);

wherein aryl, and 5 to 10-membered heteroaryl in each case independently from one another are unsubstituted or mono- or polysubstituted with one or more substituents selected from F; Cl; Br; I; CN; $C_{1-6}$-alkyl; $C_{1-6}$-alkenyl; $C_{1-6}$-alkynyl; $C_{1-6}$-alkynyl-C(H)(OH)$CH_3$; $C_{1-6}$-alkynyl-C($CH_3$)$_2$OH; $CF_3$; $CF_2H$; $CFH_2$; $CF_2Cl$; $CFCl_2$; $C_{1-6}$-alkylene-$CF_3$; $C_{1-6}$-alkylene-$CF_2H$; $C_{1-6}$-alkylene-$CFH_2$; $C_{1-6}$-alkylene-OH; $C_{1-6}$-alkylene-$OCH_3$; C(O)—$C_{1-6}$-alkyl; C(O)—OH; C(O)—$OC_{1-6}$-alkyl; C(O)—N(H)(OH); C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; O—$C_{3-6}$-cycloalkyl; O-(3 to 7-membered heterocycloalkyl); $NH_2$; N(H)($C_{1-6}$-alkyl); N($C_{1-6}$-alkyl)$_2$; N(H)—C(O)—$C_{1-6}$-alkyl; N($C_{1-6}$-alkyl)-C(O)—$C_{1-6}$-alkyl; N(H)—C(O)—$NH_2$; N(H)—C(O)—N(H)($C_{1-6}$-alkyl); N(H)—C(O)—N($C_{1-6}$-alkyl)$_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$—$C_{1-6}$-alkyl; $SCF_3$; S—$C_{1-6}$-alkyl; S(O)—$C_{1-6}$-alkyl; S(O)$_2$—$C_{1-6}$-alkyl; S(O)$_2$—$C_{3-6}$-cycloalkyl; S(O)$_2$—$C_{1-6}$-alkylene-$C_{3-6}$-cycloalkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; $C_{1-6}$-alkylene-$C_{3-6}$-cycloalkyl; 3 to 7-membered heterocycloalkyl; $C_{1-6}$-alkylene-(3 to 7-membered heterocycloalkyl); phenyl or 5 or 6-membered heteroaryl;

in the form of the free compound or a physiologically acceptable salt thereof.

In a preferred embodiment, $C_{1-6}$-alkyl, $C_{1-10}$-alkyl, $C_{1-6}$-alkylene, $C_{3-10}$-cycloalkyl and 3 to 7 membered heterocycloalkyl in each case independently from one another are unsubstituted or mono- or polysubstituted with one or more substituents selected from F; Cl; Br; I; CN; $C_{1-6}$-alkyl; $CF_3$; $CF_2H$; $CFH_2$; $CF_2Cl$; $CFCl_2$; OH; ═O; $OCF_3$; $OCF_2H$; $OCFH_2$; $OCF_2Cl$; $OCFCl_2$; O—$C_{1-6}$-alkyl; $C_{3-6}$-cycloalkyl; pyridinyl; or 3 to 7-membered heterocycloalkyl; and/or aryl, and 5 to 10-membered heteroaryl in each case independently from one another are unsubstituted or mono- or polysubstituted with one or more substituents selected from F; Cl; Br; I; CN; $C_{1-6}$-alkyl; $C_{2-6}$-alkenyl; $C_{2-6}$-alkynyl, preferably —C≡C—$CH_3$; —C≡C—CH($CH_3$)(OH); —C≡C—C($CH_3$)$_2$(OH); $CF_3$; $CF_2H$; $CFH_2$; $CF_2Cl$; $CFCl_2$; $C_{1-6}$-alkylene-$CF_3$; $C_{1-6}$-alkylene-$CF_2H$; $C_{1-6}$-alkylene-$CFH_2$; C(O)—$C_{1-6}$-alkyl; C(O)—OH; C(O)—$OC_{1-6}$-alkyl; $NH_2$; OH; ═O; $C_{1-6}$-alkylene-OH, $C_{1-6}$-alkylene being branched or unbranched; $C_{1-6}$-alkylene-O—$C_{1-6}$-alkyl; $OCF_3$; $OCF_2H$; $OCFH_2$; $OCF_2Cl$; $OCFCl_2$; O—$C_{1-6}$-alkyl; O—$C_{3-6}$-cycloalkyl; O-(3 to 7-membered heterocycloalkyl); $SCF_3$; S—$C_{1-6}$-alkyl; S(O)—$C_{1-6}$-alkyl; S(O)$_2$—$C_{1-6}$-alkyl; S(O)$_2$—$C_{3-6}$-cycloalkyl; S(O)$_2$—$C_{1-6}$-alkylene-$C_{3-6}$-cycloalkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; $C_{1-6}$-alkylene-$C_{3-6}$-cycloalkyl; 3 to 7-membered heterocycloalkyl; $C_{1-6}$-alkylene-(3 to 7-membered heterocycloalkyl); phenyl or 5 or 6-membered heteroaryl.

In another preferred embodiment, $R^1$ represents aryl, or 5 to 10-membered heteroaryl, or —$CH_2$-(3 to 7 membered heterocycloalkyl), or C(═O)—N(H)—$CH_2$-aryl; and/or $R^3$, and $R^4$, represent $C_{1-6}$-alkyl; and/or $R^6$ and $R^7$, together with the carbon atoms joining them, form —C—($CH_2$)$_m$—C—, wherein m is 1, 2, 3 or 4, or —C—O—($CH_2$)$_m$—C—, wherein m is 1, 2, 3 or 4.

In another preferred embodiment, $R^1$ represents (i)phenyl; naphthyl, pyridyl, preferably 2-pyridyl, 3-pyridyl or 4-pyridyl, imidazopyridyl, pyrrolopyridyl, pyrazolopyridyl, dihydropyrrolopyrazolyl; spiro[cyclopropane-1,3'-indoline], pyrimidinyl, pyridazinyl, pyrazinyl, pyrrolyl, —$CH_2$-pyrrolidinyl; imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclo-penta[c]pyrazolyl, benzofuranyl, benzoimidazolyl, benzothienyl, dihydrobenzodioxinyl, benzothiadiazolyl, benzothiazolyl, benzotriazolyl, benzooxazolyl, benzooxadiazolyl, quinazolinyl, quinoxalinyl, carbazolyl, quinolinyl, dihydroquinolinonyl; dibenzofuranyl, dibenzothienyl, imidazothiazolyl, indazolyl, indolizinyl, indolyl, indolinyl, isoquinolinyl, naphthyridinyl, oxazolyl, oxadiazolyl, phenazinyl, phenothiazinyl, phthalazinyl, purinyl, phenazinyl, tetrazolyl, triazinyl or —C(═O)—NH—$CH_2$-phenyl; or (ii) aryl, which is selected from the group consisting of phenyl and naphthyl, in either case unsubstituted or mono- or polysubstituted with one or more substituents selected from F; Cl; Br; I; —$CH_3$; —$CH_2$—$CH_3$; O—$CH_3$; —$CF_3$; —$C_{3-10}$-cycloalkyl; —$CH_2$—$C_{3-10}$-cycloalkyl; S(═O)$_2$—$C_{3-10}$-cycloalkyl; S(═O)$_2$—$CH_2$—$C_{3-10}$-cycloalkyl; S(═O)$_2$—$CH_3$; S(═O)$_2$—$CH_2$—$CH_3$; —$CH_2$—$CH_2$—O—$CH_2$—; —O—$CH_3$; —C≡C—$CH_3$; —$CH_2$—$CH_2$—C(═O)—N(H)—; —$CH_2$—$CH_2$—C(═O)—N($CH_3$)—; C(═O)—$CH_3$; —CH═$CH_2$; $NH_2$; or —$CH_2$—$CH_2$—OH; or heteroaryl, which is pyridinyl, unsubstituted or mono- or polysubstituted with one or more substituents selected from F; Cl; Br; I; —$CH_3$; —$CH_2$—$CH_3$; O—$CH_3$; —$CF_3$; —$C_{3-10}$-cycloalkyl; —$CH_2$—$C_{3-10}$-cycloalkyl; S(═O)$_2$—$C_{3-10}$-cycloalkyl; S(═O)$_2$—$CH_2$—$C_{3-10}$-cycloalkyl; S(═O)$_2$—$CH_3$; S(═O)$_2$—$CH_2$—$CH_3$; —$CH_2$—$CH_2$—O—$CH_2$—; —O—$CH_2$—$CH_2$—O—; —C≡C—$CH_3$; —$CH_2$—$CH_2$—C(═O)—N(H)—; C(═O)—$CH_3$; —CH═$CH_2$; $NH_2$; or —$CH_2$—$CH_2$—OH; or any of the following structures (II), (III), (IV), (V) or (VI), (II)

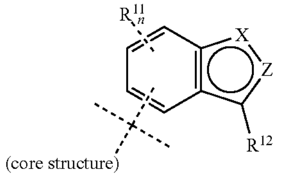

(III)

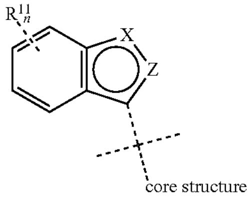

(IV)

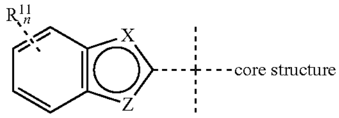

(V)

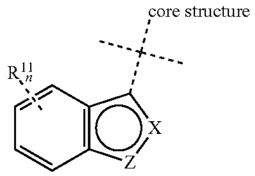

(VI)

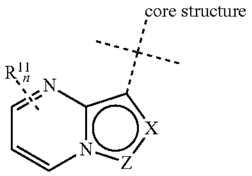

wherein X represents S, O, N, N—$R^{13}$ or C—$R^{13}$; preferably O, N, N—$R^{13}$ or C—$R^{13}$; very preferably N, N—$R^{13}$ or C—$R^{13}$; Z represents S, O, N, N—$R^{13}$ or C—$R^{13}$; preferably O, N, N—$R^{13}$ or C—$R^{13}$; very preferably N, N—$R^{13}$ or C—$R^{13}$; $R^{11}$, $R^{12}$ and $R^{13}$ represent, independently from one another, H; F; Cl; Br; I; CN; $C_{1-10}$-alkyl; $C_{3-10}$-cycloalkyl; 3 to 7 membered heterocycloalkyl; S(O)—($C_{1-10}$-alkyl); S(O)—($C_{3-10}$-cycloalkyl); S(O)-(3 to 7-membered heterocycloalkyl); S(O)$_2$—($C_{1-10}$-alkyl); S(O)$_2$—($C_{3-10}$-cycloalkyl); S(O)$_2$-(3 to 7-membered heterocycloalkyl); P(O)—($C_{1-10}$-alkyl)$_2$; P(O($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)$_2$; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; S—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—$NH_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)—3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl); wherein $C_{3-10}$-cycloalkyl and 3 to 7 membered heterocycloalkyl can optionally be bridged via $C_{1-6}$-alkylene; and n represents 0, 1, 2 or 3; or wherein $R^{11}$, $R^{12}$ and $R^{13}$ represent, independently from one another, F; Cl; Br; I; —$CH_3$; O—$CH_3$; —$CF_3$; —$CH_2$—C(H)$F_2$; —$C_{3-10}$-cycloalkyl; —$CH_2$—$C_{3-10}$-cycloalkyl; S(═O)$_2$—$C_{3-10}$-cycloalkyl; S(═O)$_2$—$CH_2$—$C_{3-10}$-cycloalkyl; S(═O)$_2$—$CH_3$; S(═O)$_2$—$CH_2$—$CH_3$; S(═O)$_2$—CH($CH_3$)$_2$; —$CH_2$—$CH_2$—O—$CH_3$; —C≡C—$CH_3$; —C≡C—CH(OH)($CH_3$); —C≡C—C(OH)($CH_3$)$_2$; C(═O)—$CH_3$; or —$CH_2$—$CH_2$—OH; and n represents 0, 1, 2 or 3.

Together with the carbon atom carrying residue $R^{12}$ on the one hand and the two carbon atoms of the adjacent phenyl moiety on the other hand, X and Z according to structure (II) form an aromatic system.

Together with the carbon atom connecting structures (III), (IV) and (V) to the core structure on the one hand and the two carbon atoms of the adjacent phenyl moiety on the other hand, X and Z form an aromatic system.

Together with the carbon atom connecting structure (VI) to the core structure on the one hand and the carbon and nitrogen atoms of the adjacent pyrimidinyl moiety on the other hand, X and Z form an aromatic system.

In another preferred embodiment, $R^1$ represents any of the following structures

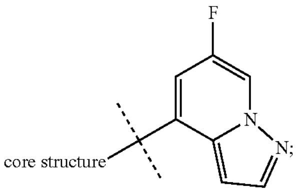

;

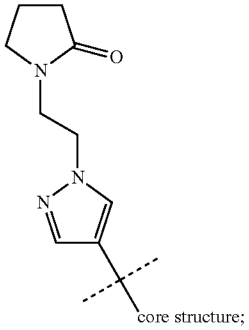

;

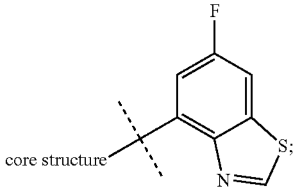

;

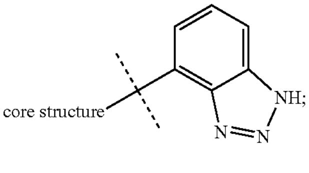

;

-continued

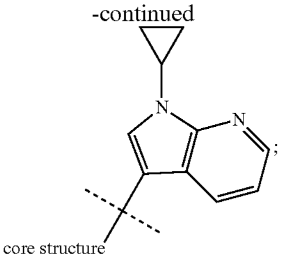

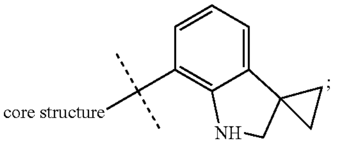

optionally monosubstituted with F or $CH_3$

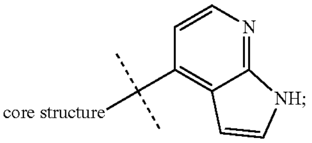

optionally monosubstituted with F or $CH_3$

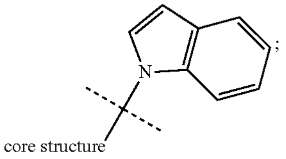

optionally monosubstituted with F or $CH_3$

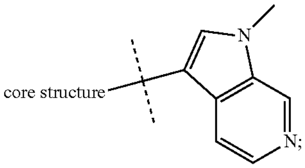

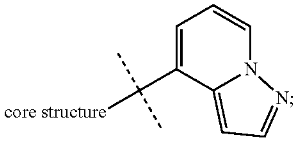

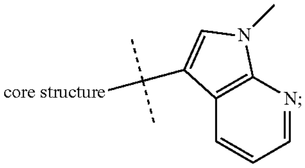

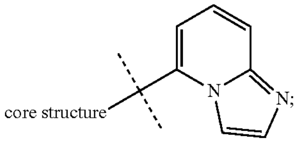

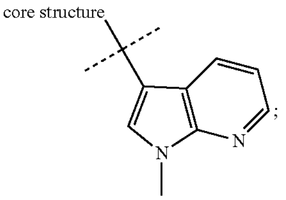

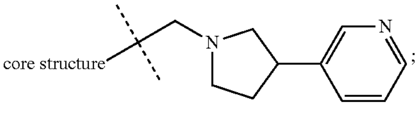

-continued

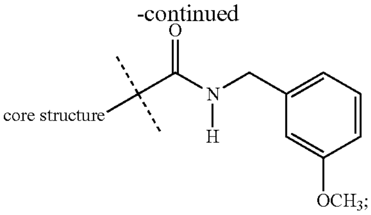

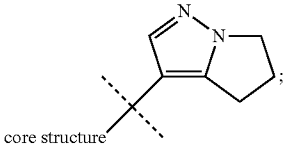

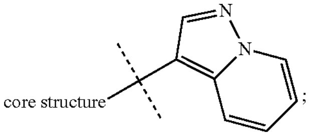

or optionally monosubstituted with F or $CH_3$

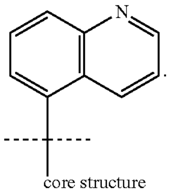

In another preferred embodiment, $R^1$ represents phenyl, naphthyl, pyridyl, preferably 2-pyridyl, 3-pyridyl or 4-pyridyl, imidazopyridyl, pyrrolopyridyl, pyrazolopyridyl, dihydropyrrolopyrazolyl, spiro[cyclopropane-1,3'-indoline], pyrimidinyl, pyridazinyl, pyrazinyl, pyrrolyl, —$CH_2$-pyrrolidinyl; imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclo-penta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dihydroquinolinonyl, dihydrobenzodioxinyl, dibenzofuranyl, dibenzothienyl, imidazothiazolyl, indazolyl, indolizinyl, indolyl, indolinyl, isoquinolinyl, naphthyridinyl, oxazolyl, oxadiazolyl, phenazinyl, phenothiazinyl, phthalazinyl, purinyl, phenazinyl, tetrazolyl, triazinyl or —C(═O)—NH—$CH_2$-phenyl; and/or $R^3$ and $R^4$ represent —$C_{1-6}$-alkyl; preferably —$C_{1-3}$-alkyl; more preferably —$C_{1-2}$-alkyl; particularly preferably —$CH_3$; and/or $R^5$ represents F; Cl; $C_{1-6}$-alkyl; O—$C_{1-6}$-alkyl; or $C_{3-10}$-cycloalkyl; preferably F; Cl; $CF_3$; $CHF_2$; —$CH_2CH_2CH_3$; —$CH_2CH_3$; —$CH_3$; —$OCH_2CH_2CH_3$; —$OCH_2CH_3$; —$OCH_3$ or $C_{3-10}$-cycloalkyl; more preferably F; Cl; $CF_3$; $CHF_2$; —$CH_2CH_2CH_3$; —$CH_2CH_3$; —$CH_3$; —$OCH_2CH_2CH_3$; —$OCH_2CH_3$; —$OCH_3$ or cyclopropyl; and/or $R^6$ represents H; F; Cl; $C_{1-6}$-alkyl; O—$C_{1-6}$-alkyl; or $C_{3-10}$-cycloalkyl; preferably H; F; Cl; $OCF_3$; or $CHF_2$; and/or $R^7$ represents H; F; Cl; OH; $C_{1-6}$-alkyl; S—$C_{1-6}$-alkyl; or $C_{3-10}$-cycloalkyl; preferably H; F; Cl; $CH_2CH_3$; —$CH_3$; $CF_3$; —$SCH_3$; OH; or —$C(CH_3)_2$—OH; or $R^6$ and $R^7$, together with the carbon atoms they are attached to, form tetrahydrofuranyl or cyclopentyl; and/or $R^{10}$ represents $C_{1-6}$-alkyl; or $C_{3-10}$-cycloalkyl; preferably $—CH_2CH_2CH_3$; $—CH_2CH_3$; $—CH_3$; or cyclopropyl; more preferably $—CH_2CH_3$; $—CH_3$; or cyclopropyl.

In a preferred embodiment, the compound according to the present invention is present in form of the free compound. For the purpose of specification, "free compound" preferably means that the compound according to the present invention is not present in form of a salt. Methods to determine whether a chemical substance is present as the free compound or as a salt are known to the skilled artisan such as $^4N$ or $^{15}N$ solid state NMR, x-ray diffraction, x-ray powder diffraction, IR, Raman, XPS. $^1H$-NMR recorded in solution may also be used to consider the presence of protonation.

In another preferred embodiment, the compound according to the present invention is present in form of a physiologically acceptable salt. For the purposes of this specification, the term "physiologically acceptable salt" preferably refers to a salt obtained from a compound according to the present invention and a physiologically acceptable acid or base.

According to the present invention, the compound according to the present invention may be present in any possible form including solvates, cocrystals and polymorphs. For the purposes of this specification, the term "solvate" preferably refers to an adduct of (i) a compound according to the present invention and/or a physiologically acceptable salt thereof with (ii) distinct molecular equivalents of one or more solvents.

Further, the compound according to the present invention may be present in form of the racemate, enantiomers, diastereomers, tautomers or any mixtures thereof.

The present invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2H$ (deuterium), $^3H$ (tritium), $^{13}C$ and $^{14}C$. Isotopic isomers of a compound of the invention can generally be prepared by conventional procedures known to a person skilled in the art.

According to the present invention, the terms "$C_{1-10}$-alkyl", "$C_{1-8}$-alkyl", "$C_{1-6}$-alkyl" and "$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, $C_{1-10}$-alkyl, $C_{1-8}$-alkyl, $C_{1-6}$-alkyl and $C_{1-4}$-alkyl are saturated. In another preferred embodiment, $C_{1-10}$-alkyl, $C_{1-8}$-alkyl, $C_{1-6}$-alkyl and $C_{1-4}$-alkyl are not saturated. According to this embodiment, $C_{1-10}$-alkyl, $C_{1-8}$-alkyl, $C_{1-6}$-alkyl and $C_{1-4}$-alkyl comprise at least one C—C double bond (a C═C-bond) or at least one C—C triple bond (a C≡C-bond). In still another preferred embodiment, $C_{1-10}$-alkyl, $C_{1-8}$-alkyl, $C_{1-6}$-alkyl and $C_{1-4}$-alkyl are (i) saturated or (ii) not saturated, wherein $C_{1-10}$-alkyl, $C_{1-8}$-alkyl, $C_{1-6}$-alkyl and $C_{1-4}$-alkyl comprise at least one, preferably one, C—C triple bond (a C≡C-bond). Preferred $C_{1-10}$-alkyl groups are selected from methyl, ethyl, ethenyl (vinyl), n-propyl, 2-propyl, 1-propynyl, 2-propynyl, propenyl ($—CH_2CH═CH_2$, $—CH═CH—CH_3$, $—C(═CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl ($—CH_2CH═CH_2$, $—CH═CH—CH_3$, $—C(═CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl. Preferred $C_{1-8}$-alkyl groups are selected from methyl, ethyl, ethenyl (vinyl), n-propyl, 2-propyl, 1-propynyl, 2-propynyl, propenyl ($—CH_2CH═CH_2$, $—CH═CH—CH_3$, $—C(═CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl ($—CH_2CH═CH_2$, $—CH═CH—CH_3$, $—C(═CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl. Preferred $C_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl ($—CH_2CH═CH_2$, $—CH═CH—CH_3$, $—C(═CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl.

Particularly preferred $C_{1-6}$-alkyl groups are selected from $C_{1-4}$-alkyl groups. Preferred $C_{1-4}$-alkyl groups are selected from methyl, ethyl, ethenyl (vinyl), n-propyl, 2-propyl, 1-propynyl, 2-propynyl, propenyl ($—CH_2CH═CH_2$, $—CH═CH—CH_3$, $—C(═CH_2)—CH_3$), n-butyl, 1-butynyl, 2-butynyl, 1-butenyl, 2-butenyl, isobutyl, sec-butyl, tert-butyl and 3-methylbut-1-ynyl.

Further according to the present invention, the terms "$C_{1-6}$-alkylene"; "$C_{1-4}$-alkylene" and "$C_{1-2}$-alkylene" relate to a linear or branched, preferably linear, and preferably saturated aliphatic residues which are preferably selected from the group consisting of methylene ($—CH_2—$), ethylene ($—CH_2CH_2—$), propylene ($—CH_2CH_2CH_2—$ or $—C(CH_3)_2—$), butylene ($—CH_2CH_2CH_2CH_2—$), pentylene ($—CH_2CH_2CH_2CH_2CH_2—$) and hexylene ($—CH_2CH_2CH_2CH_2CH_2CH_2—$); more preferably methylene ($—CH_2—$) and ethylene ($—CH_2CH_2—$) and most preferably methylene ($-CH_2-$). Preferably, $C_{1-6}$-alkylene is selected from $C_{1-4}$-alkylene, more preferably from $C_{1-2}$-alkylene.

Still further according to the present invention, the terms "$C_{3-10}$-cycloalkyl" and "$C_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or polysubstituted. Preferably, $C_{3-10}$-cycloalkyl and $C_{3-6}$-cycloalkyl are saturated. The $C_{3-10}$-cycloalkyl and $C_{3-6}$-cycloalkyl can be bound to the respective superordinate general structure via any desired and possible ring member of the cycloalkyl group. The $C_{3-10}$-cycloalkyl and $C_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or poly substituted. Further, $C_{3-10}$-cycloalkyl and $C_{3-6}$-cycloalkyl can be singly or multiply bridged such as, for example, in the case of adamantyl, bicyclo[2.2.1]heptyl or bicyclo[2.2.2]octyl. However, preferably, $C_{3-10}$-cycloalkyl and $C_{3-6}$-cycloalkyl are neither condensed with further ring systems nor bridged. More preferably, $C_{3-10}$-cycloalkyl and $C_{3-6}$-cycloalkyl are neither condensed with further ring systems nor bridged and are saturated. Preferred $C_{3-10}$-cycloalkyl groups are selected from the group consisting of cyclopropyl, cyclobutyl, cyclopentyl, cyclohexyl, cyclopentenyl, cyclohexenyl, cycloheptyl, cyclooctyl, cyclononyl, cyclodecyl, adamantly, cyclopentenyl, cyclohexenyl, cycloheptenyl, cyclooctenyl, bicyclo[2.2.1]heptyl and bicyclo[2.2.2]octyl. Particularly preferred $C_{3-10}$-cycloalkyl groups are selected from $C_{3-6}$-cycloalkyl groups. Preferred $C_{3-6}$-cycloalkyl groups are selected from the group consisting of cyclopropyl, cyclobutyl, cyclopentyl, cyclohexyl, cyclopentenyl and cyclohexenyl. Particularly preferred $C_{3-6}$-cycloalkyl groups are selected from the group consisting of cyclopropyl, cyclobutyl, cyclopentyl and cyclohexyl, most preferably cyclopropyl.

According to the present invention, the term "3 to 7-membered heterocycloalkyl" preferably means heterocycloaliphatic saturated or unsaturated (but not aromatic) residues having 3 to 7, i.e. 3, 4, 5, 6 or 7 ring members, wherein in each case at least one, if appropriate also two or three carbon atoms are replaced by a heteroatom or a heteroatom group each selected independently of one another from the group consisting of O, S, S(═O), S(═O)$_2$, N, NH and N($C_{1-4}$-alkyl) such as N($CH_3$), wherein the carbon atoms of the ring can be unsubstituted or mono- or polysubstituted. Preferably, 3 to 7-membered heterocycloalkyl is saturated. The 3 to 7-membered heterocycloalkyl group can also be condensed with further saturated or (partially) unsaturated cycloalkyl or heterocyclyl, aromatic or heteroaromatic ring systems. However, more preferably, 3 to 7-membered heterocycloalkyl is not condensed with further ring systems. Still more preferably, 3 to 7-membered heterocycloalkyl is not condensed with further ring systems and are saturated. The 3 to 7-membered heterocycloalkyl can be bound to the superordinate general structure via any desired and possible ring member of the heterocycloaliphatic residue if not indicated otherwise. In a preferred embodiment, 3 to 7-membered heterocycloalkyl are bound to the superordinate general structure via a carbon atom.

Preferred 3 to 7-membered heterocycloalkyl groups are selected from the group consisting of azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, tetrahydrofuranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. More preferably, 3 to 7-membered heterocycloalkyl groups are selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl. Particularly preferred 3 to 7-membered heterocycloalkyl groups are selected from the group consisting of tetrahydropyranyl, oxetanyl, oxiranyl, and tetrahydrofuranyl.

According to the present invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or polysubstituted. In a preferred embodiment, aryl is condensed with a further ring system. Examples of condensed aryl residues are 2H-benzo[b][1,4]oxazin-3(4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl. Preferably, aryl is selected from the group consisting of phenyl, 1-naphthyl, 2-naphthyl, 1H-benzo[d]imidazolyl, 2H-benzo[b][1,4]oxazin-3(4H)-onyl, 2,3-dihydro-1H-indenyl, tetrahydronaphthalenyl, isochroman, 1,3-dihydroisobenzofuranylfluorenyl and anthracenyl, each of which can be respectively unsubstituted or mono- or polysubstituted. In another preferred embodiment, aryl is not condensed with any further ring system. A particularly preferred aryl is phenyl, unsubstituted or mono- or polysubstituted.

According to the present invention, the terms "5- to 10-membered heteroaryl" and "5- to 6-membered heteroaryl", respectively, preferably mean a mono- or bicyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 10-membered heteroaryl and 5- to 6-membered heteroaryl, respectively, is bound to the superordinate general structure via a carbon atom of the heterocycle. In another preferred embodiment, the 5- to 10-membered heteroaryl and 5- to 6-membered heteroaryl, respectively, is bound to the superordinate general structure via a heteroatom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or poly substituted, if not indicated otherwise. In a preferred embodiment, the heteroaryl is part of a bi- or polycyclic, preferably bicyclic, system. In another preferred embodiment, the heteroaryl is not part of a bi- or polycyclic system. Preferably, the 5- to 10-membered heteroaryl is selected from the group consisting of pyridyl, preferably 2-pyridyl, 3-pyridyl or 4-pyridyl, imidazopyridyl, pyrrolopyridyl, pyrazolopyridyl, dihydropyrrolopyrazolyl, spiro[cyclopropane-1,3'-indoline]; pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclo-penta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dihydroquinolinonyl, dihydrobenzodioxinyl, dibenzofuranyl, dibenzothienyl, imidazothiazolyl, indazolyl, indolizinyl, indolyl, indolinyl, isoquinolinyl, naphthyridinyl, oxazolyl, oxadiazolyl, phenazinyl, phenothiazinyl, phthalazinyl, purinyl, phenazinyl, tetrazolyl and triazinyl.

The compounds according to the present invention are defined by substituents, for example by $R^3$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R^3$=a $C_{1-10}$-alkyl ($1^{st}$ generation substituent), then the $C_{1-10}$-alkyl can for its part be substituted, for example with a N(H)($C_{1-6}$-alkyl) ($2^{nd}$ generation substituent). This produces the functional group $R^3$=($C_{1-10}$-alkyl-NH—$C_{1-6}$-alkyl). The NH—$C_{1-6}$-alkyl can then for its part be resubstituted, for example with Cl ($3^{rd}$ generation substituent). Overall, this produces the functional group $R^3$=$C_{1-10}$-alkyl-NH—$C_{1-6}$-alkyl, wherein the $C_{1-6}$-alkyl of the NH—$C_{1-6}$-alkyl is substituted by Cl. However, in a preferred embodiment, the $3^{rd}$ generation substituents may not be resubstituted, i.e. there are then no $4^{th}$ generation substituents. More preferably, the $2^{nd}$ generation substituents may not be resubstituted, i.e. there are no $3^{rd}$ generation substituents.

If a residue occurs multiply within a molecule, then this residue can have respectively different meanings for various substituents: if, for example, both $R^3$ and $R^4$ denote $C_{1-6}$-alkyl, then $C_{1-6}$-alkyl can e.g. represent ethyl for $R^3$ and can represent methyl for $R^4$.

In connection with the terms "$C_{1-10}$-alkyl", "$C_{1-6}$-alkyl", "$C_{1-4}$-alkyl", "$C_{3-10}$-cycloalkyl", "$C_{3-6}$-cycloalkyl", "3 to 7 membered heterocycloalkyl", "$C_{1-6}$-alkylene", "$C_{1-4}$-alkylene" and "$C_{1-2}$-alkylene", the term "substituted" refers in the sense of the present invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$ or disubstituted as in the case of 1,1-difluorocyclohexyl, or at various points, as in the case of CH(OH)—CH=CH—$CHCl_2$ or 1-chloro-3-fluorocyclohexyl. The multiple substitution can be carried out using the same or using different substituents.

In relation to the terms "aryl", "phenyl", "heteroaryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the present invention, preferably $C_{1-10}$-alkyl, $C_{1-6}$-alkyl, $C_{1-4}$-alkyl, $C_{3-10}$-cycloalkyl, $C_{3-6}$-cycloalkyl, 3 to 7 membered heterocycloalkyl, $C_{1-6}$-alkylene, $C_{1-4}$-alkylene and $C_{1-2}$-alkylene in each case independently from one another are unsubstituted or mono- or polysubstituted with one or more substituents selected from F; Cl; Br; I; CN; $C_{1-6}$-alkyl; $CF_3$; $CF_2H$; $CFH_2$; $CF_2Cl$; $CFCl_2$; C(O)—$C_{1-6}$-alkyl; C(O)—OH; C(O)—$OC_{1-6}$-alkyl; C(O)—$NH_2$; C(O)—N(H)($C_{1-6}$-alkyl); C(O)—N($C_{1-6}$-alkyl)$_2$; OH; =O; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—S(O)$_2$—$NH_2$; O—S(O)$_2$—N(H)($C_{1-6}$-alkyl); O—S(O)$_2$—N($C_{1-6}$-alkyl)$_2$; $NH_2$; N(H)($C_{1-6}$-alkyl); N($C_{1-6}$-alkyl)$_2$; N(H)—C(O)—$C_{1-6}$-alkyl; N(H)—C(O)—O—$C_{1-6}$-alkyl; N(H)—C(O)—$NH_2$; N(H)—C(O)—N(H)($C_{1-6}$-alkyl); N(H)—C(O)—N($C_{1-6}$-alkyl)$_2$; N($C_{1-6}$-alkyl)-C(O)—$C_{1-6}$-alkyl; N($C_{1-6}$-alkyl)-C(O)—O—$C_{1-6}$-alkyl; N($C_{1-6}$-alkyl)-C(O)—$NH_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$OH; N(H)—S(O)$_2$—$C_{1-6}$-alkyl; N(H)—S(O)$_2$—O—$C_{1-6}$-alkyl; N(H)—S(O)$_2$—$NH_2$; N(H)—S(O)$_2$—N(H)($C_{1-6}$-alkyl); N(H)—S(O)$_2$N($C_{1-6}$-alkyl)$_2$; N($C_{1-6}$-alkyl)-S(O)$_2$—OH; N($C_{1-6}$-alkyl)-S(O)$_2$—$C_{1-6}$-alkyl; N($C_{1-6}$-alkyl)-S(O)$_2$—O—$C_{1-6}$-alkyl; N($C_{1-6}$-alkyl)-S(O)$_2$—$NH_2$; N($C_{1-6}$-alkyl)-S(O)$_2$—N(H)($C_{1-6}$-alkyl); N($C_{1-6}$-alkyl)-S(O)$_2$—N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; 3 to 7-membered heterocycloalkyl; phenyl; 5 or 6-membered heteroaryl; O—$C_{3-6}$-cycloalkyl; O-(3 to 7-membered heterocycloalkyl); O-phenyl; O-(5 or 6-membered heteroaryl); C(O)—$C_{3-6}$-cycloalkyl; C(O)-(3 to 7-membered heterocycloalkyl); C(O)-phenyl; C(O)-(5 or 6-membered heteroaryl); S(O)$_2$—($C_{3-6}$-cycloalkyl); S(O)$_2$-(3 to 7-membered heterocycloalkyl); S(O)$_2$-phenyl and S(O)$_2$-(5 or 6-membered heteroaryl).

Preferred substituents of $C_{1-10}$-alkyl, $C_{1-6}$-alkyl, $C_{1-4}$-alkyl, $C_{3-10}$-cycloalkyl, $C_{3-6}$-cycloalkyl, 3 to 7 membered heterocycloalkyl, $C_{1-6}$-alkylene and $C_{1-4}$-alkylene are selected from the group consisting of F; Cl; Br; I; CN; $C_{1-6}$-alkyl; $CF_3$; $CF_2H$; $CFH_2$; C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; O—$C_{1-6}$-alkyl; $NH_2$; N(H)($C_{1-6}$-alkyl); N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; $C_{3-6}$-cycloalkyl; 3 to 7-membered heterocycloalkyl; phenyl and 5 or 6-membered heteroaryl; and particularly preferably F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl. According to this embodiment, $C_{1-10}$-alkyl, $C_{1-6}$-alkyl, $C_{1-4}$-alkyl, $C_{3-10}$-cycloalkyl, $C_{3-6}$-cycloalkyl, 3 to 7 membered heterocycloalkyl, are preferably each independently from one another unsubstituted, mono- di- or trisubstituted, more preferably unsubstituted or monosubstituted or disubstituted with a substituent selected from the group consisting of F; Cl; Br; I; CN; $C_{1-6}$-alkyl; $CF_3$; $CF_2H$; $CFH_2$; C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; O—$C_{1-6}$-alkyl; $NH_2$; N(H)($C_{1-6}$-alkyl); N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; $C_{3-6}$-cycloalkyl; 3 to 7-membered heterocycloalkyl; phenyl and 5 or 6-membered heteroaryl. Preferably, $C_{1-6}$-alkylene groups and $C_{1-4}$-alkylene groups are unsubstituted.

According to the present invention, preferably aryl, phenyl and 5 or 6-membered heteroaryl in each case independently from one another are unsubstituted or mono- or polysubstituted with one or more substituents selected from F; Cl; Br; I; CN; $C_{1-6}$-alkyl; $C_{1-6}$-alkenyl; $C_{1-6}$-alkynyl; $C_{1-6}$-alkynyl-C(H)(OH)$CH_3$; $C_{1-6}$-alkynyl-C($CH_3$)$_2$OH; $CF_3$; $CF_2H$; $CFH_2$; $CF_2Cl$; $CFCl_2$; $C_{1-6}$-alkylene-$CF_3$; $C_{1-6}$-alkylene-$CF_2H$; $C_{1-6}$-alkylene-$CFH_2$; $C_{1-6}$-alkylene-OH; $C_{1-6}$-alkylene-$OCH_3$; C(O)—$C_{1-6}$-alkyl; C(O)—OH; C(O)—O$C_{1-6}$-alkyl; C(O)—N(H)(OH); C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; O—$C_{3-6}$-cycloalkyl; O-(3 to 7-membered heterocycloalkyl); $NH_2$; N(H)($C_{1-6}$-alkyl); N($C_{1-6}$-alkyl)$_2$; N(H)—C(O)—$C_{1-6}$-alkyl; N($C_{1-6}$-alkyl)-C(O)—$C_{1-6}$-alkyl; N(H)—C(O)—$NH_2$; N(H)—C(O)—N(H)($C_{1-6}$-alkyl); N(H)—C(O)—N($C_{1-6}$-alkyl)$_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$—$C_{1-6}$-alkyl; $SCF_3$; S—$C_{1-6}$-alkyl; S(O)—$C_{1-6}$-alkyl; S(O)$_2$—$C_{1-6}$-alkyl; S(O)$_2$—$C_{3-6}$-cycloalkyl; S(O)$_2$—$C_{1-6}$-alkylene-$C_{3-6}$-cycloalkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; $C_{1-6}$-alkylene-$C_{3-6}$-cycloalkyl; 3 to 7-membered heterocycloalkyl; $C_{1-6}$-alkylene-(3 to 7-membered heterocycloalkyl); phenyl and 5 or 6-membered heteroaryl.

Preferred substituents of aryl, phenyl and 5 or 6-membered heteroaryl are selected from the group consisting of F; Cl; Br; I; CN; $C_{1-6}$-alkyl; $C_{1-6}$-alkenyl; $C_{1-6}$-alkynyl; $C_{1-6}$-alkynyl-C(H)(OH)$CH_3$; $C_{1-6}$-alkynyl-C($CH_3$)$_2$OH; $C_{1-6}$-alkylene-OH; $CF_3$; $CF_2H$; $CFH_2$; $C_{1-4}$-alkylene-$CF_3$; $C_{1-4}$-alkylene-$CF_2H$; $C_{1-4}$-alkylene-$CFH_2$; OH; $OCF_3$; $OCF_2H$; $OCFH_2$; O—$C_{1-6}$-alkyl; O—$C_{3-6}$-cycloalkyl; $NH_2$; $C_{3-6}$-cycloalkyl; 3 to 7-membered heterocycloalkyl; $C_{1-6}$-alkylene-(3 to 7-membered heterocycloalkyl); S(O)$_2$—$C_{1-6}$-alkyl; and S(O)$_2$—$C_{3-6}$-cycloalkyl. According to this embodiment, aryl, phenyl and 5 or 6-membered heteroaryl are preferably each independently from one another unsubstituted, mono- di- or trisubstituted, more preferably unsubstituted or monosubstituted or disubstituted.

In a particularly preferred embodiment, the compound according to the present invention is selected from the group consisting of 1 3,5,11,11-tetramethyl-6-(1-(methylsulfonyl)-1H-indol-4-yl)-8,9,10,11-tetrahydrofuro[3,2-f][1,2,4]triazolo[4,3-a]quinoxaline 2 6-(1-(ethylsulfonyl)-1H-indol-4-yl)-3,5,11,11-tetramethyl-8,9,10,11-tetrahydrofuro[3,2-f][1,2,4]triazolo[4,3-a]quinoxaline 3 6-(5-chloro-2-methoxypyridin-3-yl)-3,5,11,11-tetramethyl-8,9,10,11-tetrahydrofuro[3,2-f][1,2,4]triazolo[4,3-a]quinoxaline 4 2-(6-fluoro-4-(3,5,11,11-tetramethyl-8,9,10,11-tetrahydrofuro[3,2-f][1,2,4]triazolo[4,3-a]quinoxalin-6-yl)-1H-indol-1-yl)ethan-1-ol 5 6-(1-(cyclopropylsulfonyl)-1H-indol-4-yl)-3,5,11,11-tetramethyl-8,9,10,11-tetrahydrofuro[3,2-f][1,2,4]triazolo[4,3-a]quinoxaline 6 6-(1-(2,2-difluoroethyl)-1H-indol-4-yl)-3,5,11,11-tetramethyl-8,9,10,11-tetrahydrofuro[3,2-f][1,2,4]triazolo[4,3-a]quinoxaline 7 6-(1-(isopropylsulfonyl)-1H-indol-4-yl)-3,5,11,11-tetramethyl-8,9,10,11-tetrahydrofuro[3,2-f][1,2,4]triazolo[4,3-a]quinoxaline 8 3,5,11,11-tetramethyl-6-(3-methyl-1H-indol-7-yl)-8,9,10,11-tetrahydrofuro[3,2-f][1,2,4]triazolo[4,3-a]quinoxaline 9 6-(6-fluoro-1-(methylsulfonyl)-1H-indol-4-yl)-3,5,11,11-tetramethyl-8,9,10,11-tetrahydrofuro[3,2-f][1,2,4]triazolo[4,3-a]quinoxaline 10 6-(1-(2,2-difluoroethyl)-1H-indol-4-yl)-3,11,11-trimethyl-5-(trifluoromethyl)-8,9,10,11-tetrahydrofuro[3,2-f][1,2,4]triazolo[4,3-a]quinoxaline 11 6-(1-(2,2-difluoroethyl)-6-fluoro-1H-indazol-4-yl)-3,11,11-trimethyl-5-(trifluoromethyl)-8,9,10,11-tetrahydrofuro[3,2-f][1,2,4]triazolo[4,3-a]quinoxaline 12 6-(6-fluoro-1-(methylsulfonyl)-1H-indol-4-yl)-3,11,11-trimethyl-5-(trifluoromethyl)-8,9,10,11-tetrahydrofuro[3,2-f][1,2,4]triazolo[4,3-a]quinoxaline 13 6-(3-cyclopropyl-5-fluoro-1H-indol-7-yl)-5-fluoro-3,11,11-trimethyl-8,9,10,11-tetrahydrofuro[3,2-f][1,2,4]triazolo[4,3-a]quinoxaline 14 5-fluoro-6-(5-fluoro-3-methyl-1H-indol-7-yl)-3,11,11-trimethyl-8,9,10,11-tetrahydrofuro[3,2-f][1,2,4]triazolo[4,3-a]quinoxaline 15 5-fluoro-3,11,11-trimethyl-6-(3-methyl-1H-indol-7-yl)-8,9,10,11-tetrahydrofuro[3,2-f][1,2,4]triazolo[4,3-a]quinoxaline 16 5-fluoro-6-(1H-indol-4-yl)-3,11,11-trimethyl-8,9,10,11-tetrahydrofuro[3,2-f][1,2,4]triazolo[4,3-a]quinoxaline 17 5-fluoro-6-(6-fluoro-1-(methylsulfonyl)-1H-indol-4-yl)-3,11,11-trimethyl-8,9,10,11-tetrahydrofuro[3,2-f][1,2,4]triazolo[4,3-a]quinoxaline 18 5-fluoro-6-(6-fluoro-1-methyl-1H-indol-4-yl)-3,11,11-trimethyl-8,9,10,11-tetrahydrofuro[3,2-f][1,2,4]triazolo[4,3-a]quinoxaline 19 5-chloro-6-(1-(ethylsulfonyl)-1H-indol-4-yl)-3,11,11-trimethyl-8,9,10,11-tetrahydrofuro[3,2-f][1,2,4]triazolo[4,3-a]quinoxaline 20 5-chloro-6-(1-(cyclopropylsulfonyl)-1H-indol-4-yl)-3,11,11-trimethyl-8,9,10,11-tetrahydrofuro[3,2-f][1,2,4]triazolo[4,3-a]quinoxaline 21 5-chloro-6-(1-(2,2-difluoroethyl)-6-fluoro-1H-indazol-4-yl)-3,11,11-trimethyl-8,9,10,11-tetrahydrofuro[3,2-f][1,2,4]triazolo[4,3-a]quinoxaline 22 5-chloro-6-(5-chloro-2-methoxypyridin-3-yl)-3,11,11-trimethyl-8,9,10,11-tetrahydrofuro[3,2-f][1,2,4]triazolo[4,3-a]quinoxaline 23 5-chloro-6-(1-(2,2-difluoroethyl)-1H-indol-4-yl)-3,11,11-trimethyl-8,9,10,11-tetrahydrofuro[3,2-f][1,2,4]triazolo[4,3-a]quinoxaline 24 5-chloro-6-(1-(isopropylsulfonyl)-1H-indol-4-yl)-3,11,11-trimethyl-8,9,10,11-tetrahydrofuro[3,2-f][1,2,4]triazolo[4,3-a]quinoxaline 25 5-chloro-6-(4-fluoro-1H-indazol-6-yl)-3,11,11-trimethyl-8,9,10,11-tetrahydrofuro[3,2-f][1,2,4]triazolo[4,3-a]quinoxaline 26 6-Ethyl-9-fluoro-8-(5-fluoro-3-methyl-1H-indol-7-yl)-1,4,4-trimethyl-5H-[1,2,4]triazolo[4,3-a]quinoxaline 27 8-(1-Cyclopropyl-6-fluoro-1H-indol-4-yl)-6-ethyl-9-fluoro-1,4,4-trimethyl-5H-[1,2,4]triazolo[4,3-a]quinoxaline 28 6-Ethyl-9-fluoro-8-(1H-indol-4-yl)-1,4,4-trimethyl-5H-[1,2,4]triazolo[4,3-a]quinoxaline 29 6-Ethyl-9-fluoro-8-(6-fluoro-1-methylsulfonyl-1H-indol-4-yl)-1,4,4-trimethyl-5H-[1,2,4]triazolo[4,3-a]quinoxaline 30 6-Ethyl-9-fluoro-8-(5-fluoro-3-tetrahydro-furan-3-yl-1H-indol-7-yl)-1,4,4-trimethyl-5H-[1,2,4]triazolo[4,3-a]quinoxaline 31 2-[7-(6-Ethyl-9-fluoro-1,4,4-trimethyl-5H-[1,2,4]triazolo[4,3-a]quinoxalin-8-yl)-5-fluoro-1H-indol-3-yl]-ethanol 32 6-Ethyl-9-fluoro-8-[2-methoxy-5-(trifluoromethyl)-pyridin-3-yl]-1,4,4-trimethyl-5H-[1,2,4]triazolo[4,3-a]quinoxaline 33 8-(6-Fluoro-1-methylsulfonyl-1H-indol-4-yl)-1,4,4,6-tetramethyl-9-(trifluoromethyl)-5H-[1,2,4]triazolo[4,3-a]quinoxaline 34 8-(5-Fluoro-3-prop-1-ynyl-1H-indol-7-yl)-1,4,4,6-tetramethyl-9-(trifluoromethyl)-5H-[1,2,4]triazolo[4,3-a]quinoxaline 35 2-[6-Fluoro-4-[1,4,4,6-tetramethyl-9-(trifluoromethyl)-5H-[1,2,4]triazolo[4,3-a]quinoxalin-8-yl]-1H-indol-1-yl]-ethanol 36 8-(1-Cyclopropyl-6-fluoro-1H-indol-4-yl)-9-fluoro-1,4,4,6-tetramethyl-5H-[1,2,4]triazolo[4,3-a]quinoxaline 37 9-Fluoro-8-(6-fluoro-1-methylsulfonyl-1H-indol-4-yl)-1,4,4,6-tetramethyl-5H-[1,2,4]triazolo[4,3-a]quinoxaline 38 9-Fluoro-8-(5-fluoro-3-methyl-1H-indol-7-yl)-1,4,4,6-tetramethyl-5H-[1,2,4]triazolo[4,3-a]quinoxaline 39 9-Fluoro-8-(1H-indol-4-yl)-1,4,4,6-tetramethyl-5H-[1,2,4]triazolo[4,3-a]quinoxaline 40 4-[5-Fluoro-7-(9-fluoro-1,4,4,6-tetramethyl-5H-[1,2,4]triazolo[4,3-a]quinoxalin-8-yl)-1H-indol-3-yl]-but-3-yn-2-ol 41 9-Fluoro-1,4,4,6-tetramethyl-8-(1-methylsulfonyl-1H-indol-4-yl)-5H-[1,2,4]triazolo[4,3-a]quinoxaline 42 9-Fluoro-8-(5-fluoro-3-prop-1-ynyl-1H-indol-7-yl)-1,4,4,6-tetramethyl-5H-[1,2,4]triazolo[4,3-a]quinoxaline 43 4-[5-Fluoro-7-(9-fluoro-1,4,4,6-tetramethyl-5H-[1,2,4]triazolo[4,3-a]quinoxalin-8-yl)-1H-indol-3-yl]-2-methyl-but-3-yn-2-ol 44 8-(3-Cyclopropyl-5-fluoro-1H-indol-7-yl)-9-fluoro-1,4,4,6-tetramethyl-5H-[1,2,4]triazolo[4,3-a]quinoxaline 45 9-Fluoro-1,4,4,6-tetramethyl-8-pyrazolo[1,5-a]pyridin-4-yl-5H-[1,2,4]triazolo[4,3-a]quinoxaline 46 2-[5-Fluoro-7-(9-fluoro-1,4,4,6-tetramethyl-5H-[1,2,4]triazolo[4,3-a]quinoxalin-8-yl)-1H-indol-3-yl]-ethanol 47 2-[5-Fluoro-4-(9-fluoro-1,4,4,6-tetramethyl-5H-[1,2,4]triazolo[4,3-a]quinoxalin-8-yl)-1H-indol-1-yl]-ethanol 48 9-Fluoro-8-imidazo[1,2-a]pyridin-5-yl-1,4,4,6-tetramethyl-5H-[1,2,4]triazolo[4,3-a]quinoxaline 49 5-fluoro-6-(5-fluoro-3-methyl-1H-indol-7-yl)-3,11,11-trimethyl-8,9,10,11-tetrahydro-7H-cyclopenta[f][1,2,4]triazolo[4,3-a]quinoxaline 50 6-(1-cyclopropyl-6-fluoro-1H-indol-4-yl)-5-fluoro-3,11,11-trimethyl-8,9,10,11-tetrahydro-7H-cyclopenta[f][1,2,4]triazolo[4,3-a]quinoxaline 51 5-fluoro-6-(6-fluoro-1-(methylsulfonyl)-1H-indol-4-yl)-3,11,11-trimethyl-8,9,10,11-tetrahydro-7H-cyclopenta[f][1,2,4]triazolo[4,3-a]quinoxaline 52 5-fluoro-6-(5-fluoro-3-(tetrahydrofuran-3-yl)-1H-indol-7-yl)-3,11,11-trimethyl-8,9,10,11-tetrahydro-7H-cyclopenta[f][1,2,4]triazolo[4,3-a]quinoxaline 53 9-Fluoro-8-(6-fluoro-1H-indol-4-yl)-1,4,4-trimethyl-6-(trifluoromethyl)-5H-[1,2,4]triazolo[4,3-a]quinoxaline 54 9-Fluoro-1,4,4-trimethyl-8-(1-methylsulfonyl-1H-indol-4-yl)-6-(trifluoromethyl)-5H-[1,2,4]triazolo[4,3-a]quinoxaline 55 9-Fluoro-8-[6-fluoro-1-(2-methoxy-ethyl)-1H-indol-4-yl]-1,4,4-trimethyl-6-(trifluoromethyl)-5H-[1,2,4]triazolo[4,3-a]quinoxaline 56 9-Fluoro-1,4,4-trimethyl-8-(1H-pyrrolo[2,3-b]pyridin-4-yl)-6-(trifluoromethyl)-5H-[1,2,4]triazolo[4,3-a]quinoxaline 57 8-[1-(2,2-Difluoro-ethyl)-6-fluoro-1H-indazol-4-yl]-9-fluoro-1,4,4-trimethyl-6-(trifluoromethyl)-5H-[1,2,4]triazolo[4,3-a]quinoxaline 58 9-Fluoro-8-[6-fluoro-1-(2-methoxy-ethyl)-1H-indazol-4-yl]-1,4,4-trimethyl-6-(trifluoromethyl)-5H-[1,2,4]triazolo[4,3-a]quinoxaline 59 8-(5-Fluoro-3-methyl-1H-indol-7-yl)-1,4,4,9-tetramethyl-6-methylsulfanyl-5H-[1,2,4]triazolo[4,3-a]quinoxaline 60 1,4,4,9-Tetramethyl-8-(3-methyl-1H-indol-7-yl)-5H-[1,2,4]triazolo[4,3-a]quinoxalin-6-ol 61 2-[9-Fluoro-8-(5-fluoro-3-methyl-1H-indol-7-yl)-1,4,4-trimethyl-5H-[1,2,4]triazolo[4,3-a]quinoxalin-6-yl]-propan-2-ol 62 6-Fluoro-8-(6-fluoro-pyrazolo[1,5-a]pyridin-4-yl)-1,4,4,9-tetramethyl-5H-[1,2,4]triazolo[4,3-a]quinoxaline 63 8-(5-Chloro-2-methoxy-pyridin-3-yl)-9-(difluoromethyl)-7-fluoro-1,4,4-trimethyl-5H-[1,2,4]triazolo[4,3-a]quinoxaline 64 7-Fluoro-1,4,4-trimethyl-8-(1-methyl-1H-pyrrolo[2,3-b]pyridin-3-yl)-9-(trifluoromethyl)-5H-[1,2,4]triazolo[4,3-a]quinoxaline 65 8-(5,6-Dihydro-4H-pyrrolo[1,2-b]pyrazol-3-yl)-7,9-difluoro-1,4,4-trimethyl-5H-[1,2,4]triazolo[4,3-a]quinoxaline 66 8-(5-Chloro-2-methoxy-pyridin-3-yl)-9-cyclopropyl-7-fluoro-1,4,4-trimethyl-5H-[1,2,4]triazolo[4,3-a]quinoxaline 67 7,9-Difluoro-1,4,4-trimethyl-8-naphthalen-1-yl-5H-[1,2,4]triazolo[4,3-a]quinoxaline 68 8-(Benzofuran-4-yl)-7,9-difluoro-1,4,4-trimethyl-5H-[1,2,4]triazolo[4,3-a]quinoxaline 69 7,9-Difluoro-8-(3-fluoro-5-vinyl-phenyl)-1,4,4-trimethyl-5H-[1,2,4]triazolo[4,3-a]quinoxaline 70 7,9-Difluoro-8-(3-fluoro-5-methyl-phenyl)-1,4,4-trimethyl-5H-[1,2,4]triazolo[4,3-a]quinoxaline 71 8-(5-Chloro-2-methoxy-pyridin-3-yl)-7-fluoro-1,4,4,9-tetramethyl-5H-[1,2,4]triazolo[4,3-a]quinoxaline 72 6-Fluoro-8-(6-fluoro-pyrazolo[1,5-a]pyridin-4-yl)-9-methoxy-1,4,4-trimethyl-5H-[1,2,4]triazolo[4,3-a]quinoxaline 73 8-(5-Fluoro-1H-indol-1-yl)-1,4,4,9-tetramethyl-5H-[1,2,4]triazolo[4,3-a]quinoxaline 74 8-(3-Ethyl-5-fluoro-phenyl)-7,9-difluoro-1,4,4-trimethyl-5H-[1,2,4]triazolo[4,3-a]quinoxaline 75 8-(5-Chloro-2-methoxy-pyridin-3-yl)-9-(difluoro-methyl)-1,4,4-trimethyl-5H-[1,2,4]triazolo[4,3-a]quinoxaline 76 7-Chloro-8-(5-chloro-2-methoxy-pyridin-3-yl)-6-fluoro-1,4,4,9-tetramethyl-5H-[1,2,4]triazolo[4,3-a]quinoxaline 77 8-(1-Cyclopropyl-1H-indol-3-yl)-6-fluoro-9-methoxy-1,4,4-trimethyl-5H-[1,2,4]triazolo[4,3-a]quinoxaline 78 7,9-Difluoro-8-(3-fluoro-5-methoxy-phenyl)-1,4,4-trimethyl-5H-[1,2,4]triazolo[4,3-a]quinoxaline 79 8-(5-Chloro-2-methoxy-pyridin-3-yl)-6,7-difluoro-1,4,4,9-tetramethyl-5H-[1,2,4]triazolo[4,3-a]quinoxaline 80 7-Fluoro-8-(5-fluoro-2-methoxy-pyridin-3-yl)-1,4,4,9-tetramethyl-5H-[1,2,4]triazolo[4,3-a]quinoxaline 81 9-(Difluoro-methyl)-6-fluoro-1,4,4-trimethyl-8-pyrazolo[1,5-a]pyridin-4-yl-5H-[1,2,4]triazolo[4,3-a]quinoxaline 82 6-Chloro-8-(5-chloro-2-methoxy-pyridin-3-yl)-7-fluoro-1,4,4,9-tetramethyl-5H-[1,2,4]triazolo[4,3-a]quinoxaline 83 8-(5-Chloro-2-methoxy-pyridin-3-yl)-1,4,4,9-tetramethyl-7-(trifluoromethyloxy)-5H-[1,2,4]triazolo[4,3-a]quinoxaline 84 [3-(7,9-Difluoro-1,4,4-trimethyl-5H-[1,2,4]triazolo[4,3-a]quinoxalin-8-yl)-5-fluoro-phenyl]-amine 85 9-(Difluoro-methyl)-7-fluoro-1,4,4-trimethyl-8-(1-methyl-1H-pyrrolo[2,3-b]pyridin-3-yl)-5H-[1,2,4]triazolo[4,3-a]quinoxaline 86 7-Fluoro-8-(2-methoxy-5-methyl-pyridin-3-yl)-1,4,4,9-tetramethyl-5H-[1,2,4]triazolo[4,3-a]quinoxaline 87 1-Ethyl-7,9-difluoro-4,4-dimethyl-8-[(3-pyridin-3-yl-pyrrolidin-1-yl)-methyl]-5H-[1,2,4]triazolo[4,3-a]quinoxaline 88 7,9-Difluoro-1,4,4-trimethyl-8-quinolin-5-yl-5H-[1,2,4]triazolo[4,3-a]quinoxaline 89 8-(4-Fluoro-1H-indol-1-yl)-1,4,4,9-tetramethyl-5H-[1,2,4]triazolo[4,3-a]quinoxaline 90 7,9-Difluoro-8-[2-methoxy-5-(trifluoromethyl)-pyridin-3-yl]-1,4,4-trimethyl-5H-[1,2,4]triazolo[4,3-a]quinoxaline 91 9-Ethyl-6-fluoro-1,4,4-trimethyl-8-pyrazolo[1,5-a]pyridin-4-yl-5H-[1,2,4]triazolo[4,3-a]quinoxaline 92 7,9-Difluoro-1,4,4-trimethyl-8-pyrazolo[1,5-a]pyridin-3-yl-5H-[1,2,4]triazolo[4,3-a]quinoxaline 93 1,4,4,9-Tetramethyl-8-(5-methyl-1H-indol-1-yl)-5H-[1,2,4]triazolo[4,3-a]quinoxaline 94 7-Fluoro-9-methoxy-1,4,4-trimethyl-8-(1-methyl-1H-pyrrolo[2,3-b]pyridin-3-yl)-5H-[1,2,4]triazolo[4,3-a]quinoxaline 95 8-(1H-Indol-1-yl)-1,4,4,9-tetramethyl-5H-[1,2,4]triazolo[4,3-a]quinoxaline 96 7,9-Difluoro-8-(1H-indol-3-yl)-1,4,4-trimethyl-5H-[1,2,4]triazolo[4,3-a]quinoxaline 97 9-(Difluoro-methyl)-7-fluoro-8-(7-fluoro-1H-indol-3-yl)-1,4,4-trimethyl-5H-[1,2,4]triazolo[4,3-a]quinoxaline 98 5-(7-Fluoro-1,4,4,9-tetramethyl-5H-[1,2,4]triazolo[4,3-a]quinoxalin-8-yl)-1-methyl-3,4-dihydro-1H-quinolin-2-one 99 7,9-Difluoro-1,4,4-trimethyl-8-(1-methyl-1H-pyrrolo[2,3-c]pyridin-3-yl)-5H-[1,2,4]triazolo[4,3-a]quinoxaline 100 7,9-Difluoro-8-(5-fluoro-spiro[1,2-dihydro-indole-3,1'-cyclopropane]-7-yl)-1,4,4-trimethyl-5H-[1,2,4]triazolo[4,3-a]quinoxaline 101 8-(5-Chloro-2-methoxy-pyridin-3-yl)-9-cyclopropyl-6-fluoro-1,4,4-trimethyl-5H-[1,2,4]triazolo[4,3-a]quinoxaline 102 3-(7,9-Difluoro-1,4,4-trimethyl-5H-[1,2,4]triazolo[4,3-a]quinoxalin-8-yl)-5-fluoro-phenol 103 8-(5-Ethyl-2-methoxy-pyridin-3-yl)-7-fluoro-1,4,4,9-tetramethyl-5H-[1,2,4]triazolo[4,3-a]quinoxaline 104 8-(5-Cyclopropyl-2-methoxy-pyridin-3-yl)-7-fluoro-1,4,4,9-tetramethyl-5H-[1,2,4]triazolo[4,3-a]quinoxaline 105 7,9-Difluoro-1,4,4-trimethyl-8-(1H-pyrrolo[2,3-b]pyridin-4-yl)-5H-[1,2,4]triazolo[4,3-a]quinoxaline 106 8-(2,3-Dihydro-[1,4]benzodioxin-5-yl)-7-fluoro-1,4,4,9-tetramethyl-5H-[1,2,4]triazolo[4,3-a]quinoxaline 107 6-Fluoro-9-methoxy-1,4,4-trimethyl-8-(1-methylsulfonyl-1H-indol-3-yl)-5H-[1,2,4]triazolo[4,3-a]quinoxaline 108 1-[2-[4-(7,9-Difluoro-1,4,4-trimethyl-5H-[1,2,4]triazolo[4,3-a]quinoxalin-8-yl)-1H-pyrazol-1-yl]-ethyl]-pyrrolidin-2-one 109 7,9-Difluoro-1,4,4-trimethyl-8-spiro[1,2-dihydro-indole-3,1'-cyclopropane]-7-yl-5H-[1,2,4]triazolo[4,3-a]quinoxaline 110 4-(7,9-Difluoro-1,4,4-trimethyl-5H-[1,2,4]triazolo[4,3-a]quinoxalin-8-yl)-6-fluoro-benzothiazole 111 8-(1H-Benzotriazol-4-yl)-6-fluoro-1,4,4,9-tetramethyl-5H-[1,2,4]triazolo[4,3-a]quinoxaline 112 8-(1-Cyclopropyl-1H-pyrrolo[2,3-b]pyridin-3-yl)-6-fluoro-9-methoxy-1,4,4-trimethyl-5H-[1,2,4]triazolo[4,3-a]quinoxaline 113 8-(3-Chloro-2-methoxy-phenyl)-7,9-difluoro-1,4,4-trimethyl-5H-[1,2,4]triazolo[4,3-a]quinoxaline 114 4-(7,9-Difluoro-1,4,4-trimethyl-5H-[1,2,4]triazolo[4,3-a]quinoxalin-8-yl)-2-fluoro-phenol 115 5-(7-Fluoro-1,4,4,9-tetramethyl-5H-[1,2,4]triazolo[4,3-a]quinoxalin-8-yl)-3,4-dihydro-1H-quinolin-2-one 116 1-Cyclopropyl-6-fluoro-8-(6-fluoro-pyrazolo[1,5-a]pyridin-4-yl)-4,4,9-trimethyl-5H-[1,2,4]triazolo[4,3-a]quinoxaline 117 8-(5-Chloro-2-methoxy-pyridin-3-yl)-7-(difluoro-methyl)-9-fluoro-1,4,4-trimethyl-5H-[1,2,4]triazolo[4,3-a]quinoxaline 118 8-(5-Chloro-2-methoxy-pyridin-3-yl)-1,4,4-trimethyl-9-(trifluoromethyl)-5H-[1,2,4]triazolo[4,3-a]quinoxaline 119 7,9-Difluoro-1,4,4-trimethyl-8-(1-methyl-1H-pyrrolo[2,3-b]pyridin-4-yl)-5H-[1,2,4]triazolo[4,3-a]quinoxaline 120 1,4,4,9-Tetramethyl-8-(4-methyl-1H-indol-1-yl)-5H-[1,2,4]triazolo[4,3-a]quinoxaline 121 7,9-Difluoro-8-(2-fluoro-3-methoxy-phenyl)-1,4,4-trimethyl-5H-[1,2,4]triazolo[4,3-a]quinoxaline 122 7,9-Difluoro-N-[(3-methoxyphenyl)-methyl]-1,4,4-trimethyl-5H-[1,2,4]triazolo[4,3-a]quinoxaline-8-carboxylic acid amide in the form of the free compound or a physiologically acceptable salt thereof.

The compounds according to the present invention can be synthesized by standard reactions in the field of organic chemistry known to the person skilled in the art or in a manner as described herein (cf. Reaction Scheme 1 below) or analogously. The reaction conditions in the synthesis routes described herein are known to the skilled person and are for some cases also exemplified in the Examples described herein.

Reaction scheme 1

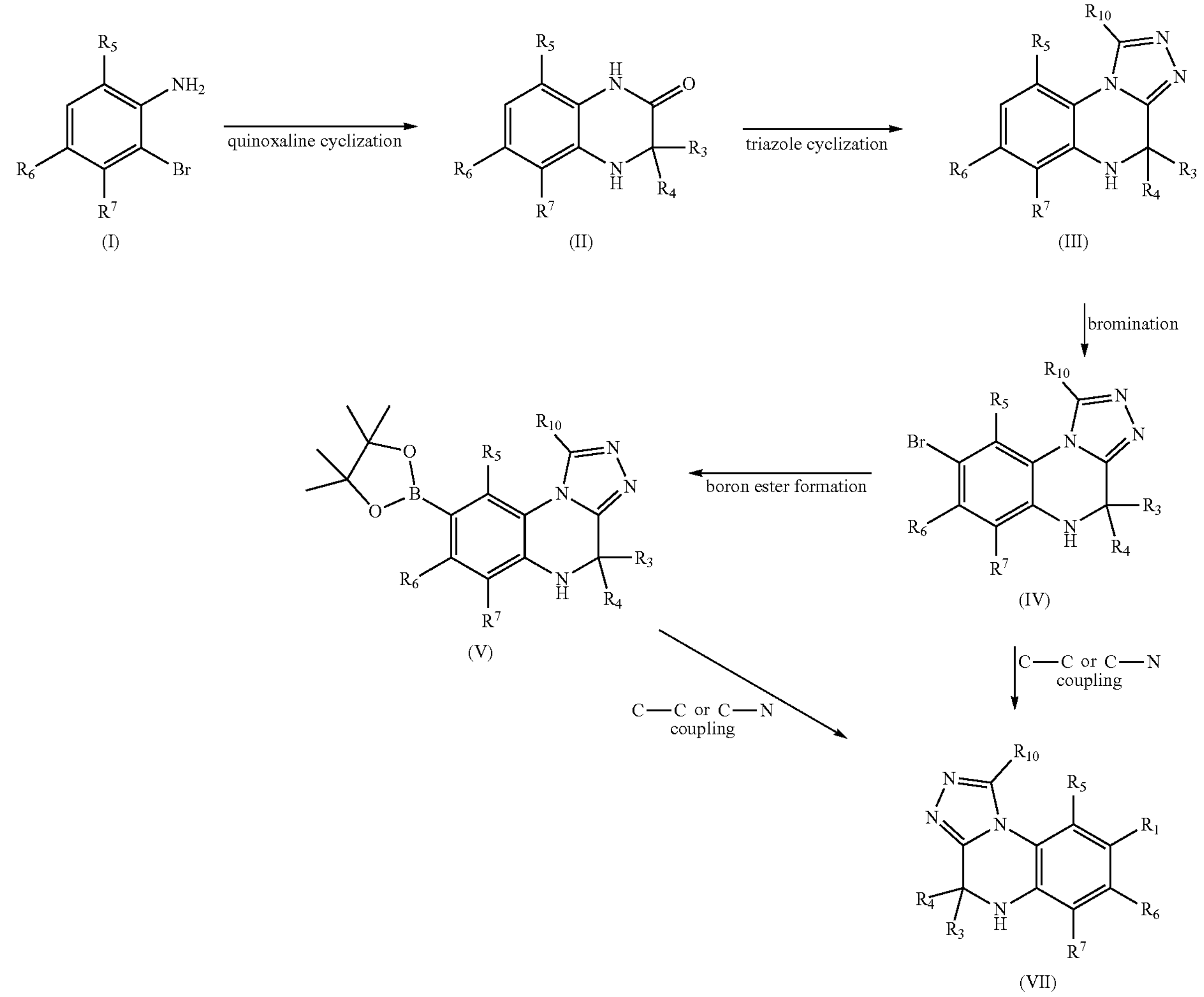

$R^1$ in compounds of formula (VII) can be introduced by subjecting a compound of formula (IV) in a metal catalyzed C—C or C—N coupling reaction. Metal catalyzed C—C coupling reactions are known in the art (cf. *Metal Catalyzed Cross-Coupling Reactions and More,* 3 Volume Set Wiley, 2014; *Angew. Chem. Int. Ed.,* 2012, 51, 5062-5085). Favorable C—C coupling reactions are palladium catalyzed cross coupling reactions (cf. Angew. Chem., 2005, 117, 4516-4563). Metal catalyzed C—N coupling reactions are generally known in the art (Current Organic Synthesis, 2011, 8, 53). Favorable C—N coupling reactions are palladium and copper catalyzed cross-coupling reactions (Chem. Rev., 2016, 116, 12564; Chem. Soc. Rev., 2014, 43, 3525; Chem. Sci., 2010, 1, 13). Triazole cyclization of compound (II) gives access to compounds of general formula (III). Triazole formation on quinoxalines is known in the art (cf. *Heterocycles,* 1992, 34, 771-780; *Biological and Pharmaceutical Bulletin,* 2005, 28, 1216-1220).

Electrophilic aromatic bromination of compound (III) gives compound (IV). Bromination reactions of aromatic compounds are generally known (cf. *Science of Synthesis*, Compounds with One Saturated Carbon-Heteroatom Bond, Volume 35, Houben-Weyl, 2007). Copper mediated quinoxaline cyclization of compound (I) to compound (II) is known in the art (cf. *Adv. Synth. Catal.,* 2010, 352, 2531-2537). Compounds of formula (I) are commercially available or can be prepared according to methods known in the art.

The compounds according to the present invention can be produced in the manner described here or in an analogous manner.

In a preferred embodiment, the compounds according to the present invention are modulators of the glucocorticoid receptor. In the sense of the present invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 μM ($10 \cdot 10^{-6}$ mol/L) or at most 10 μM; more preferably at most 1 μM; still more preferably at most 500 nM ($10^{-9}$ mol/L); yet more preferably at most 300 nM; even more preferably at most 100 nM; most preferably at most 10 nM; and in particular at most 1 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Glucocorticoid Receptor Cell-Based Assays

Potential selective glucocorticoid receptor modulators of this intervention can be tested for modulation of the activity of the glucocorticoid receptor using cell-based assays. These assays involve a Chinese hamster ovary (CHO) cell line which contains fragments of the glucocorticoid receptor as well as fusion proteins. The glucocorticoid receptor fragments used are capable of binding the ligand (e.g. beclomethasone) to identify molecules that compete for binding with glucocorticoid receptor ligands. In more detail, the glucocorticoid receptor ligand binding domain is fused to the DNA binding domain (DBD) of the transcription factor GAL4 (GAL4 DBD-GR) and is stably integrated into a CHO cell line containing a GAL4-UAS-Luciferase reporter construct. To identify selective glucocorticoid receptor modulators, the reporter cell line is incubated with the molecules using an 8-point half-log compound dilution curve for several hours. After cell lysis the luminescence that is produced by luciferase after addition of the substrate is detected and EC50 or IC50 values can be calculated. Engagement of molecules which induce gene expression via glucocorticoid receptor binding to the DNA leads to expression of the luciferase gene under the control of the fusion protein GAL4 DBD-GR and therefore to a dose-dependent increase of the luminescence signal. Binding of molecules which repress beclomethasone-induced gene expression of the luciferase gene under the control of the fusion protein GAL4 DBD-GR leads to a dose-dependent reduction of the luminescence signal.

In a preferred embodiment, the compound according to the present invention exhibits in a cellular target engagement assay for agonistic or antagonistic potency on the glucocorticoid receptor an EC50 or IC50 value on the glucocorticoid receptor of at most 1 μM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the present invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

Preferably, the compounds according to the present invention are useful as selective modulators of the glucocorticoid receptor.

Therefore, the compounds according to the present invention are preferably useful for the in vivo treatment or prevention of diseases in which participation of the glucocorticoid receptor is implicated.

The present invention therefore further relates to a compound according to the present invention for use in the modulation of glucocorticoid receptor activity.

Therefore, another aspect of the present invention relates to a compound according to the present invention for use in the treatment and/or prophylaxis of a disorder which is mediated at least in part by the glucocorticoid receptor. Still another aspect of the present invention relates to a method of treatment of a disorder which is mediated at least in part by the glucocorticoid receptor comprising the administration of a therapeutically effective amount of a compound according to the present invention to a subject in need thereof, preferably a human.

A further aspect of the invention relates to the use of a compound according to the present invention as medicament. Another aspect of the present invention relates to a pharmaceutical dosage form comprising a compound according to the present invention. Preferably, the pharmaceutical dosage form comprises a compound according to the present invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik und angrenzende Gebiete, Editio Cantor Aulendoff).

The pharmaceutical dosage form according to the present invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the present invention is preferably prepared with the aid of conventional means, devices, methods and processes known in the art. The amount of the compound according to the present invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the present invention are administered per kg of the patient's body weight.

The glucocorticoid receptor is believed to have potential to modify a variety of diseases or disorders in mammals such as humans. These include in particular inflammatory diseases.

Another aspect of the present invention relates to a compound according to the present invention for use in the treatment and/or prophylaxis of pain and/or inflammation; more preferably inflammatory pain.

A further aspect of the present invention relates to a method of treatment of pain and/or inflammation; more preferably inflammatory pain.

EXAMPLES

The following abbreviations are used in the descriptions of the experiments:

AcOH=acetic acid; Ac=acetyl group; Ataphos=bis(di-tert-butyl(4 dimethylaminophenyl)phosphine)dichloropalladium(II); Ar=argon; BISPIN (or Bis-Pin)=bis(pinacolato) diborane; Cp*=Pentamethylcyclopentadienyl, dba=dibenzylideneacetone; DCM=dichloromethane; DIPEA=N,N-diisopropylethylamine; DMADMF=N,N-dimethylformamide dimethylacetal; DMAP=4-(dimethylamino)-pyridine; DMF=N,N-dimethylformamid; DMSO=dimethylsulfoxid; dppf=1,1'; bis(diphenylphosphanyl)ferrocene; EtOAc=ethyl acetate; EtOH=ethanol;

h=hour; LDA=lithiumdiisopropylamide; LiHMDS=lithium bis(trimethylsilyl)amide; MeOH=methanol; min=minute; n-BuLi=n-butyllithium; pin=(pinacolato)borane; RT=room temperature; Rt=retention time; tert=tertiary; TEA=triethylamine; THF=tetrahydrofuran; p-TSA=para-toluene sulfonic acid; TMSCl=trimethylsilyl chloride; Xant-phos=4,5-bis(diphenylphosphino)-9,9-dimethylxanthene, X-Phos=2-dicyclohexylphosphino-2',4',6'-triisopropylbi-phenyl Synthesis of 6-fluoro-4-(4,4,5,5-tetramethyl-1,3,2-dioxaborolan-2-yl)-1H-indole (Intermediate A-1)

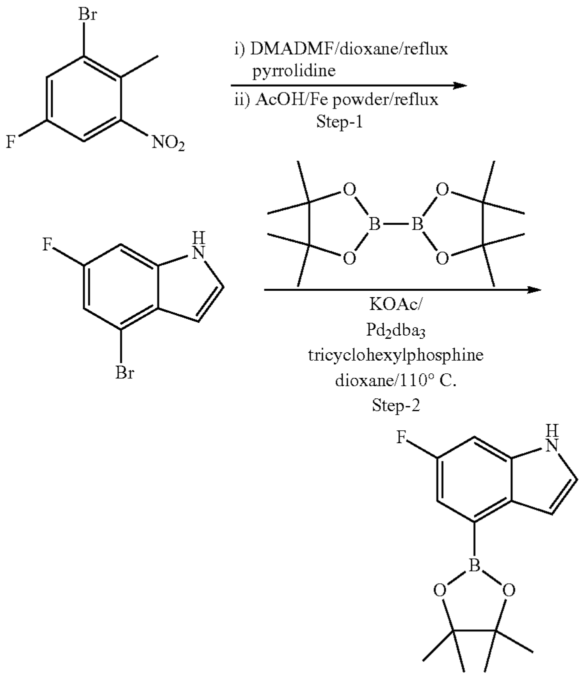

intermediate A-1

Step 1: To a stirring solution of 2-bromo-4-fluoro-6-nitrotoluene (4.69 g, 20 mmol, 1 eq) in 1,4-dioxane (25 ml) was slowly added N,N-dimethylformamide dimethylacetal (13.3 mL, 100 mmol, 5 eq) and pyrrolidine (1.47 mL, 20 mmol, 1 eq). The reaction mixture was then stirred for 18 h at 100° C. The reaction mixture was concentrated to a dark residue. To this residue were added AcOH (30 mL) and iron powder (11 g, 200 mmol, 10 eq) and then the reaction mixture was refluxed for 1 h. The reaction mixture was then cooled to RT and then filtered through a celite bed. The filtrate was neutralised by 50% sodium hydroxide solution and then extracted with EtOAc (2×100 mL). Combined organic layers was washed with water (100 mL), brine (100 mL), dried over anhydrous $Na_2SO_4$ and evaporated to get the crude which was purified by column chromatography to afford 4-bromo-6-fluoro-1H-indole (1.3 g, 30%) as brown liquid.

Step 2: To a stirring suspension of 4-bromo-6-fluoro-1H-indole (1.1 g, 5.1 mmol, 1 eq), bis(pinacolato)diborane (2.6 g, 10.2 mmol, 2 eq) and potassium acetate (2.0 g, 20.4 mmol, 4 eq) in 1,4-dioxan (20 mL) was deoxygenated by Ar for 10 min. $Pd_2(dba)_3$ (0.07 g, 0.07 mmol. 0.015 eq) and tricyclohexylphosphine (0.102 g, 0.36 mmol, 0.07 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude material which was purified by column chromatography to afford 6-fluoro-4-(4,4,5,5-tetramethyl-1,3,2-dioxaborolan-2-yl)-1H-indole (1.1 g, 82%) as light yellow solid.

Synthesis of 6-fluoro-1-(methylsulfonyl)-4-(4,4,5,5-tetramethyl-1,3,2-dioxaborolan-2-yl)-1H-indole (Intermediate A-2)

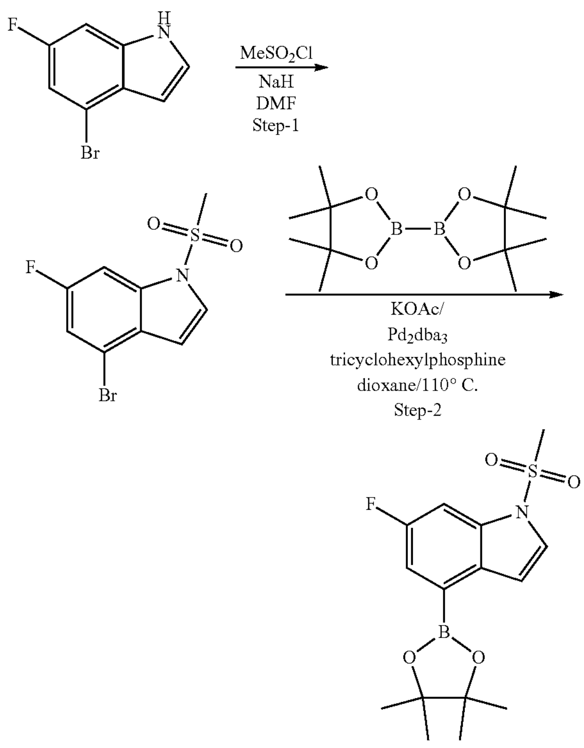

intermediate A-2

Step 1: To a stirring solution of 4-bromo-6-fluoro-1H-indole (0.18 g, 0.841 mmol, 1 eq) in DMF (5 mL) was portion wise added sodium hydride (60%, 0.07 g, 1.68 mmol, 2 eq) at 0° C. The reaction mixture was then stirred for 30 min at RT. Methanesulfonylchloride (0.114 ml, 1.26 mmol, 1.5 eq) was then added to the reaction mixture at 0° C. The reaction mixture was stirred for 2 h at RT. Reaction mixture was diluted with EtOAc (50 mL). Combined organic layers were washed with water (5×10 mL), brine (10 mL), dried over anhydrous $Na_2SO_4$ and the solvent was evaporated under reduced pressure. Crude product was purified by column chromatography to afford 4-bromo-6-fluoro-1-(methylsulfonyl)-1H-indole (0.1 g, 41%) as off-white solid.

Step 2: To a stirring suspension of 4-bromo-6-fluoro-1-(methylsulfonyl)-1H-indole (1.2 g, 3.53 mmol, 1 eq) in 1,4-dioxan (20 mL), bis-pinacolatodiborane (1.79 g, 7.06 mmol, 2 eq) and potassium acetate (1.39 g, 10.62 mmol, 4 eq) were added and the mixture was deoxygenated by Ar for 10 min. $Pd_2(dba)_3$ (0.048 g, 0.052 mmol. 0.015 eq) and triclyclohexylphosphine (0.071 g, 0.25 mmol, 0.07 eq) was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude product which was purified by column chromatography to afford 6-fluoro-1-(methylsulfonyl)-4-(4,4,5,5-tetramethyl-1,3,2-dioxaborolan-2-yl)-1H-indole (1.0 g, 80%) as light yellow solid.

Synthesis of 6-fluoro-4-(4,4,5,5-tetramethyl-1,3,2-dioxaborolan-2-yl)-1-(2,2,2-trifluoroethyl)-1H-indole (Intermediate A-11)

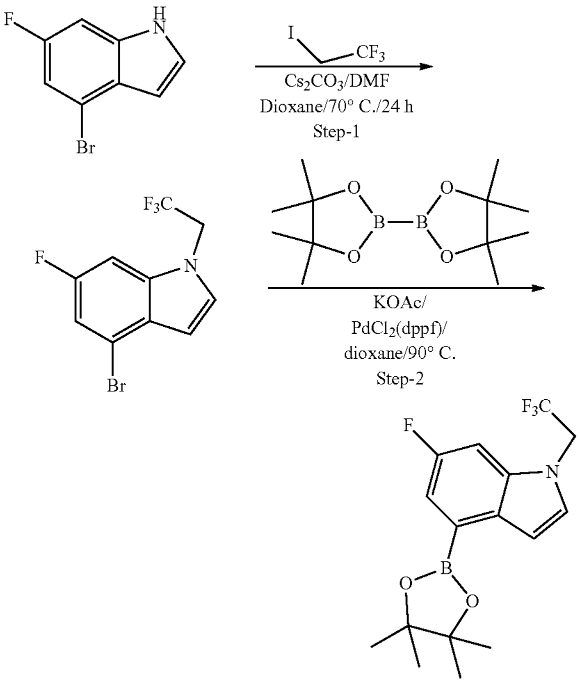

intermediate A-11

Step 1: To a solution of 4-bromo-6-fluoro-1H-indole (2.0 g, 9.345 mmol, 1 eq.) in DMF (25 mL) was added $Cs_2CO_3$ (15.18 g, 46.72 mmol, 5 eq.) and 1,1,1-trifluoro-2-iodoethane (5.8 g, 28.037 mmol, 3.0 eq) in a sealed tube. The reaction mixture was refluxed at 50° C. for 24 h. The reaction mixture was filtered through sintered and the filtrate was diluted with EtOAc (100 mL). Organic layer was washed with cold water (3×50 mL), brine (25 mL), dried over anhydrous $Na_2SO_4$ and the solvent was evaporated to get the crude product, which was purified by flash column chromatography to afford mixture which further purified by Prep HPLC to afford 4-bromo-6-fluoro-1-(2,2,2-trifluoroethyl)-1H-indole (0.400 g, 14%) as off white solid.

Step 2: To a stirred solution of 4-bromo-6-fluoro-1-(2,2,2-trifluoroethyl)-1H-indole (0.450 g, 1.52 mmol, 1 eq), bis(pinacolato)diborane (0.461 g, 1.824 mmol, 1.2 eq) and potassium acetate (0.446 g, 4.56 mmol, 3 eq) in 1,4-dioxan (20 mL) was deoxygenated by Ar for 10 min. PdCl2(dppf)·DCM (0.124 g, 0.152 mmol. 0.1 eq) was then added to the reaction mixture and stirred at 90° C. for another 16 h. The reaction mixture was filtered through celite bed. Filtrate was concentrated under reduced pressure to get crude 6-fluoro-4-(4,4,5,5-tetramethyl-1,3,2-dioxaborolan-2-yl)-1-(2,2,2-trifluoroethyl)-1H-indole which was used in next step without further purification.

Synthesis of 1-(methylsulfonyl)-4-(4,4,5,5-tetramethyl-1,3,2-dioxaborolan-2-yl)-1H-indole (Intermediate A-12)

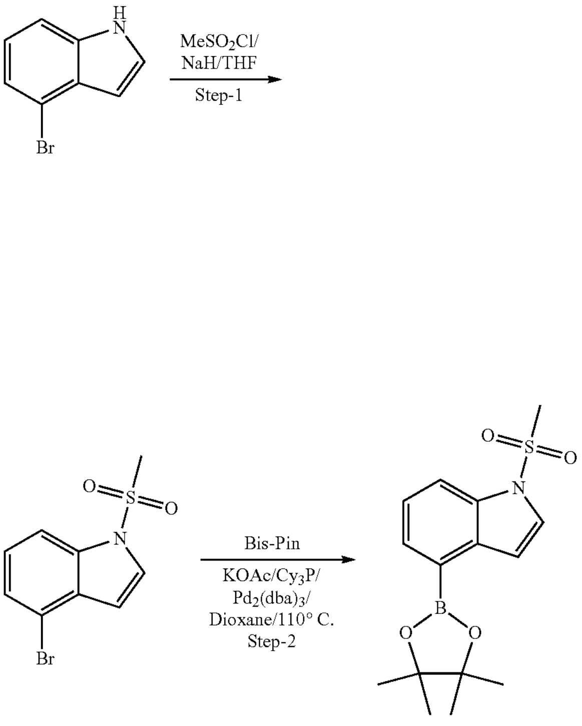

intermediate A-12

Step 1: To a stirring solution of 4-bromo-1H-indole (1.0 g, 5.1 mmol, 1 eq) in DMF (20 ml) was portion wise added sodium hydride (60%, 0.245 g, 10.2 mmol, 2 eq) at 0° C. The reaction mixture was then stirred for 30 min at RT. Methanesulfonylchloride (0.584 ml, 7.6 mmol, 1.5 eq) then added to the reaction mixture at 0° C. The reaction mixture was stirred for 2 h at RT. Reaction mixture was diluted with EtOAc (100 mL). Combined organic layers was washed with water (5×20 mL), brine (20 mL), dried over anhydrous $Na_2SO_4$ and the solvent was evaporated under reduced pressure. The crude product was purified by column chromatography to afford 4-bromo-1-(methylsulfonyl)-1H-indole (0.532 g, 38%) as off white solid.

Step 2: To a stirring suspension of 4-bromo-1-(methylsulfonyl)-1H-indole (0.36 g, 1.31 mmol, 1 eq), bis(pinacolato)diborane (0.66 g, 2.62 mmol, 2 eq) and potassium acetate (0.57 g, 5.25 mmol, 4 eq) in 1,4-dioxan (10 L1) was deoxygenated by Ar for 10 min. $Pd_2(dba)_3$ (0.018 g, 0.019 mmol. 0.015 eq) and tricyclohexylphosphine (0.027 g, 0.094 mmol, 0.072 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude material which was purified by column chromatography to afford 1-(methylsulfonyl)-4-(4,4,5,5-tetramethyl-1,3,2-dioxaborolan-2-yl)-1H-indole (0.31 g, 73%) as off white solid.

Synthesis of 5-fluoro-3-methyl-7-(4,4,5,5-tetramethyl-1,3,2-dioxaborolan-2-yl)-1H-indole (Intermediate A-15)

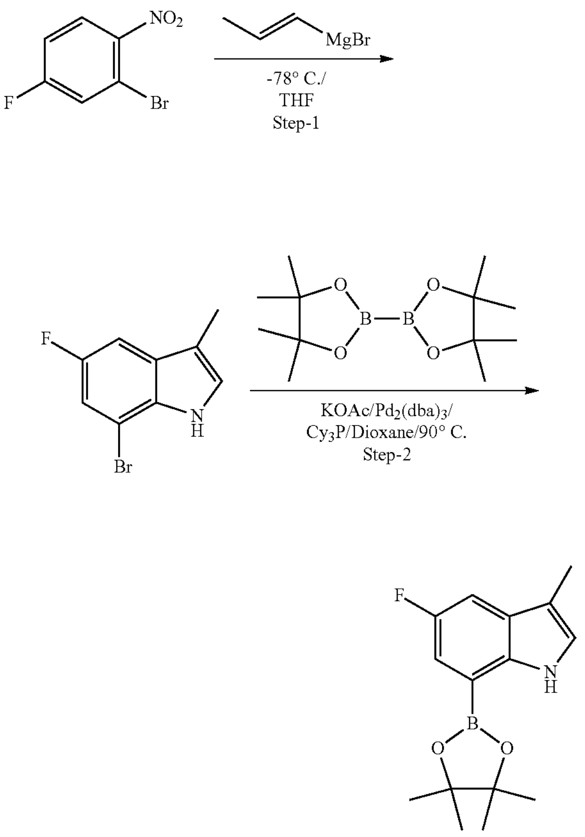

intermediate A-15

Step 1: To a solution of 2-bromo-4-fluoro-1-nitrobenzene (0.5 g, 2.27 mmol, 1 eq.) in THF (20 mL) was added (E)-prop-1-en-1-ylmagnesium bromide (0.5 M in THF) (13.6 mL, 6.818 mmol, 3 eq) at −60° C. under nitrogen atmosphere. Then the reaction mixture was stirred at the same temperature for 4 h. The reaction was quenched with saturated ammonium chloride solution at −60° C. Then the resulting mixture was extracted with EtOAc (2×100 mL), washed with brine solution and concentrated under reduced pressure to give the crude product which was purified by flash column chromatography to afford 7-bromo-5-fluoro-3-methyl-1H-indole (0.3 g, 58%) as dense yellow liquid.

Step 2: To a solution of 7-bromo-5-fluoro-3-methyl-1H-indole (0.8 g, 3.669 mmol, 1 eq) in 1,4-dioxane (15.0 mL) were added KOAC (1.43 g, 14.67 mmol, 4 eq) and bispincolatediborane (1.12 g, 7.33 mmol, 2 eq). The solution was degassed with Ar for 20 min followed by addition of $Pd_2(dba)3$ (0.16 g, 0.183 mmol, 0.05 eq) and $Cy_3P$ (0.082 g, 0.293 mmol, 0.08 eq). The reaction mixture was refluxed for 16 h. After completion of reaction (monitored by TLC), solvent was evaporated under reduced pressure to get the crude product which was purified by column chromatography to afford 5-fluoro-3-methyl-7-(4,4,5,5-tetramethyl-1,3,2-dioxaborolan-2-yl)-1H-indole (0.7 g, 70%), as brown solid.

Synthesis of 3-cyclopropyl-5-fluoro-7-(4,4,5,5-tetramethyl-1,3,2-dioxaborolan-2-yl)-1H-indole (Intermediate A-16)

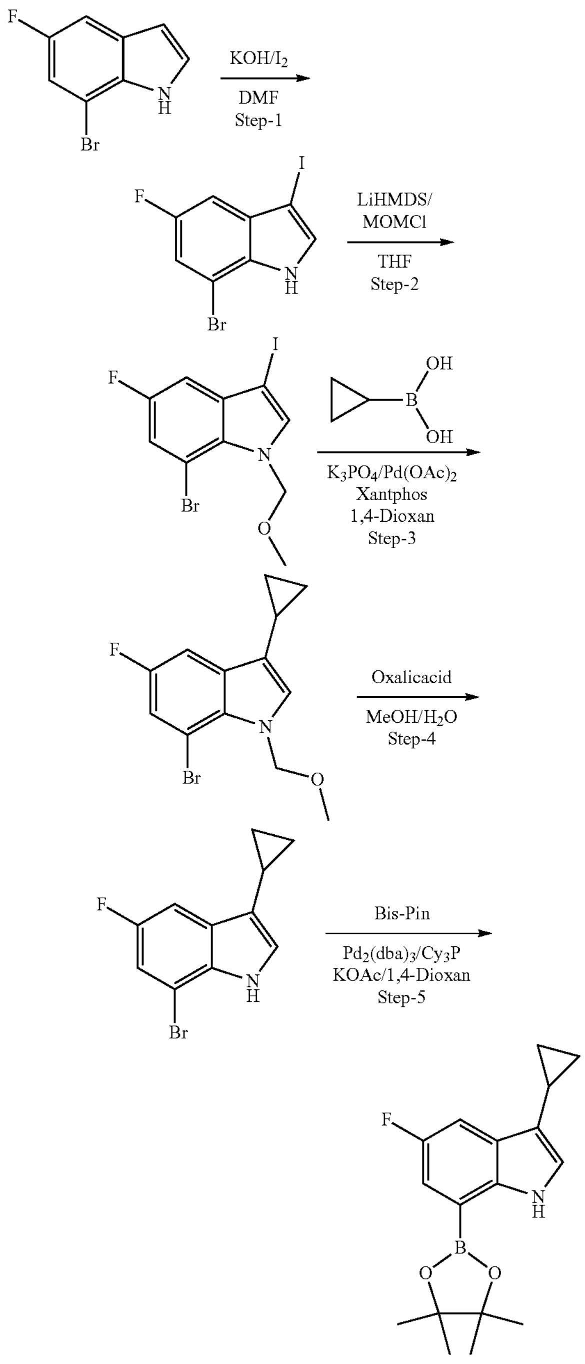

intermediate A-16

Step 1: To a stirring solution of 7-bromo-5-fluoroindole (7.0 g, 32.7 mmol, 1 eq) in DMF (175 mL) was added powdered potassium hydroxide (4.56 g, 81.77 mmol, 2.5 eq). The reaction mixture was then stirred for 30 min at RT. Iodine (12.46 g, 49.06 mmol, 1.5 eq) was then added to the reaction mixture and finally stirred for 2 h at RT. The reaction mixture was diluted with EtOAc (1000 mL) and washed with water (5×100 mL) followed brine (100 mL). The organic layer was dried over anhydrous $Na_2SO_4$ and the solvent was evaporated to get the crude product, which was purified by column chromatography to afford 7-bromo-5-fluoro-3-iodo-1H-indole (6.2, 56%) as brown solid.

Step 2: To a stirring solution of 7-bromo-5-fluoro-3-iodo-1H-indole (6.2 g, 18.23 mmol, 1 eq) in THF (109 mL) was added drop wise LiHMDS (1M) (91.15 mL, 91.15 mmol, 5 eq) at −78° C. under inert atmosphere. The reaction mixture was stirred for 30 min at same condition. MOMCl (5.83 g, 72.94 mmol, 4 eq) was then added to the reaction mixture at −78° C. The reaction mixture was allowed to warm up to RT and then stirred for 16 h. The reaction mixture was quenched by addition of saturated solution of ammonium chloride (100 mL). Organic layer was separated and the aqueous layer was extracted with EtOAc (100 mL). The combined organic layers were washed with brine (100 mL). The organic layer was dried over anhydrous $Na_2SO_4$ and the solvent was evaporated to get the crude product, which was purified by column chromatography to afford 7-bromo-5-fluoro-3-iodo-1-(methoxymethyl)-1H-indole (5.4 g, 57%) as off white solid.

Step 3: To a stirred suspension of 7-bromo-5-fluoro-3-iodo-1-(methoxymethyl)-1H-indole (2.7 g, 7.03 mmol, 1 eq), cyclopropylboronic acid (1.84 g, 2.03 mmol, 3 eq) and $K_3PO_4$ (4.5 g, 21.05 mmol, 3 eq) in 1,4-dioxan (45 mL) was deoxygenated by Ar for 10 min. $Pd(OAc)_2$ (0.08 g, 0.3525 mmol, 0.05 eq) and xantphos (0.407 g, 0.713 mmol, 0.1 eq) were then added to the reaction mixture and again deoxygenated for 10 min. Finally the reaction mixture was stirred at 100° C. for 16 h. The reaction mixture was cooled to RT and then filtered through celite bed. The filtrate was concentrated under reduced pressure to get the crude material which was purified by column chromatography to afford 7-bromo-3-cyclopropyl-5-fluoro-1-(methoxymethyl)-1H-indole (0.65 g, 31%) as off white solid.

Step 4: To a stirring solution of 7-bromo-3-cyclopropyl-5-fluoro-1-(methoxymethyl)-1H-indole (1.25 g, 4.19 mmol, 1 eq) in mixture of MeOH and water (3:1) (66 mL) was added oxalic acid (1.13 g, 12.58 mmol, 3 eq). The reaction mixture was then stirred at 90° C. for 18 h. The reaction mixture was cooled to RT and concentrated under reduced pressure to get the residue. The residue was diluted with EtOAc (100 mL) and washed with water (2×40 mL) and brine (40 mL). The organic layer was dried over anhydrous $Na_2SO_4$ and the solvent was evaporated to get the crude product, which was purified by column chromatography to afford 7-bromo-3-cyclopropyl-5-fluoro-1H-indole (0.57 g, 54%) as color less liquid.

Step 5: To a stirring suspension of 7-bromo-3-cyclopropyl-5-fluoro-1H-indole (0.57 g, 2.24 mmol, 1 eq), bis-pinacolatodiborane (1.7 g, 6.73 mmol, 3 eq) and potassium acetate (0.66 g, 6.73 mmol, 3 eq) in 1,4-dioxan (20 mL) was deoxygenated by Ar for 10 min. $Pd_2(dba)_3$ (0.031 g, 0.033 mmol. 0.015 eq) and triclyclohexylphosphine (0.047 g, 0.168 mmol, 0.075 eq) was then added to the reaction mixture and again deoxygenated by Ar for 10 min. The reaction mixture was then stirred for 14 h at 110° C. The reaction mixture was then cooled to RT and then filtered through celite bed. Filtrate was concentrated under reduced pressure to get the crude material which was purified by column chromatography to afford 3-cyclopropyl-5-fluoro-7-(4,4,5,5-tetramethyl-1,3,2-dioxaborolan-2-yl)-1H-indole (0.35 g, 52%) as off white solid.

Synthesis of 2-(6-fluoro-4-(4,4,5,5-tetramethyl-1,3,2-dioxaborolan-2-yl)-1H-indol-1-yl)ethanol (Intermediate A-20)

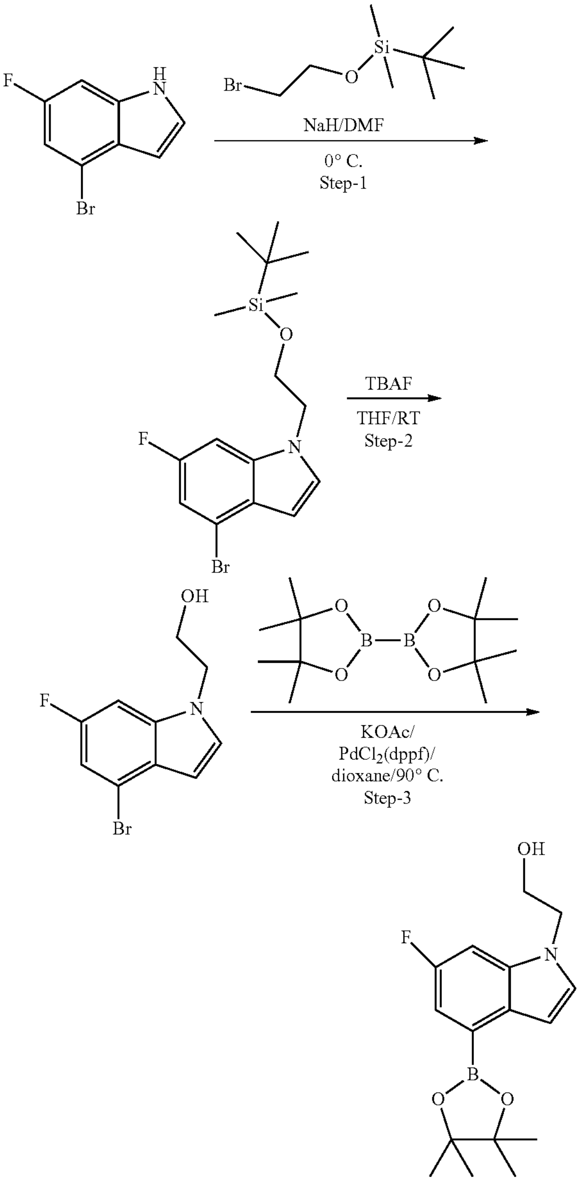

intermediate A-20

Step 1: To a solution of 4-bromo-6-fluoro-1H-indole (0.5 g, 2.34 mmol, 1 eq.) in DMF (5 mL) was added sodium hydride (0.130 g, 2.80 mmol, 1.2 eq) at 0° C. The solution was stirred at RT for 30 min followed by addition of (2-bromoethoxy)(tert-butyl)dimethylsilane (1.17 g, 4.67 mmol, 2.0 eq) and reaction mixture was stirred at RT for 2 h. After completion of reaction (monitored by LCMS), reaction mixture was diluted with EtOAc (20 mL) and organic layer was washed with cold water (5×10 mL), brine (10 mL), dried over anhydrous $Na_2SO_4$ and the solvent was evaporated under reduced pressure. Crude product was purified by column chromatography to afford 4-bromo-1-(2-((tert-butyldimethylsilyl)oxy)ethyl)-6-fluoro-1H-indole (0.85 g, 98%) as brown liquid having (2-bromoethoxy)(tert-butyl)dimethylsilane as impurity.

Step 2: To a stirred solution of 4-bromo-1-(2-((tert-butyldimethylsilyl)oxy)ethyl)-6-fluoro-1H-indole (1.3 g, 3.49 mmol, 1 eq.) in THF (15 mL) was added TBAF (3.49 mL) (1M) at RT and the mixture was stirred for 16 h. After completion of reaction (monitored by LCMS & TLC), reaction mixture was diluted with EtOAc (20 mL) and organic layer was washed with cold water (5×10 mL), brine (10 mL), dried over anhydrous $Na_2SO_4$ and the solvent was evaporated under reduced pressure. Crude product was purified by column chromatography to afford 2-(4-bromo-6-fluoro-1H-indol-1-yl)ethanol (0.55 g, 61%) as brown liquid.

Step 3: To a stirred solution of 2-(4-bromo-6-fluoro-1H-indol-1-yl)ethanol (0.55 g, 2.13 mmol, 1 eq), bis(pinacolato) diborane (0.647 g, 2.55 mmol, 1.2 eq) and potassium acetate (0.626 g, 6.393 mmol, 3 eq) in 1,4-dioxan (20 mL) was deoxygenated by Ar for 10 min. $PdCl_2$ (dppf) DCM (0.173 g, 0.213 mmol. 0.1 eq) was then added to the reaction mixture and the mixture was stirred at 90° C. for 16 h. After completion of reaction (monitored by TLC), reaction mixture was filtered through celite bed. Filtrate was concentrated under reduced pressure to get the crude product which was used in next step without further purification.

Synthesis of 2-(6-fluoro-4-(4,4,5,5-tetramethyl-1,3,2-dioxaborolan-2-yl)-1H-indazol-1-yl)ethanol (Intermediate A-21)

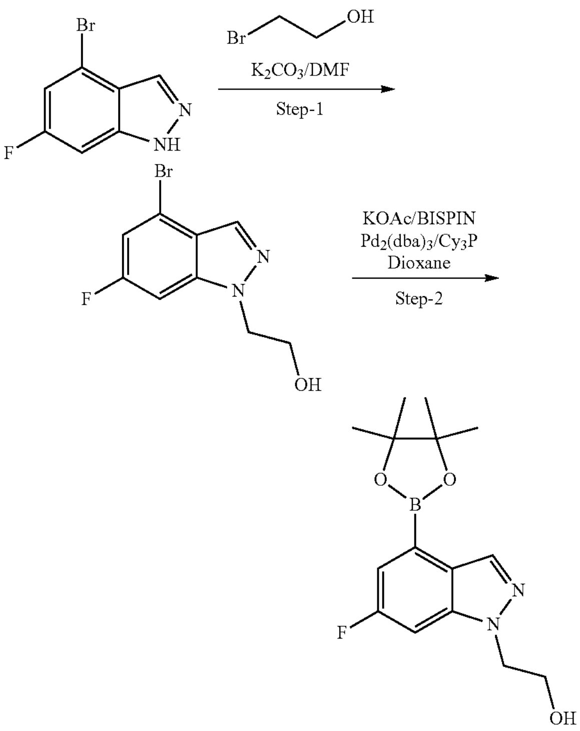

intermediate A-21

Step 1: To a stirred solution of 4-bromo-6-fluoro-1H-indazole (0.2 g, 0.93 mmol, 1 eq) in DMF (5 mL) was added $K_2CO_3$ (0.38 g, 2.79 mmol, 3.0 eq) at RT and the mixture was stirred for 20 min. Then 2-bromo-ethanol (0.07 mL, 0.93 mmol, 1 eq) was added and the mixture was stirred for 16 h at 50° C. After completion of the reaction (monitored by TLC), the reaction mass quenched with ice cold water and extracted with EtOAc (3×20 mL), washed with $H_2O$ (3×20 mL), brine (25 mL), dried over $Na_2SO_4$ and concentrated. The crude product was purified by column chromatography to afford 2-(4-bromo-6-fluoro-1H-indazol-1-yl) ethanol (0.12 g, 50%) as white solid.

Step 2: To a solution of 2-(4-bromo-6-fluoro-1H-indazol-1-yl)ethanol (0.9 g, 3.473 mmol, 1 eq) in 1,4-dioxane (60.0 mL) were added KOAc (1.02 g, 10.419 mmol, 3 eq) and bispincolatediborane (1.76 g, 6.947 mmol, 2.0 eq). The solution was degassed with Ar for 20 min followed by addition of $Pd_2(dba)_3$ (0.17 g, 0.173 mmol, 0.05 eq) and $Cy_3P$ (0.077 g, 0.277 mmol, 0.08 eq). The reaction mixture was refluxed for 16 h. After completion of reaction (monitored by TLC), solvent was evaporated under reduced pressure to get the crude product which was purified by column chromatography to afford -(6-fluoro-4-(4,4,5,5-tetramethyl-1,3,2-dioxaborolan-2-yl)-1H-indol-1-yl)ethanol (0.95 g, 89%) as brown solid.

Synthesis of 1-(methylsulfonyl)-4-(4,4,5,5-tetramethyl-1,3,2-dioxaborolan-2-yl)-1H-indazole (Intermediate A-22)

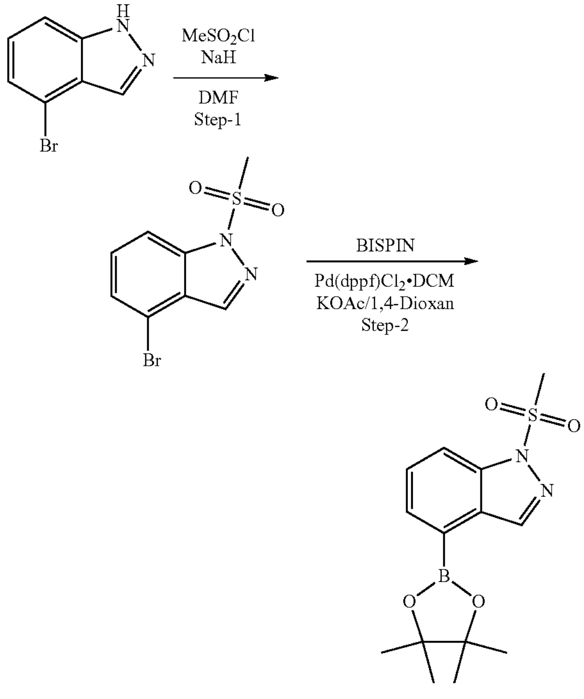

intermediate A-22

Step 1: To a stirring solution of 4-bromo-1H-indazole (1.0 g, 5.07 mmol, 1 eq) in DMF (25 ml) was portion wise added sodium hydride (60%, 0.406 g, 10.152 mmol, 2 eq) at 0° C. The reaction mixture was stirred for 30 min at RT. Methanesulfonylchloride (0.59 mL, 7.6 mmol, 1.5 eq) was added to the reaction mixture at 0° C. The reaction mixture was stirred for 2 h at RT. Reaction mixture was diluted with EtOAc (150 mL). Combined organic layers were washed with water (5×30 mL), brine (30 mL), dried over anhydrous $Na_2SO_4$ and the solvent was evaporated under reduced pressure. Crude product was purified by column chromatography (230-400 mesh silica gel 10% EtOAc/hexane; $R_f$-value-0.5) to afford 4-bromo-1-(methylsulfonyl)-1H-indazole (0.95 g, 69%) as light yellow solid.

Step 2: To a stirring suspension of 4-bromo-1-(methylsulfonyl)-1H-indazole (0.95, 3.45 mmol, 1 eq), bis(pinacolato)diborane (1.75 g, 6.91 mmol, 2 eq) and potassium acetate (1.01 g, 10.36 mmol, 3 eq) in 1,4-dioxane (35 mL) was deoxygenated by Ar for 10 min. Pd(dppf)$Cl_2$·DCM (0.141 g, 0.1727 mmol. 0.05 eq) was added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 10% EtOAc/hexane; $R_f$-value-0.45) to afford 1-(methylsulfonyl)-4-(4,4,5,5-tetramethyl-1,3,2-dioxaborolan-2-yl)-1H-indazole (0.9 g, 85.4%) as off white solid.

Synthesis of 6-fluoro-1-(2-methoxyethyl)-4-(4,4,5,5-tetramethyl-1,3,2-dioxaborolan-2-yl)-1H-indole (Intermediate A-24)

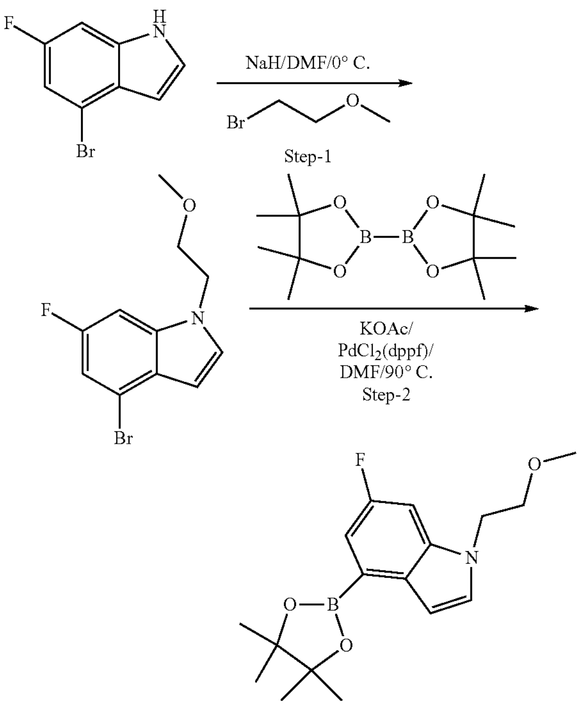

intermediate A-24

Step 1: To a stirring solution of 4-bromo-6-fluoro-1H-indole (0.5 g, 2.34 mmol, 1 eq) in DMF (5 mL) was portion wise added sodium hydride (0.112 g, 2.8 mmol, 1.2 eq.) at 0° C. The reaction mixture was then stirred for 30 min at RT. 1-Bromo-2-methoxyethane (0.812 mL, 5.84 mmol, 2.5 eq) was then added to the reaction mixture at 0° C. The reaction mixture was stirred for 2 h at RT. Reaction mixture was diluted with EtOAc (50 mL). Combined organic layers were washed with water (5×10 mL), brine (10 mL), dried over anhydrous $Na_2SO_4$ and the solvent was evaporated under reduced pressure. Crude product was purified by column chromatography (230-400 mesh silica gel 20% EtOAc/hexane; $R_f$-value-0.6) to afford 4-bromo-6-fluoro-1-(2-methoxyethyl)-1H-indole (0.63 g, 99%) as brown gum.

Step 2: To a stirring suspension of 4-bromo-6-fluoro-1-(2-methoxyethyl)-1H-indole (0.8 g, 2.94 mmol, 1 eq), bis-pinacolatodiborane (1.2 g, 4.4 mmol, 1.5 eq.) and potassium acetate (0.865 g, 8.823 mmol, 3 eq.) in 1,4-dioxan (20 mL) was deoxygenated by Ar for 10 min. $PdCl_2$(dppf)·DCM (0.239 g, 0.29 mmol. 0.01 eq.) q) was then added and the reaction mixture was stirred for 14 h at 90° C. The reaction mixture was cooled to RT and then filtered through celite bed. Filtrate was concentrated under reduced pressure to get the crude product which was purified by column chromatography (230-400 mesh silica gel 5% EtOAc/hexane; $R_f$-value-0.6) to afford 6-fluoro-1-(2-methoxyethyl)-4-(4,4,5,5-tetramethyl-1,3,2-dioxaborolan-2-yl)-1H-indole (0.93 g, 99%) as light brown gummy solid.

Synthesis of 1-cyclopropyl-6-fluoro-4-(4,4,5,5-tetramethyl-1,3,2-dioxaborolan-2-yl)-1H-indole (Intermediate A-27)

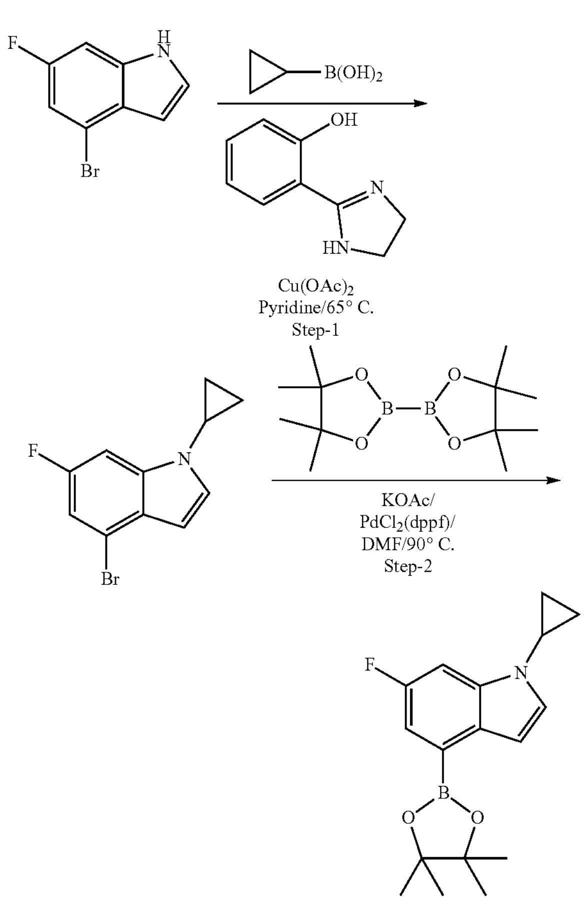

intermediate A-27

Step 1: To a stirring solution of 4-bromo-6-fluoro-1H-indole (5.4 g, 25.23 mmol, 1 eq) in toluene (45 mL) were added cyclopropylboronic acid (4.33 g, 50.46 mmol, 2 eq), $Cu(OAc)_2$ (0.46 g, 2.52 mmol, 0.1 eq), 2-(4,5-dihydro-1H-imidazol-2-yl)phenol (0.41 g, 2.52 mmol, 0.1 eq) and pyridine (6.0 g, 75.7 mmol, 3 eq). The reaction mixture was stirred for 24 h at 65° C. Solvent was removed under reduced pressure and azitrope by MeOH twice. The residue was purified by column chromatography (230-400 mesh silica gel; 10% EtOAc/hexane; $R_f$-value-0.6) to afford 4-bromo-1-cyclopropyl-6-fluoro-1H-indole (0.85 g, 13%) as brown liquid.

Step 2: To a stirring suspension of 4-bromo-1-cyclopropyl-6-fluoro-1H-indole (0.85 g, 3.35 mmol, 1 eq), bis(pinacolato)diborane (1.7 g, 6.7 mmol, 2 eq) and potassium acetate (1.31 g, 13.38 mmol, 4 eq) in 1,4-dioxan (20 mL) was deoxygenated by Ar for 10 min. $Pd_2(dba)_3$ (0.046 g, 0.05 mmol. 0.015 eq) and Ttricyclohexylphosphine (0.067 g, 0.24 mmol, 0.072 eq) was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 20% EtOAc/hexane; $R_f$-value-0.6) to afford 1-cyclopropyl-6-fluoro-4-(4,4,5,5-tetramethyl-1,3,2-dioxaborolan-2-yl)-1H-indole (0.61 g, 61%) as light yellow solid.

1H-NMR (400 MHz; DMSO-$D_6$, 20° C.): δ 7.45 (dd, 1H), 7.35 (d, 1H), 7.15 (dd, 1H), 6.67 (d, 1H), 3.41 (m, 1H), 1.32 (12H), 1.03-1.08 (2H), 0.82-0.92 (2H).

Synthesis of 5-fluoro-7-(4,4,5,5-tetramethyl-1,3,2-dioxaborolan-2-yl)-1H-indole (Intermediate A-71)

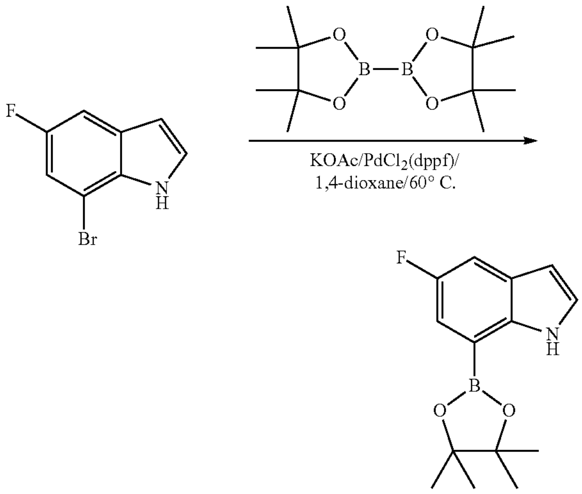

intermediate A-71

A mixture of 7-bromo-5-fluoro-1H-indole (1 g, 4.7 mmol, 1 eq), bis(pinacolato)diborane (2.02 g, 7.9 mmol, 1.7 eq), potassium acetate (917 mg, 9.4 mmol, 2 eq), 1,1'-Bis(diphenylphosphino)ferrocene palladium(II)dichloride DCM complex (382 mg, 0.467 mmol, 0.1 eq) in 1,4-dioxane (13 mL) was degassed with nitrogen, and the reaction mixture was stirred at 60° C. After completion of the reaction (monitored by LCMS), a sat. sodium bicarbonate solution was added to the reaction mixture, which was then extracted with EtOAc (2×). The combined organic layers were washed with brine, dried over anhydrous $MgSO_4$ and evaporated under reduced pressure. The crude product was purified by column chromatography (silica gel; EtOAc/cyclo-Hexane as eluent) to afford 5-fluoro-7-(4,4,5,5-tetramethyl-1,3,2-dioxaborolan-2-yl)-1H-indole (940 mg, 77%).

Synthesis of 4-fluoro-6-(4,4,5,5-tetramethyl-1,3,2-dioxaborolan-2-yl)-1H-indazole (Intermediate A-74)

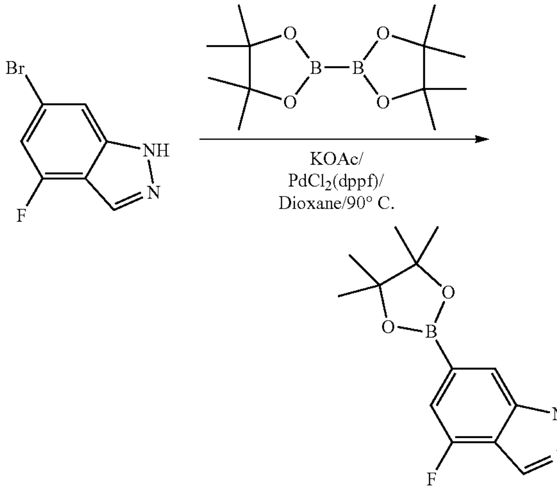

intermediate A-74

A stirring suspension of 6-bromo-4-fluoro-1H-indazole (300 mg, 1.4 mmol, 1 eq), bis(pinacolato)diborane (602 mg, 2.37 mmol, 1.7 eq) and potassium acetate (274 mg, 2.79 mmol, 2 eq) in 1,4-dioxan (14 mL) was deoxygenated with Ar for 10 min. [1,1'-Bis(diphenylphosphino)ferrocene]dichloropalladium(II), complex with dichloromethane (228 mg, 0.279 mmol. 0.2 eq) and water (0.002 mL) were then added to the reaction mixture and the reaction mixture was stirred for 2 h at 90° C. The reaction mixture then cooled to RT and EtOAc and a sat. sodium bicarbonate solution were added. After extraction with EtOAc, the combined organic layers were washed with brine, dried over anhydrous sodium sulfate, and concentrated under reduced pressure to afford 4-fluoro-6-(4,4,5,5-tetramethyl-1,3,2-dioxaborolan-2-yl)-1H-indazole (crude), which was further used without purification.

Synthesis of 2-(5-fluoro-4-(4,4,5,5-tetramethyl-1,3,2-dioxaborolan-2-yl)-1H-indol-1-yl)ethan-1-ol (Intermediate A-76)

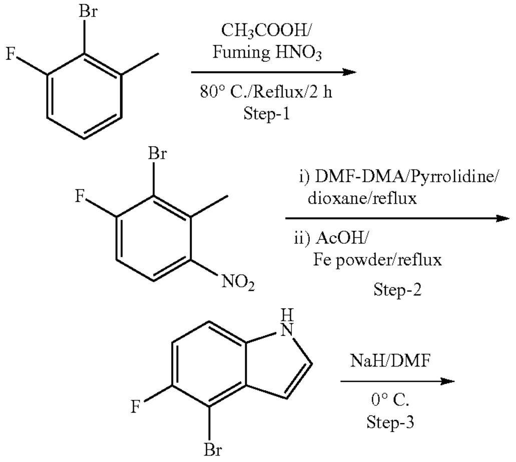

-continued

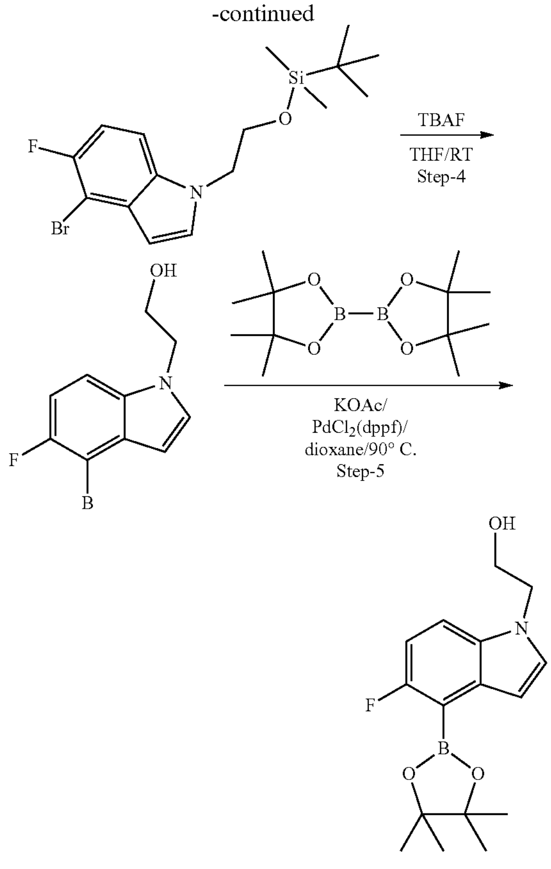

intermediate A-76

Step 1: To a stirring solution of 2-bromo-1-fluoro-3-methylbenzene (1.0 g, 5.29 mmol, 1 eq) in 5 mL acetic acid was added fuming $HNO_3$ (5 mL) very slowly at RT in small portions. The reaction mixture was then stirred for 2 h at 80° C. After completion (monitored by LCMS & TLC), the reaction mixture was cooled to RT and poured into crushed ice. A solid precipitate was formed and filtered off, and the solid obtained was dissolved in ethyl acetate (100 mL). The organic layer was washed with water (50 mL) and brine (50 mL), dried over anhydrous $Na_2SO_4$ and evaporated under reduced pressure. The crude residue was purified by column chromatography to afford 2-bromo-1-fluoro-3-methyl-4-nitrobenzene (0.6 g, 48%) as a yellow solid.

Step 2: To a stirring solution of 2-bromo-1-fluoro-3-methyl-4-nitrobenzene (3.0 g, 12.68 mmol, 1 eq) in 1,4-dioxane (25 mL) were slowly added N,N-dimethylformamide dimethylacetal (7.6 g, 64.10 mmol, 5 eq) and pyrrolidine (0.9 g, 12.82 mmol, 1 eq), and the reaction mixture was stirred for 18 h at 100° C. The reaction mixture was then concentrated and to the residue were added acetic acid (30 mL) and iron powder (7.17 g, 128 mmol, 10 eq). The reaction mixture was refluxed for 2 h, cooled to room temperature and filtered through a celite bed. The filtrate was neutralised by 50% sodium hydroxide solution and extracted by ethyl acetate (2×250 mL). The combined organic layers were washed with water (100 mL) and brine (100 mL), dried over anhydrous $Na_2SO_4$ and evaporated under reduced pressure. The crude residue was purified by column chromatography (230-400 mesh silica gel; 20% ethyl acetate/hexane) to afford compound 4-bromo-5-fluoro-1H-indole (1.7 g, 63%) as a brown liquid.

Step 3: To a solution of 4-bromo-5-fluoro-1H-indole (0.5 g, 2.336 mmol, 1 eq.) in DMF (5 mL) was added sodium hydride (0.130 g, 2.80 mmol, 1.2 eq) at 0° C., and the solution was stirred at RT for half an hour, followed by addition of (2-bromoethoxy)(tert-butyl)dimethylsilane (1.17 g, 4.67 mmol, 2.0 eq) and the reaction mixture was stirred at RT for 2 h. After completion (monitored by LCMS), the reaction mixture was diluted with ethyl acetate (20 mL) and the organic layer was washed with cold water (5×10 mL) and brine (10 mL), dried over anhydrous $Na_2SO_4$ and evaporated under reduced pressure. The crude residue was purified by column chromatography to afford 4-bromo-1-{2-[(tert-butyldimethylsilyl)oxy]ethyl}-5-fluoro-1H-indole (0.85 g, 98%) as a brown liquid.

Step 4: To a stirred solution of 4-bromo-1-{2-[(tert-butyldimethylsilyl)oxy]ethyl}-5-fluoro-1H-indole (4.0 g, 10.75 mmol, 1 eq.) in THF (15 mL) was added TBAF (4 mL, 1M) at RT and the reaction was stirred over night. After completion (monitored by LCMS & TLC), the reaction mixture was diluted with ethyl acetate (100 mL) and the organic layer was washed with cold water (5×50 mL) and brine (10 mL), dried over anhydrous $Na_2SO_4$ and evaporated under reduced pressure. The crude residue was purified by column chromatography (100-200 mesh silica gel; 30% ethyl acetate/hexane) to afford 2-(4-bromo-5-fluoro-1H-indol-1-yl)ethan-1-ol (1.3 g, 48%) as a brown liquid.

Step 5: A stirred solution of 2-(4-bromo-5-fluoro-1H-indol-1-yl)ethan-1-ol (1.3 g, 5.038 mmol, 1 eq), bis(pinacolato)diborane (1.52 g, 6.046 mmol, 1.2 eq) and potassium acetate (1.48 g, 15.114 mmol, 3 eq) in 1,4-dioxane (50 mL) was deoxygenated with argon gas for 10 min. $PdCl_2$(dppf) ·DCM (0.411 g, 0.504 mmol. 0.1 eq) was then added to the reaction mixture, which was stirred at 90° C. for another 16 h. After completion (monitored by TLC), the reaction mixture was filtered through a celite bed. The filtrate was concentrated under reduced pressure and the crude residue was purified by column chromatography (100-200 mesh silica gel; 30% ethyl acetate/hexane) to afford 2-(5-fluoro-4-(4,4,5,5-tetramethyl-1,3,2-dioxaborolan-2-yl)-1H-indol-1-yl)ethan-1-ol (1.45 g, 91.77%) as a light brown semi solid material.

Synthesis of 2-(5-fluoro-4-(4,4,5,5-tetramethyl-1,3,2-dioxaborolan-2-yl)-1H-indol-1-yl)ethan-1-ol (Intermediate A-77)

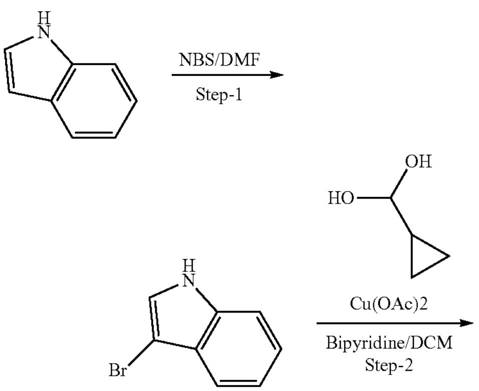

-continued

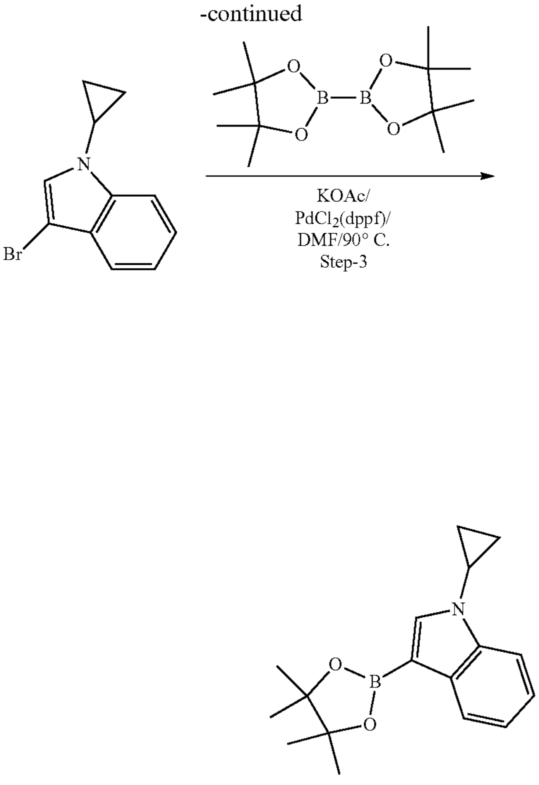

intermediate A-77

Step 1: To a stirred solution of indole (5.0 g, 42.73 mmol, 1 eq) in DMF (20 mL) at 0° C. was added portion wise over 10 min solid N-bromosuccinimide (8.36 g, 47.0 mmol, 1.1 eq), and the reaction mixture was stirred for 30 min at 0° C. After completion (monitored by LCMS), the reaction mixture was diluted with ethyl acetate (100 mL) and the organic layer was washed with water (3×200 mL) and brine (250 mL), dried over anhydrous $Na_2SO_4$ and evaporated under reduced pressure at low temperature to afford 3-bromo-1H-indole (1.1 g, 62%) as an off-white solid Step 2: To a stirred solution of 3-bromo-1H-indole (4 g, 20.5 mmol, 1 eq) in DCM, cyclopropyl boronic acid (3.5 g, 41.025 mmol, 2.0 eq), copper(II) acetate (5.58 g, 30.76 mmol, 1.5 eq) and pyridine (4 mL, 41.025 mmol, 2 eq.) were added and the reaction mixture was stirred at rt for 48 h. After completion (monitored by TLC), the reaction mixture was filtered through a celite bed. The filtrate was concentrated under reduced pressure to afford the crude material which was purified by flash column chromatography (100-200 mesh silica gel; 5% EtOAC-Hex) to yield 3-bromo-1-cyclopropyl-1H-indole (2.0 g, 41%) as an off-white solid.

Step 3: A stirred solution of 3-bromo-1-cyclopropyl-1H-indole (1 g, 4.25 mmol, 1 eq), bis(pinacolato)diborane (1.62 g, 6.38 mmol, 1.5 eq) and potassium acetate (1.25 g, 12.76 mmol, 3 eq) in 1,4-dioxane (20 mL) was deoxygenated with argon gas for 10 min. $PdCl_2$(dppf)·DCM (0.173 g, 0.212 mmol. 0.05 eq) was then added and the reaction mixture was heated at 90° C. for 16 h. After completion (monitored by TLC), the reaction mixture was filtered through a celite bed. The filtrate was concentrated under reduced pressure to afford the crude material which was purified by flash column chromatography (100-200 mesh silica gel; 5% EtOAC-Hex) to yield 1-cyclopropyl-3-(tetramethyl-1,3,2-dioxaborolan-2-yl)-1H-indole (0.8 g, 66%) as an off-white solid.

Synthesis of 7-fluoro-1-methanesulfonyl-3-(tetramethyl-1,3,2-dioxaborolan-2-yl)-1H-indole (Intermediate A-78)

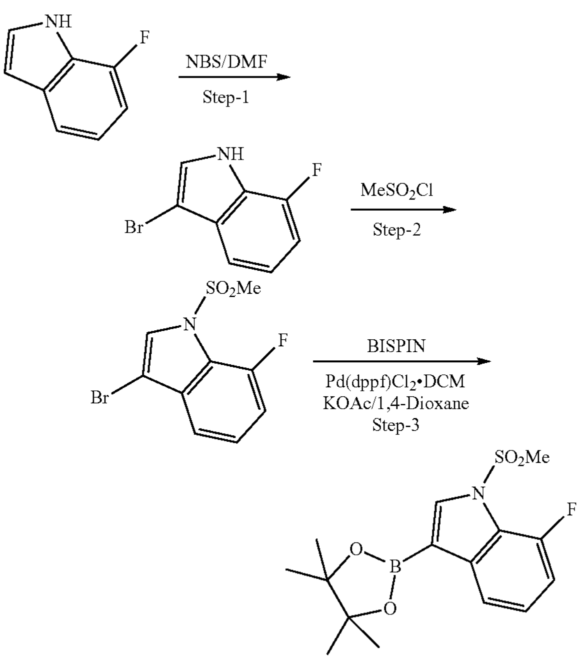

intermediate A-78

Step 1: To a suspension of 7-fluoro-1H-indole (2 g, 14 mmol, 1 eq) in DMF (20 mL) was added NBS (2.88 g, 16.2 mmol, 1.1 eq) at 0° C., and the reaction was stirred at RT for 2 h. After completion, the compound was extracted with ethyl acetate (50 mL). The combined organic layers was washed with water (150 mL) and brine (150 mL), dried over anhydrous $Na_2SO_4$ and evaporated at low temperature to afford 3-bromo-7-fluoro-1H-indole (2 g, 65%).

Step 2: To a stirred solution of 3-bromo-7-fluoro-1H-indole (2 g, 9.3 mmol, 1 eq) in dimethyl formamide (30 mL) was portion wise added sodium hydride (60%, 0.409 g, 10.2 mmol, 1.1 eq) at 0° C., and the reaction mixture was stirred for 10 min. Methanesulfonylchloride (0.86 ml, 11.2 mmol, 1.2 eq) was then added to the reaction mixture at 0° C., and the reaction mixture was stirred for 2 h at room temperature. Then, the reaction mixture was diluted with ethyl acetate (150 mL), and the combined organic layers were washed with water (5×30 mL) and brine (30 mL), dried over anhydrous $Na_2SO_4$ and evaporated under reduced pressure. The crude residue was purified by column chromatography (230-400 mesh silica gel; 10% ethyl acetate/hexane) to afford 3-bromo-7-fluoro-1-methanesulfonyl-1H-indole (2 g, 74%).

Step 3: A stirring suspension of 3-bromo-7-fluoro-1-methanesulfonyl-1H-indole (1.7 g, 5.8 mmol, 1 eq), bis (pinacolato)diborane (1.7 g, 6.9 mmol, 1.2 eq) and potassium acetate (1.7 g, 17.4 mmol, 3 eq) in 1,4-dioxane (45 mL) was deoxygenated with argon gas for 10 min. Pd(dppf) $Cl_2$·DCM (0.47 g, 0.58 mmol, 0.1 eq) was added to the reaction mixture which was again deoxygenated with argon for 10 min. The reaction mixture was then stirred for 14 h at 110° C. The reaction mixture was cooled to room temperature and filtered through a celite bed. The filtrate was concentrated under reduced pressure to get the crude material which was purified by column chromatography (230-400 mesh silica gel; 10% ethyl acetate/hexane) to afford 7-fluoro-1-methanesulfonyl-3-(tetramethyl-1,3,2-dioxaborolan-2-yl)-1H-indole (1 g, 51%) as an off-white solid.

Synthesis of 7-fluoro-1-methanesulfonyl-3-(tetramethyl-1,3,2-dioxaborolan-2-yl)-1H-indole (Intermediate A-79)

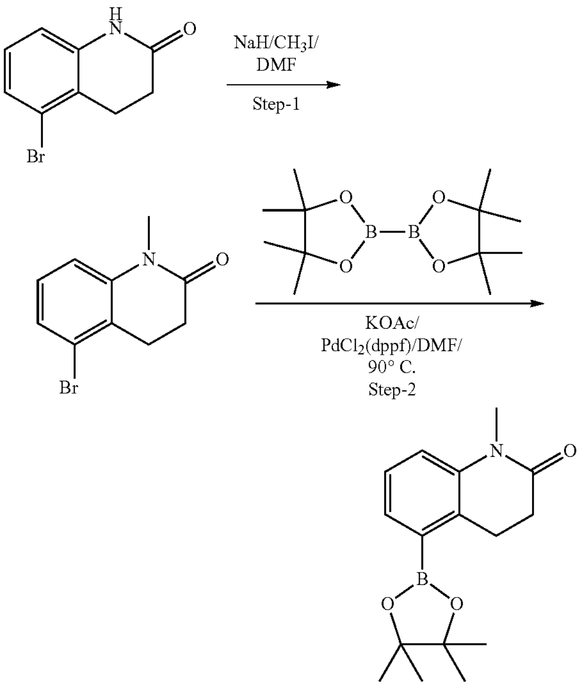

intermediate A-79

Step 1: To an ice-cooled stirred solution of NaH (0.21 g, 4.42 mmol, 2.0 eq.) in DMF (51 mL) was added 5-bromo-3,4-dihydroquinolin-2(1H)-one (0.5 g, 2.21 mmol, 1.0 eq) and the mixture was stirred for 20 min, Then, iodomethane (0.4 ml, 6.63 mmol, 3.0 eq.) was added and the reaction mixture was stirred at rt for 2 h. After completion (monitored by TLC), the reaction mixture was concentrated, diluted with water, extracted with EtOAc (200 mLx2) and washed with brine (50 mL). The organic layer was dried over anhydrous $Na_2SO_4$, filtered and evaporated under reduced pressure to yield 5-bromo-1-methyl-1,2,3,4-tetrahydroquinolin-2-one (0.52 g, 98%) as an off-white solid.

Step 2: A stirred solution of 5-bromo-1-methyl-1,2,3,4-tetrahydroquinolin-2-one (0.5 g, 0.208 mmol, 1 eq), bis (pinacolato)diborane (1.06 g, 0.416 mmol, 2.0 eq) and potassium acetate (0.612 g, 0.624 mmol, 3 eq) in 1,4-dioxane (20 mL) was deoxygenated with argon gas for 10 min. $PdCl_2$(dppf)·DCM (0.085 g, 0.104 mmol. 0.05 eq) was then added and the reaction mixture was stirred 90° C. for another 16 h. After completion (monitored by TLC), the reaction mixture was filtered through a celite bed. The filtrate was concentrated under reduced pressure to afford the crude material which was purified by flash column chromatography (100-200 mesh silica gel; 5% EtOAc-Hex) to yield 1-methyl-5-(tetramethyl-1,3,2-dioxaborolan-2-yl)-1,2,3,4-tetrahydroquinolin-2-one (0.5 g, 84%) as an off-white solid.

Synthesis of 5-ethyl-2-methoxy-3-(tetramethyl-1,3,2-dioxaborolan-2-yl)pyridine (Intermediate A-80)

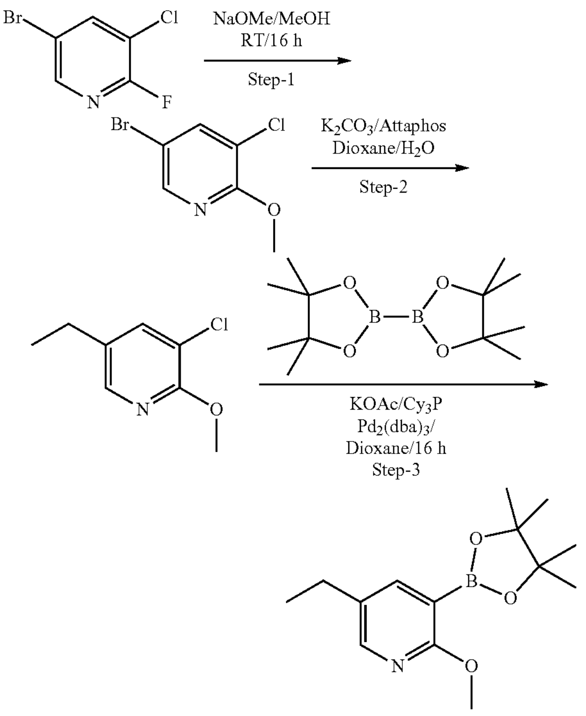

intermediate A-80

Step 1: To a solution of 5-bromo-3-chloro-2-fluoropyridine (5.0 g, 23.809 mmol, 1 eq) in MeOH (30 mL), NaOMe (15 mL) was added at RT, and the reaction was stirred at RT for 16 h. After completion (monitored by TLC), the reaction mixture was evaporated under reduced pressure. The residue was dissolved in water and extracted with EtOAc. The organic layer was washed with brine, dried over $Na_2SO_4$, filtered and evaporated under reduced pressure to afford crude 5-bromo-3-chloro-2-methoxypyridine (4.8 g, 90%) as a brown gum.

Step 2: To a solution of 5-bromo-3-chloro-2-methoxypyridine (2.0 g, 9.009 mmol, 1 eq) in a water:dioxane mixture (17 mL), $K_2CO_3$ (3.72 g, 27.027 mmol, 3 eq) and ethyl boronic acid (0.6 g, 8.108 mmol, 0.9 eq) were added at RT. After degassing the reaction mixture for 15 min, Attaphos (0.319 g, 0.4504 mmol, 0.05 eq) was added and the reaction was refluxed for 16 h. After completion (monitored by TLC), the reaction mixture was filtered and evaporated under reduced pressure. The crude residue was purified by column chromatography to afford 3-chloro-5-ethyl-2-methoxypyridine (0.78 g, 51%) as an off-white solid.

Step 3: To a solution of 3-chloro-5-ethyl-2-methoxypyridine (0.8 g, 4.67 mmol, 1 eq) in dioxane (20.0 mL) were added KOAc (1.37 g, 14.01 mmol, 3 eq) and bispincolatediborane (2.36 g, 9.35 mmol, 2 eq) The solution was degassed with argon for 20 min, followed by addition of $Pd_2$(dba)3 (0.23 g, 0.233 mmol, 0.05 eq) and $Cy_3P$ (0.104 g, 0.373 mmol, 0.08 eq). The reaction mixture was refluxed for 16 h. After completion (monitored by TLC), the reaction mixture was evaporated under reduced pressure. The crude residue was purified by column chromatography to afford 5-ethyl-2-methoxy-3-(tetramethyl-1,3,2-dioxaborolan-2-yl) pyridine (0.68 g, 55%) as a brown solid.

Synthesis of 5-cyclopropyl-2-methoxy-3-(tetramethyl-1,3,2-dioxaborolan-2-yl)pyridine (Intermediate A-81)

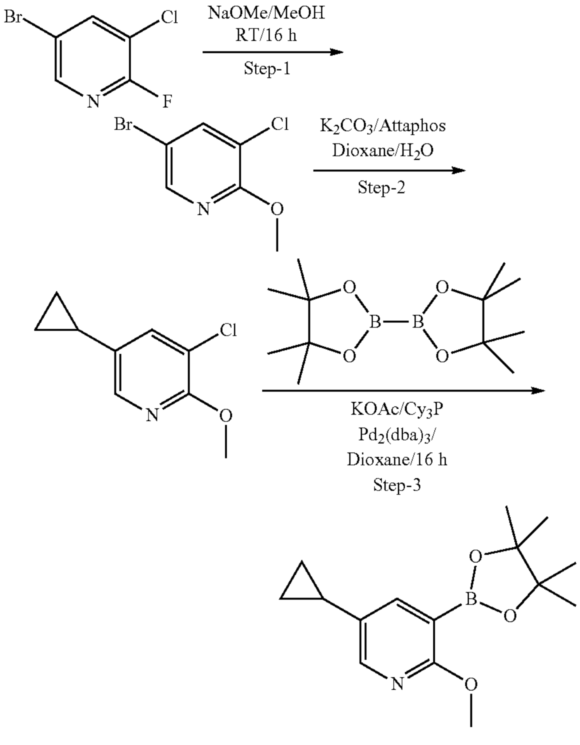

intermediate A-81

Step 1: To a solution of 5-bromo-3-chloro-2-fluoropyridine (5.0 g, 23.809 mmol, 1 eq) in MeOH (30 mL), NaOMe (15 mL) was added at RT, and the reaction was stirred at RT for 16 h. After completion (monitored by TLC), the reaction mixture was evaporated under reduced pressure. The residue was dissolved in water and extracted with EtOAc. The organic layer was washed with brine, dried over $Na_2SO_4$, filtered and evaporated under reduced pressure to afford crude 5-bromo-3-chloro-2-methoxypyridine (4.8 g, 90%) as a brown gum.

Step 2: To a solution of 5-bromo-3-chloro-2-methoxypyridine (2.0 g, 9.009 mmol, 1 eq) in a water:dioxane mixture (17 ml), $K_2CO_3$ (3.72 g, 27.027 mmol, 3 eq) and cyclopropyl boronic acid (0.697 g, 8.108 mmol, 0.9 eq) were added at RT. After degassing the reaction mixture for 15 min, Attaphos (0.319 g, 0.4504 mmol, 0.05 eq) was added and the reaction mixture was refluxed for 16 h. After completion (monitored by TLC), the reaction mixture was filtered and evaporated under reduced pressure. The crude residue was purified by column chromatography to afford 3-chloro-5-cyclopropyl-2-methoxypyridine (1.5 g, 91%) as an off-white solid.

Step 3: To a solution of 3-chloro-5-cyclopropyl-2-methoxypyridine (1 g, 5.46 mmol, 1 eq) in dioxane (20.0 mlL were added KOAc (1.6 g, 16.38 mmol, 3 eq) and Bispincolatediborane (2.76 g, 10.957 mmol, 2 eq) The solution was degassed with argon for 20 min, followed by addition of $Pd_2(dba)_3$ (0.27 g, 0.273 mmol, 0.05 eq) and $Cy_3P$ (0.122 g, 0.436 mmol, 0.08 eq). The reaction mixture was refluxed for 16 h. After completion (monitored by TLC), the reaction mixture was evaporated under reduced pressure. The crude residue was purified by column chromatography to afford 5-cyclopropyl-2-methoxy-3-(tetramethyl-1,3,2-dioxaborolan-2-yl)pyridine (0.8 g, 53%), as a brown solid.

Synthesis of 2-(2,3-dihydro-1,4-benzodioxin-5-yl)-4,4,5,5-tetramethyl-1,3,2-dioxaborolane (Intermediate A-82)

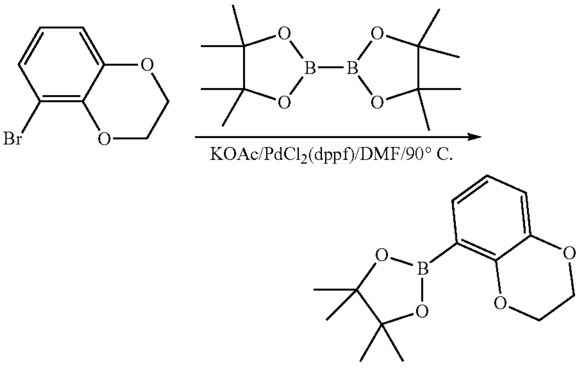

intermediate A-82

A stirred solution of 5-bromo-2,3-dihydrobenzo[b][1,4]dioxine (0.2 g, 0.93 mmol, 1 eq), bis(pinacolato)diborane (0.282 g, 1.116 mmol, 1.2 eq) and potassium acetate (0.273 g, 2.7 mmol, 3 eq) in 1,4-dioxane (20 mL) was deoxygenated with argon gas for 10 min. $PdCl_2$(dppf)·DCM (0.075 g, 0.093 mmol. 0.1 eq) was added and the reaction mixture was stirred at 90° C. for another 16 h. After completion (monitored by TLC), the reaction mixture was filtered through a celite bed. The filtrate was concentrated under reduced pressure to afford the crude material which was used in the next step without any purification.

Synthesis of 1-cyclopropyl-3-(tetramethyl-1,3,2-dioxaborolan-2-yl)-1H-pyrrolo[2,3-b]pyridine (Intermediate A-83)

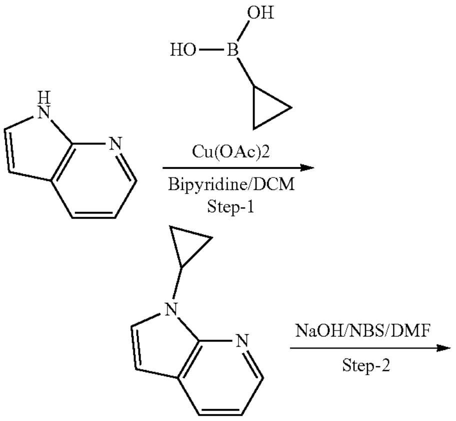

-continued

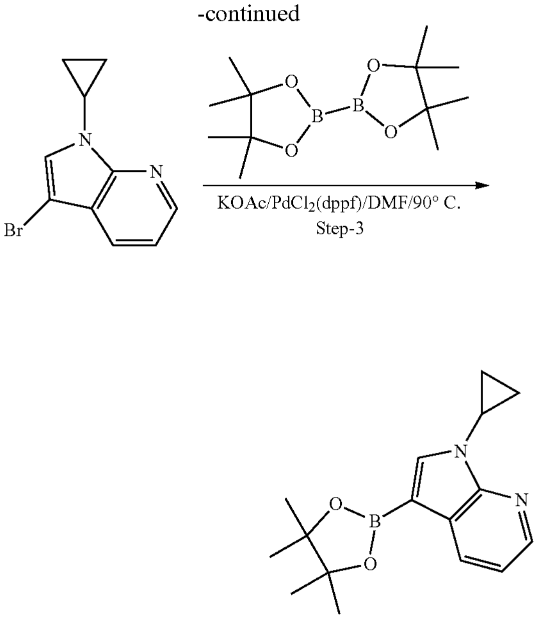

intermediate A-83

Step 1: To a stirred solution of 1H-pyrrolo[2,3-b]pyridine (2 g, 16.94 mmol, 1 eq) in DCM, cyclopropyl boronic acid (2.8 g, 33.89 mmol, 2.0 eq), copper(II)acetate (4.6 g, 25.42 mmol, 1.5 eq), $Na_2CO_3$ (3.6 g, 33.89 mmol, 2 eq.) and bipyridine (2.6 g, 16.94 mmol, 1 eq.) were added and the reaction mixture was stirred at reflux temperature for 48 h. After completion (monitored by TLC), the reaction mixture was filtered through a celite bed. The filtrate was concentrated under reduced pressure and the crude material was purified by flash column chromatography (100-200 mesh silica gel; 20% EtOAc-Hex) to afford 1-cyclopropyl-1H-pyrrolo[2,3-b]pyridine (1.4 g, 52%) as an off white solid.

Step 2: A stirred solution of 1-cyclopropyl-1H-pyrrolo[2,3-b]pyridine (1.6 g, 10.12 mmol, 1 eq) in DMF (20 mL) at 0° C. was treated with NaOH (0.445 g, 11.13 mmol, 1.1 eq) and portion wise over 10 min solid N-bromosuccinimide (1.98 g, 11.13 mmol, 1.1 eq) was added. The reaction mixture was stirred for 30 min at 0° C. After completion (monitored by LCMS), the reaction mixture was diluted with ethyl acetate (50 mL) and the organic layers were washed with water (3x50 mL) and brine (50 mL), dried over anhydrous $Na_2SO_4$ and evaporated under reduced pressure at low temperature to afford 3-bromo-1-cyclopropyl-1H-pyrrolo[2,3-b]pyridine (2.2 g, 92%) as an off-white solid.

Step 3: A stirred solution of 3-bromo-1-cyclopropyl-1H-pyrrolo[2,3-b]pyridine (0.96 g, 4.05 mmol, 1 eq), bis(pinacolato)diborane (1.52 g, 6.08 mmol, 1.5 eq) and potassium acetate (1.19 g, 12.16 mmol, 3 eq) in 1,4-dioxane (20 mL) was deoxygenated with argon gas for 10 min. $PdCl_2$(dppf)·DCM (0.165 g, 0.202 mmol. 0.05 eq) was then added and the reaction mixture was stirred at 120° C. for another 16 h. After completion (monitored by TLC), the reaction mixture was filtered through a celite bed. The filtrate was concentrated under reduced pressure and the crude material was purified by flash column chromatography (100-200 mesh silica gel; 5% EtOAc-Hex) to afford 11-cyclopropyl-3-(tetramethyl-1,3,2-dioxaborolan-2-yl)-1H-pyrrolo[2,3-b]pyridine (0.4 g, 33%) as an off-white solid.

Synthesis of 5-(tetramethyl-1,3,2-dioxaborolan-2-yl)-1,2,3,4-tetrahydroquinolin-2-one (Intermediate A-84)

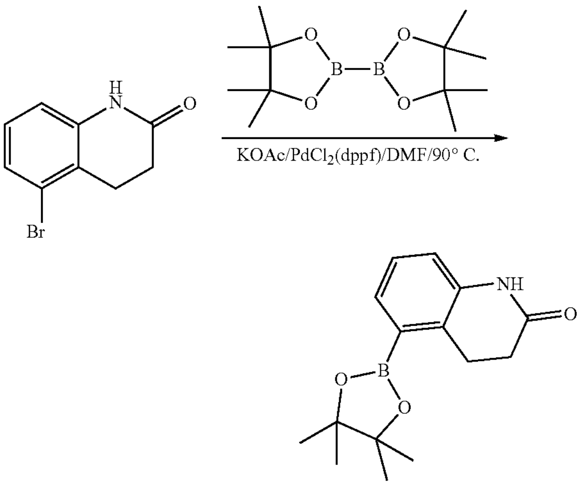

intermediate A-84

A stirred solution of 5-bromo-3,4-dihydroquinolin-2(1H)-one (0.25 g, 0.11 mmol, 1 eq), bis(pinacolato)diborane (0.56 g, 2.21 mmol, 2.0 eq) and potassium acetate (0.325 g, 0.3.31 mmol, 3 eq) in 1,4-dioxane (10 mL) was deoxygenated with argon gas for 10 min. $PdCl_2$(dppf)·DCM (0.045 g, 0.055 mmol. 0.05 eq) was then added and the reaction mixture was stirred at 90° C. for another 16 h. After completion (monitored by TLC), the reaction mixture was filtered through a celite bed. The filtrate was concentrated under reduced pressure and the crude residue was purified by flash column chromatography (100-200 mesh silica gel; 5% EtOAc-Hex) to afford 5-(tetramethyl-1,3,2-dioxaborolan-2-yl)-1,2,3,4-tetrahydroquinolin-2-one (0.28 g, 93%) as an off-white solid.

The intermediates in Table 1 were synthesized in analogy to Intermediate A-1 to Intermediate A-84.

| Intermediate | Synthesized in analogy to | Structure |
|---|---|---|
| Int-A-30 | Int-A-2 | 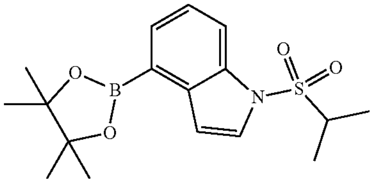 [SMILES: CC(C)S(=O)(=O)n1ccc2c(B3OC(C)(C)C(C)(C)O3)cccc21] |
| Int-A-42 | Int-A-11 | 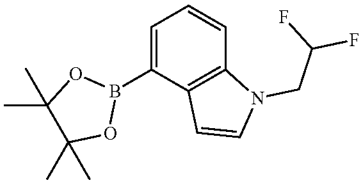 [SMILES: CC1(C)OB(c2cccc3c2ccn3CC(F)F)OC1(C)C] |

-continued

| Inter-mediate | Synthe-sized in analogy to | Structure |
|---|---|---|
| Int-A-47 | Int-A-2 | 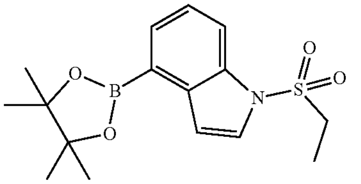 [SMILES: CCS(=O)(=O)n1ccc2c(B3OC(C)(C)C(C)(C)O3)cccc21] |
| Int-A-48 | Int-A-2 | 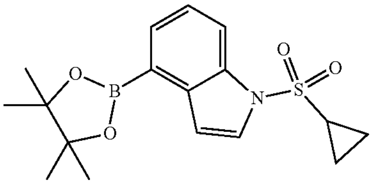 [SMILES: CC1(C)OB(c2cccc3c2ccn3S(=O)(=O)C2CC2)OC1(C)C] |
| Int-A-56 | Int-A-11 | 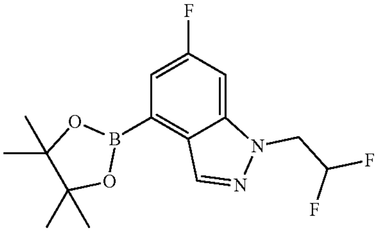 [SMILES: CC1(C)OB(c2cc(F)cc3c2cnn3CC(F)F)OC1(C)C] |
| Int-A-58 | Int-A-22 | 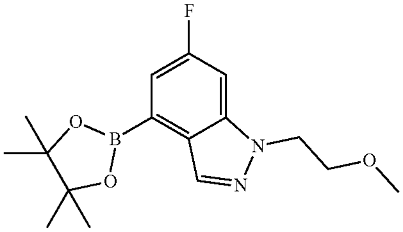 |
| Int-A-73 | Int-A-21 | 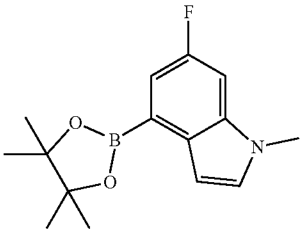 |

The Intermediates in Table 2 are commercially available:

| Name | Structure |
|---|---|
| indole-4-boronic acid | 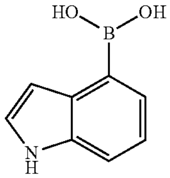 |
| 3-methyl-7-(4,4,5,5-tetramethyl-1,3,2-dioxaborolan-2-yl)-1H-indole | 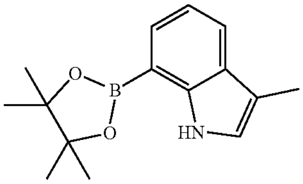 |
| 2-methoxy-3-(4,4,5,5-tetramethyl-1,3,2-dioxaborolan-2-yl)-5-(trifluoromethyl)pyridine | 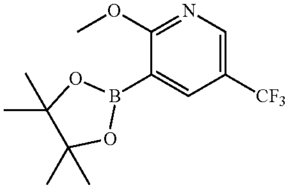 [SMILES: COc1ncc(C(F)(F)F)cc1B1OC(C)(C)C(C)(C)O1] |
| 4-(4,4,5,5-tetramethyl-1,3,2-dioxaborolan-2-yl)-1H-pyrrolo[2,3-b]pyridine | 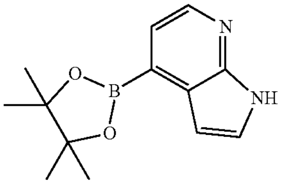 [SMILES: CC1(C)OB(c2ccnc3[nH]ccc23)OC1(C)C] |
| 1-methyl-3-(4,4,5,5-tetramethyl-1,3,2-dioxaborolan-2-yl)pyrrolo[2,3-b]pyridine | 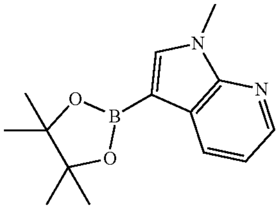 [SMILES: Cn1cc(B2OC(C)(C)C(C)(C)O2)c2cccnc21] |
| 3-(4,4,5,5-tetramethyl-1,3,2-dioxaborolan-2-yl)-5,6-dihydro-4H-pyrrolo[1,2-b]pyrazole | 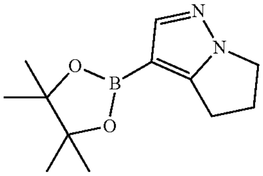 [SMILES: CC1(C)OB(c2cnn3c2CCC3)OC1(C)C] |
| Naphthalene-1-boronic acid | 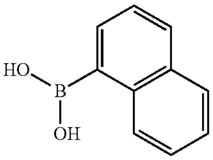 [SMILES: OB(O)c1cccc2ccccc12] |
| (3-Fluoro-5-vinylphenyl)boronic acid | 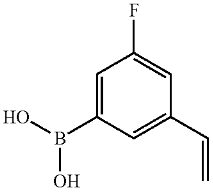 |
| (3-fluoro-5-methylphenyl)boronic acid | 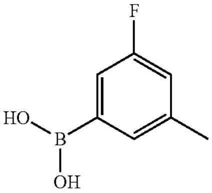 |

-continued

| Name | Structure |
| --- | --- |
| 5-chloro-2-methoxy-3-(4,4,5,5-tetramethyl-1,3,2-dioxaborolan-2-yl)pyridine | 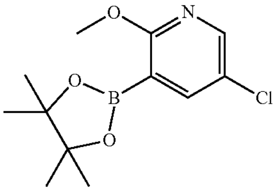 [SMILES: COc1ncc(Cl)cc1B1OC(C)(C)C(C)(C)O1] |
| 5-fluoro-1H-indole | 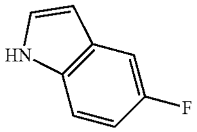 |
| (3-fluoro-5-ethylphenyl)boronic acid | 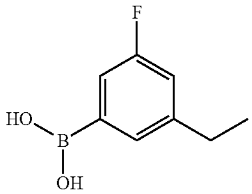 |
| (3-fluoro-5-methoxy-phenyl)boronic acid | 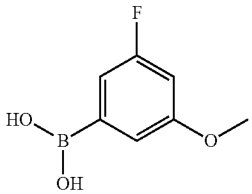 |
| 5-fluoro-2-methoxy-3-(4,4,5,5-tetramethyl-1,3,2-dioxaborolan-2-yl)pyridine | 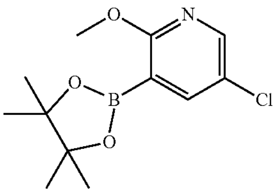 [SMILES: COc1ncc(Cl)cc1B1OC(C)(C)C(C)(C)O1] |
| (3-amino-5-fluoro-phenyl)boronic acid | 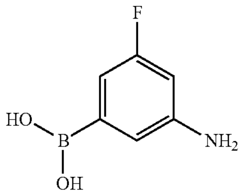 [SMILES: Nc1cc(F)cc(B(O)O)c1] |
| 1-methyl-3-(4,4,5,5-tetramethyl-1,3,2-dioxaborolan-2-yl)pyrrolo[2,3-c]pyridine | 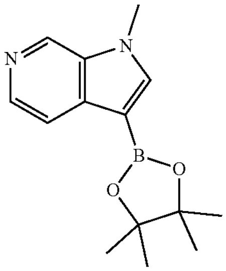 [SMILES: Cn1cc(B2OC(C)(C)C(C)(C)O2)c2ccncc21] |

-continued

| Name | Structure |
| --- | --- |
| 2-methoxy-5-methyl-3-(4,4,5,5-tetramethyl-1,3,2-dioxaborolan-2-yl)pyridne | 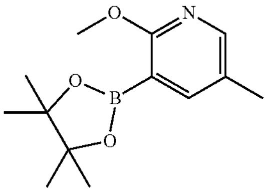 |
| quinolin-5-ylboronic acid | 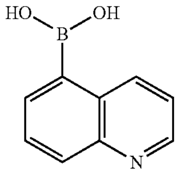 [SMILES: OB(O)c1cccc2ncccc12] |
| 4-fluoro-1H-indole | 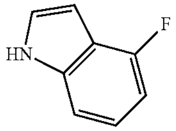 |
| 3-(4,4,5,5-tetramethyl-1,3,2-dioxaborolan-2-yl)pyrazolo[1,5-a]pyridine | 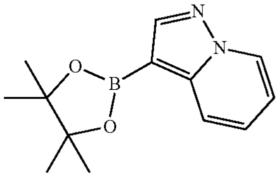 [SMILES: CC1(C)OB(c2cnn3ccccc23)OC1(C)C] |
| 5-methyl-1H-indole | 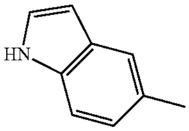 |
| 1-(methylsulfonyl)-3-(4,4,5,5-tetramethyl-1,3,2-dioxaborolan-2-yl)-1H-indole | 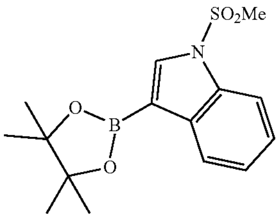 [SMILES: CC1(C)OB(c2cn(S(C)(=O)=O)c3ccccc23)OC1(C)C] |
| (3-fluoro-5-hydroxy-phenyl)boronic acid | 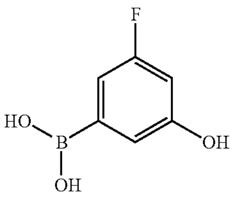 [SMILES: OB(O)c1cc(O)cc(F)c1] |
| (3-chloro-2-methoxyphenyl)boronic acid | 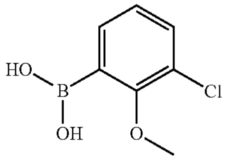 |

-continued

| Name | Structure |
|---|---|
| (3-fluoro-4-methoxy-phenyl)boronic acid | 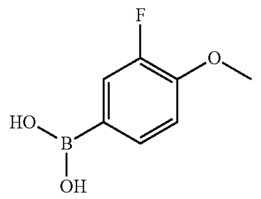 |
| 1-methyl-4-(4,4,5,5-tetramethyl-1,3,2-dioxaborolan-2-yl)pyrrolo[2,3-b]pyridine | 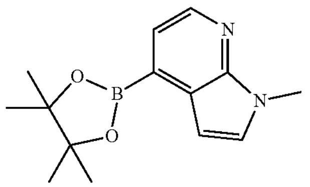 |
| 4-methyl-1H-indole | 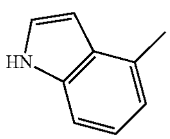 |
| (2-fluoro-3-methoxyphenyl)boronic acid | 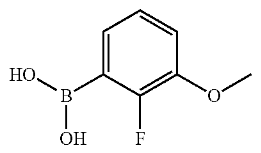 |

Synthesis of 8-bromo-7,9-difluoro-1,4,4-trimethyl-4,5-dihydro-[1,2,4]triazolo[4,3-a]quinoxaline (Intermediate B-1)

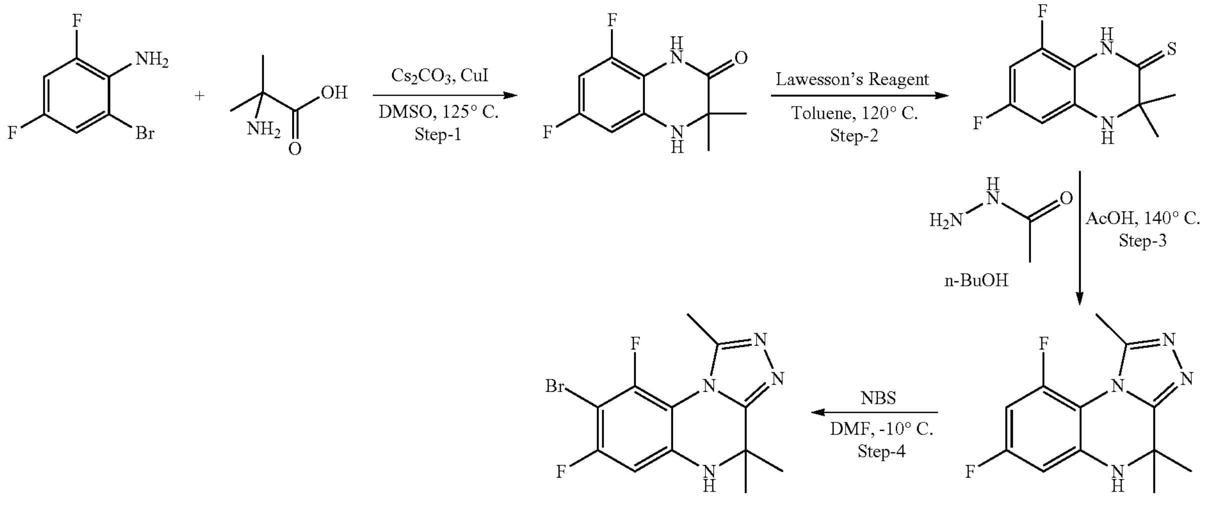

intermediate B-1

Step 1: A suspension of 2-bromo-4,6-difluoroaniline (25 g, 120.19 mmol, 1 eq.), 2-amino-2-methylpropanoic acid (24.75 g, 240.38 mmol, 2 eq.), $K_3PO_4$ (50.96 g, 240.38 mmol, 2 eq.) and CuI (2.29 g, 12.02 mmol, 0.1 eq.) in dry DMSO (375 mL) in a sealed tube were deoxygenated with Ar for 20 min. Reaction mixture was then stirred at 125° C. for 16 h. After completion of the reaction, it was filtered through celite bed and washed by EtOAc (100 mL). The filtrate was diluted with EtOAc (500 mL) and washed with water (3×150 mL), brine (200 mL), dried over anhydrous $Na_2SO_4$ and evaporated under reduced pressure. Crude product was purified by column chromatography to afford 6,8-difluoro-3,3-dimethyl-3,4-dihydroquinoxalin-2(1H)-one (34.0 g, 67%) as brown solid.

Step 2: To a solution of 6,8-difluoro-3,3-dimethyl-3,4-dihydroquinoxalin-2(1H)-one (34.0 g, 160 mmol, 1 eq.) in toluene (650 mL) was added Lawesson's reagent (97.3 g, 240 mmol, 1.5 eq.) at RT and the reaction mixture was refluxed at 120° C. for 40 min. After completion of reaction, the reaction mixture was quenched with sat. $NaHCO_3$ solution (250 mL) followed by extraction with EtOAc (3×150 mL). Combined organic layers was washed with water (300 mL), brine (200 mL), dried over anhydrous $Na_2SO_4$ and evaporated to get the crude product which was purified by column chromatography to afford 6,8-difluoro-3,3-dimethyl-3,4-dihydroquinoxaline-2(1H)-thione (26 g, 66%) as yellow solid.

Step 3: To a solution of 6,8-difluoro-3,3-dimethyl-3,4-dihydroquinoxaline-2(1H)-thione (5.0 g, 21.9 mmol, 1 eq.) in n-BuOH (60 mL) is added acetohydrazide (5.35 g, 72.3 mmol, 3.3 eq) followed by addition of AcOH (6 mL) and then the reaction mixture is stirred at 140° C. for 16 h. After completion of reaction, reaction mixture is concentrated and the residue was diluted with EtOAc (150 mL). Combined organic layers washed with water (100 mL), brine (100 mL), dried over anhydrous $Na_2SO_4$ and evaporated to get the crude product which was purified by column chromatography to afford 7,9-difluoro-1,4,4-trimethyl-4,5-dihydro-[1,2,4]triazolo[4,3-a]quinoxaline (4.5 g, 82%) as off white solid.

Step 4: To the stirred solution of 7,9-difluoro-1,4,4-trimethyl-4,5-dihydro-[1,2,4]triazolo[4,3-a]quinoxaline (4.5 g, 18 mmol, 1 eq.) in DMF (40 mL) was added N-bromosuccinimide (3.5 g, 19.8 mmol, 1.1 eq) portion wise. Reaction mixture was allowed to warm to RT and stirred for 2 h. Reaction mixture was diluted with EtOAc (300 mL). Combined organic layers was washed with water (5×50 mL), brine (50 mL), dried over anhydrous $Na_2SO_4$ and evaporated under reduced pressure. Crude product was purified by column chromatography to afford 8-bromo-7,9-difluoro-1,4,4-trimethyl-4,5-dihydro-[1,2,4]triazolo[4,3-a]quinoxaline (4.0 g, 61%) as brown solid.

Synthesis of 8-bromo-7-fluoro-1,4,4,9-tetramethyl-4,5-dihydro-[1,2,4]triazolo[4,3-a]quinoxaline (Intermediate B-3)

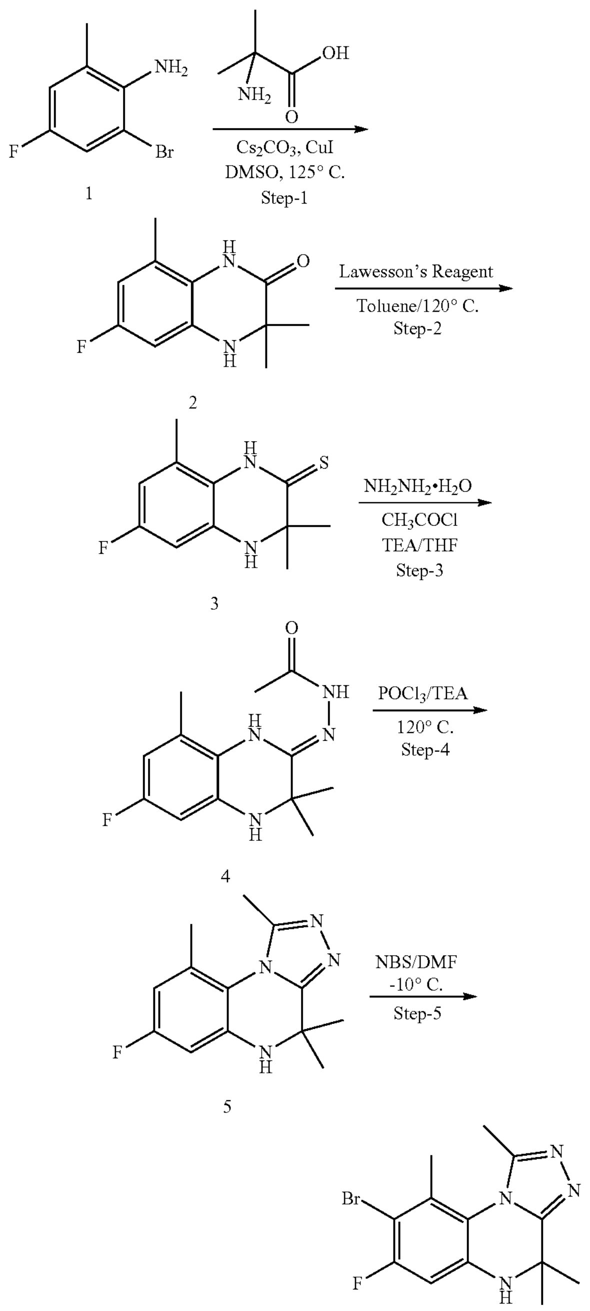

1, 2, 3, 4, 5

Intermediate B-3

Step 1: A suspension of 2-bromo-4-fluoro-6-methyl aniline (5 g, 24.5 mmol, 1 eq.), 2-aminoisobutaric acid (5.05 g, 49 mmol, 2 eq.), $Cs_2CO_3$ (15.92 g, 49 mmol, 2 eq.) and cuprous iodide (0.466 g, 2.45 mmol, 0.1 eq.) in dry DMSO (75 mL) in a sealed tube were deoxygenated with Ar for 20 min. Reaction mixture was then stirred at 125° C. for 16 h. The reaction mixture was filtered through celite bed and washed with EtOAc (100 mL). The filtrate was diluted with EtOAc (200 mL) and washed with water (3×100 mL), brine (100 mL), dried over anhydrous $Na_2SO_4$ and evaporated under reduced pressure to get the crude product which was purified by column chromatography to afford 6-fluoro-3,3,8-trimethyl-3,4-dihydroquinoxalin-2(1H)-one (3.0 g, 59%) as brown solid.

Step 2: To a solution of 6-fluoro-3,3,8-trimethyl-3,4-dihydroquinoxalin-2(1H)-one (3.66 g, 17.6 mmol, 1 eq.) in toluene (75 mL) was added Lawesson's reagent (10.67 g, 26.2 mmol, 1.5 eq.) at RT and the reaction mixture was stirred at 120° C. for 40 min. The reaction mixture was quenched with sat. $NaHCO_3$ solution (100 mL) followed by extraction with EtOAc (2×100 mL). Combined organic layers were washed with water (100 mL), brine (100 mL), dried over anhydrous $Na_2SO_4$ and the solvent was evaporated to get the crude product which was purified by column chromatography to afford 6-fluoro-3,3,8-trimethyl-3,4-dihydroquinoxaline-2(1H)-thione (2.8 g, 71%) as yellow solid.

Step 3: To a stirring solution of 6-fluoro-3,3,8-trimethyl-3,4-dihydroquinoxaline-2(1H)-thione (5.50 g, 24.55 mmol, 1 eq) in THF (30 mL) was drop wise added hydrazine hydrate (5.17 mL, 122.76 mmol, 5 eq) at 0° C. The reaction mixture was then stirred for 16 h at RT. TEA (16.7 ml, 122.76 mmol, 5 eq) was added to the reaction mixture and stirred for another 10 min. Acetyl chloride (5.78 g, 73.65 mmol, 3 eq) was added to the reaction mixture very slowly at 0° C. and then stirred for 2 h at RT. The reaction mixture was diluted with water (50 mL) and extracted with DCM (5×100 mL). The combine organic layers were washes with brine (100 mL). The organic layer was dried over $Na_2SO_4$, concentrated under reduced pressure to get the crude material which was washed with diethyl ether to afford N'-(6-fluoro-3,3,8-trimethyl-3,4-dihydroquinoxalin-2(1H)-ylidene)acetohydrazide (5.5 g, 85%) as a white solid.

Step 4: N'-(6-fluoro-3,3,8-trimethyl-3,4-dihydroquinoxalin-2(1H)-ylidene)acetohydrazide (5.5 g, 20.8 mmol, 1 eq) was taken in round bottom flax (50 mL) and then cooled to −10° C. Phosphorus oxychloride (18.4 ml, 197.6 mmol, 9.5 eq) was then added drop wise to the compound followed by drop wise addition of TEA (2.9 ml, 20.8 mmol, 1 eq).

After that the reaction mixture was stirred at −10° C. for 10 min and then 10 min at RT and finally heated to reflux for 4 h. The reaction mixture was cooled to 0° C. and then crushed ice was drop wise added with constant stirring. To this aqueous part was then slowly added cold ammonium solution (100 mL). The aqueous layer was extracted with DCM (2×100 mL). The combined organic layers were washed with brine (100 mL). The organic layer was dried over anhydrous $Na_2SO_4$, concentrated under reduced pressure to get the crude material. Crude product was purified by column chromatography to afford 7-fluoro-1,4,4,9-tetramethyl-4,5-dihydro-[1,2,4]triazolo[4,3-a]quinoxaline (3.0 g, 59%) as yellow solid.

Step 5: A stirred solution of 7-fluoro-1,4,4,9-tetramethyl-4,5-dihydro-[1,2,4]triazolo[4,3-a]quinoxaline (4.0 g, 16.2 mmol, 1 eq) in DMF (40 mL) at −10° C. is treated portion wise over 10 min with solid N-bromosuccinimide (3.1 g, 17.1 mmol, 1.05 eq). The reaction mixture was allowed to warm to RT and stirred for 1.5 h. The reaction mixture was diluted with EtOAc (300 mL) and the organic layers were washed with water (5×50 mL), brine (50 mL), dried over anhydrous $Na_2SO_4$ and the solvent was evaporated under reduced pressure. The crude product was purified by column chromatography to afford 8-bromo-7-fluoro-1,4,4,9-tetramethyl-4,5-dihydro-[1,2,4]triazolo[4,3-a]quinoxaline (3.3 g, 63%) as off white solid.

Synthesis of 8-bromo-7-fluoro-1,4,4-trimethyl-9-(trifluoromethyl)-4,5-dihydro-[1,2,4]triazolo[4,3-a]quinoxaline (Intermediate B-4)

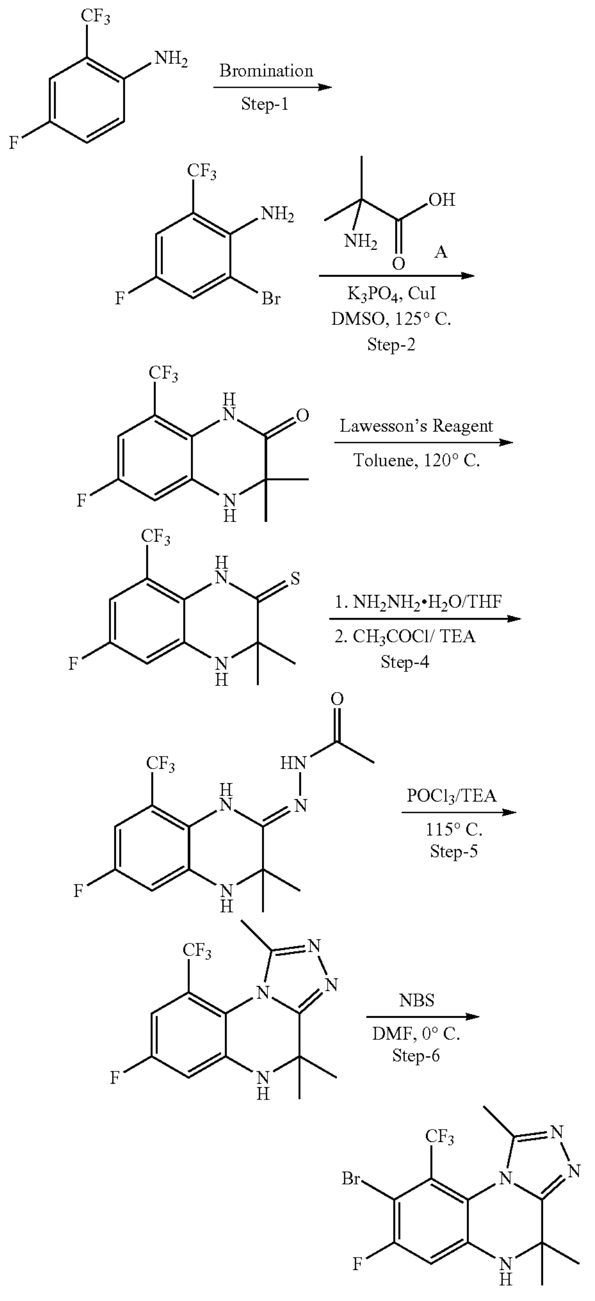

intermediate B-4

Step 1: To a solution of 4-fluoro-2-trifluoromethyl-phenylamine (50 g, 0.279 mol) in DCM (550 mL) was added solution of $Br_2$ (15.1 ml, 0.29 mol) in DCM (100 mL) drop-wise at 0° C. and the resulting reaction mixture was stirred at 0° C. for 2 h. The reaction mixture was diluted with water (1000 mL) and extracted with EtOAc (2×500 mL). Combined organic layers were washed with water (2×500 mL) followed by brine (250 mL), dried over anhydrous $Na_2SO_4$ and concentrated to afford crude product. Which was purified by column chromatography to afford 2-bromo-4-fluoro-6-trifluoromethyl-phenylamine (50 g, 69.4%) as brown liquid.

Step 2: To the stirred suspension of 2-bromo-4-fluoro-6-trifluoromethyl-phenylamine (25 g, 0.097 mol) in dry DMSO (375 mL) was added 2-amino-2-methyl-propionic acid (20 g, 0.194 mol) followed by $K_3PO_4$ (41.1 g, 0.194 mol) at RT. Resulting reaction mixture was degassed with nitrogen for 30 min, then CuCl (0.96 g, 0.0097 mol) was added and the reaction mixture was stirred at 140° C. for 16 h. The reaction mixture was cooled to RT and filtered through celite. Celite bed was washed with EtOAc (500 mL). Resulting filtrate was poured into ice cold water (1000 mL). Resulting aqueous layer was extracted with EtOAc (2×250 mL). Total organic part was washed with water (2×500 mL), brine (250 mL), dried over anhydrous $Na_2SO_4$ and the solvent was evaporated under reduced pressure to afford crude product which was purified by column chromatography to afford 6-fluoro-3,3-dimethyl-8-trifluoromethyl-3,4-dihydro-1H-quinoxalin-2-one (16 g, 63%) as brown solid.

Step 3: To a solution of 6-fluoro-3,3-dimethyl-8-trifluoromethyl-3,4-dihydro-1H-quinoxalin-2-one (26 g, 0.0992 mol) in toluene (390 mL) was added Lawesson's reagent (60.14 g, 0.1488 mol) at RT and the reaction mixture was refluxed at 120° C. for 2 h. The reaction mixture was concentrated. Obtained solid residue was quenched with sat. $NaHCO_3$ solution (1500 mL) and resulting aqueous layer was extracted with EtOAc (3×500 mL). Combined organic layers were washed with water (1000 mL), brine (1000 mL), dried over anhydrous $Na_2SO_4$ and the solvent was evaporated to get the crude product. Obtained crude product was purified by column chromatography to afford 6-fluoro-3,3-dimethyl-8-trifluoromethyl-3,4-dihydro-1H-quinoxaline-2-thione (26 g, 94.3%) as yellow solid.

Step 4: To a stirring solution of 6-fluoro-3,3-dimethyl-8-trifluoromethyl-3,4-dihydro-1H-quinoxaline-2-thione (29.5 g, 0.106 mol) in THF (750 mL) was drop wise added hydrazine hydrate (15.91 g, 0.318 mol) at 0° C. The reaction mixture was stirred at RT for 16 h. TEA (101.19 mL, 0.742 mol) and acetyl chloride (30.14 ml, 0.424 mol) were added subsequently to the reaction mixture drop-wise at 0° C. and the mixture was stirred for 2 h at RT. The reaction mixture was diluted with water (500 mL) and extracted with 10% MeOH-DCM (5×500 mL). The total organic part was washed with brine (250 mL), dried over $Na_2SO_4$ and concentrated under reduced pressure to afford acetic acid (6-fluoro-3,3-dimethyl-8-trifluoromethyl-3,4-dihydro-1H-quinoxalin-2-ylidene)-hydrazide (30 g, 88.9%) as an off white solid.

Step 5: Acetic acid (6-fluoro-3,3-dimethyl-8-trifluoromethyl-3,4-dihydro-1H-quinoxalin-2-ylidene)-hydrazide (17 g, 0.053 mol) was taken in a round bottom flask and then cooled to −10° C. Phosphorus oxalylchloride (24.7 mL, 0.265 mol) was then added drop wise to the compound followed by drop wise addition of TEA (7.36 ml, 0.053 mol). After that the reaction mixture was stirred at −10° C. for 10 min and then for 10 min at RT and finally the mixture was heated to reflux for 4 h. The reaction mixture was cooled to 0° C. and quenched with crushed ice water (250 mL). The aqueous part was then basified using cold ammonium solution (250 mL) drop-wise. Resulting basic aqueous layer was then extracted with EtOAc (3×500 mL). Total organic part was washed with brine (250 mL), dried over anhydrous $Na_2SO_4$ and concentrated under reduced pressure to afford crude product. Obtained crude product was purified by trituration using MTBE to afford 7-fluoro-1,4,4-trimethyl-9-trifluoromethyl-4,5-dihydro-[1,2,4]triazolo[4,3-a]quinoxaline (8.5 g, 53%) as yellow solid.

Step 6: To a solution of 7-fluoro-1,4,4-trimethyl-9-trifluoromethyl-4,5-dihydro-[1,2,4]triazolo[4,3-a]quinoxaline (5.9 g, 19.64 mmol) in DMF (177 mL) was added NBS (3.84 g, 21.61 mol) portion wise at −10° C. Resulting reaction mixture was stirred at RT for 16 h. The reaction mixture was diluted with water (500 mL) and extracted with EtOAc (2×750 mL). Combined organic layers were washed with water (750 mL) followed by brine (400 mL), dried over anhydrous $Na_2SO_4$ and concentrated to afford crude product. Obtained crude product was purified by column chromatography to afford 8-bromo-7-fluoro-1,4,4-trimethyl-9-trifluoromethyl-4,5-dihydro-[1,2,4]triazolo[4,3-a]quinoxaline (3 g, 40%) as off white solid.

Synthesis of 8-bromo-6-fluoro-1,4,4,9-tetramethyl-4,5-dihydro-[1,2,4]triazolo[4,3-a]quinoxaline (Intermediate B-7)

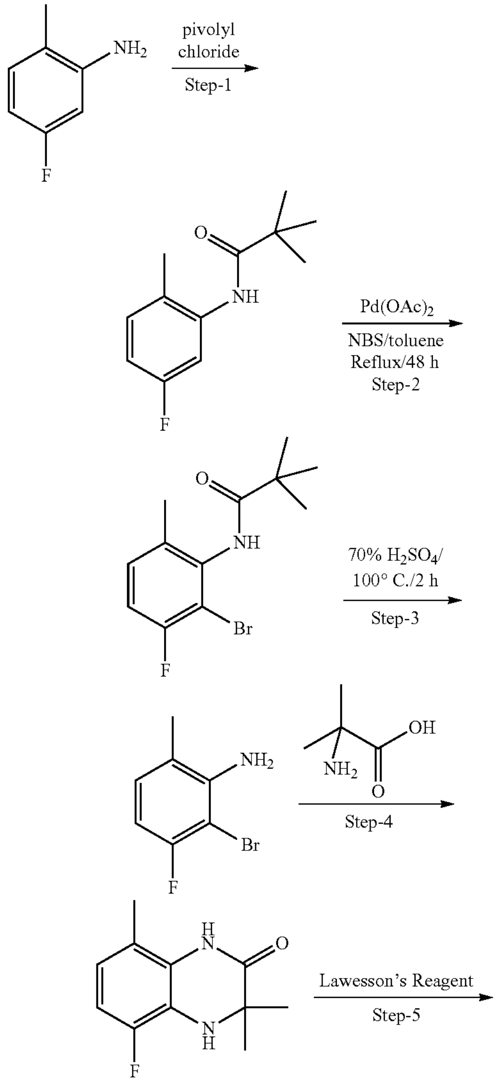

-continued

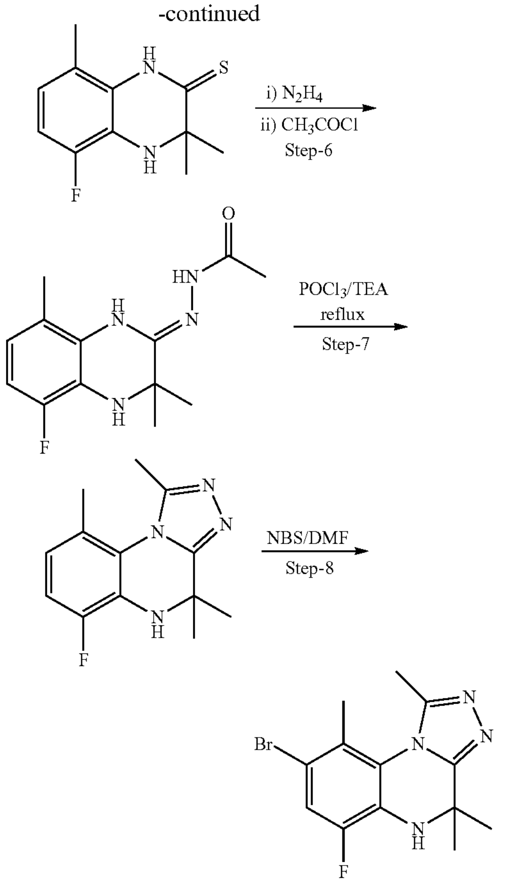

intermediate B-7

Step 1: To a stirred solution of 5-fluoro-2-methyl-phenylamine (100 g, 0.8 mol) in DCM (1500 mL) was added pyridine (129 mL, 1.6 mol) followed by DMAP (1 g, 0.008 mol) at RT. To this reaction mixture was added drop wise pivolyl chloride (109 mL, 0.88 mol) at 0° C. Resulting reaction mixture was stirred at 0° C. for 2 h. After completion of starting material reaction mixture was poured into ice cooled 1(N) HCl solution (1500 mL) and stirred for 30 min. The two layers were separated and the organic layer was washed with 1(N) HCl solution (1000 mL) followed by saturated $NaHCO_3$ solution (1000 mL) followed by brine (1000 mL) and then dried over anhydrous $Na_2SO_4$ and concentrated under reduced pressure to afford crude product. Crude product was triturated using hexane to afford N-(5-Ffluoro-2-methyl-phenyl)-2,2-dimethyl-propionamide (158 g, 95%) as white solid.

Step 2: To a stirring solution N-(5-fluoro-2-methyl-phenyl)-2,2-dimethyl-propionamide (90 g, 0.43 mol) in toluene (2000 mL) was added para-toluene sulphonic acid monohydrate (82.0 g, 0.43 mol), $Pd(OAC)_2$ (9.66 g, 0.043 mol) followed by N-bromo succinimide (84.5 g, 0.473 mol) at RT. Resulting reaction mixture was stirred at RT for 48 h. Reaction monitoring TLC in 20% EA-Hex, showed formation of desired product (Rf=0.4) along with the ~60% un-reacted SM (Rf=0.5). Reaction mixture was then concentrated, obtained residue was diluted with EtOAc and washed with water (twice). Total organic layer was dried over anhydrous $Na_2SO_4$ and concentrated to afford crude product. Two combined batches of crude product (obtained from 90 g and 100 g reaction of N-(5-fluoro-2-methyl-phenyl)-2,2-dimethyl-propionamide) were purified by flash chromatography to afford N-(2-bromo-3-fluoro-6-methyl-phenyl)-2,2-dimethyl-propionamide (60 g, 23%) as white solid and recovered un-reacted N-(5-fluoro-2-methyl-phenyl)-2,2-dimethyl-propionamide (125 g).

Step 3: To a pre cooled solution of 70% $H_2SO_4$ in water (430 mL) was added N-(2-bromo-3-fluoro-6-methyl-phenyl)-2,2-dimethyl-propionamide (60 g, 0.208 mol) portion wise at 0° C. Resulting reaction mixture was stirred at RT for 10 min and then heated to 100° C. for 2 h. After completion of starting material (monitored by TLC in 10% EA-Hex, Rf=0.8) reaction mixture was cooled to 0° C. and pH adjusted to ~10 with 10% NaOH solution. Resulting basic aqueous was extracted with EtOAc (3×500 mL). Total organic layers were washed with water followed by brine, dried over anhydrous $Na_2SO_4$ and concentrated to afford crude product. Crude product was purified by column chromatography to afford 2-bromo-3-fluoro-6-methyl-phenylamine (36 g, 85%) as pale yellow liquid.

Step 4: To the stirred suspension of 2-bromo-3-fluoro-6-methyl-phenylamine (36 g, 0.1764 mol) in dry DMSO (540 mL) was added 2-amino-2-methyl-propionic acid (16.9 g, 0.164 mol) followed by $K_3PO_4$ (75 g, 0.353 mol) at RT. Resulting reaction mixture was degassed with nitrogen for 30 min, then CuCl (1.75 g, 0.0176 mol) was added and reaction mixture was heated at 140° C. for 5 h. After completion of the starting material (monitored by TLC, 20% EA-Hexane, Rf 0.4) reaction mixture was cooled to RT and filtered through celite. Celite bed was washed with EtOAc (500 mL). Resulting filtrate was poured into ice cold water (2500 mL). Resulting aqueous layer was extracted with EtOAc (2×750 mL). Total organic part was washed with water (2×750 mL), followed by brine (500 mL), dried over anhydrous $Na_2SO_4$ and evaporated under reduced pressure to afford crude product. Obtained crude product was triturated with hexane and filtered and dried to afford 5-fluoro-3,3,8-trimethyl-3,4-dihydro-1H-quinoxalin-2-one (19 g, 52%) as brown solid.

Step 5: To a solution of 5-fluoro-3,3,8-trimethyl-3,4-dihydro-1H-quinoxalin-2-one (19 g, 91.2 mmol) in toluene (380 mL) was added Lawesson's reagent (55.5 g, 137 mmol) at RT and the reaction mixture was refluxed at 120° C. for 1 h. After completion of starting material (monitored by TLC in 20% EA-Hexane, Rf 0.7), the reaction mass was cooled to RT and quenched with sat. NaH $CO_3$ solution (250 mL) and resulting aqueous layer was extracted with EtOAc (3×250 mL). Combined organic layers were washed with water (250 mL), followed by brine (250 mL), dried over anhydrous $Na_2SO_4$ and the solvent was evaporated to afford crude product. Obtained crude product was purified by column chromatography to afford 5-fluoro-3,3,8-trimethyl-3,4-dihydro-1H-quinoxaline-2-thione (19 g, 93%) as yellow solid.

Step 6: To a stirred solution of 5-fluoro-3,3,8-trimethyl-3,4-dihydro-1H-quinoxaline-2-thione (20.5 g, 91.5 mmol) in THF (512 mL) was added drop wise hydrazine hydrate (13.5 mL, 274.5 mmol) at 0° C. The reaction mixture was stirred at RT for 16 h. TEA (64 mL, 457.5 mmol) followed acetyl chloride (21.5 mL, 274.5 mmol) were added to the reaction mixture drop-wise at 0° C. and stirred for 2 h at RT. After completion of starting material (monitored by LCMS) reaction mixture diluted with water (500 mL) and extracted by 10% MeOH-DCM (5×500 mL). The total organic part was washed by brine (250 mL), dried over $Na_2SO_4$ and concentrated under reduced pressure to afford acetic acid (5-fluoro-3,3,8-trimethyl-3,4-dihydro-1H-quinoxalin-2-ylidene)-hydrazide (21 g, 87%, crude) as pale yellow solid.

Step 7: Acetic acid (5-fluoro-3,3,8-trimethyl-3,4-dihydro-1H-quinoxalin-2-ylidene)-hydrazide (10.5 g, 0.04 mol) was taken in round bottom flax (100 mL) and then cooled to −10° C. Then phosphorus oxalylchloride (18.5 ml, 0.2 mol) was added drop wise followed by drop wise addition of TEA (5.6 ml, 0.04 mol). After that the reaction mixture was stirred at −10° C. for 10 min and then 10 min at RT and finally at reflux condition for 1 h. After completion of starting material (monitored by LCMS) reaction mixture cooled to 0° C. and quenched with crushed ice water (100 mL). The aqueous part was then basified using cold aqueous ammonia solution (100 mL) drop-wise. Resulting basic aqueous was then extracted with EtOAc (3×150 mL). Total organic part was washed with brine (150 mL), dried over anhydrous $Na_2SO_4$ and concentrated under reduced pressure to afford crude compound. Crude product co-distillation with MTBE twice, then trituration with hexane and dried to afford 6-fluoro-1,4,4,9-tetramethyl-4,5-dihydro-[1,2,4]triazolo[4,3-a]quinoxaline (6 g, 61%) as pale yellow solid.

Step 8: To a solution of 6-fluoro-1,4,4,9-tetramethyl-4,5-dihydro-[1,2,4]triazolo[4,3-a]quinoxaline (12 g, 0.048 mol) in DMF (360 mL) was added NBS (9.39 g, 0.0528 mol) portion wise at −10° C. Resulting reaction mixture was stirred at RT for 4 h. After completion of starting material (monitored by LCMS), reaction mixture was diluted with water (500 mL) and extracted with EtOAc (2×500 mL). Combined organic layers were washed with water (750 mL) followed by brine (400 mL), dried over anhydrous $Na_2SO_4$ and concentrated to afford crude compound. Obtained crude product was purified by column chromatography followed by trituration using MTBE to afford 8-bromo-6-fluoro-1,4,4,9-tetramethyl-4,5-dihydro-[1,2,4]triazolo[4,3-a]quinoxaline (9.1 g, 57%) as off white solid.

Synthesis of 8-bromo-9-ethyl-6-fluoro-1,4,4-trimethyl-4,5-dihydro-[1,2,4]triazolo[4,3-a]quinoxaline (Intermediate B-9)

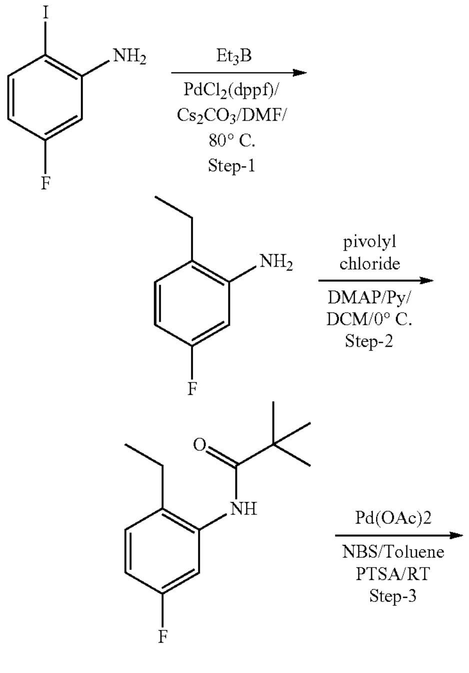

-continued

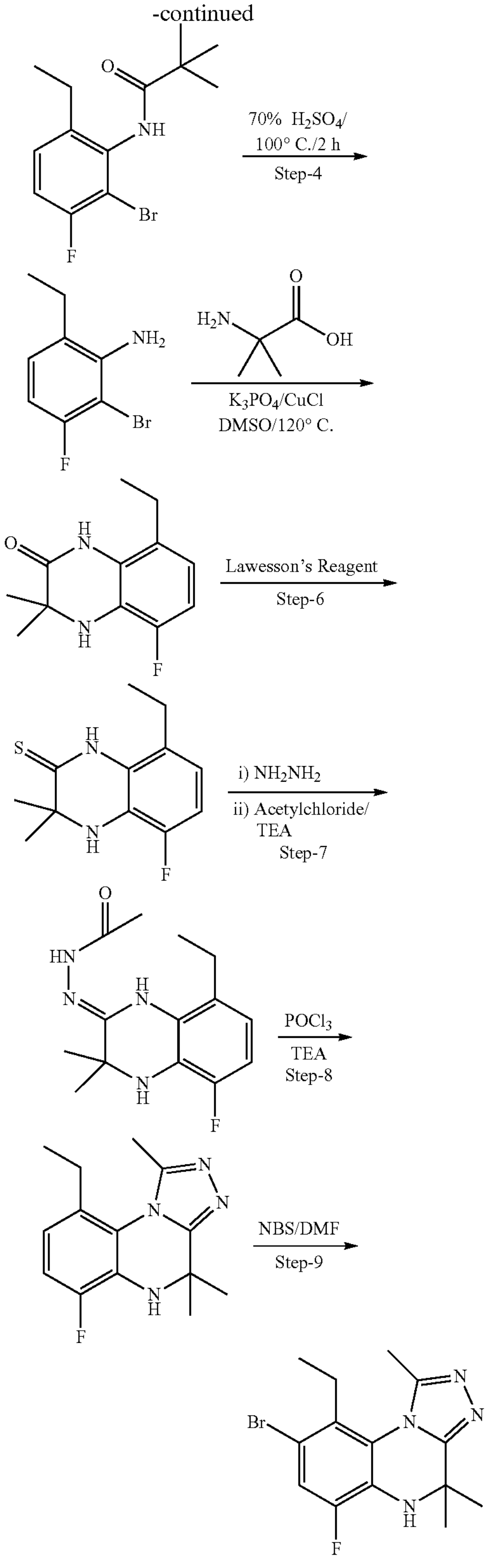

intermediate B-9

Step 1: A stirring suspension of Pd(dppf)$Cl_2$·DCM (1.03 g, 1.27 mmol, 0.1 eq) and $Cs_2CO3$ (16.5 g, 50.63 mmol, 4 eq) in DMF (78 mL) was deoxygenated by Ar for 5 min. 5-Fluoro-2-iodoaniline (3.0 g, 12.65 mmol, 1 eq) and triethylborane (1M) (16.45 mL, 16.45 mmol, 1.5 eq) was added to the reaction mixture and again deoxygenated by Ar for 10 min. Finally the reaction mixture was stirred for 16 h at 70° C. The reaction mixture was cooled to RT and then diluted with EtOAc (100 mL). The organic layer was washed with water (5×20 mL) and brine (20 mL), dried over $Na_2SO_4$, concentrated under reduced pressure to get the crude product. Crude product was purified by column chromatography (230-400 mesh silica gel; 10% EtOAc/hexane; $R_f$-value-0.5) to afford 2-ethyl-5-fluoroaniline (1.20 g, 68%) as off white solid.

Step 2: To a stirring solution of 2-ethyl-5-fluoroaniline (2.0 g, 14.38 mmol 1 eq), pyridine (2.31 mL, 28.77 mmol, 2 eq), and DMAP (0.018 g, 0.144 mmol, 0.01 eq) in DCM (50 mL) was drop wise added pivolyl chloride (1.91 g, 15.82 mmol, 1.1 eq) at 0° C. The reaction mixture was then stirred for another 1 h at 0° C. and then poured into ice cooled HCl (20 ml) (1M) solution. The organic layer was separated and the aqueous layer was extracted with $Et_2O$ (2×20 mL). The combined organic layer was washed with water (2×20 mL) and brine (20 mL). The organic layer was dried over anhydrous $Na_2SO_4$, concentrated under reduced pressure to get the crude material. Crude product was purified by column chromatography (230-400 mesh silica gel; 10% EtOAc/hexane; $R_f$-value-0.5) to afford N-(2-ethyl-5-fluorophenyl)pivalamide (2.3 g, 72%) as off white solid.

Step 3: To a stirring solution of N-(2-ethyl-5-fluorophenyl)pivalamide (25.0 g, 112.1 mmol, 1 eq), in toluene (500 mL) was added p-TSA (19.3 g, 112.1 mmol, 1 eq), Pd$(Oac)_2$ (2.52 g, 11.21 mmol, 0.1 eq) and NBS (21.5 g, 123.3 mmol, 1.1 eq) respectively at RT. The reaction mixture was stirred for 48 h at RT under air. Solvent was evaporated and the residue was dissolved in EtOAc (1000 mL) and washed with water (2×200 mL) followed by brine (200 mL). The organic layer was dried over anhydrous $Na_2SO_4$, concentrated under reduced pressure to get the crude material. Crude product was purified by column chromatography (230-400 mesh silica gel; 10% EtOAc/hexane; $R_f$-value-0.45) to afford N-(2-bromo-6-ethyl-3-fluorophenyl)pivalamide (5.0 g, 15%) as off white solid.

Step 4: 70% $H_2SO_4$ (70 mL) was added to N-(2-bromo-6-ethyl-3-fluorophenyl)pivalamide (9.2 g, 30.46 mmol, 1 eq) in a round bottom flask at 0° C. The reaction mixture was stirred for 20 min at 0° C. and for 2 h 110° C. The reaction mixture then cooled to 0° C. and basified by 20%-NaOH solution up to pH~14. The aqueous part was extracted with EtOAc (3×150 mL). The combined organic layers were washed with water (2×100 mL) and brine (100 mL). The organic layer was dried over anhydrous $Na_2SO_4$, concentrated under reduced pressure to get the crude material. Crude product was purified by column chromatography (230-400 mesh silica gel; 5% EtOAc/hexane; $R_f$-value-0.5) to afford 2-bromo-6-ethyl-3-fluoroaniline (5.9 g, 89%) as brown liquid.

Step 5: A suspension of 2-bromo-6-ethyl-3-fluoroaniline (4.9 g, 22.47 mmol, 1 eq), 2-amino-2-methylpropanoic acid (4.63 g, 44.94 mmol, 2 eq), $K_3PO_4$ (9.54 g, 44.94 mmol, 2 eq) and cuprous chloride (0.22 g, 2.247 mmol, 0.1 eq) in dry DMSO (75 mL) in a sealed tube was deoxygenated with Ar for 20 min. Reaction mixture was then stirred at 140° C. for 2 h. After completion of the reaction, the reaction mixture cooled to RT and filtered through celite bed and washed with EtOAC (100 mL). The filtrate was diluted with EtOAc (500 mL) and washed with water (3×150 mL), brine (200 mL), dried over anhydrous $Na_2SO_4$ and the solvent was evaporated under reduced pressure. Crude product was purified by column chromatography (230-400 mesh silica gel; 20%

EtOAc/hexane; $R_f$-value-0.4) to afford 8-ethyl-5-fluoro-3,3-dimethyl-3,4-dihydroquinoxalin-2(1H)-one (2.83 g, 57%) light brown solid.

Step 6: To a solution of 8-ethyl-5-fluoro-3,3-dimethyl-3,4-dihydroquinoxalin-2(1H)-one (3.4 g, 15.3 mmol, 1 eq.) in toluene (110 mL) was added Lawesson's reagent (8.03 g, 19.89 mmol, 1.3 eq.) at RT and the reaction mixture was refluxed at 120° C. for 40 min. After completion of reaction (monitored by TLC), the reaction mixture was quenched with sat. NaH $CO_3$ solution (80 mL) followed by extraction with etOAc (2×70 mL). Combined organic layers were washed with water (80 mL), brine (80 mL), dried over anhydrous $Na_2SO_4$ and the solvent was evaporated to get the crude product which was purified by column chromatography (230-400 mesh silica gel; 20% EtOAc/hexane; $R_f$-value-0.6) to afford 8-ethyl-5-fluoro-3,3-dimethyl-3,4-dihydroquinoxaline-2(1H)-thione (3.0 g, 82%) as yellow solid.

Step 7: To a stirring solution of 8-ethyl-5-fluoro-3,3-dimethyl-3,4-dihydroquinoxaline-2(1H)-thione (3.0 g, 12.58 mmol, 1 eq) in THF (50 mL) was drop wise added hydrazine hydrate (3.03 mL, 62.93 mmol, 5 eq) at 0° C. The reaction mixture was stirred for 16 h at RT. TEA (8.56 mL, 62.93 mmol, 5 eq) was added to the reaction mixture and stirred for another 10 min. Acetyl chloride (2.7 ml, 37.74 mmol, 3 eq) was added to the reaction mixture very slowly at 0° C. and then stirred for 2 h at RT. The reaction mixture was diluted with water (100 mL) and extracted with DCM (3×100 mL). The combined organic layer was washed with brine (100 mL). The organic layer was dried over $Na_2SO_4$, concentrated under reduced pressure to get the crude material which purified by washing with diethyl ether to afford the N'-(8-ethyl-5-fluoro-3,3-dimethyl-3,4-dihydroquinoxalin-2(1H)-ylidene)acetohydrazide (3.4 g, 97%) as off white solid.

Step 8: N'-(8-ethyl-5-fluoro-3,3-dimethyl-3,4-dihydroquinoxalin-2(1H)-ylidene)acetohydrazide (3.4 g, 12.23 mmol, 1 eq) was taken in round bottom flax (100 mL) and cooled to −10° C. Phosphorus oxychloride (11.7 mL, 122.3 mmol, 10 eq) was then added drop wise to the compound followed by drop wise addition of TEA (1.66 mL, 12.23 mmol, 1 eq). The reaction mixture was stirred at −10° C. for 10 min and then for 10 min at RT and finally heated to reflux for 2 h. The reaction mixture was cooled to 0° C. and then drop wise added into crushed ice with constant stirring. To this aqueous part was slowly added cold ammonium solution up to pH~12. The aqueous part was extracted with DCM (3×100 mL). The combined organic layer was washed with brine (100 mL). The organic layer was dried over anhydrous $Na_2SO_4$, concentrated under reduced pressure to get the crude material. Crude product was purified by column chromatography (230-400 mesh silica gel; 5% MeOH/DCM; $R_f$-value-0.4) to afford 9-ethyl-6-fluoro-1,4,4-trimethyl-4,5-dihydro-[1,2,4]triazolo[4,3-a]quinoxaline (1.4 g, 44%) as light yellow solid.

Step 9: A stirred solution of 9-ethyl-6-fluoro-1,4,4-trimethyl-4,5-dihydro-[1,2,4]triazolo[4,3-a]quinoxaline (1.4 g, 5.38 mmol, 1 eq) in DMF (30 mL) at −10° C. was treated portion wise over 10 min with solid N-bromosuccinimide (1.01 g, 5.65 mmol, 1.05 eq). Reaction mixture was allowed to warm to RT and stirred for 1.5 h. After completion of reaction (monitored by LCMS), reaction mixture was diluted with EtOAc (300 mL) and organic layers was washed with water (5×50 mL), brine (50 mL), dried over anhydrous $Na_2SO_4$ and evaporated under reduced pressure. Crude product was purified by silica gel (230-400) column chromatography (5% MeOH/DCM; $R_f$-value-0.4) to afford 8-bromo-9-ethyl-6-fluoro-1,4,4-trimethyl-4,5-dihydro-[1,2,4]triazolo[4,3-a]quinoxaline (1.45 g, 80%) as off white solid.

1H-NMR (400 MHz; DMSO-$D_6$, 20° C.): δ 7.54-7.56 (1H), 6.69 (s, 1H), 2.82-2.85 (2H), 2.38 (s, 3H), 1.46 (bs, 3H), 0.94-0.97 (3H)

Synthesis of 8-bromo-6-fluoro-9-methoxy-1,4,4-trimethyl-4,5-dihydro-[1,2,4]triazolo[4,3-a]quinoxaline (Intermediate B-10)

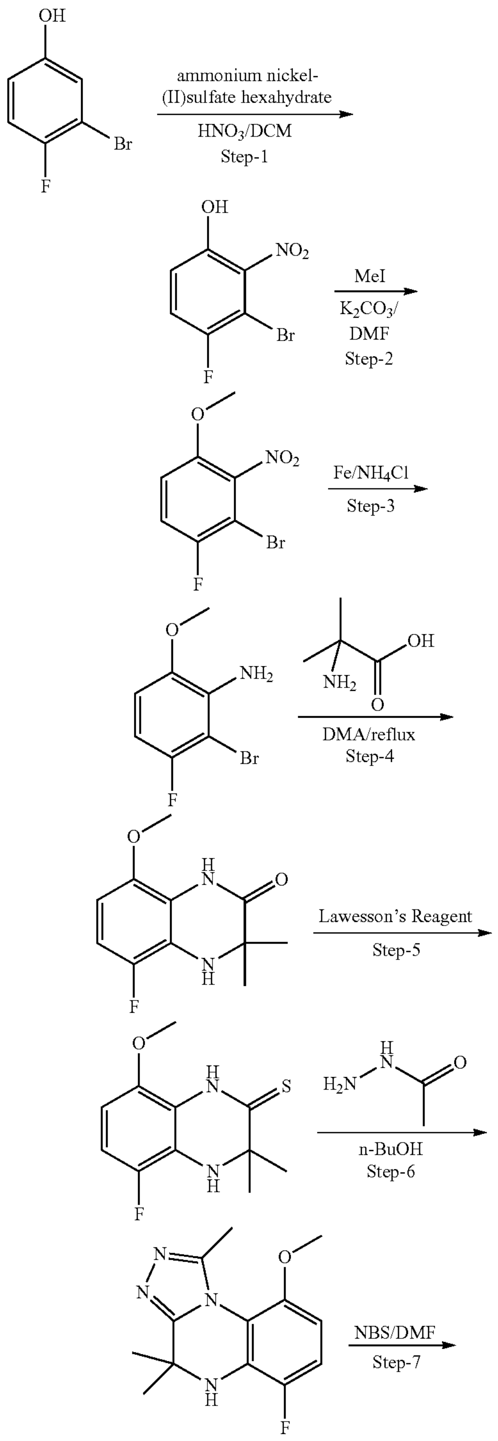

-continued

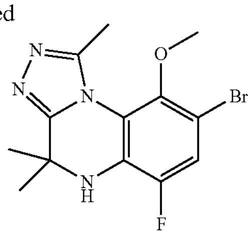

intermediate B-10

Step 1: To an ice cold solution of 3-bromo-4-fluorophenol (100 g, 523.56 mmol, 1 eq) and ammonium nickel(II) sulfate hexahydrate (103.4 g, 261.77 mmol, 0.5 eq) in DCM (1000 mL) fuming nitric acid was added drop wise and the reaction mixture was stirred at same temperature for 3 h (TLC). Reaction mixture was poured into crushed ice and diluted with DCM. The extracted organic layer was washed with brine; the organic layer was dried over $Na_2SO_4$ and concentrated. The crude product was purified by column chromatography (230-400 mesh silica gel, TLC system: EtOAc/hexane (2:8); $R_f$=0.2) to give 3-bromo-4-fluoro-2-nitrophenol (35 g, 28%).

Step 2: To a stirred solution of 3-bromo-4-fluoro-2-nitrophenol (35 g, 148.30 mmol, 1 eq) in ACN (40 mL) potassium carbonate (61.48 g, 444.91 mmol, 3 eq) and iodo methane (63.15 g, 444.91 mmol, 3 eq) were added and the reaction mixture was heated at 80° C. for 4 h. After completion (monitored by TLC) the reaction mixture was diluted with EtOAc and washed with water. The extracted organic layer was washed with brine, dried over anhydrous $Na_2SO_4$ and concentrated under reduced pressure. The crude product was purified by column chromatography (230-400 mesh silica gel, TLC system: EtOAc/hexane (2:8); $R_f$=0.6) to give 2-bromo-1-fluoro-4-methoxy-3-nitrobenzene (35 g, 94%).

Step 3: To a stirred solution of 2-bromo-1-fluoro-4-methoxy-3-nitrobenzene (35 g, 140 mmol, 1 eq) in EtOH and water (300 mL, 1:1), iron powder (78.17 g, 1400 mmol, 10 eq) and ammonium chloride (74.886 g, 1400 mmol, 10 eq) were added. The reaction mixture was heated to reflux for 12 h. After completion (monitored by TLC) the reaction mixture was filtered through a pad of celite. The filtrate was concentrated under reduced pressure to get crude product. The crude product was purified by column chromatography (230-400 mesh silica gel, TLC system: EtOAc/hexane (2:8); $R_f$=0.6) to give 2-bromo-3-fluoro-6-methoxyaniline (30 g, 97%).

Step 4: A suspension of 2-bromo-3-fluoro-6-methoxyaniline (30 g, 136.36 mmol, 1 eq), 2-aminoisobutaric acid (44.65 g, 340.83 mmol, 2.5 eq), DBU (49.70 g, 272.21 mmol, 2 eq) and copper iodide (2.59 g, 13.59 mmol, 0.1 eq.) in dry DMA (300 mL) in a round bottom flask was deoxygenated with Ar for 20 min. Reaction mixture was then stirred at 120° C. for 16 h. After completion of the reaction, (monitored by TLC), it was filtered through a pad of celite and washed with EtOAc (500 mL), washed with water (3×500 mL), brine (500 mL), dried over anhydrous $Na_2SO_4$ and evaporated under reduced pressure to get the crude product which was purified by column chromatography (230-400 mesh silica gel; TLC system: EtOAc/hexane (2:8); $R_f$=0.3) to give 5-fluoro-8-methoxy-3,3-dimethyl-3,4-dihydroquinoxalin-2(1H)-one (14 g, 46%) as brown solid.

Step 5: To a solution of 5-fluoro-8-methoxy-3,3-dimethyl-3,4-dihydroquinoxalin-2(1H)-one (14 g, 62.22 mmol, 1 eq) in toluene (150 mL) was added Lawesson's reagent (37.75 g, 93.33 mmol, 1.5 eq) at RT and the reaction mixture was refluxed at 120° C. for 1 h. After completion of reaction (monitored by TLC), the reaction mixture was quenched with sat. $NaHCO_3$ solution (200 mL) followed by extraction with EtOAc (2×200 mL). Combined organic layers were washed with water (300 mL), brine (100 mL), dried over anhydrous $Na_2SO_4$ and the solvent was evaporated to get the crude product which was purified by column chromatography using 230-400 mesh silica gel and 10% EtOAc in hexane as an eluting solvent to afford 5-fluoro-8-methoxy-3,3-dimethyl-3,4-dihydroquinoxaline-2(1H)-thione (10 g, 67%) as a yellow solid. TLC system: EtOAc/hexane (2:8); $R_f$=0.4).

Step 6: To a solution of 5-fluoro-8-methoxy-3,3-dimethyl-3,4-dihydroquinoxaline-2(1H)-thione (10 g, 41.61 mmol, 1 eq) in n-BuOH (100 mL) was added acetic hydrazide (10.80 g, 145.93 mmol, 3.5 eq) followed by addition of acetic acid (10 mL) and then the reaction mixture was stirred at 140° C. for 16 h. After completion of reaction (monitored by TLC) reaction mixture was diluted with water (100 mL) and extracted with EtOAc (2×50 mL). Combined organic layers were washed with water (100 mL), brine (100 mL), dried over anhydrous $Na_2SO_4$ and evaporated to get the crude product which was purified by column chromatography using 5% MeOH in DCM as an eluting solvent and 230-400 silica gel to afford 6-fluoro-9-methoxy-1,4,4-trimethyl-4,5-dihydro-[1,2,4]triazolo[4,3-a]quinoxaline (3.5 g, 32%) as off white solid (TLC system, 5% MeOH in DCM, $R_f$-0.2).

Step 7: A stirred solution of 6-fluoro-9-methoxy-1,4,4-trimethyl-4,5-dihydro-[1,2,4]triazolo[4,3-a]quinoxaline (3.5 g, 13.34 mmol, 1 eq) in DMF (30 mL) at 0° C. was treated portion wise over 10 min with solid N-bromosuccinamide (2.48 g, 13.93 mmol, 1.05 eq). Reaction mixture was allowed to warm to RT and stirred for 30 min. After completion of reaction (monitored by LCMS), reaction mixture was diluted with EtOAc (50 mL) and organic layers were washed with water (3×100 mL), brine (100 mL), dried over anhydrous $Na_2SO_4$ and the solvent was evaporated under reduced pressure. Crude product was purified by column chromatography using 1.5% MeOH in DCM as an eluting solvent and 230-400 silica gel to afford 8-bromo-6-fluoro-9-methoxy-1,4,4-trimethyl-4,5-dihydro-[1,2,4]triazolo[4,3-a]quinoxaline (1.9 g, 42%) as off white solid (TLC system, 5% MeOH in DCM, $R_f$-0.4).

1H-NMR (400 MHz; DMSO-$D_6$, 20° C.): δ 7.58 (d, 1H), 6.73 (s, 1H), 3.56 (s, 3H), 2.44 (s, 3H), 1.49 (s, 3H), 1.46 (s, 3H).

Synthesis of 8-bromo-1-cyclopropyl-6-fluoro-4,4,9-trimethyl-4,5-dihydro-[1,2,4]triazolo[4,3-a]quinoxaline (Intermediate B-12)

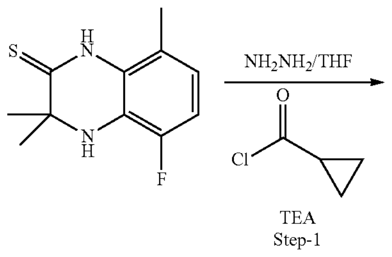

-continued

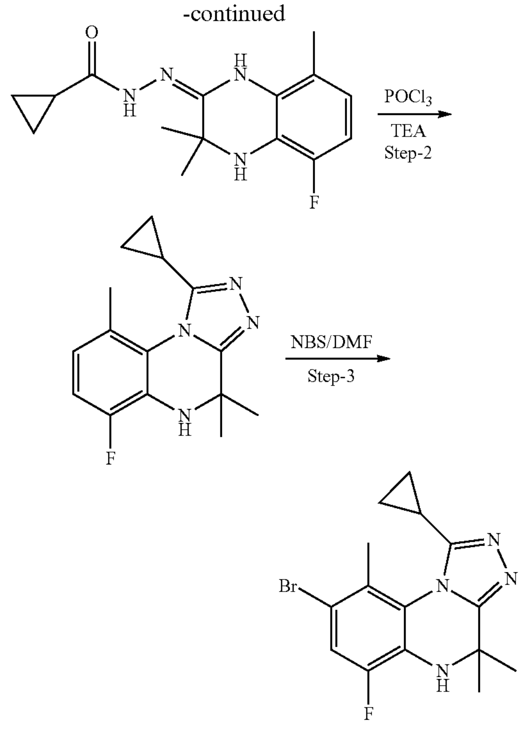

intermediate B-12

Step 1: To a stirring solution of 5-fluoro-3,3,8-trimethyl-3,4-dihydroquinoxaline-2(1H)-thione (1.7 g, 7.58 mmol, 1 eq) in THF (40 mL) was drop wise added hydrazine hydrate (1.72 mL, 37.94 mmol, 5 eq) at 0° C. The reaction mixture was stirred for 16 h at RT. TEA (5.13 mL, 37.94 mmol, 5 eq) was added to the reaction mixture and stirred for another 10 min. Cyclopropanecarbonyl chloride (2.39 g, 22.76 mmol, 3 eq) was added to the reaction mixture very slowly at 0° C. and then stirred for 2 h at RT. The reaction mixture was diluted with water (100 mL) and extracted with DCM (3×100 mL). The combined organic layers were with brine (100 mL). The organic layer was dried over $Na_2SO_4$, concentrated under reduced pressure to get the crude product which was purified by washing with diethyl ether to afford N'-(5-fluoro-3,3,8-trimethyl-3,4-dihydroquinoxalin-2(1H)-ylidene)cyclopropanecarbohydrazide (2.1 g, 95%) as off white solid.

Step 2: N'-(5-fluoro-3,3,8-trimethyl-3,4-dihydroquinoxalin-2(1H)-ylidene)cyclopropanecarbohydrazide (1.44 g, 4.96 mmol, 1 eq) was taken in a round bottom flax (50 mL) and then cooled to −10° C. Phosphorus oxychloride (4.7 mL, 49.65 mmol, 10 eq) was then added drop wise to the compound followed by drop wise addition of TEA (10.67 mL, 4.96 mmol, 1 eq). After that the reaction mixture was stirred at −10° C. for 10 min and then 10 min at RT and finally at reflux condition for 2 h. The reaction mixture was cooled to 0° C. and then it was drop wise added into crushed ice with constant stirring. To this aqueous part was slowly added cold ammonium solution up to pH~12. The aqueous part was extracted with DCM (3×50 mL). The combined organic layer were washed with brine (50 mL). The organic layer was dried over anhydrous $Na_2SO_4$, concentrated under reduced pressure to get the crude product. Crude product was purified by column chromatography (230-400 mesh silica gel; 5% MeOH/DCM; Rr-value-0.4) to afford 1-cyclopropyl-6-fluoro-4,4,9-trimethyl-4,5-dihydro-[1,2,4]triazolo[4,3-a]quinoxaline (0.24 g, 18%) as light yellow solid.

Step 3: A stirred solution of 1-cyclopropyl-6-fluoro-4,4,9-trimethyl-4,5-dihydro-[1,2,4]triazolo[4,3-a]quinoxaline (0.55 g, 2.02 mmol, 1 eq) in DMF (15 mL) at −10° C. was treated portion wise over 10 min with solid N-bromosuccinimide (0.36 g, 2.02 mmol, 1 eq). Reaction mixture was allowed to warm to RT and stirred for 1.5 h. After completion of reaction (monitored by LCMS), reaction mixture was diluted with EtOAc (80 mL) and organic layers were washed with water (5×20 mL), brine (20 mL), dried over anhydrous $Na_2SO_4$ and solvent was evaporated under reduced pressure. Crude product was purified by silica gel (230-400) column chromatography (5% MeOH/DCM; $R_f$-value-0.4) to afford 8-bromo-1-cyclopropyl-6-fluoro-4,4,9-trimethyl-4,5-dihydro-[1,2,4]triazolo[4,3-a]quinoxaline (0.55 g, 78%) as off white solid.

1H-NMR (400 MHz; DMSO-$D_6$, 20° C.): δ 7.58 (d, 1H), 6.58 (s, 1H), 2.45 (s, 3H), 1.71-1.77 (1H), 1.44 (bs, 6H), 1.02-1.27 (4H).

Synthesis of 8-bromo-9-(difluoromethyl)-7-fluoro-1,4,4-trimethyl-4,5-dihydro-[1,2,4]triazolo[4,3-a]quinoxaline (Intermediate B-28)

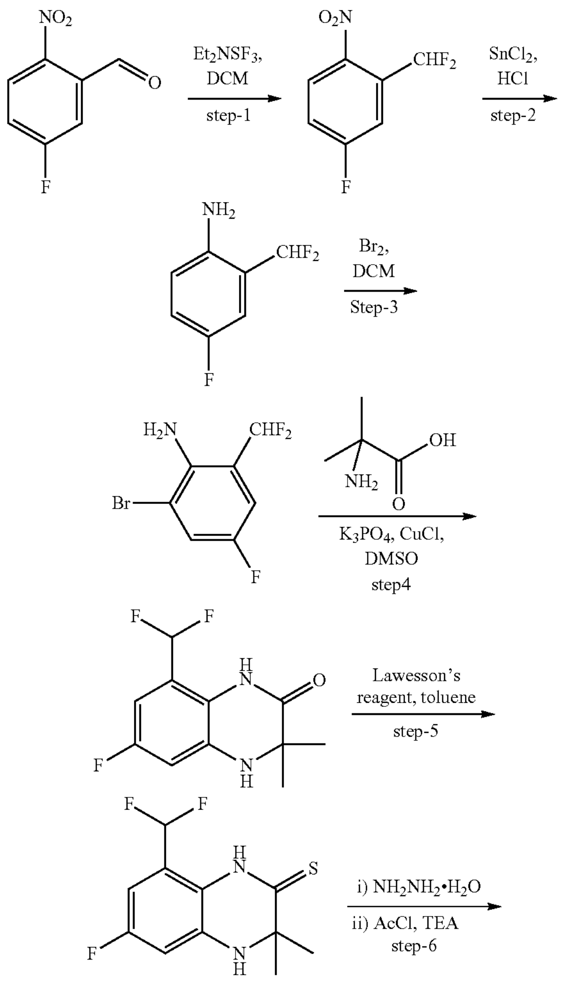

-continued

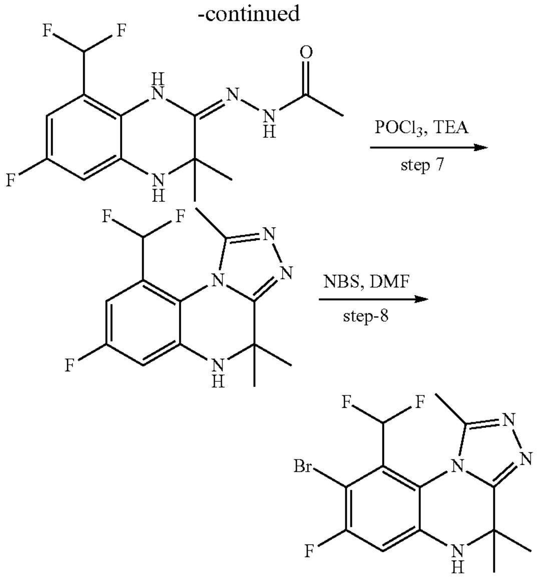

intermediate B-28

Step 1: To a stirred solution of 5-fluoro-2-nitro-benzaldehyde (20.0 g, 118.27 mmol) in DCM (600 mL) was added DAST (23.3 ml, 177.51 mmol) at 0° C. The reaction mixture was stirred at ambient temperature for 4 h. After completion of the reaction, the reaction mixture was quenched with sat. $NaHCO_3$ solution and was extracted with DCM (2×500 mL). The combined organic layers were washed with water (500 mL) followed by brine (500 mL), were then dried over anhydrous $Na_2SO_4$ and concentrated. The crude material was purified by column chromatography using 2-3% EtOAc/hexane to afford 2-difluoromethyl-4-fluoro-1-nitro-benzene (22.0 g, 88%) as a yellow liquid.

Step 2: To a stirred solution of 2-difluoromethyl-4-fluoro-1-nitro-benzene (22.0 g, 115.16 mmol) in ethanol (372 mL) was added $SnCl_2 \cdot 2H_2O$ (103.7 g, 460.46 mmol) followed by con. HCl (76 mL) at 0° C. The reaction mixture was stirred at ambient temperature for 2 h. After completion of the reaction the reaction mixture was concentrated, the residue was basified with 5N NaOH solution and was extracted with MTBE (2×500 mL). The combined organic layers were washed with water (500 mL) followed by brine (500 mL), were dried over anhydrous $Na_2SO_4$ and concentrated. The crude material was purified by column chromatography using 2-3% EtOAc/hexane to afford 2-difluoromethyl-4-fluoro-phenylamine (12.5 g, 41%) as a yellow gummy liquid.

Step 3: To a solution of 2-difluoromethyl-4-fluoro-phenylamine (8.0 g, 49.64 mmol) in DCM (150 mL) was added a solution of bromine (3.84 mL, 74.47 mmol) in DCM (100 ml) dropwise at 0° C. The resulting reaction mixture was stirred at ambient temperature for 16 h. After completion of the reaction (monitored by TLC in 10% EA-Hexane, Rf=0.7), the reaction mixture was quenched with saturated $NaHCO_3$ solution. The two layers were separated, the aqueous layer was then extracted with DCM (2×200 mL). The combined organic layers were washed with water (2×500 ml) and brine (250 ml) and were then dried over anhydrous $Na_2SO_4$ and concentrated under reduced pressure. Three batches of this reaction were performed in parallel, which were afterwards combined to give the crude compound. This combined crude material was purified by column chromatography (100-200 mesh silica gel and 5% EtOAc/hexane as eluent) to afford to afford 2-bromo-6-difluoromethyl-4-fluoro-phenylamine (18.0 g, 51%) as a white solid.

Step 4: To the stirred suspension of 2-bromo-6-difluoromethyl-4-fluoro-phenylamine (18.0 g, 73.77 mmol) in dry DMSO (270 mL) was added 2-amino-2-methyl-propionic acid (15.2 g, 147.54 mmol) followed by $K_3PO_4$ (31.31 g, 147.54 mmol) at ambient temperature. The resulting reaction mixture was degassed with nitrogen for 30 minutes, then cuprous chloride (730 mg, 7.37 mmol) was added and reaction mixture was heated at 125° C. for 16 h. After completion of the reaction (monitored by TLC, 20% EA-Hexane, Rf 0.4), the reaction mixture was cooled to ambient temperature and was filtered through celite. The celite bed was washed with EtOAc (2×200 mL). The resulting filtrate was poured into ice cold water (500 mL). The resulting aqueous layer was extracted with EtOAc (2×250 mL). The combined organic layers were washed with water (3×200 mL) and brine (400 ml), were dried over anhydrous $Na_2SO_4$ and the solvent was evaporated under reduced pressure to afford the crude mixture. The crude mixture was purified by column chromatography (100-200 mesh silica gel and 15% EtOAc/hexane as eluent) to afford 8-difluoromethyl-6-fluoro-3,3-dimethyl-3,4-dihydro-1H-quinoxalin-2-one (9.0 g, 50%) as a brown solid.

Step 5: To a stirred solution of 8-difluoromethyl-6-fluoro-3,3-dimethyl-3,4-dihydro-1H-quinoxalin-2-one (9.0 g, 36.88 mmol) in toluene (300 ml) was added Lawesson's reagent (22.39 g, 55.32 mmol) at ambient 53uinoxaline and the reaction mixture was then heated to 120° C. for 3 h. After completion of the reaction (monitored by TLC in 20% EA-Hexane, Rf 0.6) the reaction mixture was cooled to ambient temperature and was then concentrated under reduced pressure. The obtained residue was quenched with sat. $NaHCO_3$ solution (500 ml) and the resulting aqueous layer was extracted with EtOAc (3×250 ml). The combined organic layers were washed with water (500 ml) and brine (250 ml), were dried over anhydrous $Na_2SO_4$ and then evaporated to dryness under reduced pressure. The crude material was purified by column chromatography (100-200 mesh silica gel and 20% EtOAc/hexane as eluent) to afford 8-difluoromethyl-6-fluoro-3,3-dimethyl-3,4-dihydro-1H-quinoxaline-2-thione (9.0 g, 94%) as a yellow solid.

Step 6: To a stirred solution of 8-difluoromethyl-6-fluoro-3,3-dimethyl-3,4-dihydro-1H-quinoxaline-2-thione (9.0 g, 34.57 mmol) in THF (60 ml) was added dropwise hydrazine hydrate (5.19 g, 103.73 mmol) at 0° C. The reaction mixture was stirred at ambient temperature for 16 h. TEA (24.2 ml, 172.89 mmol) followed acetyl chloride (7.4 ml, 103.73 mmol) were added to the reaction mixture dropwise at 0° C. and the resulting reaction mixture was then stirred for 2 h at ambient temperature. After completion of the reaction (monitored by LCMS) the reaction mixture was diluted with water and extracted with 10% MeOH-DCM (5×100 ml). The combined organic layers were washed by brine, dried over $Na_2SO_4$ and concentrated under reduced pressure to afford acetic acid (8-difluoromethyl-6-fluoro-3,3-dimethyl-3,4-dihydro-1H-quinoxalin-2-ylidene)-hydrazide (9.0 g, 87%, crude) as pale yellow solid.

Step 7: Acetic acid (8-difluoromethyl-6-fluoro-3,3-dimethyl-3,4-dihydro-1H-quinoxalin-2-ylidene)-hydrazide (9.0 g, 30 mmol) in a round bottom flask was cooled to −10° C. Phosphorus oxalylchloride (13.98 ml, 150 mmol) was added dropwise, followed by the dropwise addition of triethyl amine (4.2 ml, 30 mmol). The reaction mixture was stirred at −10° C. for 10 minutes and then 10 minutes at RT and finally under reflux for 2 h. After completion of the reaction (monitored by LCMS) the reaction mixture was cooled to 0° C. and was quenched with crushed ice in water (200 ml). The aqueous part was then basified by adding cold aqueous ammonia solution (500 ml) dropwise. The resulting basic aqueous layer was then extracted with EtOAc (3x250 ml). The combined organic layers were washed with brine, dried over anhydrous $Na_2SO_4$ and were concentrated under reduced pressure to afford the crude compound. The obtained crude was co-distilled with MTBE twice, then triturated with hexane and dried to afford 9-difluoromethyl-7-fluoro-1,4,4-trimethyl-4,5-dihydro-[1,2,4]triazolo[4,3-a]quinoxaline (4.5 g, 53%) as a pale yellow solid.

Step 8: To a solution of 9-difluoromethyl-7-fluoro-1,4,4-trimethyl-4,5-dihydro-[1,2,4]triazolo[4,3-a]quinoxaline (11.0 g, 39.0 mmol) in DMF (180 mL) was added NBS (7.2 g, 40.2 mmol) portion wise at 0° C. The resulting reaction mixture was stirred at 0° C. for 1 h. After completion of the reaction (monitored by LCMS) the reaction mixture was diluted with water (400 mL) and was extracted with EtOAc (2x400 mL). The combined organic layers were washed with water (2x200 mL) and brine, dried over anhydrous $Na_2SO_4$ and concentrated under reduced pressure. The crude was purified via column chromatography (100-200 mesh silica gel and 5% MeOH/DCM as eluent) to afford 8-bromo-9-difluoromethyl-7-fluoro-1,4,4-trimethyl-4,5-dihydro-[1,2,4]triazolo[4,3-a]quinoxaline (7.2 g, 65%) as an off white solid.

$^1$H-NMR (400 MHz, DMSO-$d_6$): δ=6.91-6.64 (m, 2H), 4.58 (s, 1H), 2.56 (s, 3H), 1.58 (brs, 3H), 1.24 (brs, 3H).

Synthesis of 8-bromo-6,7-difluoro-1,4,4,9-tetramethyl-4,5-dihydro-[1,2,4]triazolo[4,3-a]quinoxaline (Intermediate B-38)

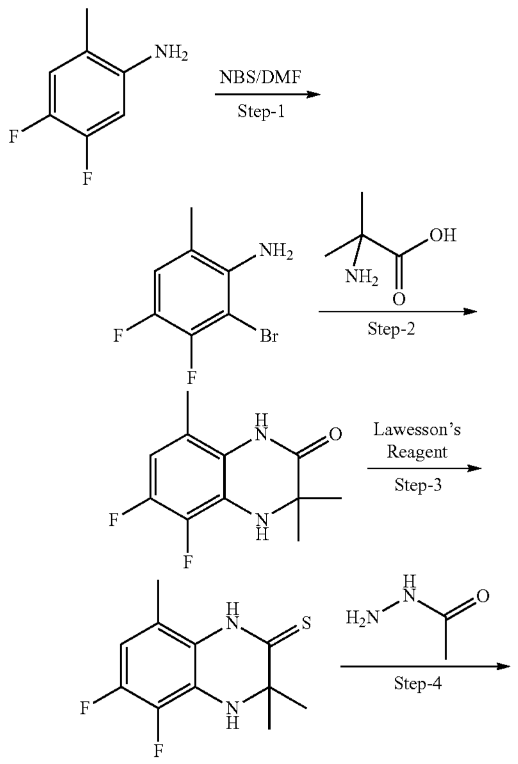

-continued

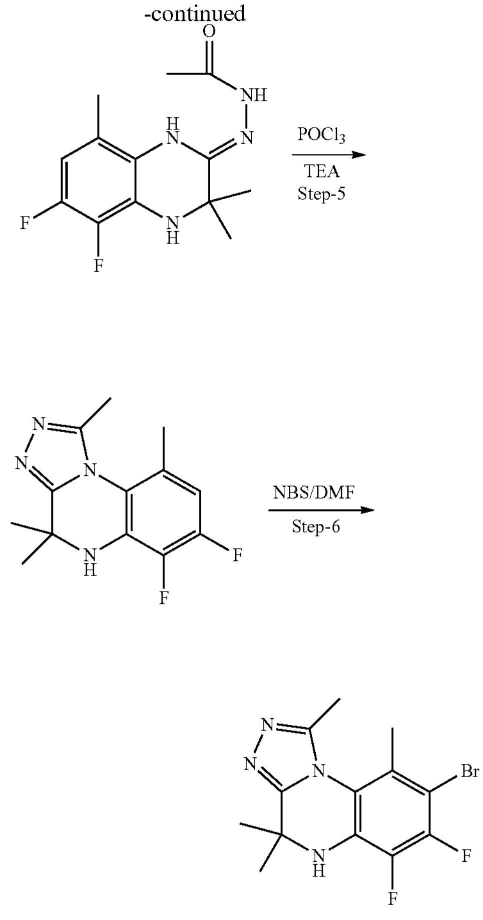

intermediate B-38

Step 1: To a suspension of 4,5-difluoro-2-methylaniline (0.5 g, 3.49 mmol, 1 eq) in DCM (30 ml), $Br_2$ (0.55 g, 0.17 ml, 3.49 mmol, 1 eq) in DCM (20 ml) was added at 0° C. Then the reaction was stirred at RT for 2 h. After completion of starting material, the reaction mass was quenched with saturated $NaHCO_3$ solution (50 ml). The organic layer was separated and aqueous layer was extracted with DCM (50 ml). Combined organic layers was washed with water (150 ml), followed by brine (150 ml), dried over anhydrous $Na_2SO_4$ and the solvent was evaporated to afford crude product which was purified by column chromatography (230-400 mesh silica gel; 10% EtOAc/hexane; $R_f$-value-0.6) to afford 2-bromo-3,4-difluoro-6-methylaniline (0.4 g, 52%).

Step 2: A suspension of 2-bromo-3,4-difluoro-6-methylaniline (0.25 g, 1.13 mmol, 1 eq), 2-aminobutyric acid (0.23 g, 2.26 mmol, 2 eq) in DMA (10 ml) in a sealed tube was deoxygenated with Ar for 20 min. DBU (0.35 ml, 2.26 mmol, 2 eq) and CuI (0.02 g, 0.113 mmol, 0.1 eq) were added and reaction mixture was stirred at 140° C. for 16 h. After completion of the reaction, it was filtered through celite bed and washed by EtOAc (100 ml). The filtrate was diluted with EtOAc (100 ml) and washed with water (3x150 ml), brine (200 ml), dried over anhydrous $Na_2SO_4$ and the solvent was evaporated under reduced pressure to get the crude product which was purified by column chromatography (100-200 mesh silica gel; 30% EtOAc/hexane; $R_f$-value-0.4) to afford 5,6-difluoro-3,3,8-trimethyl-3,4-dihydroquinoxalin-2(1H)-one (0.2 g, 75%).

Step 3: To a solution of 5,6-difluoro-3,3,8-trimethyl-3,4-dihydroquinoxalin-2(1H)-one (3.66 g, 17.6 mmol, 1 eq) in toluene (75 ml) was added Lawesson's reagent (10.67 g, 26.2 mmol, 1.5 eq) at RT and the reaction mixture was heated at 120° C. for 40 min. After completion of reaction (monitored by TLC), the reaction mixture was quenched with sat. $NaHCO_3$ solution (100 ml) followed by extraction with EtOAc (2×100 ml). Combined organic layers were washed with water (100 ml), brine (100 ml), dried over anhydrous $Na_2SO_4$ and the solvent was evaporated to get the crude product which was purified by column chromatography (230-400 mesh silica gel; 20% EtOAc/hexane; $R_f$-value-0.4) to afford 5,6-difluoro-3,3,8-trimethyl-3,4-dihydroquinoxaline-2(1H)-thione (2.8 g, 71%) as yellow solid.

Step 4: To a stirring solution of 5,6-difluoro-3,3,8-trimethyl-3,4-dihydroquinoxaline-2(1H)-thione (5.50 g, 24.55 mmol, 1 eq) in THF (30 ml) was drop wise added hydrazine hydrate (5.17 ml, 122.76 mmol, 5 eq) at 0° C. The reaction mixture then stirred for 16 h at RT. TEA (16.7 ml, 122.76 mmol, 5 eq) was added to the reaction mixture and stirred for another 10 min. Acetyl chloride (5.78 g, 73.65 mmol, 3 eq) was added very slowly at 0° C. and then the mixture was stirred for 2 h at RT. The reaction mixture was diluted with water (50 ml) and extracted by DCM (5×100 ml). The combined organic layers were washed by brine (100 ml). The organic layer was dried over $Na_2SO_4$, concentrated under reduced pressure to get the crude material which purified by washing with diethyl ether to afford N'-(5,6-difluoro-3,3,8-trimethyl-3,4-dihydroquinoxalin-2(1H)-ylidene)acetohydrazide (5.5 g, 85%) as a white solid.

Step 5: N'-(5,6-difluoro-3,3,8-trimethyl-3,4-dihydroquinoxalin-2(1H)-ylidene)acetohydrazide (5.5 g, 20.8 mmol, 1 eq) was taken in round bottom flax (50 ml) and then cooled to −10° C. Phosphorus oxychloride (18.4 ml, 197.6 mmol, 9.5 eq) was then added drop wise to the compound followed by drop wise addition of TEA (2.9 ml, 20.8 mmol, 1 eq). After that the reaction mixture was stirred at −10° C. for 10 min and then 10 min at RT and finally at reflux condition for 4 h. The reaction mixture was cooled to 0° C. and then drop wise added into crushed ice with constant stirring. To this aqueous part was slowly added cold ammonium solution (100 ml). The aqueous part was extracted by DCM (2×100 ml). The combined organic layer was washed by brine (100 ml). The organic layer was dried over anhydrous $Na_2SO_4$, concentrated under reduced pressure to get the crude product which was purified by column chromatography (230-400 mesh silica gel; 5% MeOH/DCM; $R_f$-value-0.4) to afford 6,7-difluoro-1,4,4,9-tetramethyl-4,5-dihydro-[1,2,4]triazolo[4,3-a]quinoxaline (3.0 g, 59%) as yellow solid.

Step 6: A stirred solution of 6,7-difluoro-1,4,4,9-tetramethyl-4,5-dihydro-[1,2,4]triazolo[4,3-a]quinoxaline (4.0 g, 16.2 mmol, 1 eq) in DMF (40 ml) at −10° C. was treated portion wise over 10 min with solid N-bromosuccinimide (3.1 g, 17.1 mmol, 1.05 eq). Reaction mixture was allowed to warm to RT and stirred for 1.5 h. After completion of reaction (monitored by LCMS), reaction mixture was diluted with EtOAc (300 ml) and organic layers were washed with water (5×50 ml), brine (50 ml), dried over anhydrous $Na_2SO_4$ and the solvent was evaporated under reduced pressure to get the crude product which was purified by silica gel (230-400) column chromatography (5% MeOH/DCM; $R_f$-value-0.3) to afford 8-bromo-6,7-difluoro-1,4,4,9-tetramethyl-4,5-dihydro-[1,2,4]triazolo[4,3-a]quinoxaline (3.3 g, 63%) as off white solid.

Synthesis of 8-bromo-1,4,4,9-tetramethyl-4,5-dihydro-[1,2,4]triazolo[4,3-a]quinoxaline (Intermediate B-40)

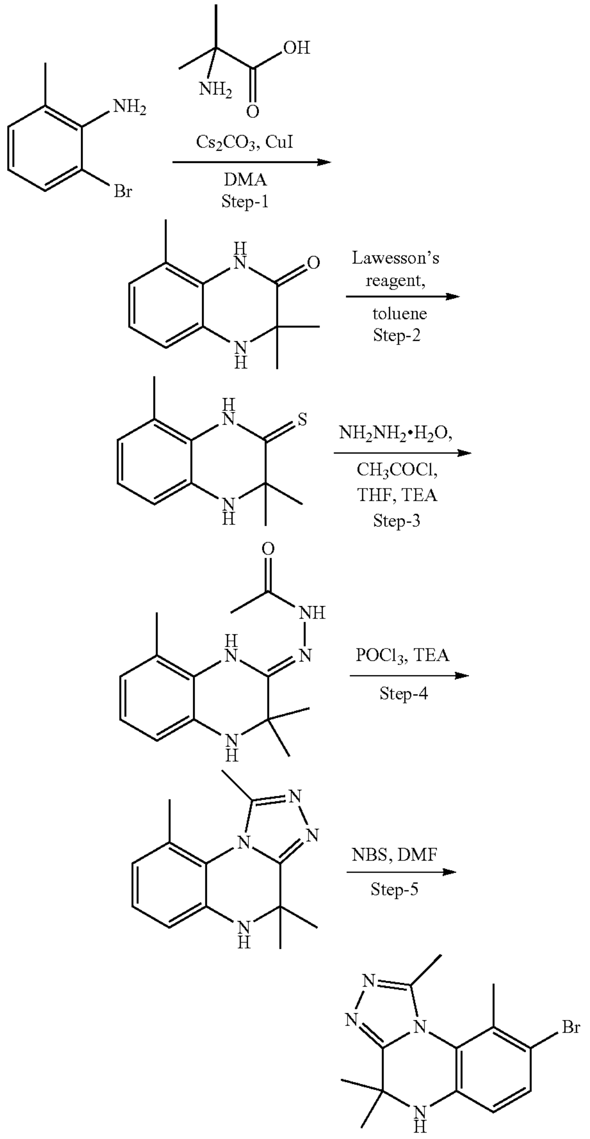

intermediate B-40

Step 1: A suspension of 2-bromo-6-methylaniline (1.0 g, 54.0 mmol, 1.0 eq) and 2-aminobutyric acid (1.1 g, 10.8 mmol, 2.0 eq) in DMSO (10 ml) in a sealed tube was deoxygenated with Ar for 20 minutes. $K_3PO_4$ (2.3 g, 10.8 mmol, 2.0 eq) and CuCl (53.0 mg, 5.4 mmol, 0.1 eq) were then added. The reaction mixture was then stirred at 140° C. for 16 h. After completion of the reaction, the reaction mixture was filtered through a celite bed and the celite bed was washed with EtOAc (100 ml). The filtrate was diluted with EtOAc (100 ml) and was washed with water (3×150 ml) and brine (200 ml), dried over anhydrous $Na_2SO_4$ and was then evaporated under reduced pressure to obtain the crude compound, which was purified by column chromatography (100-200 mesh silica gel; 30% EtOAc/hexane; $R_f$-value-0.4) to afford 3,3,8-trimethyl-3,4-dihydroquinoxalin-2(1H)-one (0.6 g, 60%).

Step 2: To a solution of 3,3,8-trimethyl-3,4-dihydroquinoxalin-2(1H)-one (7.0 g, 36.0 mmol, 1.0 eq) in toluene (75 ml) was added Lawesson's reagent (22.0 g, 55 mmol, 1.5 eq.) at ambient temperature and the reaction mixture was then refluxed at 120° C. for 40 minutes. After completion of the reaction (monitored by TLC), the reaction mixture was quenched with sat. $NaHCO_3$ solution (100 ml) followed by extraction with EtOAc (2×100 ml). The combined organic layers were washed with water (100 ml) and brine (100 ml), were dried over anhydrous $Na_2SO_4$ and evaporated under reduced pressure to obtain the crude compound which was purified by column chromatography (230-400 mesh silica gel; 20% EtOAc/hexane; $R_f$-value-0.4) to afford 3,3,8-trimethyl-3,4-dihydroquinoxaline-2(1H)-thione (5.0 g, 66%) as a yellow solid.

Step 3: To a stirring solution of compound 3,3,8-trimethyl-3,4-dihydroquinoxaline-2(1H)-thione (5.0 g, 62.4 mmol, 1 eq) in THF (30 ml) was added dropwise hydrazine hydrate (6.0 ml, 121.0 mmol, 5 eq) at 0° C. The reaction mixture was then stirred for 16 h at ambient temperature. TEA (16.5 ml, 122.7 mmol, 5 eq) was then added to the reaction mixture and the reaction mixture was stirred for another 10 minutes. Acetyl chloride (5.65 g, 73.65 mmol, 3 eq) was then added to the reaction mixture very slowly at 0° C. and the resulting reaction mixture was then stirred for 2 h at ambient temperature. The reaction mixture was then diluted with water (50 ml) and extracted with DCM (5×100 ml). The combined organic layers were washed with brine (100 ml), dried over $Na_2SO_4$ and concentrated under reduced pressure to obtain the crude material which was purified by washing with diethyl ether to afford N'-(3,3,8-trimethyl-3,4-dihydroquinoxalin-2(1H)-ylidene)acetohydrazide (2.0 g, 34%) as a white solid.

Step 4: N'-(3,3,8-trimethyl-3,4-dihydroquinoxalin-2(1H)-ylidene)acetohydrazide (6.0 g, 24 mmol, 1 eq) was taken up in a round bottom flask (50 ml) and was then cooled to −10° C. Phosphorus oxychloride (23.0 ml, 243 mmol, 10 eq) was then added dropwise to the compound followed by drop wise addition of TEA (3.5 ml, 24 mmol, 1 eq). After that the reaction mixture was stirred at −10° C. for 10 minutes and then 10 minutes at ambient temperature and finally at reflux for 4 h. The reaction mixture was then cooled to 0° C. and was then added dropwise into crushed ice in water under constant stirring. To this was then slowly added cold ammonia solution (100 ml). The aqueous part was then extract with DCM (2×100 mL). The combined organic layers were washed with brine (100 ml), dried over anhydrous $Na_2SO_4$ and concentrated under reduced pressure to obtain the crude compound, which was purified by column chromatography (230-400 mesh silica gel; 5% MeOH/DCM; $R_f$-value-0.4) to afford 1,4,4,9-tetramethyl-4,5-dihydro-[1,2,4]triazolo[4,3-a]quinoxaline (3.2 g, 58.6%) as a yellow solid.

Step 5: A stirred solution of 1,4,4,9-tetramethyl-4,5-dihydro-[1,2,4]triazolo[4,3-a]quinoxaline (3.2 g, 14 mmol, 1.00 eq) in DMF (40 ml) at −10° C. is treated with solid N-bromosuccinimide (2.7 g, 15 mmol, 1.05 eq) portionwise over 10 minutes. The reaction mixture was allowed to warm to ambient temperature and was then stirred for 1.5 h. After completion of the reaction (monitored by LCMS) the reaction mixture was diluted with EtOAc (300 ml) and was washed with water (5×50 ml) and brine (50 ml), dried over anhydrous $Na_2SO_4$ and evaporated under reduced pressure to obtain the crude compound, which was purified by silica gel (230-400) column chromatography (5% MeOH/DCM; $R_f$-value-0.3) to afford 8-bromo-1,4,4,9-tetramethyl-4,5-dihydro-[1,2,4]triazolo[4,3-a]quinoxaline (2.0 g, 48%) as an off white solid.

Synthesis of 8-bromo-9-(difluoromethyl)-6-fluoro-1,4,4-trimethyl-4,5-dihydro-[1,2,4]triazolo[4,3-a]quinoxaline (Intermediate B-43)

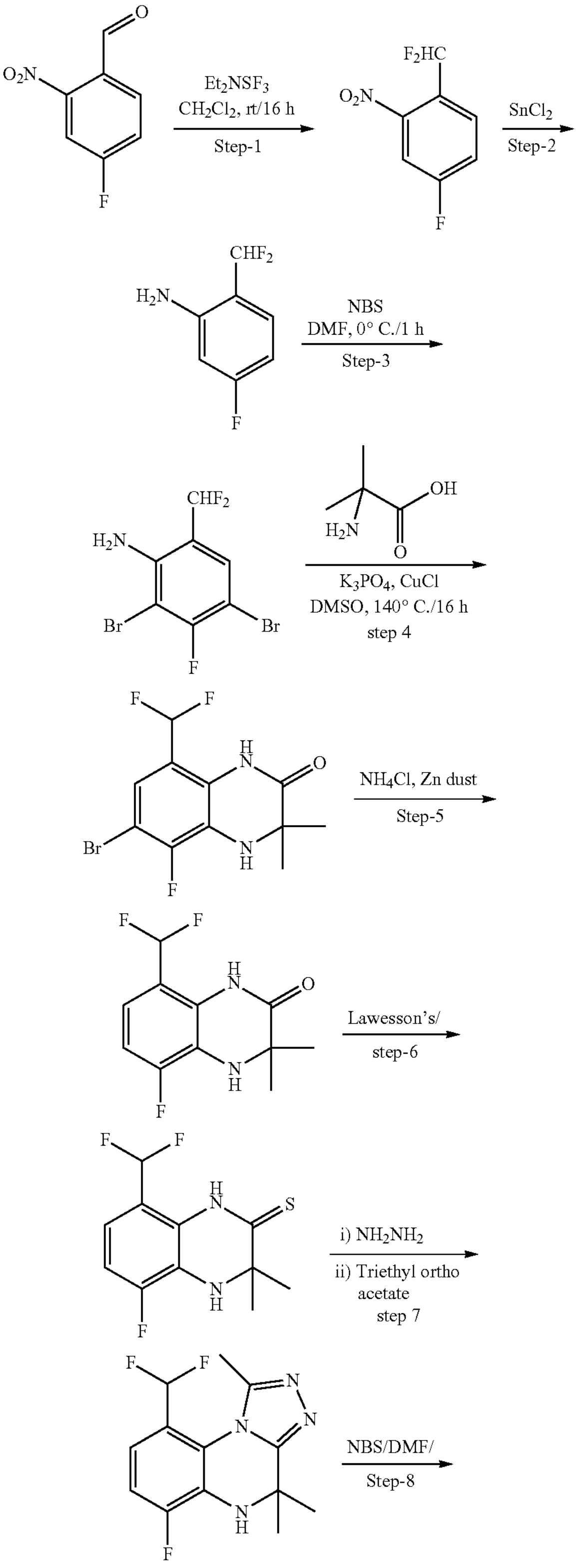

-continued

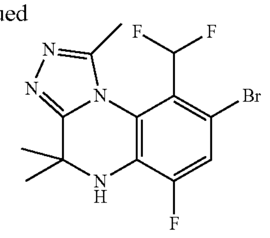

intermediate B-43

Step 1: To a stirred solution of 4-fluoro-2-nitrobenzaldehyde (20 g, 118.27 mmol, 1 eq) in DCM (600 mL) was added DAST (23.26 ml, 177.51 mmol, 1.5 eq) at 0° C. The reaction mixture was stirred at RT for 4 h. After completion of starting material reaction mixture was quenched with sat.$NaHCO_3$ solution and extracted with DCM (2×500 mL). Combined organic layers was washed with water (500 mL) followed by brine (500 mL), dried over anhydrous $Na_2SO_4$ and concentrated. Crude product was purified by column chromatography using 2-3% EtOAC/hexane to afford 1-(difluoromethyl)-4-fluoro-2-nitrobenzene (22 g, 88%) as yellow liquid.

Step 2: To a stirred solution of 1-(difluoromethyl)-4-fluoro-2-nitrobenzene (10 g, 52.16 mmol, 1 eq) in EtOH (372 mL) was added $SnCl_2·2H_2O$ (47 g, 209.46 mmol, 4 eq) followed by con. HCl (35 mL) at 0° C. The reaction mixture was stirred at RT for 2 h. After completion of starting material reaction mixture was concentrated, residue was basified with 5N NaOH solution and extracted with MTBE (2×500 mL). Combined organic layers were washed with water (500 mL) followed by brine (500 mL), dried over anhydrous $Na_2SO_4$ and concentrated. Crude product was purified by column chromatography using 2-3% EtOAc/hexane to afford 2-(difluoromethyl)-5-fluoroaniline (7.0 g, 83%) as yellow gummy liquid.

Step 3: To a solution of 2-(difluoromethyl)-5-fluoroaniline (4 g, 24 mmol, 1.0 eq) in DMF (40 mL) was added NBS (13 g, 74 mmol, 3.0 eq) portion wise at −10° C. Resulting reaction mixture was stirred at 0° C. for 1 h. After completion of starting material (monitored by LCMS), reaction mixture was diluted with water (100 mL) and extracted with EtOAc (2×100 mL). Combined organic layers were washed with water (2×100 mL) and brine, dried over anhydrous $Na_2SO_4$ and concentrated to get crude 2,4-dibromo-6-(difluoromethyl)-3-fluoroaniline (7 g, 85%) was used for the next step without further purification.

Step 4: A suspension of crude 2,4-dibromo-6-(difluoromethyl)-3-fluoroaniline (8 g, 25.2 mmol, 1 eq) in DMSO (80 ml), 2-aminobutyric acid (5.2 g, 50 mmol, 2 eq) was added at RT. The reaction mixture was then deoxygenated with Ar for 20 min. $K_3PO_4$ (10.6 g, 50 mmol, 2 eq) and CuCl (0.024 g, 2.5 mmol, 0.1 eq) were added and reaction mixture was then stirred at 140° C. for 16 h. After completion of the reaction, it was filtered through celite bed and washed by EtOAc (100 ml). The filtrate was diluted with EtOAc (100 ml) and washed with water (3×150 ml), brine (200 ml), dried over anhydrous $Na_2SO_4$ and the solvent was evaporated under reduced pressure to get crude product which was purified by column chromatography (100-200 mesh silica gel; 30% EtOAc/hexane; $R_f$-value-0.4) to afford 6-bromo-8-(difluoromethyl)-5-fluoro-3,3-dimethyl-3,4-dihydroquinoxalin-2(1H)-one (1.5 g, 20%).

Step 5: To a stirring solution of 6-bromo-8-(difluoromethyl)-5-fluoro-3,3-dimethyl-3,4-dihydroquinoxalin-2(1H)-one (3.0 g, 9.3 mmol, 1 eq) in a mixture of 1,4-dioxan and water (1:1) (100 ml), was added $NH_4Cl$ (7.47 g, 139.0 mmol, 15 eq) and zinc dust (9.08 g, 139.0 mmol, 15 eq). The reaction mixture was stirred for 16 h at reflux. The reaction mixture was cooled to RT and then filtered through sintered funnel. The filtrate was concentrated under reduced pressure to get the product, which was dissolved in EtOAc (100 ml) and washed by water (2×30 ml) followed by brine (30 ml). The organic layer was dried over $Na_2SO_4$, concentrated under reduced pressure to get 8-(difluoromethyl)-5-fluoro-3,3-dimethyl-3,4-dihydroquinoxalin-2(1H)-one (2.0 g, 90%) as off white solid.

Step 6: To a solution of 8-(difluoromethyl)-5-fluoro-3,3-dimethyl-3,4-dihydroquinoxalin-2(1H)-one (1 g, 4.09 mmol, 1 eq) in toluene (10 ml) was added Lawesson's reagent (2.48 g, 6.14 mmol, 1.5 eq) at RT and the reaction mixture was refluxed at 120° C. for 40 min. After completion of reaction (monitored by TLC), the reaction mixture was quenched with sat. $NaHCO_3$ solution (100 ml) followed by extraction with EtOAc (2×100 ml). Combined organic layers were washed with water (100 ml), brine (100 ml), dried over anhydrous $Na_2SO_4$ and the solvent was evaporated to get the crude product which was purified by column chromatography (230-400 mesh silica gel; 20% etOAc/hexane; $R_f$-value-0.4) to afford 8-(difluoromethyl)-5-fluoro-3,3-dimethyl-3,4-dihydroquinoxaline-2(1H)-thione (0.6 g, 65%) as yellow solid.

Step 7: To a stirring solution of 8-(difluoromethyl)-5-fluoro-3,3-dimethyl-3,4-dihydroquinoxaline-2(1H)-thione (2.5 g, 9.6 mmol, 1 eq) in THF (30 ml) was drop wise added hydrazine hydrate (2.4 ml, 48 mmol, 5 eq) at 0° C. The reaction mixture then stirred for 16 h at RT. Then the reaction mixture was concentrated under reduced pressure to get the crude material. Then triethyl ortho acetate (20 ml) was added to the reaction mixture. The reaction mixture was stirred at 140° C. for 16 h. After completion of reaction (monitored by TLC), reaction mixture was diluted with water (50 ml) and extracted by DCM (5×100 ml). The combined organic layer was washed by brine (100 ml). The organic layer was dried over $Na_2SO_4$, concentrated under reduced pressure to get the crude product which was purified by column chromatography (230-400 mesh silica gel; 5% MeOH/DCM; $R_f$-value-0.4) to afford 9-(difluoromethyl)-6-fluoro-1,4,4-trimethyl-4,5-dihydro-[1,2,4]triazolo[4,3-a]quinoxaline (2.0 g, 74%) as a off white solid.

Step 8: A stirred solution of 9-(difluoromethyl)-6-fluoro-1,4,4-trimethyl-4,5-dihydro-[1,2,4]triazolo[4,3-a]quinoxaline (2.0 g, 7.08 mmol, 1 eq) in DMF (30 ml) at −10° C. was treated portion wise over 10 min with solid N-bromosuccinimide (1.3 g, 7.79 mmol, 1.05 eq). Reaction mixture was allowed to warm to RT and stirred for 1.5 h. After completion of reaction (monitored by LCMS), reaction mixture was diluted with EtOAc (300 ml) and organic layers were washed with water (5×50 ml), brine (50 ml), dried over anhydrous $Na_2SO_4$ and the solvents were evaporated under reduced pressure to get the crude product which was purified by silica gel (230-400) column chromatography (5% MeOH/DCM; $R_f$-value-0.3) to afford 8-bromo-9-(difluoromethyl)-6-fluoro-1,4,4-trimethyl-4,5-dihydro-[1,2,4]triazolo[4,3-a]quinoxaline (1.5 g, 75%) as off white solid.

Synthesis of 8-bromo-9-cyclopropyl-7-fluoro-1,4,4-trimethyl-4,5-dihydro-[1,2,4]triazolo[4,3-a]quinoxaline (Intermediate B-44)

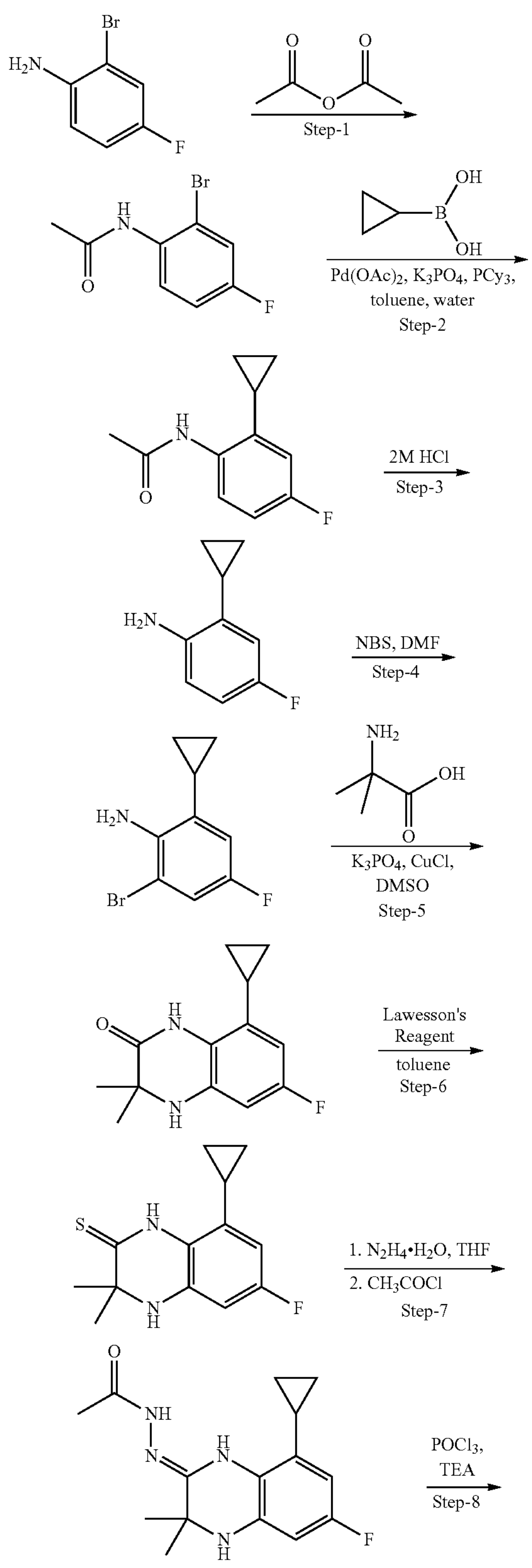

-continued

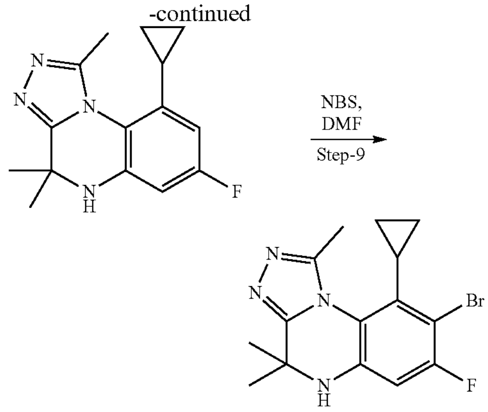

intermediate B-44

Step 1: 2-Bromo-4-fluoro-phenylamine (20.0 g, 0.105 mol) was dissolved in acetic anhydride (10 mL) at 10° C. and was stirred at ambient temperature for 3 h. After completion of the reaction (monitored by TLC, 10% ethylacetate/hexane) the thick reaction mass was diluted with n-hexane and was filtered. The solid material was washed with n-hexane and was then dried under vacuum to afford N-(2-bromo-4-fluoro-phenyl)-acetamide (20.0 g, 82%) as an off white solid.

Step 2: To a stirred solution of N-(2-bromo-4-fluoro-phenyl)-acetamide (65.0 g, 0.28 mol) in a mixture of toluene-water (1:1, 1.3 L) was added tricyclohexyl phosphine (7.85 g, 0.03 mol) followed by the addition of $K_3PO_4$ (208.2 g, 0.98 mol) at ambient temperature. This mixture was then degassed with Ar for 30 minutes. Cyclopropyl boronic acid (31.2 g, 0.37 mol) followed by $Pd(Oac)_2$ (3.2 g, 0.01 mol) was added and the reaction mixture was heated to 100° C. for 16 h. After consumption of the starting material (monitored by TLC, 20% EA-Hexane, Rf 0.4) the reaction mixture was cooled to ambient temperature, diluted with EtOAc (1 L), washed with water (2×500 ml) followed by brine (500 ml) and was then dried over anhydrous $Na_2SO_4$ and concentrated under reduced pressure to afford the crude compound. The obtained crude compound was purified by column chromatography (100-200 mesh silica gel and 15-20% EtOAc/hexane as eluent) to afford N-(2-cyclopropyl-4-fluoro-phenyl)-acetamide (51.5 g, 95%) as a brownish solid.

Step 3: A stirred suspension of N-(2-cyclopropyl-4-fluoro-phenyl)-acetamide (4) (52.0 g, 0.269 mol) in HCl (2.1 L, 2M) was heated to 90° C. for 16 h. After completion of reaction (monitored by TLC, 20% EA-Hexane, Rf 0.6), it was cooled to ambient temperature and was basified to pH~13-14 with NaOH solution (2M). The mixture was extracted with EtOAc (1 L). The organic layer was then washed with water (2×500 ml) and brine (500 ml), dried over anhydrous $Na_2SO_4$ and was concentrated under reduced pressure to afford 2-cyclopropyl-4-fluoro-phenylamine (40.0 g, crude) as a dark brown liquid.

Step 4: To a stirred solution of 2-cyclopropyl-4-fluoro-phenylamine (20.0 g, 0.132 mol) in DMF (350 ml) was added NBS (85.0 g, 0.477 mol) portion wise at −10° C. The resulting reaction mixture was stirred at 0° C. for 1 h. After completion of reaction (monitored by TLC, 20% EtOAc/hex) the reaction mixture was diluted with water (1 L) and was extracted with MTBE (2×750 ml). The combined organic layers were washed with cold brine (3×500 ml), dried over anhydrous $Na_2SO_4$ and concentrated under reduced pressure. The obtained crude material was purified by column chromatography (100-200 mesh silica gel and 5-10% EtOAc/hexane as eluent) to afford 2-bromo-6-cyclopropyl-4-fluoro-phenylamine (20.2 g, 65% over two steps) as a brownish liquid.

Step 5: To a stirred suspension of 2-bromo-6-cyclopropyl-4-fluoro-phenylamine (20.0 g, 86.88 mmol) in dry DMSO (300 mL) was added 2-amino-2-methyl-propionic acid (17.9 g, 173.94 mmol) followed by $K_3PO_4$ (36.9 g, 173.94 mmol) at ambient temperature. The resulting reaction mixture was degassed with Ar for 30 minutes. Then, CuCl (860 mg, 8.69 mmol) was added and the reaction mixture was heated to 140° C. for 16 h. After consumption of the starting material (monitored by TLC, 30% EA-Hexane, Rf 0.4) the reaction mixture was cooled to ambient temperature and was filtered through a celite bed. The celite bed was washed with EtOAc (500 ml). The organic layers were washed with water (2×750 ml) and brine (500 ml), were dried over anhydrous $Na_2SO_4$ and the solvent was evaporated under reduced pressure to afford the crude material. The obtained crude material was purified by column chromatography using 15-20% EtOAc-hexane to afford 8-cyclopropyl-6-fluoro-3,3-dimethyl-3,4-dihydro-1H-quinoxalin-2-one (10.1 g, 50%) as a brown solid.

Step 6: To a solution of 8-cyclopropyl-6-fluoro-3,3-dimethyl-3,4-dihydro-1H-quinoxalin-2-one (10.0 g, 42.7 mmol) in toluene (200 ml) was added Lawesson's reagent (25.9 g, 64.1 mmol) at ambient temperature and the reaction mixture was refluxed at 120° C. for 1 h. After completion of the reaction (monitored by TLC in 20% EA-Hexane, $R_f$ 0.7) the reaction mass was cooled to ambient temperature and was quenched with saturated $NaHCO_3$ solution (35 ml). The resulting aqueous layer was extracted with EtOAc (3×500 ml). The combined organic layers were washed with water (500 ml) followed by brine (500 ml), dried over anhydrous $Na_2SO_4$ and concentrated to afford the crude material. The obtained crude material was purified via column chromatography (using silica 100-200 mesh and 5-10% EtOAc/hexane) to afford 8-cyclopropyl-6-fluoro-3,3-dimethyl-3,4-dihydro-1H-quinoxaline-2-thione (9.5 g, 89%) as a yellow solid.

Step 7: To a stirred solution of 8-cyclopropyl-6-fluoro-3,3-dimethyl-3,4-dihydro-1H-quinoxaline-2-thione (9.0 g, 36.0 mmol) in THF (216 ml) was hydrazine hydrate (5.3 ml, 108 mmol) added dropwise at 0° C. The reaction mixture was then stirred at ambient temperature for 16 h. TEA (30.2 ml, 216.0 mmol) followed by acetyl chloride (10.3 ml, 144.0 mmol) were then added to the reaction mixture dropwise at 0° C. and the reaction mixture was stirred for 2 h at ambient temperature. After completion of the reaction (monitored by LCMS) the reaction mixture was diluted with water (300 ml) and extracted with EtOAc (2×500 ml). The combined organic layers were washed with brine (300 ml), dried over $Na_2SO_4$ and concentrated under reduced pressure to afford acetic acid [8-cyclopropyl-6-fluoro-3,3-dimethyl-3,4-dihydro-1H-quinoxalin-(2E)-ylidene]-hydrazide (9.0 g, crude) as a pale yellow solid.

Step 8: Acetic acid [8-cyclopropyl-6-fluoro-3,3-dimethyl-3,4-dihydro-1H-quinoxalin-(2E)-ylidene]-hydrazide (6.0 g, 20.66 mmol) was taken up in a round bottom flask and was cooled to −10° C. Phosphorus oxalylchloride (9.7 ml, 103.32 mmol) was added to it and the mixture was stirred at −10° C. for 15 min. TEA (2.9 ml, 20.66 mmol) was slowly added to the reaction mixture at −10° C. and the mixture was stirred for 15 min. The reaction mixture was then stirred at ambient temperature for 15 minutes, followed by heating to 120° C. for 1.5 h. After completion of the reaction (monitored by LCMS) the reaction mixture was cooled to ambient temperature, poured into crushed ice in water and basified (pH~8-9) using aqueous ammonia solution. The resulting basic aqueous layer was extracted with EtOAc (2×500 mL). The combined organic layers were washed with water (500 ml) followed by brine (500 ml), dried over anhydrous $Na_2SO_4$ and concentrated under reduced pressure. The residue was triturated with 50% MTBE-Hexane (50 mL×2) to afford 9-cyclopropyl-7-fluoro-1,4,4-trimethyl-4,5-dihydro-[1,2,4]triazolo[4,3-a]quinoxaline (5.0 g, crude) as a pale yellow solid.

Step 9: To a stirred solution of 9-cyclopropyl-7-fluoro-1,4,4-trimethyl-4,5-dihydro-[1,2,4]triazolo[4,3-a]quinoxaline (5.0 g, 18.36 mmol) in DMF (80 mL) was added NBS (3.4 g, 18.91 mol) portionwise at −10° C. The resulting reaction mixture was stirred at 0° C. for 1 h. After completion of the reaction (monitored by LCMS) the reaction mixture was diluted with water (250 ml) and extracted with EtOAc (2×250 ml). The combined organic layers were washed with cold brine (3×250 ml), dried over anhydrous $Na_2SO_4$ and were concentrated under reduced pressure. The obtained crude material was purified by column chromatography (100-200 mesh silica gel and 30-35% acetone/hexane as eluent) to afford 8-bromo-9-cyclopropyl-7-fluoro-1,4,4-trimethyl-4,5-dihydro-[1,2,4]triazolo[4,3-a]quinoxaline (1.2 g, 17% over three steps) as an off white solid.

$^1$H-NMR (400 MHz, DMSO-$d_6$): δ=6.89 (s, 1H), 6.81-6.79 (t, 1H), 2.50-2.47 (d, 3H), 2.08 (t, 1H), 1.67 (s, 3H), 1.37 (bs, 1H), 1.10 (s, 3H), 0.92 (b, 1H) 0.82 (bs, 1H), 0.01 (bs, 1H).

Synthesis of 8-bromo-9-difluoromethyl-7-fluoro-1,4,4-trimethyl-4,5-dihydro-[1,2,4]triazolo[4,3-a]quinoxaline (Intermediate B-45)

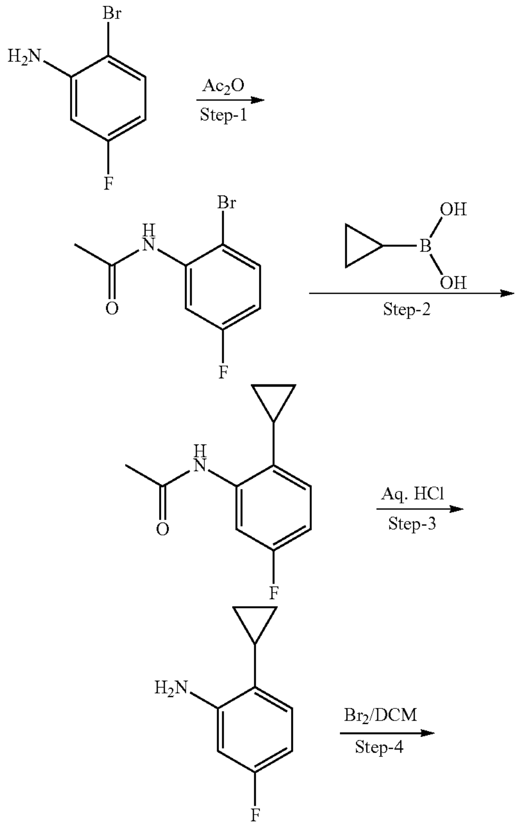

-continued

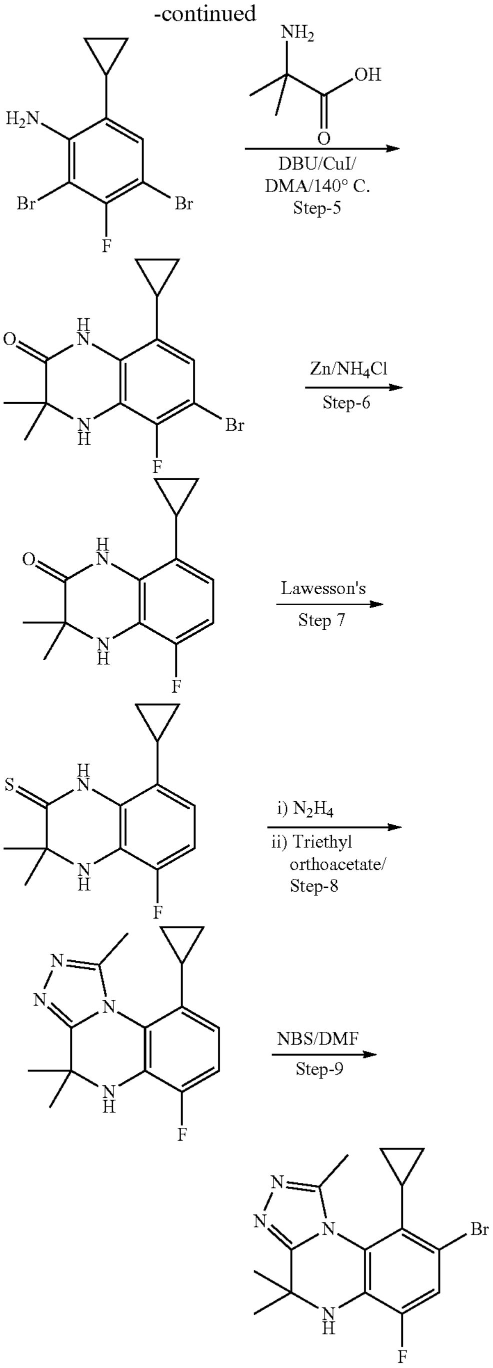

intermediate B-45

Step 1: 2-Bromo-5-fluoro-phenylamine (50 g, 0.262 mol, 1 eq) was dissolved in acetic anhydride (25 mL) at 10° C. and stirred at room temperature for 3 h. After completion of the reaction (monitored by TLC, 10% EtOAc/hexane), the thick reaction mass was diluted with n-hexane and filtered. The solid material was washed with n-hexane and dried under reduced pressure to afford N-(2-bromo-5-fluoro-phenyl)-acetamide (55 g, 90%) as an off-white solid.

Step 2: To a stirred solution of N-(2-bromo-5-fluoro-phenyl)-acetamide (50 g, 0.259 mol, 1 eq) in a toluene:water (1:1, 1 L) mixture was added tricyclohexyl phosphine (7.26 g, 0.0259 mol, 0.1 eq), followed by $K_3PO_4$ (192 g, 0.906 mol, 3.5 eq) at room temperature and the mixture was degassed with argon for 30 minutes. Cyclopropyl boronic acid (28.98 g, 0.336 mol, 1.3 eq) and subsequently $Pd(Oac)_2$ (2.9 g, 0.0129, 0.05 eq) were added and the reaction mixture was heated at 100° C. for 16 h. After completion of the reaction (monitored by TLC, 20% EtOAc-Hexane, Rf 0.4), the reaction mixture was cooled to room temperature, diluted with EtOAc (1 L), washed with water (2×500 mL) and brine (500 mL), dried over anhydrous $Na_2SO_4$ and concentrated under reduced pressure. The obtained crude residue was purified by column chromatography (100-200 mesh silica gel; 15-20% EtOAc/hexane as eluent) to afford N-(2-cyclopropyl-4-fluoro-phenyl)-acetamide (36 g, 86%) as a brownish solid.

Step 3: A stirred suspension of N-(2-cyclopropyl-4-fluoro-phenyl)-acetamide (54 g, 0.279 mol, 1 eq) in aqueous HCl (2.1 L, 2M) was heated at 90° C. for 16 h. After completion of the reaction (monitored by TLC, 20% EtOAc-Hexane, Rf 0.6), the reaction mixture was cooled to room temperature and basified to pH~13-14 with a NaOH solution (2M). This mixture was extracted with EtOAc (1 L), washed with water (2×500 mL) and brine (500 mL), dried over anhydrous $Na_2SO_4$ and concentrated under reduced pressure to afford 2-cyclopropyl-5-fluoro-phenylamine (48 g, crude) as a dark brown liquid.

Step 4: To a stirred solution of 2-cyclopropyl-5-fluoro-phenylamine (27 g, 0.18 mol, 1 eq) in DMF (480 mL) was added NBS (79.5 g, 0.447 mol, 2.5 eq) portion wise at −10° C. and the resulting reaction mixture was stirred at 0° C. for 1 h. After completion of the reaction (monitored by TLC, 20% EtOAc/hexane), the reaction mixture was diluted with water (1 L) and extracted with MTBE (2×750 ml). The combined organic layers were washed with cold brine (3×500 mL), dried over anhydrous $Na_2SO_4$ and concentrated under reduced pressure. The obtained crude residue was purified by column chromatography (100-200 mesh silica gel; 5-10% EtOAc/hexane as eluent) to afford 2,4-dibromo-6-cyclopropyl-3-fluoro-phenylamine (22 g, 45% over two steps) as a brownish liquid.

Step 5: To a stirred suspension of 2,4-dibromo-6-cyclopropyl-3-fluoro-phenylamine (20 g, 0.065 mol, 1 eq) in dry DMA (300 mL) was added 2-amino-2-methyl-propionic acid (13.35 g, 0.129 mol, 2 eq) followed by DBU (19.2 mL, 0.129 mol, 2 eq) at room temperature. The resulting reaction mixture was degassed with argon for 30 minutes, CuI (1.2 g, 0.006 mol. 0.1 eq) was added and the reaction mixture was heated at 140° C. for 16 h. After complete consumption of the starting material (monitored by TLC, 30% EtOAc-Hexane, Rf 0.4), the reaction mixture was cooled to room temperature and filtered over a bed of celite, that was then washed with EtOAc (500 mL). The organic fraction was washed with water (2×750 mL) and brine (500 mL), dried over anhydrous $Na_2SO_4$ and concentrated under reduced pressure. The obtained crude residue was purified by column chromatography (15-16% EtOAc-hexane) to afford 6-bromo-8-cyclopropyl-5-fluoro-3,3-dimethyl-3,4-dihydro-1H-quinoxalin-2-one (13 g, 64%) as a brown solid.

Step 6: To a suspension of 6-bromo-8-cyclopropyl-5-fluoro-3,3-dimethyl-3,4-dihydro-1H-quinoxalin-2-one (10 g, 0.031 mol, 1 eq) in adioxane:water (2:1, 200 mL) mixture was added Zn-powder (12.52 g, 0.191 mol, 6 eq), followed by ammonium chloride (10.25 g, 0.191 mol, 6 eq) at room temperature and the reaction was stirred at 100° C. for 16 h. After completion of the reaction (monitored by TLC, 30% EtOAc-Hexane, Rf 0.4), the reaction mixture was cooled to room temperature and filtered through a celite bed, that was then washed with EtOAc (500 mL). The organic fraction was washed with water (2×750 mL) and brine (500 mL), dried over anhydrous $Na_2SO_4$ and concentrated under reduced pressure. The obtained crude residue was purified by column chromatography using 15-20% EtOAc-hexane to afford 8-cyclopropyl-5-fluoro-3,3-dimethyl-3,4-dihydro-1H-quinoxalin-2-one (4.3 g, 59%) as a brown solid.

Step 7: To a solution of 8-cyclopropyl-6-fluoro-3,3-dimethyl-3,4-dihydro-1H-quinoxalin-2-one (4.3 g, 18.376 mmol, 1 eq) in toluene (86 mL) was added Lawesson's reagent (11.16 g, 27.564 mmol, 1.5 eq) at room temperature and the reaction mixture was refluxed at 120° C. for 1 h. After completion of the reaction (monitored by TLC in 20% EtOAc-Hexane, Rf 0.6), the reaction was cooled to room temperature and quenched with a sat. $NaHCO_3$ solution. The resulting aqueous fraction was extracted with EtOAc (3×200 mL) and the combined organic layers were washed with water (200 mL) and brine (200 mL), dried over anhydrous $Na_2SO_4$ and concentrated under reduced pressure. The obtained crude residue was purified by column chromatography (100-200 mesh silica; 5-10% EtOAc/hexane) to afford 8-cyclopropyl-5-fluoro-3,3-dimethyl-3,4-dihydro-1H-quinoxaline-2-thione (4.2 g, 92%) as a yellow solid.

Step 8: To a stirred solution of 8-cyclopropyl-5-fluoro-3,3-dimethyl-3,4-dihydro-1H-quinoxaline-2-thione (4 g, 16 mmol, 1 eq) in tetrahydrofuran (80 mL) was added hydrazine hydrate (2.35 ml, 48 mmol, 3 eq) drop wise at 0° C. and the reaction mixture was stirred at room temperature for 16 h. The solvent was then evaporated and the residue was taken up in triethyl orthoacetate and heated at 140° C. for 48 h. The reaction mixture was concentrated under reduced pressure and purified by column chromatography (100-200 mesh silica gel; 2% MeOH/DCM as eluent) to afford 9-cyclopropyl-6-fluoro-1,4,4-trimethyl-4,5-dihydro-[1,2,4]triazolo[4,3-a]quinoxaline (2.7 g, 59%) as a white solid.

Step 9: To a stirred solution of 9-cyclopropyl-6-fluoro-4,4-dimethyl-4,5-dihydro-[1,2,4]triazolo[4,3-a]quinoxaline (2.27 g, 8.345 mmol, 1 eq) in DMF (40 mL) was added NBS (1.33 g, 7.511 mmol, 0.9 eq) portion wise at −10° C. and the resulting reaction mixture was stirred at 0° C. for 1 h. After complete consumption of starting material (monitored by LCMS), the reaction mixture was diluted with water (20 mL) and extracted with EtOAc (2×30 mL). The combined organic layers were washed with water (2×50 mL) and brine, dried over anhydrous $Na_2SO_4$ and concentrated. The crude residue was combined with another batch (starting from 800 mg of 9-cyclopropyl-6-fluoro-4,4-dimethyl-4,5-dihydro-[1,2,4]triazolo[4,3-a]quinoxaline and following the same procedure as described above) and the total crude amount was then purified by column chromatography (100-200 mesh silica gel; 5% MeOH/DCM as eluent) to afford 8-bromo-9-difluoromethyl-7-fluoro-1,4,4-trimethyl-4,5-dihydro-[1,2,4]triazolo[4,3-a]quinoxaline (2.2 g, 56%) as an off-white solid.

Synthesis of 8-bromo-6-chloro-7-fluoro-1,4,4,9-tetramethyl-4,5-dihydro-[1,2,4]triazolo[4,3-a]quinoxaline (Intermediate B-51)

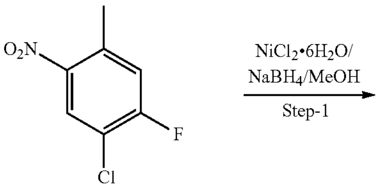

-continued

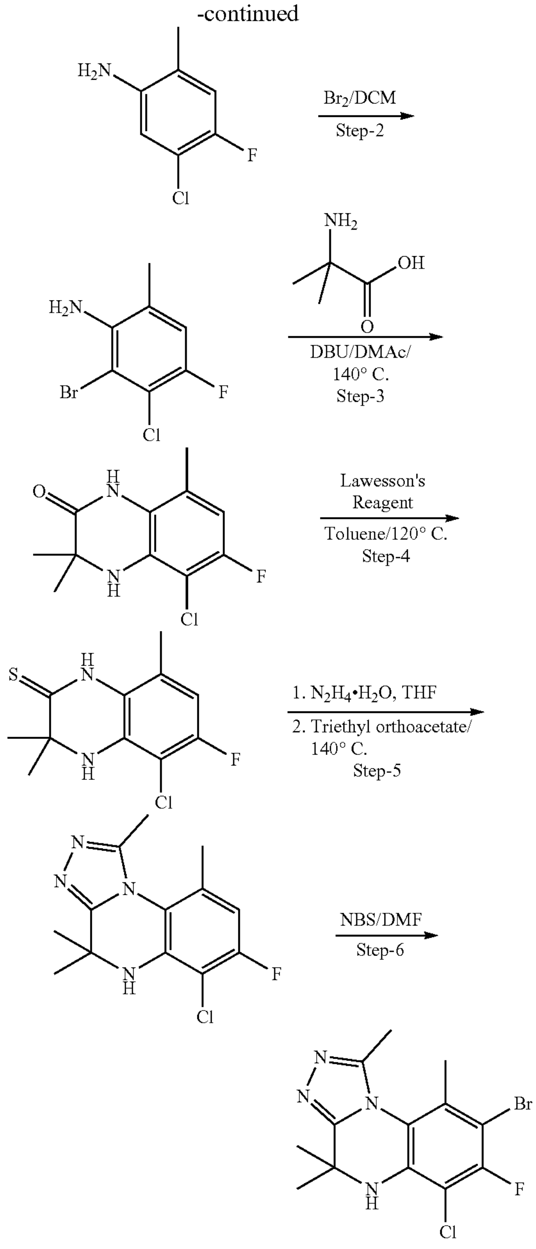

intermediate B-51

Step 1: To a stirred solution of $NiCl_2 \cdot 6H_2O$ (12.54 g, 0.0527 mol, 1 eq) in MeOH (526 mL) was added $NaBH_4$ (5.97 g, 0.158 mol, 3 eq) portion wise at 0° C. and the resulting suspension was stirred at 0° C. for 1 h. Then, 1-chloro-2-fluoro-4-methyl-5-nitro-benzene (20 g, 0.1055 mol, 2 eq) was added, followed by further addition of $NaBH_4$ (13.95 g, 0.369 mol, 7 eq) portion wise and the reaction mixture was stirred at 0° C. for 2 h. After complete consumption of starting material (monitored by TLC), the reaction mixture was concentrated and the obtained residue was diluted with 1N HCl (150 mL) followed by aqueous ammonia (150 mL) and EtOAc (200 mL). This mixture was stirred at room temperature for 15 min, filtered over a celite bed, and the obtained aqueous filtrate was extracted with EtOAc (2×250 mL). The combined organic fractions were washed with water (350 mL) and brine (250 mL), dried over anhydrous $Na_2SO_4$ and concentrated to afford 5-chloro-4-fluoro-2-methyl-phenylamine (14 g, 83%) as an off-white solid.

Step 2: To a solution of 5-chloro-4-fluoro-2-methyl-phenylamine (14 g, 0.087 mol, 1 eq) in DCM (280 mL) was added a solution of $Br_2$ (4.97 mL, 0.098 mol, 1.1 eq) in DCM (70 mL) drop-wise at 0° C. and the resulting reaction mixture was stirred at 0° C. for 2 h. After complete consumption of starting material (monitored by TLC in 10% EtOAc-Hexane), the reaction mixture was diluted with water (300 mL) and extracted with DCM (2×150 mL). The combined organic layers were washed with water (2×250 mL), a saturated sodium thiosulfate solution (2×250 mL) and brine (250 mL), dried over anhydrous $Na_2SO_4$ and concentrated under reduced pressure. The obtained crude residue was purified by column chromatography (100-200 mesh silica gel; 5% EtOAc/hexane as eluent) to yield 2-bromo-3-chloro-4-fluoro-6-methyl-phenylamine (11.2 g, 53%) as a brown solid.

Step 3: To a stirred suspension of 2-bromo-3-chloro-4-fluoro-6-methyl-phenylamine (18 g, 0.075 mol, 1 eq) in dry DMAc (270 mL) was added 2-amino-2-methyl-propionic acid (15.56 g, 0.15 mol, 2 eq), followed by DBU (22.57 mL, 0.15 mol, 2 eq) at room temperature and the resulting reaction mixture was degassed with nitrogen for 30 minutes. Then, CuI (1.43 g, 0.0075 mol, 0.1 eq) was added and the reaction mixture was heated at 140° C. for 16 h. After complete consumption of the starting material (monitored by TLC, 20% EtOAc-Hexane, Rf 0.4), the reaction mixture was cooled to room temperature and poured into ice-cold water (1 L). The resulting aqueous mixture was extracted with EtOAc (2×400 mL) and the combined organic fractions were washed with water (2×500 mL) and brine (400 mL), dried over anhydrous $Na_2SO_4$ and evaporated under reduced pressure. The obtained crude residue was triturated with hexane to afford 5-chloro-6-fluoro-3,3,8-trimethyl-3,4-dihydro-1H-quinoxalin-2-one (8 g, 44%) as a brown liquid.

Step 4: To a solution of 5-chloro-6-fluoro-3,3,8-trimethyl-3,4-dihydro-1H-quinoxalin-2-one (12 g, 0.049 mol, 1 eq) in toluene (150 mL) was added Lawesson's reagent (29.97 g, 0.074 mol, 1.5 eq) at room temperature and the reaction mixture was refluxed at 120° C. for 2 h. After complete consumption of starting material (monitored by TLC in 20% EtOAc-Hexane, Rf 0.6), the reaction mixture was quenched with a sat. $NaHCO_3$ solution (200 mL) and the resulting aqueous mixture was extracted with EtOAc (2×350 mL). The combined organic layers were washed with water (200 mL) and brine (200 mL), dried over anhydrous $Na_2SO_4$ and evaporated under reduced pressure. The obtained crude residue was purified by column chromatography (100-200 mesh silica gel; 10% EtOAc/hexane as eluent) to afford 5-chloro-6-fluoro-3,3,8-trimethyl-3,4-dihydro-1H-quinoxaline-2-thione (128 g, 93%) as a yellow solid.

Step 5: To a stirring solution of 5-chloro-6-fluoro-3,3,8-trimethyl-3,4-dihydro-1H-quinoxaline-2-thione (11 g, 0.042 mol, 1 eq) in tetrahydrofuran (275 mL) was added hydrazine hydrate (6.38 g, 0.127 mol, 3 eq) drop wise at 0° C. and the resulting reaction mixture was stirred at room temperature for 16 h. After formation of imine intermediate, the reaction mixture was concentrated and azeotroped with toluene twice. The obtained residue was dissolved in triethyl-orthoacetate (120 mL) and heated to reflux for 24 h. After complete consumption of starting material (monitored by LCMS), the reaction mixture was concentrated and the obtained crude residue was purified by column chromatography (230-400 mesh silica gel; 5% MeOH/DCM as eluent) to afford 6-chloro-7-fluoro-1,4,4,9-tetramethyl-4,5-dihydro-[1,2,4]triazolo[4,3-a]quinoxaline (8.5 g, 71%) as an off-white solid.

Step 6: To a solution of 6-chloro-7-fluoro-1,4,4,9-tetramethyl-4,5-dihydro-[1,2,4]triazolo[4,3-a]quinoxaline (8 g, 0.028 mol, 1 eq) in DMF (160 mL) was added NBS (5.07 g, 0.028 mol, 1 eq) portion wise at 0° C. and the resulting reaction mixture was stirred at room temperature for 3 h. After complete consumption of starting material (monitored by LCMS), the reaction mixture was diluted with water (500 mL) and extracted with EtOAc (2×250 mL). The combined organic layers were washed with water (2×250 mL) and brine (250 mL), dried over anhydrous $Na_2SO_4$ and concentrated under reduced pressure. The obtained crude residue was purified by column chromatography (230-400 mesh silica gel; 5% MeOH/DCM as eluent) to afford 8-bromo-6-chloro-7-fluoro-1,4,4,9-tetramethyl-4,5-dihydro-[1,2,4]triazolo[4,3-a]quinoxaline (6.2 g, 60%) as an off-white solid.

Synthesis of 8-bromo-9-(difluoromethyl)-1,4,4-trimethyl-4,5-dihydro-[1,2,4]triazolo[4,3-a]quinoxaline (Intermediate B-52)

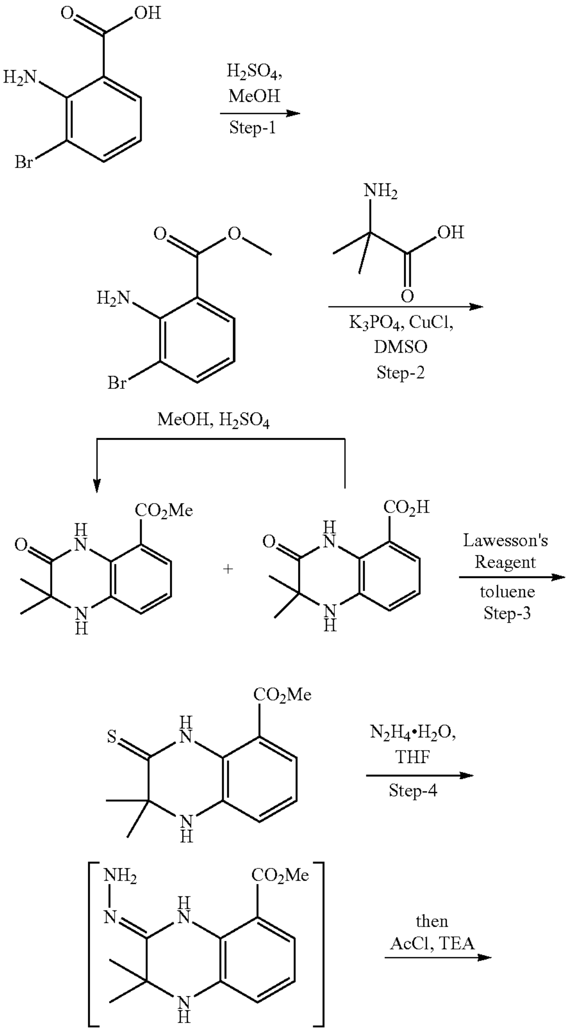

-continued

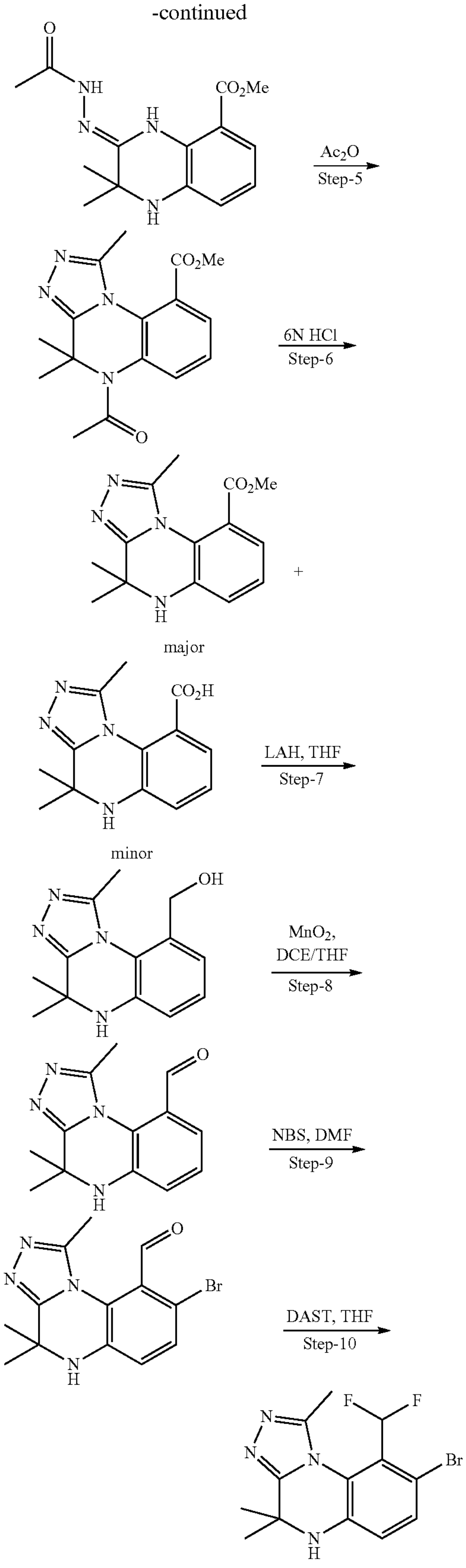

major minor intermediate B-52

Step 1: To a stirring solution of 2-amino-3-bromo-benzoic acid (100.0 g, 0.465 mol) in MeOH (1 L) was added con. $H_2SO_4$ (100 ml) at 0° C. and the mixture was heated to 80° C. for 48 h. After completion of the reaction (monitored by TLC, 5% EA-Hexane, R % 0.4) the reaction mixture was cooled to ambient temperature. The reaction mixture was then concentrated under reduced pressure, the obtained residue was basified with sat. $NaHCO_3$ solution (to pH~8-9) and was then extracted with EtOAc (2×500 ml). The combined organic layers were washed with water (250 ml) and brine (250 ml), were then dried over anhydrous $Na_2SO_4$ and concentrated under reduced pressure to afford 2-amino-3-bromo-benzoic acid methyl ester (80.0 g, 75%) as a brownish solid.

Step 2: To a stirring suspension of 2-amino-3-bromo-benzoic acid methyl ester (30.0 g, 0.131 mol) in dry DMSO (450 ml) was added 2-amino-2-methyl-propionic acid (27.1 g, 0.262 mol) followed by $K_3PO_4$ (55.6 g, 0.262 mol) at ambient temperature. The resulting reaction mixture was degassed with nitrogen for 30 minutes, then cuprous chloride (1.29 g, 0.01 mol) was added and the reaction mixture was heated to 140° C. for 4-5 h. After completion of the reaction (monitored by TLC, 20% EA-Hexane, Rf 0.4) the reaction mixture was cooled to ambient temperature and filtered through celite. The celite bed was washed with EtOAc (2×250 nil). The resulting filtrate was poured into ice cold water (800 ml). The aqueous layer was extracted with EtOAc (2×500 ml). The combined organic layers were washed with water (2×650 ml) and brine (650 ml), dried over anhydrous $Na_2SO_4$ and concentrated under reduced pressure to afford methyl 2,2-dimethyl-3-oxo-1,2,3,4-tetrahydroquinoxaline-5-carboxylate (3.0 g, crude). The aqueous layer was acidified with conc. HCl (pH~2-3) and was then extracted with EtOAc (2×500 ml). The combined organic layers were washed with brine (500 ml), dried over anhydrous $Na_2SO_4$ and were evaporated under reduced pressure to yield 2,2-dimethyl-3-oxo-1,2,3,4-tetrahydroquinoxaline-5-carboxylic acid (15.0 g). This material was dissolved in MeOH (150 nil), followed by the slow addition of conc. $H_2SO_4$ (15 ml) at 0° C. The resulting reaction mixture was then stirred at 90° C. for 50 h. The reaction mixture was concentrated and the obtained residue was basified with sat. $NaHCO_3$ solution (pH~8-9) and was then extracted with EtOAc (2×250 ml). The combined organic layers were washed with water (150 ml) and brine (150 ml), dried over anhydrous $Na_2SO_4$ and evaporated under reduced pressure to obtain methyl 2,2-dimethyl-3-oxo-1,2,3,4-tetrahydroquinoxaline-5-carboxylate (~13 g, crude). The combined batches of methyl 2,2-dimethyl-3-oxo-1,2,3,4-tetrahydroquinoxaline-5-carboxy late were triturated with hexane to afford 2,2-dimethyl-3-oxo-1,2,3,4-tetrahydro-quinoxaline-5-carboxylic acid methyl ester (13.1 g, 43%) as a brownish solid.

Step 3: To a stirring solution of 2,2-dimethyl-3-oxo-1,2,3,4-tetrahydro-quinoxaline-5-carboxylic acid methyl ester (20.0 g, 85.47 mmol) in toluene (430 ml) was added Lawesson's reagent (51.9 g, 128.21 mmol) at ambient temperature and the reaction mixture was then heated to 120° C. for 2 h. After completion of the reaction (monitored by TLC in 20% EA-Hexane, Rf 0.6) the reaction mixture was quenched with sat. $NaHCO_3$ solution (500 ml) and the resulting aqueous layer was extracted with EtOAc (2×400 ml). The combined organic layers were washed with water (500 ml) and brine (300 ml), dried over anhydrous $Na_2SO_4$ and concentrated under reduced pressure to obtain the crude compound. The obtained crude was purified by column chromatography (100-200 mesh silica gel, 7-8% EtOAc in hexane as eluent) to afford 2,2-dimethyl-3-thioxo-1,2,3,4-tetrahydro-quinoxaline-5-carboxylic acid methyl ester (16.0 g, 75%) as a yellow solid.

Step 4: To a stirring solution of 2,2-dimethyl-3-thioxo-1,2,3,4-tetrahydro-quinoxaline-5-carboxylic acid methyl ester (30.0 g, 0.12 mol) in THF (800 ml) was added hydrazine hydrate (10.6 ml, 0.22 mol) dropwise at 0° C. and the mixture was then stirred at ambient temperature for 10 h. To the reaction mixture was then added TEA (60.3 ml, 0.43 mol) dropwise at 0° C. followed by acetyl chloride (23.1 ml, 0.32 mol), and the resulting mixture was stirred for 4 h at ambient temperature. After completion of the reaction (monitored by LCMS) the reaction mixture was diluted with water (500 ml) and extracted with 10% MeOH-DCM (2×300 ml). The combined organic layers were then washed with brine (350 ml), dried over $Na_2SO_4$ and concentrated under reduced pressure. The obtained compound was then purified by column chromatography (100-200 mesh silica gel and 1.5-2% MeOH in DCM as eluent) to afford 3-(acetyl-hydrazono)-2,2-dimethyl-1,2,3,4-tetrahydro-quinoxaline-5-carboxylic acid methyl ester (20.1 g, 58%) as an off white solid.

Step 5: To 3-(acetyl-hydrazono)-2,2-dimethyl-1,2,3,4-tetrahydro-quinoxaline-5-carboxylic acid methyl ester (12.0 g, 41.35 mmol) was added acetic anhydride (200 ml) and the resulting mixture was heated to 140° C. for 8 h. After completion of the reaction (monitored by LCMS) the reaction mixture was concentrated under reduced pressure. The residue was diluted with EtOAc, washed with saturated $NaHCO_3$ solution, dried over $Na_2SO_4$ and concentrated under reduced pressure. The obtained crude material was purified by column chromatography (100-200 mesh silica gel and 1.5-2% MeOH in DCM as eluent) to afford 5-acetyl-1,4,4-trimethyl-4,5-dihydro-[1,2,4]triazolo[4,3-a]quinoxaline-9-carboxylic acid methyl ester (5.5 g, 42%) as an off white solid.

Step 6: A stirring solution of 5-acetyl-1,4,4-trimethyl-4,5-dihydro-[1,2,4]triazolo[4,3-a]quinoxaline-9-carboxylic acid methyl ester (5.4 g, 0.12 mol) in 6N HCl (200 ml) was heated to 80° C. for 6 h. After completion of the reaction (monitored by LCMS) the reaction mixture was concentrated, the residue was azeotroped with toluene (four times) followed by trituration with ether-pentane to afforded the di-hydrochloride salt of 1,4,4-Trimethyl-4,5-dihydro-[1,2,4]triazolo[4,3-a]quinoxaline-9-carboxylic acid methyl ester (5.2 g, crude) as a greenish solid.

Step 7: To a stirring solution of the di-hydrochloride salt of 1,4,4-trimethyl-4,5-dihydro-[1,2,4]triazolo[4,3-a]quinoxaline-9-carboxylic acid methyl ester (2.5 g, 7.25 mmol) in THF (70 ml) was slowly added lithium aluminium hydride (18.12 ml, 18.12 mmol, 2M in THF) at 0° C. and the resulting reaction mixture was stirred at ambient temperature for 16 h. After completion of the reaction (monitored by LCMS) the reaction mixture was quenched with saturated $Na_2SO_4$ and was then filtered through a celite bed. The celite bed was then washed with hot THF (3×50 ml). The combined filtrates were concentrated under reduced pressure and were then azeotroped with toluene (3×50 ml) to afford (1,4,4-trimethyl-4,5-dihydro-[1,2,4]triazolo[4,3-a]66uinoxaline-9-yl)-MeOH (1.9 g, crude) as a brownish solid.

Step 8: (1,4,4-Trimethyl-4,5-dihydro-[1,2,4]triazolo[4,3-a]66uinoxaline-9-yl)-MeOH (2.2 g, 9.01 mmol) was dissolved in THF-DCE (1:1, 65 ml). Manganese dioxide was added (4.7 g, 54.06 mmol) and the resulting reaction mixture was stirred at 80-90° C. for 48 h. After completion of the reaction (monitored by LCMS) the reaction mixture was filtered through a celite bed and the celite bed was washed with THF-DCE (1:1, 25 ml). The combined filtrate was concentrated under reduced pressure and the obtained crude material was purified by column chromatography (Silica gel 100-200 mesh, 2-2.5% MeOH-DCM as eluent) to afford 1,4,4-trimethyl-4,5-dihydro-[1,2,4]triazolo[4,3-a]quinoxaline-9-carbaldehyde (1.74 g, 80%) as an off white solid.

Step 9: To a stirring solution of 1,4,4-Trimethyl-4,5-dihydro-[1,2,4]triazolo[4,3-a]quinoxaline-9-carbaldehyde (2.0 g, 8.25 mmol) in DMF (30 ml) was added NBS (1.5 g, 8.50 mmol) portionwise at 0° C. and the resulting reaction mixture was then stirred at this temperature for 1 h. After completion of the reaction (monitored by LCMS) the reaction mixture was diluted with water (250 ml) and was extracted with EtOAc (2×150 ml). The combined organic layers were washed with water (2×180 ml), dried over anhydrous $Na_2SO_4$ and were then concentrated under reduced pressure. The obtained crude material was purified by column chromatography (230-400 mesh silica gel, 2-3% MeOH in DCM as eluent) to afford 8-bromo-1,4,4-trimethyl-4,5-dihydro-[1,2,4]triazolo[4,3-a]quinoxaline-9-carbaldehyde (1.1 g, 42%) as a brownish solid.

Step 10: 8-Bromo-1,4,4-trimethyl-4,5-dihydro-[1,2,4]triazolo[4,3-a]quinoxaline-9-carbaldehyde (1.0 g, 3.12 mmol) was dissolved in DCM (10 ml) and was cooled to 0° C. DAST (0.61 ml, 1.5 eq) was added and the reaction mixture was stirred at 10-15° C. for 6 h. The reaction mixture was then kept at −20° C. for 16 h. The reaction mixture was then warmed to 0° C. DAST (0.61 ml, 1.5 eq) was added and the reaction mixture was stirred for three hours. Then, DAST (0.61 ml, 1.5 eq) was added and the reaction mixture was stirred for another three hours. The reaction mixture was then quenched with sat. $NaHCO_3$ solution (pH~8-9) at 0° C. and was extracted with DCM (50 mL×2). The combined organic layers were washed with cold water (30 ml), and brine (30 ml), dried over sodium sulphate and were then concentrated under reduced pressure to obtain the crude compound. The described reaction was conducted in four batches in parallel, each using 1.0 g (3.12 mmol) of 8-bromo-1,4,4-trimethyl-4,5-dihydro-[1,2,4]triazolo[4,3-a]quinoxaline-9-carbaldehyde. The combined batches of the crude compounds were purified by column chromatography (Silica gel 230-400 mesh, 30-35% acetone in hexane as eluent) to afford 8-bromo-9-difluoromethyl-1,4,4-trimethyl-4,5-dihydro-[1,2,4]triazolo[4,3-a]quinoxaline (1.4 g, 33%) as an off white solid.

$^1$H-NMR (400 MHz, DMSO-$d_6$): δ=7.57-7.54 (d, 1H), 7.27-7.06 (t, 1H), 7.04-7.03 (m, 2H), 2.41 (s, 3H), 1.68 (brs, 3H), 1.19 (brs, 3H).

Synthesis of 8-bromo-9-difluoromethyl-7-fluoro-1,4,4-trimethyl-4,5-dihydro-[1,2,4]triazolo[4,3-a]quinoxaline (Intermediate B-53)

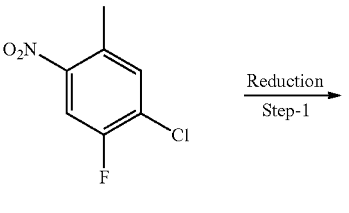

-continued

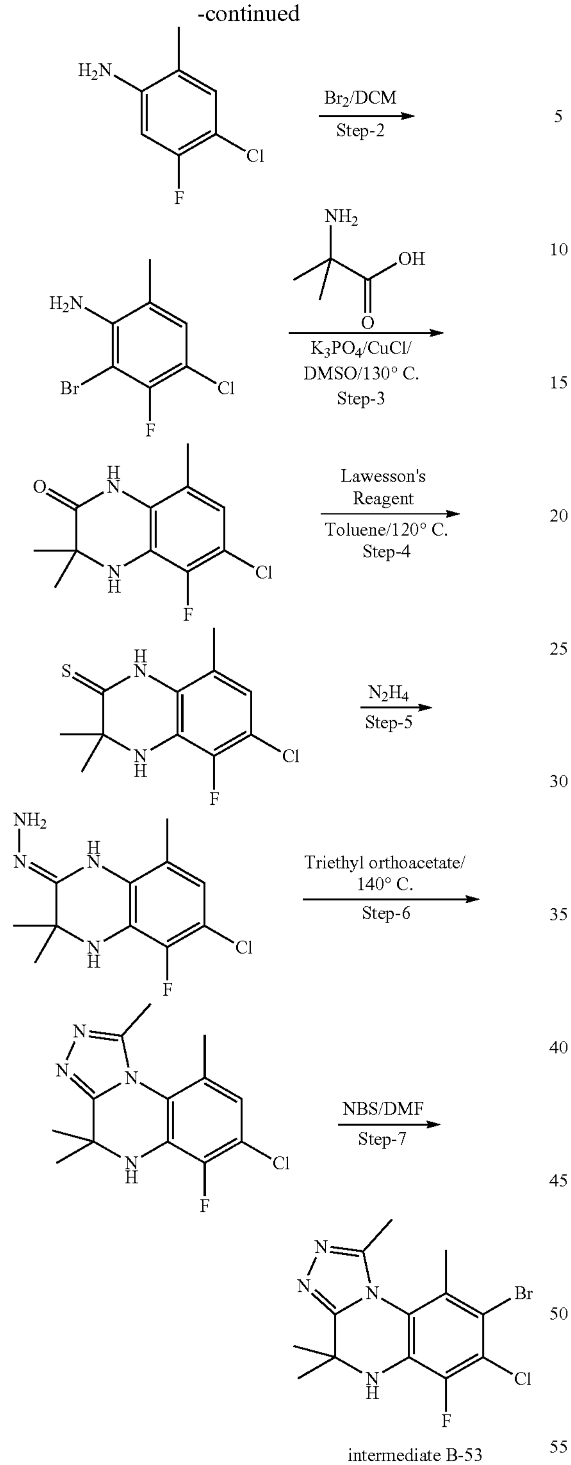

intermediate B-53

Step 1: To a stirred solution of 1-chloro-2-fluoro-5-methyl-4-nitro-benzene (10.0 g, 52.91 mmol, 1 eq) in an EtOH-water (1:1, 120 mL) mixture was added a conc. Aqueous HCl solution (6 mL), followed by addition of iron powder (10.3 g, 185.18 mmol, 3.5 eq) at room temperature and the reaction mixture was stirred for 16 h at 110° C. After completion of the reaction (monitored by TLC, 20% EtOAc/hexane, Rf 0.3), the reaction mixture was filtered through a celite bed and washed with EtOAc (200 mL×3). The combined organic fractions were concentrated under reduced pressure, diluted with EtOAc (500 mL), washed with water (100 mL×2) and brine (200 mL), dried over anhydrous $Na_2SO_4$ and concentrated under reduced pressure. The obtained crude residue was purified by column chromatography (100-200 mesh silica gel; 20% EtOAc/hexane as eluent) to afford 4-chloro-5-fluoro-2-methyl-phenylamine (7.5 g, 89%) as a light brown solid.

Step 2: To a stirred solution of 4-chloro-5-fluoro-2-methyl-phenylamine (5.5 g, 34.81 mmol, 1 eq) in DCM (150 mL) was added a solution of $Br_2$ (1.79 mL, 34.81 mmol, 1 eq) in DCM (60 mL) drop wise at 0° C. and the resulting reaction mixture was stirred at 0° C. for 2 h. After complete consumption of starting material (monitored by TLC in 20% EtOAc-Hexane, Rf 0.6), the reaction mixture was quenched with a saturated $NaHCO_3$ solution (400 mL) and the organic layer was separated. The aqueous fraction was extracted and the combined organic layers were washed with water (2×300 mL) and brine (200 mL), dried over anhydrous $Na_2SO_4$ and concentrated under reduced pressure. The obtained crude residue was purified by column chromatography (100-200 mesh silica gel; 10% EtOAc/hexane as eluent) to afford 2-bromo-3-chloro-4-fluoro-6-methyl-phenylamine (4.5 g, 54%) as a brown solid.

Step 3: To a stirred solution of 2-bromo-3-chloro-4-fluoro-6-methyl-phenylamine (5 g, 21.008 mmol, 1 eq) in dry DMAc (100 mL) were added 2-amino-2-methyl-propionic acid (4.4 g, 42.016 mmol, 2 eq) and DBU (5.46 mL, 42.016 mmol, 2 eq) at room temperature and the resulting reaction mixture was degassed with nitrogen for 30 minutes. CuI (400 mg, 2.1006 mmol, 0.1 eq) was added to this reaction mixture, which was heated at 140° C. for 16 h. After complete consumption of the starting material (monitored by TLC, 20% EtOAc-Hexane, Rf 0.3), the reaction mixture was cooled to room temperature and filtered over a celite bed, that was then washed with EtOAc (2×300 mL). The resulting filtrate was poured into ice-cold water (200 mL) and extracted with EtOAc (2×400 mL). The combined organic fractions were washed with cold water (3×100 mL) and brine (100 mL), dried over anhydrous $Na_2SO_4$ and evaporated under reduced pressure. The crude residue was purified by chromatography (100-200 mesh silica gel; 20% EtOAc/hexane as eluent) to afford 5-chloro-6-fluoro-3,3,8-trimethyl-3,4-dihydro-1H-quinoxalin-2-one (28 g, 69%) as an off-white solid.

Step 4: To a stirred solution of 6-difluoromethoxy-8-fluoro-3,3-dimethyl-3,4-dihydro-1H-quinoxalin-2-one (12 g, 49.58 mmol, 1 eq) in toluene (240 mL) was added Lawesson's reagent (30.08 g, 74.38 mmol, 1.5 eq) at room temperature and the reaction mixture was refluxed at 120° C. for 2 h. After consumption of starting material (monitored by TLC in 20% EtOAc-Hexane, Rf 0.6), the reaction mixture was concentrated under reduced pressure. The obtained solid residue was quenched with sat. $NaHCO_3$ solution (500 mL) and the resulting aqueous phase was extracted with EtOAc (3×300 mL), after which the combined organic layers were washed with water (400 mL) and brine (200 mL), dried over anhydrous $Na_2SO_4$ and evaporated under reduced pressure. The obtained crude residue was purified by column chromatography (100-200 mesh silica gel; 10% EtOAc/hexane as eluent) to afford 6-chloro-5-fluoro-3,3,8-trimethyl-3,4-dihydro-1H-quinoxaline-2-thione (11.5 g, 90%) as a yellow solid.

Step 5: To a stirred solution of [6-fluoro-3,3,8-trimethyl-3,4-dihydro-1H-quinoxaline-2-thione] (8 g, 31.007 mmol, 1 eq) in tetrahydrofuran (200 mL) was drop wise added hydrazine hydrate (6.209 g, 124 mmol, 4 eq) at 0° C. and the reaction mixture was stirred at room temperature for 16 h.

After complete consumption of starting material (monitored by TLC in 5% MeOH-DCM, Rf 0.4), the reaction mixture was concentrated to afford crude (6-chloro-5-fluoro-3,3,8-trimethyl-3,4-dihydro-1H-quinoxalin-(2E)-ylidene]-hydrazine (8 g), which was used in the next step without purification.

Step 6: To crude [6-chloro-5-fluoro-3,3,8-trimethyl-3,4-dihydro-1H-quinoxalin-(2E)-ylidene]-hydrazine (8 g, 34.06 mmol, 1 eq), triethyl orthoacetate (240 mL) was added at room temperature, and the solution was stirred at 140° C. for 48 h. After consumption of starting material (monitored by LCMS), the reaction mixture was concentrated and purified by column chromatography (100-200 mesh silica gel; 2% MeOH/DCM as eluent) to afford 7-chloro-6-fluoro-1,4,4,9-tetramethyl-4,5-dihydro-[1,2,4]triazolo[4,3-a]quinoxaline (6 g, 69% over two steps) as a white solid.

Step 7: To a stirred solution of 7-chloro-6-fluoro-1,4,4,9-tetramethyl-4,5-dihydro-[1,2,4]triazolo[4,3-a]quinoxaline (3 g, 10.686 mmol, 1 eq) in DMF (90 mL) was added NBS (1.99 g, 11.22 mmol, 1.05 eq) portion wise at 0° C. and the resulting reaction mixture was stirred at 0° C. for 1 h. After consumption of starting material (monitored by LCMS), the reaction mixture was diluted with water (60 mL) and extracted with EtOAc (2×100 mL). The combined organic layers were washed with water (2×60 mL) and brine, dried over anhydrous $Na_2SO_4$ and concentrated under reduced pressure. Three batches (3×3 g) were done in parallel and the combined crude material was purified by column chromatography (100-200 mesh silica gel; 5% MeOH/DCM as eluent) to afford 8-bromo-9-difluoromethyl-7-fluoro-1,4,4-trimethyl-4,5-dihydro-[1,2,4]triazolo[4,3-a]quinoxaline (7.6 g, 66%) as a yellow solid.

Synthesis of 6-bromo-3,5,11,11-tetramethyl-8,9,10,11-tetrahydrofuro[3,2-f][1,2,4]triazolo[4,3-a]quinoxaline (Intermediate B-54)

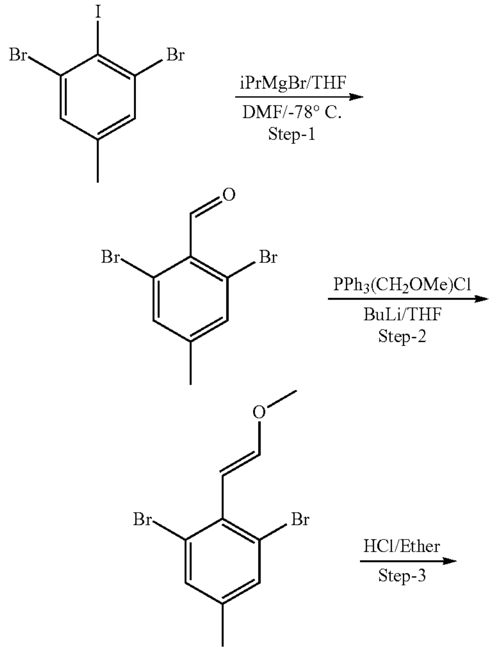

-continued

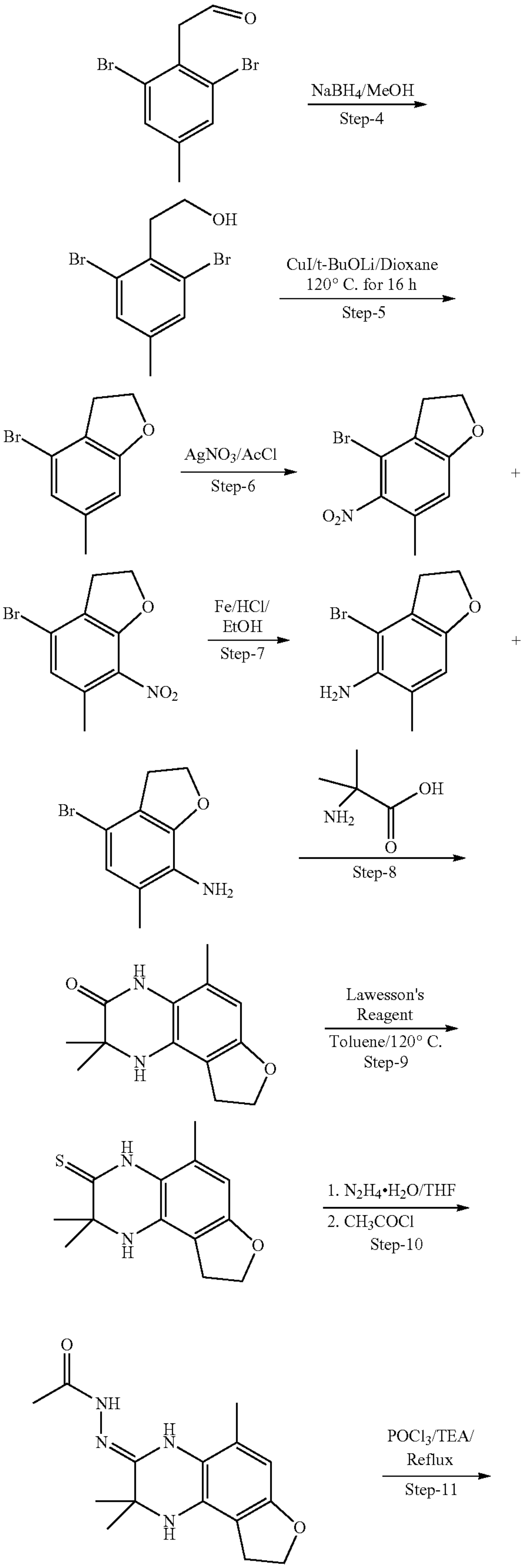

-continued

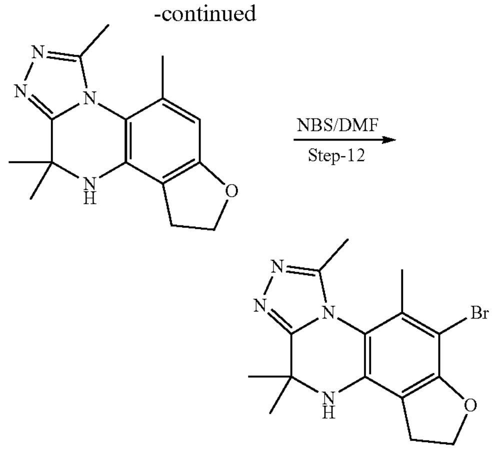

intermediate B-54

Step 1: A solution of 1,3-dibromo-2-iodo-5-methyl-benzene (140 g, 372.51 mmol) in dry THF (850 mL) was cooled to −78° C., and isopropyl magnesium bromide (279.4 mL, 558.76 mmol, 2 M in THF) was added to the reaction mixture dropwise at this temperature. The reaction mixture was stirred at room temperature for 1 h. Anhydrous DMF (95.58 ml, 1229.28 mmol) was added dropwise at −78° C. and the reaction mixture was stirred at RT for 10 min. After completion (monitored by TLC), the reaction was quenched with saturated ammonium chloride solution. The reaction mixture was diluted with diethyl ether and washed with water (2×500 mL), brine (500 mL), dried over anhydrous $Na_2SO_4$ and evaporated under reduced pressure to afford 2,6-dibromo-4-methyl-benzaldehyde (100 g crude) as a black solid, that was used crude in the next step.

Step 2: To a suspension of (methoxymethyl) triphenyl phosphonium chloride (140 g, 431.75 mmol) in anhydrous THF (700 mL) at 0° C. was added n-BuLi (179.89 mL, 431.75 mmol) dropwise and the reaction mixture was stirred for 30 min. 2,6-Dibromo-4-methyl-benzaldehyde (100 g, 359.79 mmol) was dissolved in THF (300 mL) and added to the reaction mixture dropwise at 0° C. The reaction mixture was stirred at RT for 16 h, and after completion (monitored by TLC), the reaction was quenched with saturated ammonium chloride solution. The reaction mixture was diluted with ethyl acetate and washed with water (2×500 mL), brine (500 mL), dried over anhydrous $Na_2SO_4$ and evaporated under reduced pressure. Crude was purified by column chromatography (100-200 mesh silica gel; elution with 2% EA-Hexane) to afford 1,3-dibromo-2-(2-methoxy-vinyl)-5-methyl-benzene (3) (37 g, 32.74% in two steps) as white solid.

Step 3: To a solution of 1,3-dibromo-2-(2-methoxy-vinyl)-5-methyl-benzene (37 g, 76.59 mmol) in diethyl ether (400 mL) was added conc. HCl (150 mL) dropwise at 0° C. and the reaction mixture was stirred at RT for 16 h. After completion (monitored by TLC), the reaction mixture was quenched with water (500 mL) followed by extraction with diethyl ether (2×350 mL). The combined organic layers were washed with water (300 mL) and brine (300 ml), dried over anhydrous $Na_2SO_4$ and evaporated under reduced pressure to afford (2,6-dibromo-4-methyl-phenyl)-acetaldehyde (34.6 g crude) as off-white solid.

Step 4: To a solution of (2,6-dibromo-4-methyl-phenyl)-acetaldehyde (34.6 g, 118.505 mmol) in MeOH (300 mL) at 0° C. was added sodium borohydride (8.966 g, 237.01 mmol) and the reaction mixture was stirred at RT for 1 h. After completion (monitored by TLC), the reaction mixture was diluted with water (400 mL) and extracted with ethyl acetate (3×500 mL). The combined organic layers were washed with water (300 mL) and brine (300 mL), dried over anhydrous $Na_2SO_4$ and evaporated under reduced pressure to yield the crude compound. The crude material was washed with hexane to afford 2-(2,6-dibromo-4-methyl-phenyl)-ethanol (33 g, crude) as a white solid.

Step 5: A solution of lithium tert-butoxide (26.96 g, 336.79 mmol) in 1,4-dioxane (160 mL) was stirred at RT for 30 minutes, and 2-(2,6-dibromo-4-methyl-phenyl)-ethanol (33 g, 112.25 mmol) was added. Then, the reaction mixture was degassed for 15 minutes followed by addition of CuI (2.136 μm, 11.215 mmol). After degassing once more, the reaction mixture was stirred for 16 h at 120° C. After completion (monitored by TLC), the reaction mixture was quenched with AcOH to pH=6-7, and extracted with DCM. The combined organic layers were washed with water (300 mL) and brine (300 mL), dried over anhydrous $Na_2SO_4$ and concentrated under reduced pressure. The crude material was purified by column chromatography (100-200 mesh silica gel; 1% Ethyl acetate in-Hexane) to afford 4-bromo-6-methyl-2,3-dihydro-benzofuran (20 g, 77.63% over three steps) as colorless liquid.

Step 6: To a stirred solution of 4-bromo-6-methyl-2,3-dihydro-benzofuran (20 g, 93.86 mmol) in ACN (200 mL) was added $AgNO_3$ (17.54 g, 103.25 mmol). Then AcCl (7.367 mL, 78.50 mmol) was added drop wise at 0° C. and the reaction mixture was stirred for 2 h at the same temperature. After completion (monitored by TLC), the reaction mixture was poured into ice water and extracted with ethyl acetate (3×100 mL). The combined organic layers were washed with brine (100 mL), dried over anhydrous $Na_2SO_4$ and evaporated under reduced pressure. The crude material was purified by column chromatography (100-200 mesh silica gel; 10% ethyl acetate/hexane) to afford 4-bromo-6-methyl-5-nitro-2,3-dihydro-benzofuran (20 g, 82.57%) as light yellow solid.

Step 7: To a stirred solution of 4-bromo-6-methyl-5-nitro-2,3-dihydro-benzofuran (20 g, 77.50 mmol) in a mixture of ethanol and water (1:1, 350 mL) were added conc. HCl (15.17 mL) and Fe powder (10.386 g, 186.00 mmol) at RT, and the reaction mixture was stirred at reflux for 3 h. After completion (monitored by TLC), the reaction mixture was quenched with saturated $NaHCO_3$ solution, diluted with ethyl acetate. And filtered over celite. The organic layer was separated, dried over $Na_2SO_4$ and concentrated under reduced pressure to afford 4-bromo-6-methyl-2,3-dihydro-benzofuran-5-ylamine (19 g, crude) as black solid.

Step 8: A suspension of 4-bromo-6-methyl-2,3-dihydro-benzofuran-5-ylamine (19 g, 83.30 mmol), 2-amino-2-methylpropanoic acid (17.179 g, 166.60 mmol), $K_3PO_4$ (35.36 g, 166.6 mmol) and cuprous chloride (0.824 g, 8.33 mmol) in dry DMSO (300 mL) was deoxygenated with argon for 20 min. The reaction mixture was then stirred at 140° C. for 16 h. After completion (monitored by TLC), the reaction mixture was diluted with ethyl acetate and filtered. The filtrate was partitioned between water and ethyl acetate, and the combined organic layers were washed with brine (200 mL), dried over anhydrous $Na_2SO_4$ and evaporated under reduced pressure. The crude material was purified by column chromatography (100-200 mesh silica gel; 50% ethyl acetate/hexane) to afford 5,8,8-trimethyl-1,2,8,9-tetrahydro-6H-3-oxa-6,9-diaza-cyclopenta[a]naphthalen-7-one (2.6 g 14.44% over two step) as black solid.

Step 9: To a solution of 5,8,8-trimethyl-1,2,8,9-tetrahydro-6H-3-oxa-6,9-diaza-cyclopenta[a]naphthalen-7-one (6 g, 25.83 mmol) in toluene (120 mL) was added Lawesson's reagent (15.67 g, 38.75 mmol) at RT and the reaction mixture was refluxed at 120° C. for 1 h. After completion (monitored by TLC), the reaction mixture was quenched with sat. $NaHCO_3$ solution (150 mL) and extracted with ethyl acetate (3×200 mL). The combined organic layers were washed with water (150 mL) and brine (150 mL), dried over anhydrous $Na_2SO_4$ and evaporated under reduced pressure. The crude material was purified by column chromatography (100-200 mesh silica gel; 2% MeOH-DCM) to afford 5,8,8-trimethyl-1,2,8,9-tetrahydro-6H-3-oxa-6,9-diaza-cyclopenta[a]naphthalene-7-thione (5.3 g, 82.6%) as yellow solid.

Step 10: To a stirring solution of 5,8,8-trimethyl-1,2,8,9-tetrahydro-6H-3-oxa-6,9-diaza-cyclopenta[a]naphthalene-7-thione (5.3 g, 21.34 mmol) in tetrahydrofuran (120 mL) was dropwise added hydrazine hydrate (3.12 mL, 64.02 mmol) at 0° C. and the reaction mixture was stirred at room temperature for 16 h. Triethyl amine (14.831 mL, 106.71 mmol) and acetyl chloride (4.55 mL, 64.02 mmol) were added dropwise at 0° C. and the reaction mixture was stirred for 2 h at room temperature. After completion (monitored by LCMS) the reaction mixture was diluted with water (50 mL) and extracted with 20% MeOH-DCM (5×500 mL). The combined organic layers were washed with brine (50 mL), dried over $Na_2SO_4$ and concentrated under reduced pressure. The crude material was washed with MTBE to afford acetic acid (5,8,8-trimethyl-1,2,8,9-tetrahydro-6H-3-oxa-6,9-diaza-cyclopenta[a]naphthalen-7-ylidene)-hydrazide (5.5 g, crude) as yellow solid.

Step 11: Acetic acid (5,8,8-trimethyl-1,2,8,9-tetrahydro-6H-3-oxa-6,9-diaza-cyclopenta[a]naphthalen-7-ylidene)-hydrazide (5 g, 17.34 mmol, crude) was cooled to −10° C., and $POCl_3$ (8.08 mL, 86.700 mmol) was added, followed by dropwise addition of triethyl amine (2.41 mL, 17.34 mmol). The reaction mixture was stirred at −10° C. for 10 min, 10 min at room temperature and finally for 1 h at reflux temperature (110° C.). After completion (monitored by LCMS), the reaction mixture was cooled to 0° C. and quenched with crushed ice in water (15 mL). The aqueous part was then basified (pH~10) by dropwise addition of cold aqueous ammonia solution. The resulting basic aqueous phase was then extracted with ethyl acetate (3×100 mL), and the combined organic layers were washed with brine (250 mL), dried over anhydrous $Na_2SO_4$ and concentrated under reduced pressure. The crude material was triturated with MTBE/Hexane/Ethyl acetate (4:8:1) to afford 3,4,10,10-tetramethyl-7,8,9,10-tetrahydro-6-oxa-1,2,3a,9-tetraaza-dicyclopenta[a,f]naphthalene (3.8 g crude) as off-white solid.

Step 12: To a stirred solution of 3,4,10,10-tetramethyl-7,8,9,10-tetrahydro-6-oxa-1,2,3a,9-tetraaza-dicyclopenta[a,f]naphthalene (3.3 g, 12.21 mmol) in DMF (40 mL) was added NBS (2.389 g, 13.43 mmol) portion wise at 0° C., and the resulting reaction mixture was stirred at room temperature for 4 h. After completion (monitored by LCMS), the reaction mixture was diluted with water (150 mL) and extracted with ethyl acetate (2×150 mL). The combined organic layers were washed with water (100 mL) and brine (100 mL), dried over anhydrous $Na_2SO_4$ and concentrated under reduced pressure. The crude material was triturated using MTBE/EtOAc/Heptane (4:1:5) to afford 6-bromo-3,5,11,11-tetramethyl-8,9,10,11-tetrahydrofuro[3,2-f][1,2,4]triazolo[4,3-a]quinoxaline (2.1 g) as off-white solid.

$^1$H-NMR (400 MHz, DMSO-$d_6$): δ=6.16 (s, 1H), 4.67-4.63 (t, 2H), 3.22-3.18 (t, 2H), 2.33 (s, 3H), 2.27 (s, 3H), 1.44 (bs, 6H).

Synthesis of 6-bromo-3,11,11-trimethyl-5-(trifluoromethyl)-8,9,10,11-tetrahydrofuro[3,2-f][1,2,4]triazolo[4,3-a]quinoxaline (Intermediate B-55)

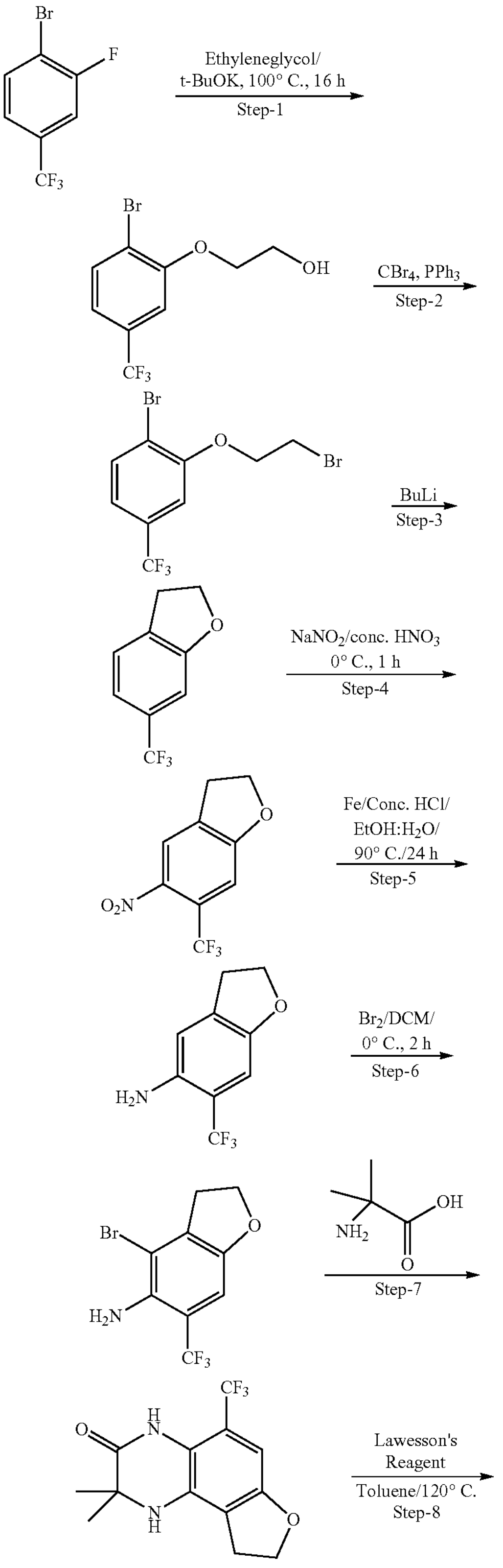

-continued

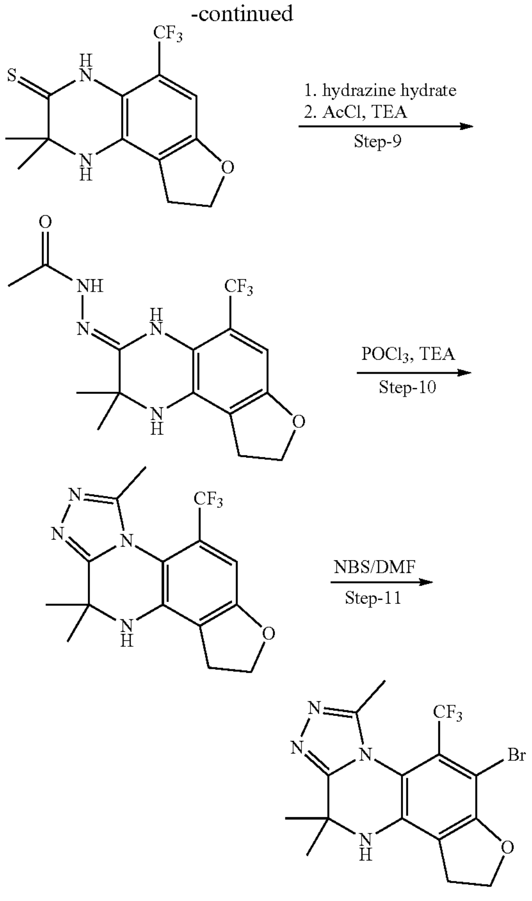

intermediate B-55

Step 1: To a stirred solution of 1-bromo-2-fluoro-4-trifluoromethyl-benzene (100 g, 0.41 mol) in ethylene glycol (1 L) was added NMP (100 mL) followed by portion wise addition of potassium tert-butoxide (161.6 g, 1.44 mol) at room temperature, and the resulting reaction mixture was stirred at 100° C. for 16 h. After completion (monitored by TLC), the reaction mixture was poured into ice water (2500 mL) and extracted with ethyl acetate (2×1250 mL). The combined organic layers were washed with water (2×750 mL) and brine (750 mL), dried over anhydrous $Na_2SO_4$ and evaporated under reduced pressure to afford 2-(2-bromo-5-trifluoromethyl-phenoxy)-ethanol (100 g, crude) as brown liquid.

Step 2: To a stirred solution of 2-(2-bromo-5-trifluoromethyl-phenoxy)-ethanol (100 g, 0.35 mol) in DCM (1.5 L) was added carbon tetrabromide (145.4 g, 0.43 mol) followed by triphenylphosphine (138 g, 0.52 mol) at 0° C., and the resulting reaction mixture was stirred at room temperature for 2 h. After completion (monitored by TLC), the reaction mixture was concentrated under reduced pressure and the obtained residue was purified by column chromatography (100-200 mesh silica gel; 5% ethyl acetate/hexane) to afford 1-bromo-2-(2-bromo-ethoxy)-4-trifluoromethyl-benzene (80 g, 56% over 2 steps) as colorless oil.

Step 3: To a stirred solution of 1-bromo-2-(2-bromo-ethoxy)-4-trifluoromethyl-benzene (80 g, 229.9 mmol) in THF (800 mL) was added n-BuLi (126.45 ml, 252.9 mmol, 2 M in hexane) dropwise at −78° C., and the resulting reaction mixture was stirred at −78° C. for 30 min. After completion (monitored by TLC), the reaction mixture was quenched with cold water and extracted with MTBE (2×500 mL). The combined organic layers were washed with water (2×450 mL) and brine (450 mL), dried over anhydrous $Na_2SO_4$ and evaporated under reduced pressure to afford 6-trifluoromethyl-2,3-dihydro-benzofuran (60 g, crude) as brown liquid.

Step 4: To a stirred solution of 6-trifluoromethyl-2,3-dihydro-benzofuran (60 g, 0.31 mol) in conc. $HNO_3$ (600 mL) was added $NaNO_2$ (44 g, 0.63 mol) portion wise at 0° C., and the resulting reaction mixture was stirred at 0° C. for 30 min. After completion (monitored by TLC), the reaction mixture was quenched with cold water (3.5 L) and extracted with ethyl acetate (2×1500 mL). The combined organic layers were washed with water (2×750 mL) and brine (750 mL), dried over anhydrous $Na_2SO_4$ and evaporated under reduced pressure. The obtained crude material was purified by column chromatography (100-200 mesh silica gel; 5% ethyl acetate/hexane) to afford 5-nitro-6-trifluoromethyl-2,3-dihydro-benzofuran (30 g, 55% over 2 steps) as off-white solid.

Step 5: To a stirred solution of 5-nitro-6-trifluoromethyl-2,3-dihydro-benzofuran (30 g, 0.128 mol) in an ethanol:water (1:1) mixture was added conc. HCl (10 mL) and Fe powder (17.95 g, 0.32 mol) at 0° C., and the resulting reaction mixture was stirred at 90° C. for 24 h. After completion (monitored by TLC), the reaction mixture was concentrated, the obtained residue was diluted with ethyl acetate and filtered. The filtrate was washed with saturated $NaHCO_3$ solution and brine, dried over anhydrous $Na_2SO_4$ and evaporated under reduced pressure. The crude material was purified by column chromatography (100-200 mesh silica gel; 10% ethyl acetate/hexane) to afford 6-trifluoromethyl-2,3-dihydro-benzofuran-5-ylamine (8 g, 30%) as off-white solid.

Step 6: To a solution of 6-trifluoromethyl-2,3-dihydro-benzofuran-5-ylamine (6.6 g, 0.0324 mol) in DCM (165 mL) was added a solution of $Br_2$ (1.74 mÖ, 0.034 mol) in DCM (33 mL) dropwise at 0° C., and the resulting reaction mixture was stirred at 0° C. for 2 h. After completion (monitored by TLC), the reaction mixture was diluted with water (200 mL) and extracted with DCM (2×150 mL). The combined organic layers were washed with water (2×150 mL) followed by a saturated solution of sodium thiosulfate (2×150 mL) and brine (150 mL), dried over anhydrous $Na_2SO_4$, and evaporated under reduced pressure. The obtained crude residue was purified by column chromatography (100-200 mesh silica gel; 10% ethyl acetate/hexane) to afford 4-bromo-6-trifluoromethyl-2,3-dihydro-benzofuran-5-ylamine (6.6 g, 72%) as brown liquid.

Step 7: To a stirred suspension of 4-bromo-6-trifluoromethyl-2,3-dihydro-benzofuran-5-ylamine (6.7 g, 0.02 mol) in dry DMSO (100 mL) was added 2-amino-2-methyl-propionic acid (4.88 g, 0.05 mol) followed by addition of $K_3PO_4$ (10.06 g, 0.05 mol) at room temperature, and the resulting reaction mixture was degassed with nitrogen for 30 minutes. Then cuprous chloride (234 mg, 0.002 mol) was added and the reaction mixture was heated at 140° C. for 16 h. After completion (monitored by TLC), the reaction mixture was cooled to room temperature and filtered over celite. The celite bed was washed with ethyl acetate (250 mL), and the resulting filtrate was poured into ice cold water (500 mL). After extraction with ethyl acetate (3×250 mL), the combined organic layers were washed with water (2×350 mL) and brine (250 mL), dried over anhydrous $Na_2SO_4$ and evaporated under reduced pressure. The crude material was purified by trituration using MTBE-Hexane to afford 8,8-dimethyl-5-trifluoromethyl-1,2,8,9-tetrahydro-6H-3-oxa-6,9-diaza-cyclopenta[a]naphthalen-7-one (4.3 g, 63%) as off-white solid.

Step 8: To a solution of 8,8-dimethyl-5-trifluoromethyl-1,2,8,9-tetrahydro-6H-3-oxa-6,9-diaza-cyclopenta[a]naphthalen-7-on] (4.3 g, 0.15 mol) in toluene (65 mL) was added Lawesson's reagent (9.1 g, 0.0225 mol) at RT and the reaction mixture was refluxed at 120° C. for 3 h. After completion (monitored by TLC), the reaction mixture was cooled to room temperature and poured into sat. $NaHCO_3$ solution (150 mL). The resulting aqueous phase was extracted with ethyl acetate (2×150 mL) and the combined organic layers were washed with brine (150 mL), dried over anhydrous $Na_2SO_4$ and evaporated under reduced pressure. The obtained crude residue was purified by column chromatography (100-200 mesh silica gel; 20% ethyl acetate/hexane) to afford 8,8-dimethyl-5-trifluoromethyl-1,2,8,9-tetrahydro-6H-3-oxa-6,9-diaza-cyclopenta[a]naphthalene-7-thione (4.4 g, 96.9%) as yellow solid.

Step 9: To a stirring solution of 8,8-dimethyl-5-trifluoromethyl-1,2,8,9-tetrahydro-6H-3-oxa-6,9-diaza-cyclopenta[a]naphthalene-7-thione (4.5 g, 0.015 mol) in tetrahydrofuran (112.5 mL) was added dropwise hydrazine hydrate (2.25 mL, 0.045 mol) at 0° C., and the reaction mixture was stirred at room temperature for 4 h. Triethyl amine (16.6 mL, 0.12 mol) and acetyl chloride (4.26 mL, 0.6 mol) were added dropwise at 0° C. and the reaction mixture was stirred for 16 h at room temperature. After completion (monitored by LCMS), the reaction mixture was diluted with water (150 mL) and extracted with 10% MeOH-DCM (2×250 mL). The combined organic layers were washed with brine (250 mL), dried over $Na_2SO_4$ and concentrated under reduced pressure to afford acetic acid (8,8-dimethyl-5-trifluoromethyl-1,2,8,9-tetrahydro-6H-3-oxa-6,9-diaza-cyclopenta[a]naphthalen-7-ylidene)-hydrazide (4.3 g, 84%) as an off-white solid.

Step 10: Acetic acid (8,8-dimethyl-5-trifluoromethyl-1,2,8,9-tetrahydro-6H-3-oxa-6,9-diaza-cyclopenta[a]naphthalen-7-ylidene)-hydrazide (4.3 g, 12.56 mmol) was taken up in a round bottom flask and then cooled to −10° C. Phosphoryl chloride (5.85 mL, 62.81 mmol) was then added dropwise to the compound followed by dropwise addition of triethyl amine (1.74 mL, 12.56 mmol). The reaction mixture was stirred at −10° C. for 10 min, 10 min at room temperature and finally under reflux conditions for 3 h. After completion (monitored by LCMS), the reaction mixture was cooled to 0° C. and quenched with crushed ice water (350 mL). The aqueous phase was then basified by dropwise addition of cold ammonium solution (25 mL), and the resulting basic aqueous phase was then extracted by ethyl acetate (3×150 mL). The combined organic layers were washed with brine (200 mL), dried over anhydrous $Na_2SO_4$ and concentrated under reduced pressure. The obtained crude residue was purified by trituration using MTBE to afford 3,10,10-trimethyl-4-trifluoromethyl-7,8,9,10-tetrahydro-6-oxa-1,2,3a,9-tetraaza-dicyclopenta[a,f]naphthalene (1.9 g, 47%) as off-white solid.

Step 11: To a solution of 3,10,10-trimethyl-4-trifluoromethyl-7,8,9,10-tetrahydro-6-oxa-1,2,3a,9-tetraaza-dicyclopenta[a,f]naphthalene (1.9 g, 5.86 mmol) in DMF (38 mL) was added NBS (1.14 g, 6.44 mmol) portion wise at −10° C., and the resulting reaction mixture was stirred at room temperature for 16 h. After completion (monitored by LCMS), the reaction mixture was diluted with water (250 mL) and extracted with ethyl acetate (2×150 mL). The combined organic layers were washed with water (2×150 mL) and brine (150 mL), dried over anhydrous $Na_2SO_4$ and concentrated under reduced pressure. The obtained crude residue was purified by column chromatography (100-200 mesh silica gel; 5% MeOH/DCM) to afford 6-bromo-3,11,11-trimethyl-5-(trifluoromethyl)-8,9,10,11-tetrahydrofuro[3,2-f][1,2,4]triazolo[4,3-a]quinoxaline (1.55 g, −65%) as off-white solid.

$^1$H-NMR (400 MHz, DMSO-$d_6$): δ=6.79 (s, 1H), 4.81-4.77 (m, 1H), 4.69-4.64 (m, 1H), 3.38-3.35 (m, 1H), 3.25-3.16 (m, 1H), 2.31 (s, 3H), 1.74 (s, 3H), 1.24 (s, 3H).

Synthesis of 6-bromo-5-fluoro-3,11,11-trimethyl-8,9,10,11-tetrahydrofuro[3,2-f][1,2,4]triazolo[4,3-a]quinoxaline (Intermediate B-56)

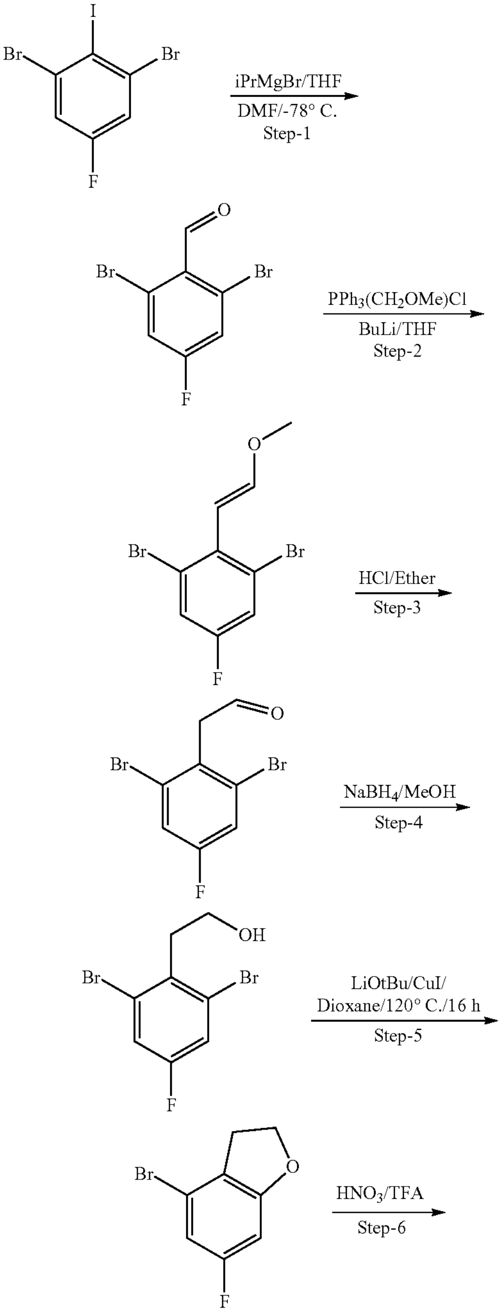

-continued

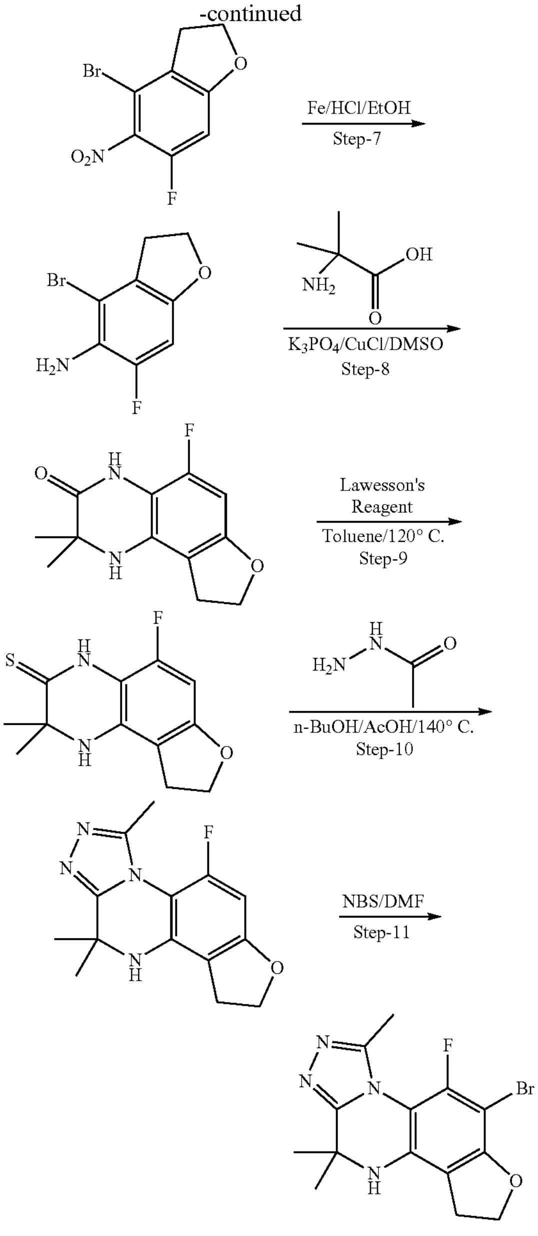

intermediate B-56

Step 1: A solution of 1,3-dibromo-5-fluoro-2-iodo-benzene (100 g, 263.30 mmol, 1 eq.) in dry THF (600 mL) was cooled to −78° C., isopropyl magnesium bromide (144.8 mL, 289.63 mmol, 1.3 eq., 2 M in THF) was added dropwise, and the reaction mixture was stirred at the same temperature for 1 h. Anhydrous DMF (54 mL, 868 mmol, 3.3 eq.) was added dropwise at −78° C. and the mixture was stirred at rt for 10 minutes. After completion, the reaction mixture was quenched with saturated ammonium chloride solution, diluted with diethyl ether and washed with water (2×500 mL) and brine (500 mL), dried over anhydrous $Na_2SO_4$ and evaporated under reduced pressure to afford 2,6-dibromo-4-fluoro-benzaldehyde (65 g, crude) as a brown solid.

Step 2: To a suspension of (methoxymethyl) triphenyl phosphonium chloride (179.0 g, 523.49 mmol, 1.2 eq.) in anhydrous THF (1000 mL) at 0° C. was added n-BuLi (130 mL, 327.18 mmol, 1.3 eq.) dropwise and the mixture was stirred for 30 min. 2,6-Dibromo-4-fluoro-benzaldehyde (130.0 g, 436.24 mmol, 1. Eq.) dissolved in THF (500 mL) was added dropwise at 0° C. and the mixture was stirred at rt for 16 h. After completion (monitored by TLC), the reaction was quenched with saturated ammonium chloride solution, diluted with ethyl acetate and washed with water (2×500 mL) and brine (500 mL), dried over anhydrous $Na_2SO_4$ and evaporated under reduced pressure. The crude residue was purified by column chromatography (100-200 mesh silica gel; Hexane) to afford 1,3-dibromo-5-fluoro-2 (2-methoxy-vinyl) benzene (50.0 g, crude) as a colorless liquid.

Step 3: To a solution of 1,3-dibromo-5-fluoro-2(2-methoxy-vinyl) benzene (44 g, 152.24 mmol, 1 eq.) in diethyl ether (500 mL) was added conc. HCl (200 mL) drop wise at 0° C. and the reaction mixture was stirred at rt for 16 h. After completion (monitored by TLC), the reaction mixture was quenched with sat. $NaHCO_3$ solution (500 mL), followed by extraction with diethyl ether (2×350 mL). The combined organic layers were washed with water (300 mL) and brine (300 ml), dried over anhydrous $Na_2SO_4$ and evaporated under reduced pressure to afford 2,6-dibromo-4-fluoro-phenyl)-acetaldehyde (36 g, crude) as a white solid.

Step 4: To a solution of 2,6-dibromo-4-fluoro-phenyl)-acetaldehyde (36 g, 116.18 mmol, 1 eq) in MeOH (400 mL) at 0° C. was added sodium borohydride (21.9 g, 62.84 mmol, 3 eq.) and the reaction mixture was stirred at rt for 1 h. After completion (monitored by TLC), the reaction mixture was diluted with water (400 mL) and extracted with ethyl acetate (3×500 mL). The combined organic layers were washed with water (300 mL) and brine (300 mL), dried over anhydrous $Na_2SO_4$ and evaporated under reduced pressure. The crude material was purified by column chromatography (100-200 mesh silica gel) to afford 2-(2,6-dibromo-4-fluoro-phenyl)-ethanol (24 g, 17% over four steps) as a white solid.

Step 5: Lithium tert-butoxide (18.53 g, 231.58 mmol, 3 eq) in 1,4-dioxane (250 mL) was stirred at rt for 30 minutes, and 2-(2,6-dibromo-4-fluoro-phenyl)-ethanol (23 g, 77.194 mmol, 1 eq.) was added to the reaction mixture. After addition of CuI (1.47 g, 4.77 mmol, 0.1 eq), the mixture was degassed for 20 minutes, and then stirred for 16 h at 120° C. After completion (monitored by TLC), the reaction mixture was concentrated, diluted with water (200 mL) and extracted with ethyl acetated (3×200 mL). The combined organic layers were washed with water (300 mL) and brine (300 mL), dried over anhydrous $Na_2SO_4$ and evaporated under reduced pressure. The crude material was purified by column chromatography (100-200 mesh silica gel; Hexane) to afford 4-bromo-6-fluoro-2,3-dihydro-benzofuran (13 g, 74%) as a colorless liquid Step 6: To an ice-cooled stirred solution of 4-bromo-6-fluoro-2,3-dihydro-benzofuran ((24.0 g, 103.47 mmol, 1 eq) in TFA (220 mL) was added conc. $HNO_3$ (9.77 g, 155.2 mmol, 1.5 eq) dropwise at 0° C. After 10 min, the ice bath was removed and the mixture was stirred at room temperature for 30 minutes. After completion (monitored by TLC), the reaction mixture was poured into ice water and extracted with ether (3×100 mL). The combined organic layers were washed with water (100 mL) and brine (100 mL), dried over anhydrous $Na_2SO_4$ and evaporated under reduced pressure. The crude residue was purified by column chromatography (100-200 mesh silica gel; 10% ethyl acetate/hexane) to afford 4-bromo-5-nitro-6-fluoro-2,3-dihydro-benzofuran (13 g, 48%) as an off-white solid.

Step 7: To a stirred solution of 4-bromo-5-nitro-6-fluoro-2,3-dihydro-benzofuran (16 g, 57.78 mmol, 1 eq) in an ethanol/water (1:1, 100 mL:100 mL) mixture were added conc. HCl (14 mL) and Fe powder (8 g, 144.5 mmol, 2.5 eq) at rt, and the reaction mixture was stirred at reflux for 3 h. After completion (monitored by TLC), the reaction mixture was filtered through a celite bed and washed with ether. The combined organic layers were concentrated at low temperature. The crude material was purified by column chromatography (100-200 mesh silica gel; 10% ethyl acetate/hexane) to afford 4-bromo-6-fluoro-2,3-dihydro-bezofuran-5-ylamine (10.5 g, 74%) as a dark brown solid.

Step 8: A suspension of 4-bromo-6-fluoro-2,3-dihydro-bezofuran-5-ylamine (16.0 g, 68.96 mmol, 1 eq.), 2-amino-2-methylpropanoic acid (14.23 g, 137.93 mmol, 2 eq.), $K_3PO_4$ (32.23 g, 151.71 mmol, 2.2 eq.) and cuprous chloride (0.682 g, 6.896 mmol, 0.1 eq.) in dry DMSO (200 mL) was deoxygenated with argon for 20 minutes, and the reaction mixture was stirred at 140° C. for 16 h. After completion, the reaction mixture was diluted with water and extracted with ethyl acetate. The combined organic layers were washed with water (2×250 mL) and brine (200 mL), dried over anhydrous $Na_2SO_4$ and concentrated under reduced pressure. The crude material was purified by column chromatography (100-200 mesh silica gel; 30% ethyl acetate/hexane) to afford 5-fluoro-7,7-dimethyl-1,6,7,9-tetrahydro-2H-3-oxa-6,9-diaza-cyclopenta(a)nephalene-8-one (10 g, 70%) as a brown solid.

Step 9: To a solution of 5-fluoro-7,7-dimethyl-1,6,7,9-tetrahydro-2H-3-oxa-6,9-diaza-cyclopenta(a)nephalene-8-one (10 g, 42.37 mmol, 1 eq.) in toluene (160 mL) was added Lawesson's reagent (25.74 g, 63.55 mmol, 1.5 eq.) at rt and the reaction mixture was refluxed at 120° C. for 1 h. After completion (monitored by TLC), the reaction mixture was quenched with saturated $NaHCO_3$ solution (150 mL) followed by extraction with ethyl acetate (3×200 mL). The combined organic layers were washed with water (150 mL) and brine (150 mL), dried over anhydrous $Na_2SO_4$ and concentrated under reduced pressure. The crude residue was purified by column chromatography (100-200 mesh silica gel; 50% DCM/hexane) to afford 5-fluoro-7,7-dimethyl-1,6,7,9-tetrahydro-2H-3-oxa-6,9-diaza-cyclopenta(a)nephalene-8-thione (8.5 g, 79%) as a yellow solid.

Step 10: To a solution of 5-fluoro-7,7-dimethyl-1,6,7,9-tetrahydro-2H-3-oxa-6,9-diaza-cyclopenta(a)nephalene-8-thione (10 g, 39.68 mmol, 1 eq.) in n-BuOH (210 mL) was added acetohydrazide (9.70 g, 130.95 mmol, 3.3 eq.), followed by acetic acid (42 mL) at rt, and the reaction mixture was stirred at 140° C. for 16 h. After completion (monitored by TLC), the reaction mixture was diluted with water (150 mL) and extracted with ethyl acetate (3×150 mL). The combined organic layers were washed with water (130 mL) and brine (130 mL), dried over anhydrous $Na_2SO_4$ and concentrated under reduced pressure. The crude material was purified by column chromatography (100-200 mesh silica gel; 5% MeOH-DCM) to afford 5-fluoro-3,11,11-trimethyl-8,9,10,11-tetrahydrofuro[3,2-f][1,2,4]triazolo[4,3-a]quinoxaline (8 g, 70%) as a white solid Step 11: To a stirred solution of 5-fluoro-3,11,11-trimethyl-8,9,10,11-tetrahydrofuro[3,2-f][1,2,4]triazolo[4,3-a]quinoxaline (3 g, 10.93 mmol, 1 eq.) in DMF (50 mL) at −10° C. was added N-bromosuccinimide (2.14 g, 12.03 mmol, 1.1 eq.) portion wise. The reaction mixture was then allowed to warm to rt and stirred for 1 h. After completion (monitored by TLC), the reaction mixture was diluted with water (50 mL) and extracted with ethyl acetate (3×100 mL). The combined organic layers were washed with water (100 mL) and brine (100 mL), dried over anhydrous $Na_2SO_4$ and evaporated under reduced pressure. The crude material was purified by column chromatography (100-200 mesh silica gel; 5% MeOH-DCM) to afford 6-bromo-5-fluoro-3,11,11-trimethyl-8,9,10,11-tetrahydrofuro[3,2-f][1,2,4]triazolo[4,3-a]quinoxaline (2.8 g, 72%) as an off-white solid.

$^1$H-NMR (400 MHz, DMSO-$d_6$): δ=6.47 (s, 1H), 4.738-4.698 (t, 2H), 3.22-3.16 (t, 2H), 2.44 (s, 3H) 1.48 (s, 6H)

Synthesis of 6-bromo-5-chloro-3,11,11-trimethyl-8,9,10,11-tetrahydrofuro[3,2-f][1,2,4]triazolo[4,3-a]quinoxaline (Intermediate B-57)

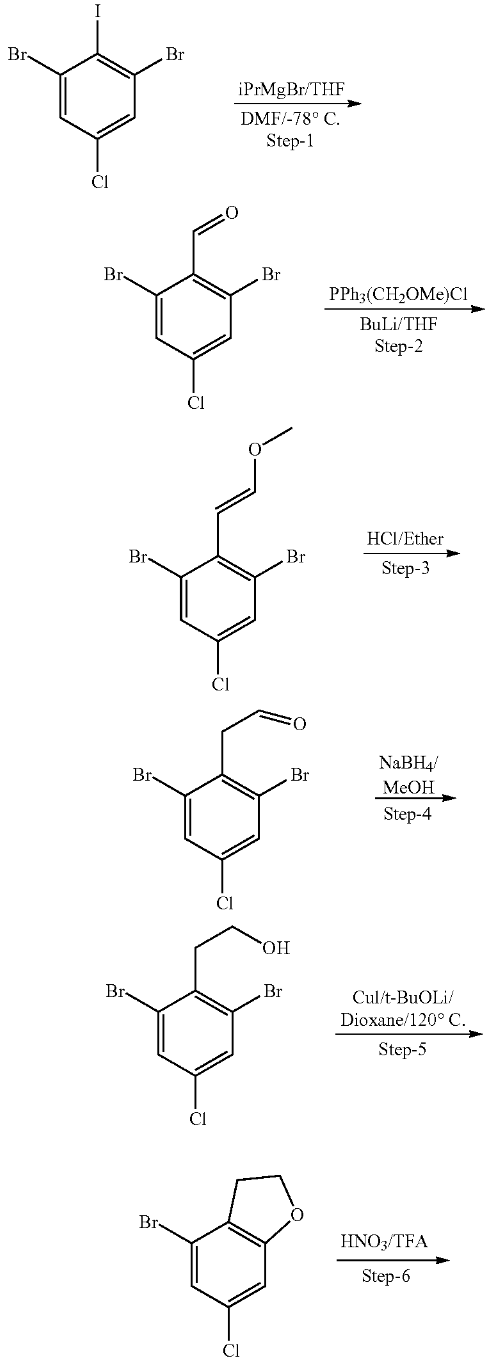

-continued

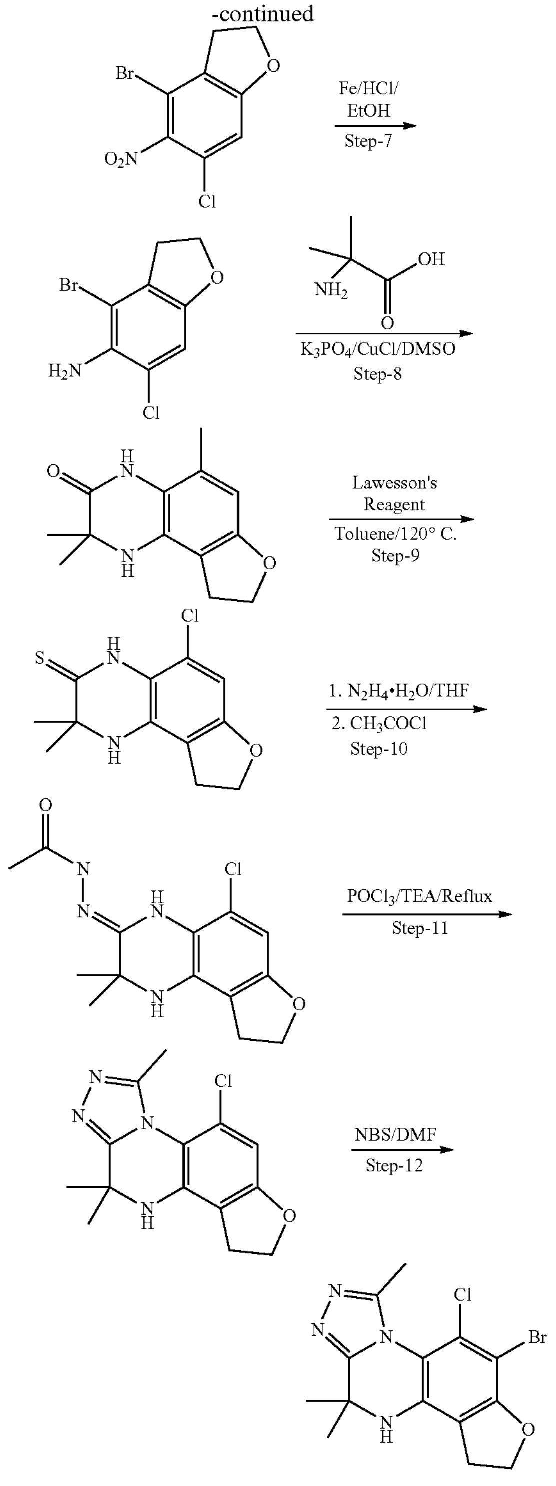

intermediate B-57

Step 1: A solution of 1,3-dibromo-5-chloro-2-iodo-benzene (25 g, 63.09 mmol, 1 eq.) in dry THF (150 mL) was cooled to −78° C., isopropyl magnesium bromide (41 mL, 82.01 mmol, 1.3 eq., 2 M in THF) was added to the reaction mixture dropwise, and the reaction mixture was stirred at the same temperature for 1 h. Anhydrous DMF (16 mL, 207.93 mmol, 3.3 eq.) was added dropwise to the reaction mixture at −78° C. and stirring was continued at RT for 10 min. After completion (monitored by TLC), the reaction was quenched with saturated ammonium chloride solution. The reaction mixture was diluted with diethyl ether and washed with water (2×500 mL) and brine (500 mL), dried over anhydrous $Na_2SO_4$ and evaporated under reduced pressure to afford 2,6-dibromo-chloro-benzaldehyde (17 g crude) as a brown solid.

Step 2: To a suspension of (methoxymethyl) triphenyl phosphonium chloride (112.0 g, 327.18 mmol, 1.3 eq.) in anhydrous THF (600 mL) at 0° C. was added n-BuLi (130 mL, 327.18 mmol, 1.3 eq.) dropwise and the mixture was stirred for 30 min. A solution of 2,6-dibromo-chloro-benzaldehyde (75.0 g, 251.67 mmol, 1. Eq.) in THF (300 mL) was then added to the reaction mixture dropwise at 0° C. and the mixture was stirred at RT for 16 h. After completion (monitored by TLC), the reaction was quenched with saturated ammonium chloride solution. The reaction mixture was diluted with ethyl acetate and washed with water (2×500 mL) and brine (500 mL), dried over anhydrous $Na_2SO_4$ and evaporated under reduced pressure. The crude residue was purified by column chromatography (100-200 mesh silica gel; Hexane) to afford 1,3-dibromo-5-chloro-2(2-methoxy-vinyl) benzene (32.0 g, 35% over two steps) as a colorless liquid.

Step 3: To a solution of 3-dibromo-5-chloro-2(2-methoxy-vinyl) benzene (25 g, 76.59 mmol, 1 eq.) in diethyl ether (250 mL) was added conc. HCl (110 mL) drop wise at 0° C. and the reaction mixture was stirred at RT for 16 h. After completion (monitored by TLC), the reaction mixture was quenched with sat. $NaHCO_3$ solution (500 mL) followed by extraction with diethyl ether (2×350 mL). The combined organic layers were washed with water (300 mL) and brine (300 mL), dried over anhydrous $Na_2SO_4$ and evaporated under reduced pressure to afford 2,6-dibromo-4-chloro-phenyl)-acetaldehyde (20 g crude) as a white solid.

Step 4: To a solution of 2,6-dibromo-4-chloro-phenyl)-acetaldehyde (50 g, 160.05 mmol, 1 eq.) in MeOH (450 mL) at 0° C. was added sodium borohydride (12.1 g, 320.11 mmol, 2.0 eq.) and the mixture was stirred at RT for 1 h. After completion (monitored by TLC), the reaction mixture was diluted with water (400 mL) and extracted with ethyl acetate (3×500 mL). The combined organic layers were washed with water (300 mL) and brine (300 mL), dried over anhydrous $Na_2SO_4$ and evaporated under reduced pressure. The crude material was purified by column chromatography (100-200 mesh silica gel) to afford 2-(2,6-dibromo-4-chloro-phenyl)-ethanol (36 g, 60% over two steps) as a white solid.

Step 5: A solution of lithium tert-butoxide (11.46 g, 143.13 mmol, 3 eq) in 1,4-dioxane (200 mL) was stirred at RT for 30 minutes. Subsequently, 2-(2,6-Dibromo-4-chloro-phenyl)-ethanol (5) (15 g, 47.71 mmol, 1 eq.) was added and the mixture was degassed for 15 minutes, followed by addition of CuI (911 mg, 4.77 mmol, 0.1 eq), degassing once more, and then the reaction mixture was stirred for 16 h at 120° C. After completion (monitored by TLC), the reaction mixture was concentrated, diluted with water (200 mL), and extracted with ethyl acetate (3×200 mL). The combined organic layers were washed with water (300 mL) and brine (300 mL), dried over anhydrous $Na_2SO_4$ and concentrated under reduced pressure. The crude residue was purified by column chromatography (100-200 mesh silica gel; Hexane) to afford 4-bromo-6-chloro-2,3-dihydro-benzofuran (8 g, 71%) as a colorless liquid.

Step 6: To an ice-cooled stirred solution of 4-bromo-6-chloro-2,3-dihydro-benzofuran (6.0 g, 25.69 mmol, 1 eq) in TFA (128 mL) was added conc. $HNO_3$ (2.5 mL, 38.55 mmol, 1.5 eq) dropwise at 0° C., and the reaction mixture was stirred for 10 minutes at 0° C. and then stirred at room temperature for 30 minutes. After completion (monitored by TLC), the reaction mixture was poured into ice water and extracted with ether (3×100 mL). The combined organic layers were washed with water (100 mL) and brine (100 mL), dried over anhydrous $Na_2SO_4$ and evaporated under reduced pressure. The crude residue was purified by column chromatography (100-200 mesh silica gel; 10% ethyl acetate/hexane) to afford 4-bromo-5-nitro-6-chloro-2,3-dihydro-benzofuran (3.5 g, 49%) as an off-white solid.

Step 7: To a stirred solution of 4-bromo-5-nitro-6-chloro-2,3-dihydro-benzofuran (3.5 g, 12.56 mmol, 1 eq) in an ethanol and water (1:1, 35 mL) mixture were added conc. HCl (2.5 mL) and Fe powder (3.5 g, 62.8 mmol, 1.2 eq) at rt, and the reaction mixture was stirred at reflux temperature for 3 h. After completion (monitored by TLC), the reaction mixture was filtered through a celite bed and washed with diethyl ether. The combined organic layers were concentrated at low temperature to afford 4-bromo-6-chloro-2,3-dihydro-benzofuran-5-ylamine (3 g, crude) as a dark brown solid.

Step 8: A suspension of 4-bromo-6-chloro-2,3-dihydro-benzofuran-5-ylamine (7.0 g, 28.16 mmol, 1 eq.), 2-amino-2-methylpropanoic acid (5.814 g, 56.34 mmol, 2 eq.), $K_3PO_4$ (13.15 g, 61.95 mmol, 2.2 eq.) and cuprous chloride (0.278 g, 2.81 mmol, 0.1 eq.) in dry DMSO (70 mL) was deoxygenated with argon for 20 min, and the reaction mixture was then stirred at 140° C. for 16 h. After completion, the reaction mixture was diluted with water and extracted with ethyl acetate. The combined organic layers were washed with water (2×250 mL) and brine (200 mL), dried over anhydrous $Na_2SO_4$ and evaporated under reduced pressure. The crude material was purified by column chromatography (100-200 mesh silica gel; 30% ethyl acetate/hexane) to afford 5-chloro-7,7-dimethyl-1,6,7,9-tetrahydro-2H-3-oxa-6,9-diaza-cyclopenta(a)nephalene-8-one (3 g, 44% over two steps) as a brown solid.

Step 9: To a solution of 5-chloro-7,7-dimethyl-1,6,7,9-tetrahydro-2H-3-oxa-6,9-diaza-cyclopenta(a)nephalene-8-one (4.8 g, 18.94 mmol, 1 eq.) in toluene (70 mL) was added Lawesson's reagent (11.53 g, 28.49 mmol, 1.5 eq.) at RT and the reaction mixture was refluxed at 120° C. for 1 h. After completion (monitored by TLC), the reaction mixture was quenched with sat. $NaHCO_3$ solution (150 mL) followed by extraction with ethyl acetate (3×200 mL). The combined organic layers were washed with water (150 mL) and brine (150 ml), dried over anhydrous $Na_2SO_4$ and evaporated under reduced pressure. The crude material was purified by column chromatography (100-200 mesh silica gel; 50% DCM/hexane) to afford 5-chloro-7,7-dimethyl-1,6,7,9-tetrahydro-2H-3-oxa-6,9-diaza-cyclopenta(a)nephalene-8-thione (4.4 g, 86.1%) as a yellow solid.

Step 10: To a stirring solution of 5-chloro-7,7-dimethyl-1,6,7,9-tetrahydro-2H-3-oxa-6,9-diaza-cyclopenta(a)nephalene-8-thione (4.0 g, 14.88 mmol, 1 eq) in tetrahydrofuran (80 mL) was added hydrazine hydrate (2.19 ml, 44.65 mmol, 3 eq) dropwise at 0° C., and the reaction mixture was stirred at room temperature for 16 h. Triethyl amine (12.45 mL, 89.28 mmol, 6 eq) and acetyl chloride (4.24 mL, 59.52 mmol, 4 eq) were then added dropwise at 0° C. and the reaction mixture was stirred for 2 h at room temperature. After completion (monitored by LCMS), the reaction mixture was diluted with water (50 mL) and extracted with 10% MeOH-DCM (5×500 mL). The combined organic layers were washed with brine (50 mL), dried over $Na_2SO_4$ and concentrated under reduced pressure to afford acetic acid 5-chloro-8,8-dimethyl-1,2,8,9-tetrahydro-6H-3-oxa-6,9-diaza-cyclopenta[a]naphthalen-(7Z)-ylidene]-hydrazide (4.3 g, crude) as a white solid.

Step 11: Acetic acid [5-chloro-8,8-dimethyl-1,2,8,9-tetrahydro-6H-3-oxa-6,9-diaza-cyclopenta[a]naphthalen-(7Z)-ylidene]-hydrazide (4 g, 12.98 mmol, crude) was cooled to −10° C., and phosphoryl chloride (6.1 mL) was added, followed by dropwise addition of triethyl amine (1.81 mL). The reaction mixture was stirred at −10° C. for 10 min, 10 min at room temperature and finally under reflux (110° C.) conditions for 1 h. After completion (monitored by LCMS), the reaction mixture was cooled to 0° C. and quenched with crushed ice water (15 mL). The aqueous fraction was then basified (pH~10) by dropwise addition of cold aqueous ammonia solution, and the resulting basic aqueous fraction was then extracted with ethyl acetate (3×100 mL). The combined organic layers were washed with brine (250 mL), dried over anhydrous $Na_2SO_4$ and concentrated under reduced pressure. The crude material was triturated with hexane to afford 4-chloro-3,10,10-trimethyl-7,8,9,10-tetrahydro-6-oxa-1,2,3a,9-tetraaza-dicyclopenta[a,f]naphthalene (2.5 g, crude) as a yellow solid.

Step 12: To a stirred solution of 4-chloro-3,10,10-trimethyl-7,8,9,10-tetrahydro-6-oxa-1,2,3a,9-tetraaza-dicyclopenta[a,f]naphthalene (2.5 g, 8.61 mmol) in DMF (40 mL) was added NBS (1.57 g, 8.87 mmol) portion wise at −10° C., and the resulting reaction mixture was stirred at room temperature for 1 h. After completion (monitored by LCMS), the reaction mixture was diluted with water (150 mL) and extracted with ethyl acetate (2×150 mL). The combined organic layers were washed with water (100 mL) and brine (100 mL), dried over anhydrous $Na_2SO_4$ and concentrated under reduced pressure. The crude residue was purified by column chromatography (100-200 mesh silica gel; 40-50% acetone/hexane) followed by trituration with MTBE to afford 6-bromo-5-chloro-3,11,11-trimethyl-8,9,10,11-tetrahydrofuro[3,2-f][1,2,4]triazolo[4,3-a]quinoxaline (2.2 g, 40% over three steps) as an off-white solid.

Synthesis of 8-bromo-6-ethyl-9-fluoro-1,4,4-trimethyl-4,5-dihydro-[1,2,4]triazolo[4,3-a]quinoxaline (Intermediate B-58)

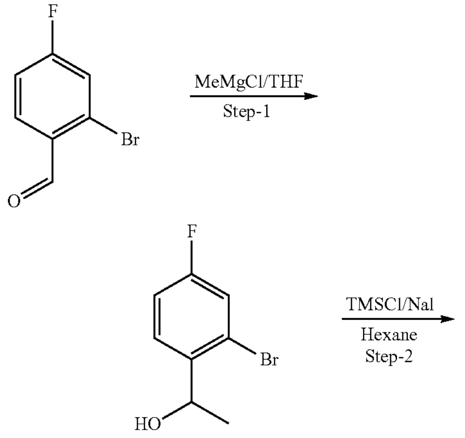

-continued

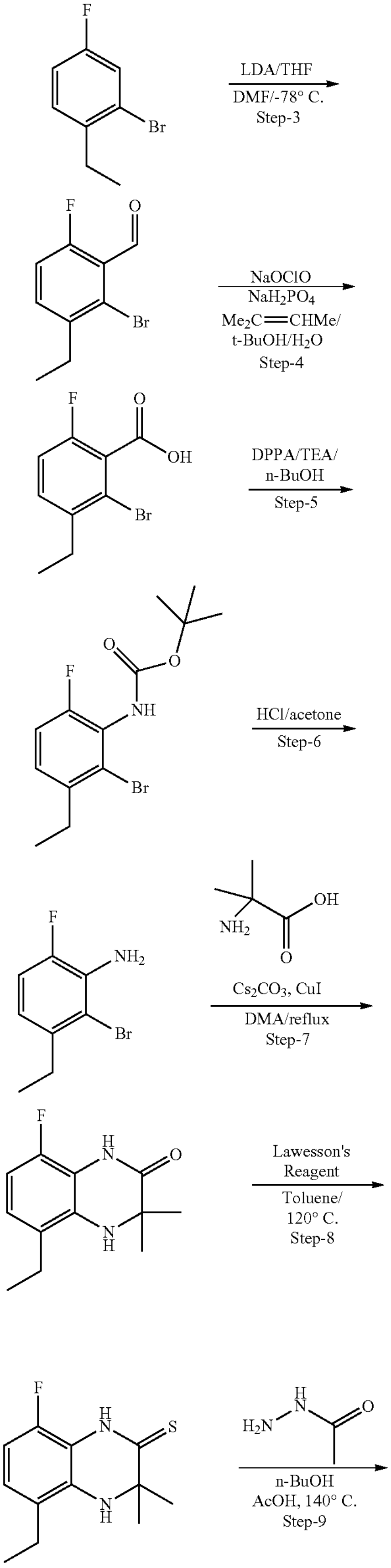

-continued

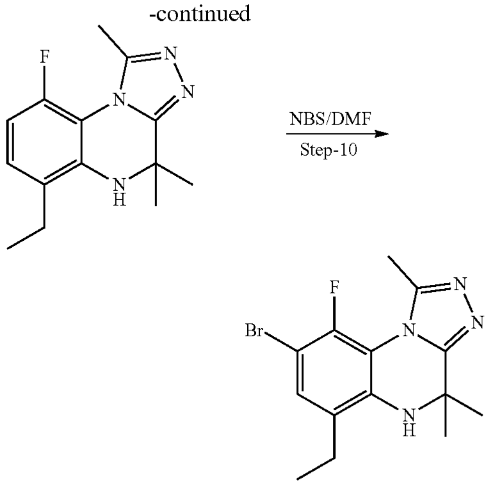

intermediate B-58

Step 1: MeMgBr solution in diethyl ether (9.3 mL, 3M, 27.09 mmol, 1.1 eq) was added dropwise to a stirred solution of 4-fluoro 2-bromo benzaldehyde (5.0 g, 24.63 mmol, 1 eq) in diethyl ether (75 mL) at −78° C. and the reaction mixture was stirred for 2 h at the same temperature. After completion (monitored by TLC), the reaction was quenched with sat. $NH_4Cl$ solution (100 mL) and the compound was extracted with ethyl acetate (2×100 mL), dried over $Na_2SO_4$ and concentrated under reduced pressure to afford 1-(2-bromo-4-fluoro-phenyl)-ethanol (4.8 g, 89.4%).

Step 2: To a stirred solution of 1-(2-bromo-4-fluoro-phenyl)-ethanol (2 g, 9.13 mmol, 1 eq) in hexane (10 mL), NaI (8.2 g, 54.7 mmol, 6 eq) was added, and the reaction mixture was stirred for 5 min at RT. Then, TMSCl (7 ml, 91.31 mmol, 10 eq) was added slowly and the reaction mixture was stirred for 18 h at RT. After completion (monitored by TLC) the reaction was quenched with sat. $NH_4Cl$ solution (50 mL) and the compound was extracted with ethyl acetate (50 mL×3), dried over $Na_2SO_4$ and concentrated under reduced pressure. The crude compound was purified by column chromatography (230-400 silica gel; hexane) to afford 2-bromo-1-ethyl-4-fluoro-benzene (1.3 g, 70%).

Step 3: To a solution of DIPA (16.0 ml, 115.74 mmol, 1.3 eq) in THF (160 mL), nBuLi (43.2 mL, 94.58 mmol, 1.2 eq) was added at −78° C. and the reaction mixture was stirred for 1 h at this temperature. Then, 2-bromo-1-ethyl-4-fluoro-benzene (16 g, 78.81 mmol, 1 eq) in THF (100 mL) was added at the same temperature. After stirring the reaction mixture for 30 min at the same temperature, DMF (16 mL) was added, and the reaction was continued for 30 min at RT. After completion (monitored by TLC), the reaction mixture was quenched with saturated $NH_4Cl$ solution (200 mL) and extracted with EA (3×200 mL). The combined organic layers were washed with water (200 mL) and brine (200 mL), dried over $Na_2SO_4$, filtered and concentrated under reduced pressure. The crude material was purified by column chromatography (100-200 silica gel; 2% ethyl acetate in hexane) as eluting solvent to afford 2-Bromo-3-ethyl-6-fluoro-benzaldehyde (10.0 g, 55%) as an off-white solid.

Step 4: $NaH_2PO_4$ (57 g, 367 mmol, 4.04 eq) and $NaClO_2$ (36 g, 403.57 mmol, 4.44 eq) were added to a solution of 2-bromo-3-ethyl-6-fluoro-benzaldehyde (21 g, 90.9 mmol, 1 eq) in a THF (275 mL):BuOH (275 mL):$H_2O$ (90 mL) mixture at 0° C. Then, 2-methyl-2-butene (42 ml, 403.57 mmol, 4.44 eq) was added, and the reaction mixture was stirred at RT for 1 h. After completion (monitor by TLC), the organic solvent was removed, and ethyl acetate (500 mL) was used for extraction. The combined organic layers were washed with water (500 mL) and brine (500 mL), dried over $Na_2SO_4$ and concentrated under reduced pressure. The crude residue was purified by trituration with pentane to afford 2-bromo-3-ethyl-6-fluoro-benzoic acid (13 g, 57.8%).

Step 5: Diphenyl phosphoryl azide (10 ml) was added to a stirred solution of 2-bromo-3-ethyl-6-fluoro-benzoic acid (5 g, 20.24 mmol, 1 eq), triethyl amine (5.6 mL, 40.48 mmol, 2 eq) and molecular sieves (10 g) in t-BuOH (200 mL), and the reaction mixture was refluxed for 16 h. After completion (monitored by TLC), the organic solvent was removed. The compound was extracted with ethyl acetate (200 mL), washed with 5% aqueous HCl (100 mL) and water (100 mL) and concentrated under reduced pressure. The crude residue was purified by column chromatography (100-200 silica gel; 5% ethyl acetate in hexane) to afford (2-Bromo-3-ethyl-6-fluoro-phenyl)-carbamic acid tert-butyl ester (2.4 g, 37.2%).

Step 6: To a cold stirred solution of (2-Bromo-3-ethyl-6-fluoro-phenyl)-carbamic acid tert-butyl ester (2.6 g, 8.17 mmol, 1 eq) in DCM (30 mL) was added TFA (5 mL), and the reaction mixture was stirred for 1 h at room temperature. After completion (monitored by TLC), the solvent was evaporated under reduced pressure. The crude material was purified by column chromatography (100-200 silica gel; 5% ethyl acetate in hexane) to afford 2-bromo-3-ethyl-6-fluoro-phenylamine (1.7 g, 95.4%).

Step 7: A suspension of 2-bromo-3-ethyl-6-fluoro-phenylamine (3.7 g, 16.96 mmol, 1 eq.), 2-aminoisobutyric acid (3.5 g, 33.93 mmol, 2 eq.), $K_3PO_4$ (7.2 g, 33.94 mmol, 2 eq.) and cuprous chloride (168 mg, 1.69 mmol, 0.1 eq.) in dry DMSO (55 mL) in a sealed tube was deoxygenated with argon for 20 min, and then the reaction mixture was stirred at 125° C. for 16 h. After completion, the reaction mixture was filtered through a celite bed and washed with ethyl acetate (100 mL). The combined organic layers were washed with water (3×100 mL) and brine (100 mL), dried over anhydrous $Na_2SO_4$ and evaporated under reduced pressure. The crude material was purified by column chromatography (230-400 mesh silica gel; 20% ethyl acetate/hexane) to afford 5-ethyl-8-fluoro-3,3-dimethyl-3,4-dihydro-1H-quinoxalin-2-one (2.8 g, 74.2%) as a brown solid.

Step 8: To a solution of 5-ethyl-8-fluoro-3,3-dimethyl-3,4-dihydro-1H-quinoxalin-2-one (3.8 g, 17.11 mmol, 1 eq.) in toluene (50 mL) was added Lawesson's reagent (10.4 g, 25.67 mmol, 1.5 eq.) at RT and the reaction mixture was refluxed at 120° C. for 1 h. After completion (monitored by TLC), the reaction mixture was quenched with sat. $NaHCO_3$ solution (100 mL), followed by extraction with ethyl acetate (2×100 mL). The combined organic layers were washed with water (100 mL) and brine (100 mL), dried over anhydrous $Na_2SO_4$ and evaporated under reduced pressure. The crude residue was purified by column chromatography (230-400 mesh silica gel; 20% ethyl acetate/hexane) to afford 5-ethyl-8-fluoro-3,3-dimethyl-3,4-dihydro-1H-quinoxaline-2-thione (3.6 g, 88%) as a yellow solid.

Step 9: To a solution of 5-ethyl-8-fluoro-3,3-dimethyl-3,4-dihydro-1H-quinoxaline-2-thione (3.4 g, 14.28 mmol, 1 eq) in n-BuOH (170 mL) was added propionic acid hydrazide (3.48 g, 47.14 mmol, 3.3 eq), followed by addition of acetic acid (17 mL) and the reaction mixture was stirred at 140° C. for 16 h. After completion (monitored by TLC), the reaction mixture was diluted with water (100 mL) and extracted with ethyl acetate (2×100 mL). The combined organic layers were washed with water (100 mL) and brine (100 mL), dried over anhydrous $Na_2SO_4$ and evaporated under reduced pressure. The crude material was purified by column chromatography (5% MeOHl/DCM) to afford 6-ethyl-9-fluoro-1,4,4-trimethyl-4,5-dihydro-[1,2,4]triazolo[4,3-a]quinoxaline (2.5 g, 67.25%) as an off-white solid.

Step 10: A stirred solution of 6-ethyl-9-fluoro-1,4,4-trimethyl-4,5-dihydro-[1,2,4]triazolo[4,3-a]quinoxaline (2.7 g, 10.38 mmol, 1 eq) in DMF (30 mL) at 0° C. is treated portion wise over 10 min with solid N-bromosuccinimide (1.94 g, 10.90 mmol, 1.05 eq). Then, the reaction mixture is allowed to warm to RT and stirred for 1 h. After completion (monitored by LCMS), the reaction mixture is diluted with ethyl acetate (100 mL) the and organic fraction is washed with water (5×100 mL) and brine (100 mL), dried over anhydrous $Na_2SO_4$ and evaporated under reduced pressure. The crude residue was purified by column chromatography (230-400 silica; 1.5% MeOH in DCM) to afford 8-bromo-6-ethyl-9-fluoro-1,4,4-trimethyl-4,5-dihydro-[1,2,4]triazolo[4,3-a]quinoxaline (2.7 g, 76.68%) as an off-white solid.

Synthesis of 8-bromo-1,4,4,6-tetramethyl-9-(trifluoromethyl)-4,5-dihydro-[1,2,4]triazolo[4,3-a]quinoxaline (Intermediate B-59)

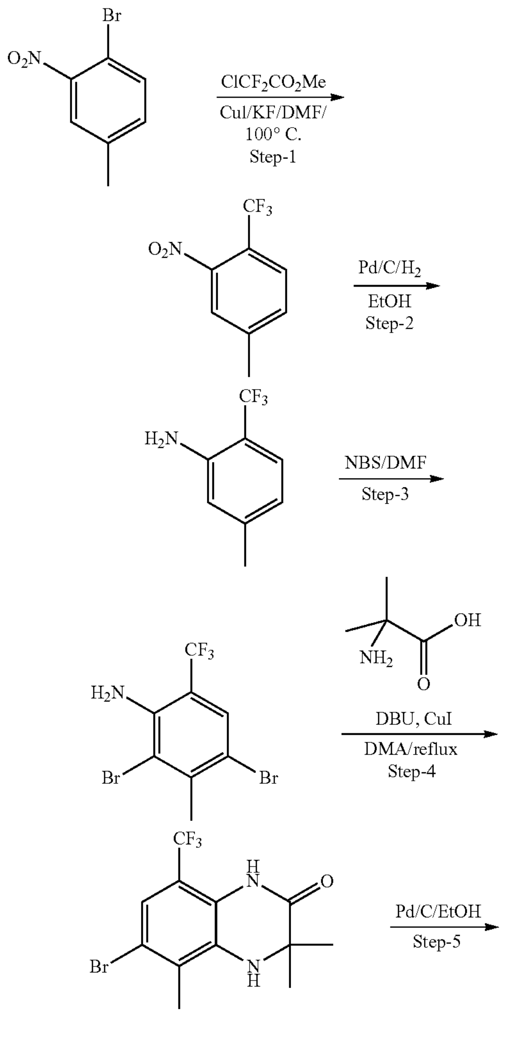

-continued

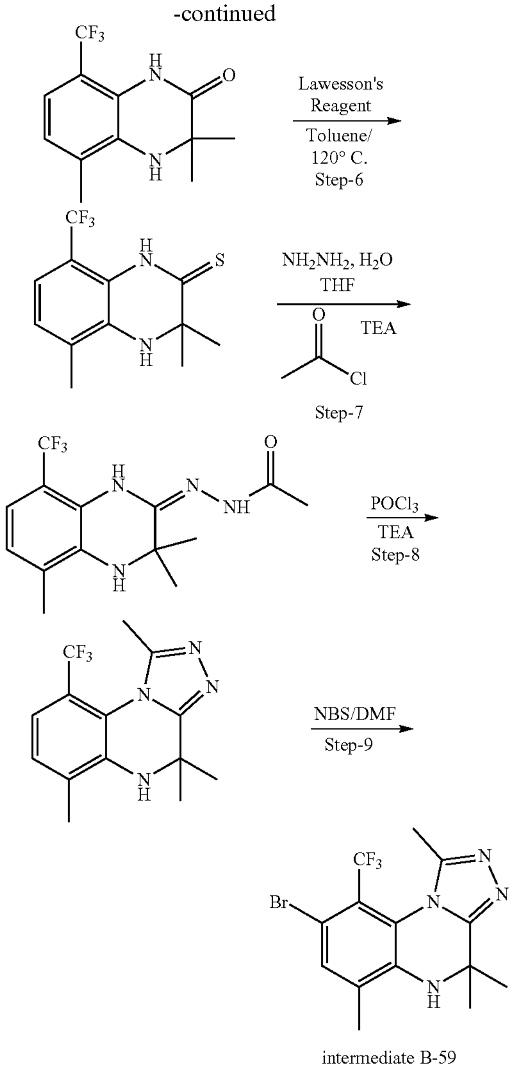

intermediate B-59

Step 1: A stirring suspension of 1-bromo-4-methyl-2-nitrobenzene (3.0 g, 13.88 mmol, 1 eq), methyl 2-chloro-2,2-difluoroacetate (4.01 g, 27.7 mmol, 2 eq) and potassium fluoride (0.966 g, 16.65 mmol, 1.2 eq) in dimethylformamide (12.5 mL) was deoxygenated with argon gas for 10 min. CuI (2.76 g, 13.88 mmol, 1 eq) was added to the reaction mixture, which was again deoxygenated with argon for 10 min, and then the reaction mixture was stirred for 48 h at 110° C. The reaction mixture was cooled to room temperature and diluted with citric acid solution (50 mL). The aqueous fraction was extracted with ethyl acetate (3×150 mL) and the combined organic layers were washed with water (3×50 mL) and brine (50 mL), dried over anhydrous $Na_2SO_4$, and concentrated under reduced pressure. The crude material. Was purified by column chromatography (230-400 mesh silica gel; 20% ethyl acetate/hexane) to afford 4-methyl-2-nitro-1-(trifluoromethyl)benzene (1.0 g, 35.14%) as a light brown liquid.

Step 2: A stirring solution of 4-methyl-2-nitro-1-(trifluoromethyl)benzene (2.5 g, 12.2 mmol, 1 eq) in ethanol (250 mL) was deoxygenated with argon gas for 10 min. Pd/C (0.5 g) was then added to the solution under argon atmosphere and the reaction mixture was again deoxygenated by argon for 10 min. After stirring for 2 h at room temperature under hydrogen atmosphere, the reaction mixture was filtered through a celite bed and washed with ethanol (100 mL). The filtrate was concentrated under reduced pressure to obtain the 5-methyl-2-(trifluoromethyl)aniline (1.5 g, 70.25%) as a colorless liquid.

Step 3: A stirred solution of 5-methyl-2-(trifluoromethyl)aniline (7.0 g, 40 mmol, 1 eq) in DMF (200 mL) at 0° C. was treated portion wise over 10 min with solid N-bromosuccinimide (15.66 g, 88 mmol, 2.2 eq). The reaction mixture was allowed to warm to RT and stirred for 1.5 h. After completion (monitored by LCMS), the reaction mixture was diluted with ethyl acetate (1000 mL) and the organic layer was washed with water (5×200 mL) and brine (200 mL), dried over anhydrous $Na_2SO_4$ and evaporated under reduced pressure to afford 2,4-dibromo-3-methyl-6-(trifluoromethyl)aniline (10.4 g, 78%) as a brown solid.

Step 4: A solution of 2,4-dibromo-3-methyl-6-(trifluoromethyl)aniline (6.0 g, 18 mmol, 1 eq), 2-aminoisobutyric acid (3.71 g, 36 mmol, 2 eq) and DBU (15.92 g, 49 mmol, 2 eq) in dry DMA (90 mL) in a sealed tube was deoxygenated with argon for 10 min. Cuprous iodide (0.358 g, 1.8 mmol, 0.1 eq) was then added to the solution, which was again deoxygenated with argon for 10 min, and the reaction mixture was stirred at 140° C. for 16 h. After completion, the reaction mixture was cooled to room temperature, diluted with ethyl acetate (400 mL), washed with water (4×100 ml) and brine (100 ml), dried over anhydrous $Na_2SO_4$ and evaporated under reduced pressure. The crude material was purified by column chromatography (230-400 mesh silica gel; 20% ethyl acetate/hexane) to afford 6-bromo-3,3,5-trimethyl-8-(trifluoromethyl)-1,2,3,4-tetrahydroquinoxalin-2-one (2.2 g, 36.26%) as a light brown solid.

Step 5: A stirring solution of 6-bromo-3,3,5-trimethyl-8-(trifluoromethyl)-1,2,3,4-tetrahydroquinoxalin-2-one (2.5 g, 12.2 mmol, 1 eq) in ethanol (250 mL) was deoxygenated with argon gas for 10 min. Pd/C (0.5 g) was added under argon atmosphere to the solution which was again deoxygenated with argon for 10 min, and then, the reaction mixture was stirred for 2 h at room temperature under hydrogen atmosphere. The reaction mixture was filtered through a celite bed and washed with ethanol (100 mL). The filtrate was concentrated under reduced pressure to yield 3,3,5-trimethyl-8-(trifluoromethyl)-1,2,3,4-tetrahydroquinoxalin-2-one (1.5 g, 70.25%) as a colorless liquid.

Step 6: To a solution of 3,3,5-trimethyl-8-(trifluoromethyl)-1,2,3,4-tetrahydroquinoxalin-2-one (1.6 g, 6.2 mmol, 1 eq.) in toluene (50 mL) was added Lawesson's reagent (3.7 g, 9.3 mmol, 1.5 eq.) at RT and the reaction mixture was refluxed at 120° C. for 40 min. After completion (monitored by TLC), the reaction mixture was quenched with sat. $NaHCO_3$ solution (50 mL) followed by extraction with ethyl acetate (2×50 mL). The combined organic layers were washed with water (50 mL) and brine (50 mL), dried over anhydrous $Na_2SO_4$ and evaporated under reduced pressure. The crude material was purified by column chromatography (230-400 mesh silica gel; 20% ethyl acetate/hexane) to afford 3,3,5-trimethyl-8-(trifluoromethyl)-1,2,3,4-tetrahydroquinoxaline-2-thione (1.4 g, 82.4%) as a yellow solid.

Step 7: To a stirring solution of 3,3,5-trimethyl-8-(trifluoromethyl)-1,2,3,4-tetrahydroquinoxaline-2-thione (1.25 g, 4.58 mmol, 1 eq) in tetrahydrofuran (25 mL) was dropwise added hydrazine hydrate (1.1 mL, 22.78 mmol, 5 eq) at 0° C., and the reaction mixture was stirred for 16 h at room temperature. Triethyl amine (3.1 mL, 22.78 mmol, 5 eq) was added and the reaction mixture was stirred for another 10 min. Acetyl chloride (1.07 g, 13.65 mmol, 3 eq) was then added very slowly at 0° C. and the reaction mixture was stirred for 2 h at room temperature. The reaction mixture was diluted with water (50 mL) and extracted with dichloromethane (5×50 mL). The combined organic layers were washed with brine (50 ml), dried over $Na_2SO_4$ and concentrated under reduced pressure. The crude material was purified by washing with diethyl ether to afford N'-[(2E)-3,3,5-trimethyl-8-(trifluoromethyl)-1,2,3,4-tetrahydroquinoxalin-2-ylidene]acetohydrazide (1.4 g, 97.3%) as an off-white solid.

Step 8: N'-[(2E)-3,3,5-trimethyl-8-(trifluoromethyl)-1,2,3,4-tetrahydroquinoxalin-2-ylidene]acetohydrazide (1.4 g, 4.458 mmol, 1 eq) was cooled to −10° C., and phosphorus oxychloride (4.27 mL, 44.58 mmol, 10 eq) was added dropwise, followed by dropwise addition of triethyl amine (0.606 mL, 4.46 mmol, 1 eq), and the reaction mixture was stirred at −10° C. for 10 min, 10 min at room temperature and under reflux conditions for 2 h. Then, the reaction mixture was cooled to 0° C. and drop wise added into crushed ice with constant stirring. To this aqueous fraction cold ammonium solution (50 mL) was slowly added, followed by extraction with dichloromethane (2×50 mL). The combined organic layers were washed with brine (50 mL), dried over anhydrous $Na_2SO_4$, and concentrated under reduced pressure. The crude material was purified by column chromatography (230-400 mesh silica gel; 5% methanol/dichloromethane) to afford 1,4,4,6-tetramethyl-9-(trifluoromethyl)-4H,5H-[1,2,4]triazolo[4,3-a]quinoxaline (0.6 g, 45.46%) as a light yellow solid.

Step 9: A stirred solution of 1,4,4,6-tetramethyl-9-(trifluoromethyl)-4H,5H-[1,2,4]triazolo[4,3-a]quinoxaline (0.6 g, 2.02 mmol, 1 eq) in DMF (20 mÖ) at −10° C. was treated portion wise over 10 min with solid N-bromosuccinimide (0.36 g, 2.02 mmol, 1 eq), and then the reaction mixture was allowed to warm to RT and stirred for 1.5 h. After completion (monitored by LCMS), the reaction mixture was diluted with ethyl acetate (150 mL) and the organic layer was washed with water (5×30 mL) and brine (30 mL), dried over anhydrous $Na_2SO_4$ and evaporated under reduced pressure. The crude residue was purified by column chromatography (230-400 mesh silica gel; 5% MeOH/DCM) to afford 8-bromo-1,4,4,6-tetramethyl-9-(trifluoromethyl)-4,5-dihydro-[1,2,4]triazolo[4,3-a]quinoxaline (0.5 g, 66%) as an off-white solid.

Synthesis of 8-bromo-9-fluoro-1,4,4,6-tetramethyl-4,5-dihydro-[1,2,4]triazolo[4,3-a]quinoxaline (Intermediate B-60)

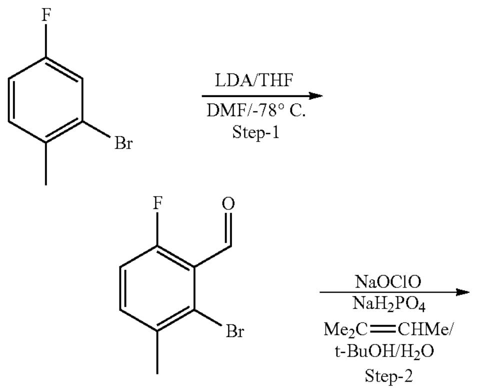

-continued

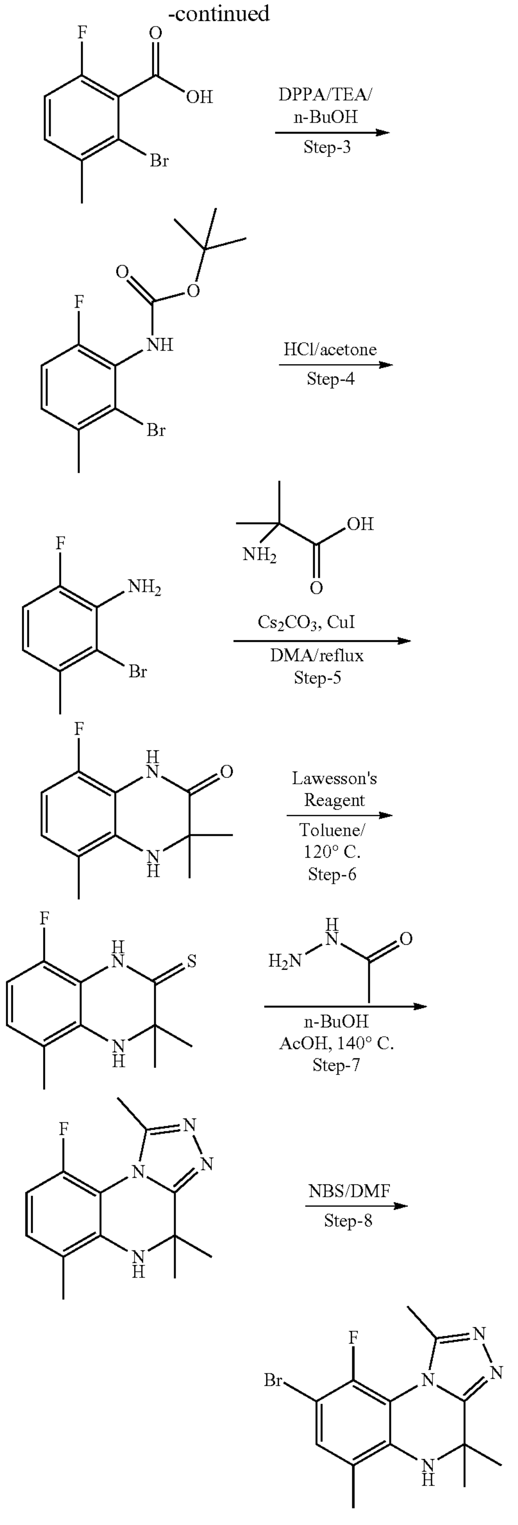

intermediate B-60

Step 1: To a stirred solution of DIPA (90.0 mL, 57.08 mol, 1.2 eq) in THF (900 mL), n-BuLi (260 mL, 52.33 mol, 1.1 eq) was added at −78° C. and the reaction was stirred for 1 h at this temperature Then, 2-bromo-4-fluoro-1-methylbenzene (90 g, 47.58 mol, 1 eq) in THF was added at the same temperature. After stirring the reaction mixture for 30 min at the same temperature, DMF (90 mL, 95.14 mol, 2 eq)

was added, and the reaction was continued for 30 min at RT. After completion (monitored by TLC), the reaction mixture was quenched with saturated $NH_4Cl$ solution (500 mL) and extracted with EA (3×500 mL). The combined organic layers were washed with water (500 mL) and brine (500 mL), dried over $Na_2SO_4$, filtered and concentrated under reduced pressure. The crude material was purified by column chromatography (100-200 silica gel; 2% ethyl acetate in hexane) to afford 2-bromo-6-fluoro-3-methyl-benzaldehyde (71 g, 68.66%) as an off-white solid.

Step 2: $NaH_2PO_4$ (220 g, 1.42 mol, 4.04 eq) and $NaClO_2$ (140 g, 1.55 mol, 4.44 eq) were added to 2-bromo-6-fluoro-3-methyl-benzaldehyde (76 g, 0.35 mol, 1 eq) in a THF (1000 mL):BuOH (1000 mL):$H_2O$ (300 mL) mixture at 0° C. Then, 2-methyl-2-butene (152 mL, 1.55 mol, 4.44 eq) was added and the reaction mixture was stirred at RT for 1 h. After completion (monitored by TLC), the organic solvent was removed, the residue was diluted with ethyl acetate (2000 mL), washed with water (1000 mL) and brine (1000 mL), dried over $Na^2SO_4$ and concentrated under reduced pressure. The compound was purified by trituration with pentane to afford 2-bromo-6-fluoro-3-methyl-benzoic acid (30 g, 37%).

Step 3: Diphenyl phosphoryl azide (50 mL) was added to a stirred solution of 2-bromo-6-fluoro-3-methyl-benzoic acid (30 g, 128.75 mmol, 1 eq) in t-BuOH (600 mL), triethyl amine (36 ml, 257.51 mmol, 2 eq) and molecular sieves (60 g) and the reaction mixture was refluxed for 16 h. After completion (monitored by TLC), the organic solvent was removed. The residue was diluted with ethyl acetate (500 mL), washed with 5% aqueous HCl (200 mL) and water (200 mL), and concentrated under reduced pressure. The compound was purified by column chromatography (100-200 silica gel; 2% ethyl acetate in hexane) to afford (2-bromo-6-fluoro-3-methyl-phenyl)-carbamic acid tert-butyl ester (16 g, 41%).

Step 4: To a cold stirred solution of (2-bromo-6-fluoro-3-methyl-phenyl)-carbamic acid tert-butyl ester (140 mg, 0.46 mmol, 1 eq) in DCM (8 mL), TFA (2 mL) was added and the reaction mixture was stirred for 1 h at room temperature. After completion (monitored by TLC), the organic solvent was evaporated under reduced pressure to obtain crude 2-bromo-6-fluoro-3-methyl-phenylamine (91 mg, 97%) which was used for the next step without any purification.

Step 5: A suspension of 2-bromo-6-fluoro-3-methyl-phenylamine (5.7 g, 27.93 mmol, 1 eq.), 2-aminoisobutyric acid (5.76 g, 55.87 mmol, 2 eq.), $K_3PO_4$ (11.86 g, 55.87 mmol, 2 eq.) and cuprous chloride (0.277 g, 2.57 mmol, 0.1 eq.) in dry DMSO (86 mL) in a sealed tube was deoxygenated with argon for 20 min, and the reaction mixture was stirred at 125° C. for 16 h. After completion (monitored by TLC), the reaction mixture was filtered through a celite bed and washed with ethyl acetate (100 mL). The organic fraction was washed with water (3×100 mL) and brine (100 mL), dried over anhydrous $Na_2SO_4$ and evaporated under reduced pressure. The crude residue was purified by column chromatography (230-400 mesh silica gel; 20% ethyl acetate/hexane) to afford 8-fluoro-3,3,5-trimethyl-3,4-dihydro-1H-quinoxalin-2-one (3.2 g, 55%) as a brown solid.

Step 6: To a solution of 8-fluoro-3,3,5-trimethyl-3,4-dihydro-1H-quinoxalin-2-one (2.4 g, 11.53 mmol, 1 eq.) in toluene (30 mL) was added Lawesson's reagent (7.0 g, 17.3 mmol, 1.5 eq.) at RT and the reaction mixture was refluxed at 120° C. for 1 h. After completion (monitored by TLC), the reaction mixture was quenched with sat. $NaHCO_3$ solution (100 mL), followed by extraction with ethyl acetate (2×100 mL). The combined organic layers were washed with water (100 mL) and brine (100 mL), dried over anhydrous $Na_2SO_4$ and evaporated under reduced pressure. The crude material was purified by column chromatography (230-400 mesh silica gel; 10% ethyl acetate in hexane) to afford 8-fluoro-3,3,5-trimethyl-3,4-dihydro-1H-quinoxaline-2-thione (2.2 g, 85%) as a yellow solid.

Step 7: To a solution of 8-fluoro-3,3,5-trimethyl-3,4-dihydro-1H-quinoxaline-2-thione (2.0 g, 8.92 mmol, 1 eq) in n-BuOH (100 mL) was added propionic acid hydrazide (2.18 g, 7.23 mmol, 3.3 eq), followed by addition of acetic acid (10 mL) and then the reaction mixture was stirred at 140° C. for 16 h. After completion (monitored by TLC), the reaction mixture was diluted with water (30 mL) and extracted with ethyl acetate (2×50 mL). The combined organic layers were washed with water (50 mL) and brine (50 mL), dried over anhydrous $Na_2SO_4$ and evaporated under reduced pressure. The crude residue was purified by column chromatography (230-400 silica gel; 1.5% MeOH in DCM) to afford 9-fluoro-1,4,4,6-tetramethyl-4,5-dihydro-[1,2,4]triazolo[4,3-a]quinoxaline (1.3 g, 59%) as an off-white solid.

Step 8: A stirred solution of 9-fluoro-1,4,4,6-tetramethyl-4,5-dihydro-[1,2,4]triazolo[4,3-a]quinoxaline (1.35 g, 5.48 mmol, 1 eq) in DMF (20 mL) at 0° C. was treated portion wise over 10 min with solid N-bromosuccinimide (1.03 g, 5.76 mmol, 1.05 eq), the reaction mixture was allowed to warm to RT and stirred for 30 min. After completion (monitored by LCMS), the reaction mixture was diluted with ethyl acetate (50 mL) and the organic fraction was washed with water (3×50 mL) and brine (50 mL), dried over anhydrous $Na_2SO_4$ and evaporated under reduced pressure. The crude material was purified by column chromatography (230-400 silica gel; 1.5% MeOH in DCM) to afford 8-bromo-9-fluoro-1,4,4,6-tetramethyl-4,5-dihydro-[1,2,4]triazolo[4,3-a]quinoxaline (1.1 g, 61.7%) as an off-white solid.

Synthesis of 6-bromo-5-fluoro-3,11,11-trimethyl-8,9,10,11-tetrahydro-7H-cyclopenta[f][1,2,4]triazolo[4,3-a]quinoxaline (Intermediate B-61)

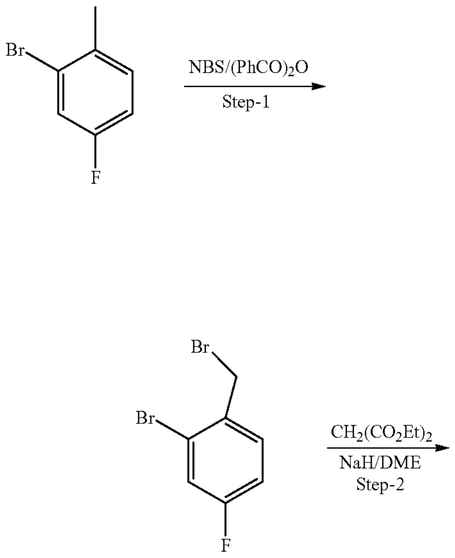

-continued

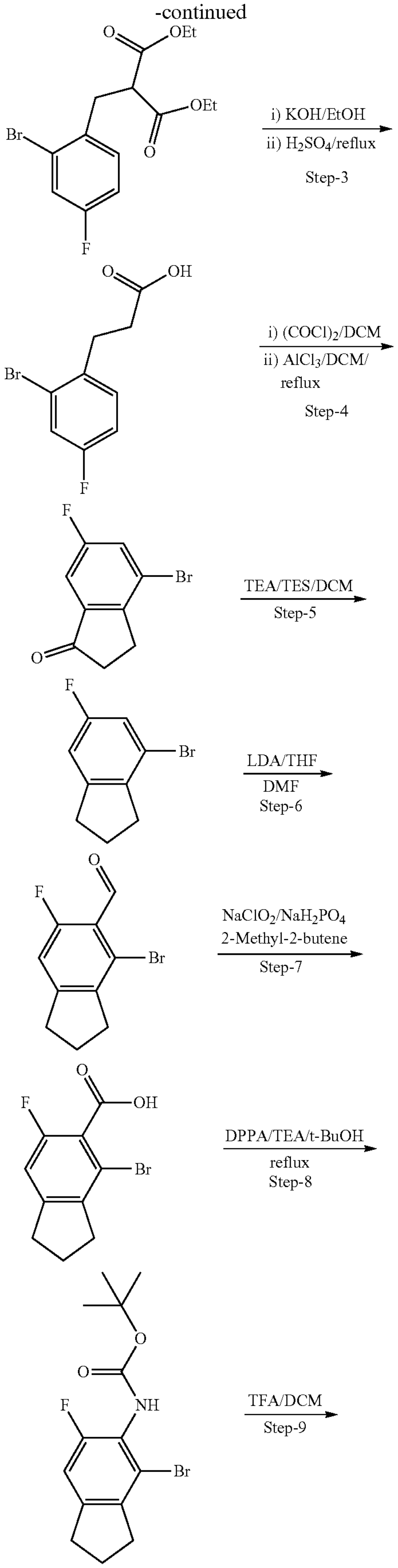

-continued

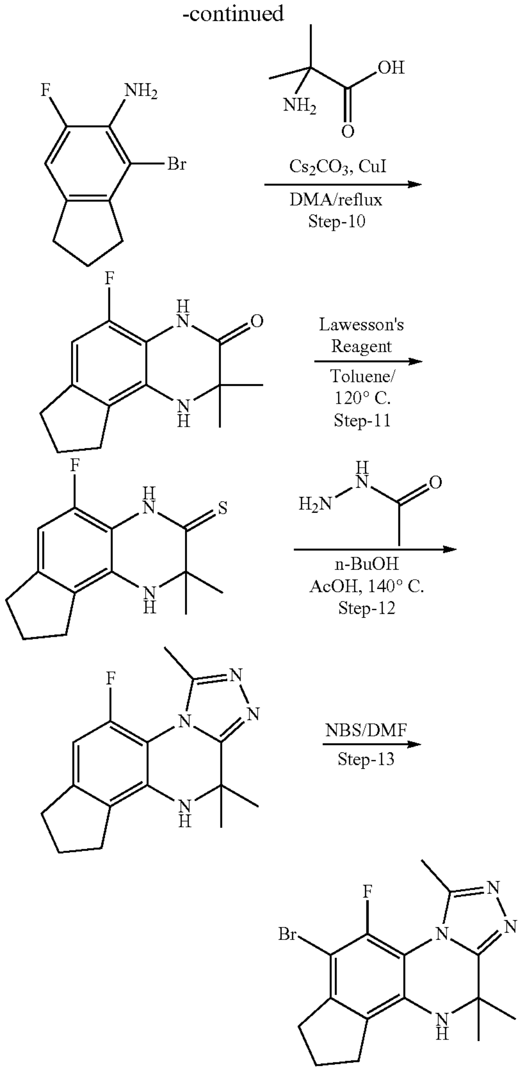

intermediate B-61

Step 1: NBS (49 g, 275.28 mmol, 1.04 eq) and benzyl peroxide (500 mg, 2.06 mmol, 0.0075 eq) were added to a stirred solution of 2-Bromo-4-fluoro-1-methyl-benzene (50 g, 264.55 mmol, 1 eq) in carbon tetrachloride (400 ml), and the reaction mixture was refluxed for 16 h in the presence of light. After completion (monitored by TLC), the reaction mixture was diluted with water (500 mL) and extracted with DCM (2×500 mL). The combined organic layers were washed with water (500 mL) and brine (500 mL), dried over anhydrous $Na_2SO_4$ and evaporated under reduced pressure. The crude residue was purified by column chromatography (100-200 silica gel; hexane) to afford 2-Bromo-1-bromomethyl-4-fluoro-benzene (52 g, 74%) as a colorless liquid.

Step 2: Diethyl malonate (68.95 g, 430.97 mmol, 1.1 eq) in DME (300 mL) was added dropwise to a stirred solution of NaH (16.4 g, 411.39 mmol, 1.05 eq) in DME (100 mL) and the reaction mixture was stirred at RT for 1 h. Then, 2-bromo-1-bromomethyl-4-fluoro-benzene (105 g, 391.8 mmol, 1 eq) in DME (200 mL) was added slowly and the reaction mixture was refluxed for 1 h. After completion (monitored by TLC), the reaction mixture was diluted with water (1000 mL) and extracted with ethyl acetate (3×500 mL). The combined organic layers were washed with water (500 mL) and brine (500 mL), dried over anhydrous $Na_2SO_4$ and evaporated under reduced pressure. The crude material was purified by column chromatography (100-200 silica gel; 5% ethyl acetate in hexane) to afford 2-(2-bromo-4-fluoro-benzyl)-malonic acid diethyl ester (100 g, 73.5%).

Step 3: A mixture of 2-(2-bromo-4-fluoro-benzyl)-malonic acid diethyl ester (89 g, 256.48 mmol, 1 eq) in THF and KOH (28.7 g, 512.96 mmol, 2 eq) in $H_2O$ (500 mL) was refluxed for 5 h. Then, THF (100 mL) was removed and the resulting mixture was dissolved in conc. $H_2SO_4$ (100 mL) and heated at 120° C. for 16 h. The reaction mixture was poured into ice-cold water (500 mL), the solid precipitate formed was filtered of and the compound was extracted with ethyl acetate (3×1000 mL), dried over anhydrous $Na_2SO_4$ and concentrated under reduced pressure to afford 3-(2-Bromo-4-fluoro-phenyl)-propionic acid (52.2 g, 82.3%) as a white solid.

Step 4: Oxalyl Chloride (33 mL, 381.78 mmol, 2 eq) was added to a stirred solution of 3-(2-bromo-4-fluoro-phenyl)-propionic acid (47.15 g, 190.89 mmol, 1 eq) in dry DCM (500 mL) under inert atmosphere, and the reaction mixture was stirred at RT for 16 h. After completion (monitored by TLC), DCM and oxalyl chloride were removed by rotary evaporator under inert atmosphere and the crude material was carried on to the next step without purification. The crude material was dissolved in dry DCM (500 mL), a suspension of anhydrous $AlCl_3$ (38.4 g, 286.33 mmol, 1.5 eq) in DCM (200 mL) was added at RT, and the reaction mixture was refluxed for 3 h. After completion, the reaction mixture was poured into ice-cold water (1000 mL) and the organic fraction was separated. The aqueous layer was extracted with DCM (2×500 mL), and the combined organic layers were washed with water (500 mL) and brine (500 mL), dried over anhydrous $Na_2SO_4$ and concentrated under reduced pressure to afford 4-bromo-6-fluoro-indan-1-one (31 g, 71%).

Step 5: Triethyl silane (79.19 g, 676.83 mmol, 2.5 eq) was added to a stirred solution of 4-bromo-6-fluoro-indan-1-one (62 g, 270.74 mmol, le q) in TFA (1000 mL) and the reaction mixture was stirred at RT for 16 h under inert atmosphere. After completion (monitored by TLC), the reaction mixture was concentrated, diluted with water (1000 mL) and extracted with ethyl acetate (2×1000 mL). The combined organic layers were washed with water (500 mL) and brine (500 mL), dried over anhydrous $Na_2SO_4$ and evaporated under reduced pressure. The crude residue was purified by column chromatography (100-200 silica gel; hexane) to afford 4-bromo-6-fluoro-indan (51 g, 88%).

Step 6: To a solution of DIPA (49.2 mL, 357.2 mmol, 1.2 eq) in THF (900 mL), nBuLi (163.7 mL, 327.43 mmol, 1.1 eq) was added at −78° C. and the reaction was stirred for 1 h at this temperature. Then, 4-bromo-6-fluoro-indan (64 g, 297.67 mmol, 1 eq) in THF was added to the mixture at the same temperature. After stirring the reaction mixture for 30 min at this temperature, DMF (65 mL) was added and the reaction was continued for 30 min at RT. After completion (monitored by TLC), the reaction mixture was quenched with saturated $NH_4Cl$ solution (500 mL) and extracted with EA (3×500 mL). The organic layer was washed with water (500 mL) and brine (500 mL), dried over $Na_2SO_4$, filtered and concentrated under reduced pressure. The crude material was purified by column chromatography using (100-200 silica gel; 2% ethyl acetate in hexane) to afford 4-bromo-6-fluoro-indan-5-carbaldehyde (54 g, 74.63%) as an off-white solid.

Step 7: $NaH_2PO_4$ (191 g, 1.22 mol, 4.04 eq) and $NaClO_2$ (121.7 g, 1.35 mol, 4.44 eq) were added to a solution of 4-bromo-6-fluoro-indan-5-carbaldehyde (74 g, 0.304 mol, 1 eq) in THF (1000 mL):BuOH (1000 mL):$H_2O$ (300 mL) ml at 0° C. Then, 2-methyl-2-butene (116 mL, 1.34 mol, 4.44 eq) was added and the reaction mixture was stirred at RT for 1 h. After completion (monitored by TLC), the organic solvent was reduced, diluted with ethyl acetate (2000 mL), washed with water (1000 mL) and brine (1000 mL), dried over $Na_2SO_4$ and concentrated under reduced pressure. The compound was purified by trituration with pentane to afford 4-bromo-6-fluoro-indan-5-carboxylic acid (35 g, 44.45%).

Step 8: Diphenyl phosphoryl azide (75 mL) was added to a stirred solution of 4-bromo-6-fluoro-indan-5-carboxylic acid (37.7 g, 145.51 mmol, 1 eq) in t-BuOH (1000 mL), triethyl amine (30.1 mL, 218.2 mmol, 1.5 eq) and molecular sieves (75 g), and the reaction mixture was refluxed for 16 h. After completion (monitored by TLC), the organic solvent was removed, and the residue diluted with ethyl acetate (1000 mL), washed with 5% aqueous HCl (500 mL) and water (500 mL) and concentrated under reduced pressure. The compound was purified by column chromatography (100-200 silica gel; 5% ethyl acetate in hexane) to afford (4-bromo-6-fluoro-indan-5-yl)-carbamic acid tert-butyl ester (21 g, 37.2%)

Step 9: To a cold stirred solution of (4-bromo-6-fluoro-indan-5-yl)-carbamic acid tert-butyl ester (40 g, 121.14 mmol, 1 eq) in DCM (750 mL), TFA (250 mL) was added, and the reaction mixture was stirred for 1 h at room temperature. After completion (monitored by TLC), the solvent was evaporated under reduced pressure and the crude compound was purified by column chromatography (100-200 silica gel; 5% ethyl acetate in hexane) to afford 4-bromo-6-fluoro-indan-5-ylamine (11 g, 39.4%).

Step 10: A suspension of 4-bromo-6-fluoro-indan-5-ylamine (12.0 g, 52.15 mmol, 1 eq.), 2-amino-2-methylpropanoic acid (10.75 g, 104.31 mmol, 2 eq.), $K_3PO_4$ (24.35 g, 114.74 mmol, 2.2 eq.) and cuprous chloride (0.516 g, 5.2 mmol, 0.1 eq.) in dry DMSO (120 mL) in a sealed tube was deoxygenated with argon for 20 min, and the reaction mixture was stirred at 140° C. for 16 h. After completion, the reaction mixture was diluted with water and extracted with ethyl acetate. The combined organic layers were washed with water (2×300 mL) and brine (200 mL), dried over anhydrous $Na_2SO_4$ and evaporated under reduced pressure. The crude residue was purified by column chromatography (100-200 mesh silica gel; 30% ethyl acetate/hexane) to afford 5-fluoro-2,2-dimethyl-1,2,4,7,8,9-hexahydro-cyclopenta(f)nephalene-3-one (6.5 g, 53%) as a brown solid.

Step 11: To a solution of 5-fluoro-2,2-dimethyl-1,2,4,7,8,9-hexahydro-cyclopenta(f)nephalene-3-one (6.5 g, 27.7 mmol, 1 eq.) in toluene (100 mL) was added Lawesson's reagent (17 g, 41.66 mmol, 1.5 eq.) at RT, and the reaction mixture was refluxed at 120° C. for 1 h. After completion (monitored by TLC), the reaction mixture was quenched with sat. $NaHCO_3$ solution (50 mL) followed by extraction with ethyl acetate (3×200 mL). The combined organic layers were washed with water (100 mL) and brine (100 mL), dried over anhydrous $Na_2SO_4$ and evaporated under reduced pressure. The crude residue was purified by column chromatography (100-200 mesh silica gel; 20% ethyl acetate/hexane) to afford 5-fluoro-2,2-dimethyl-1,2,4,7,8,9-hexahydro-cyclopenta(f)nephalene-3-thione (6.0 g, 86%) as a yellow solid.

Step 12: To a solution of 5-fluoro-2,2-dimethyl-1,2,4,7,8,9-hexahydro-cyclopenta(f)nephalene-3-thione (6.0 g, 24 mmol, 1 eq.) in n-BuOH (120 mL) was added acetohydrazide (5.8 g, 79.2 mmol, 3.3 eq.), followed by addition of acetic acid (25.7 mL) and then the reaction mixture was stirred at 140° C. for 16 h. After completion (monitored by TLC), the reaction mixture was diluted with water (150 mL) and extracted with ethyl acetate (3×250 mL). The combined organic layers were washed with water (50 mL) and brine (500 mL), dried over anhydrous $Na_2SO_4$ and evaporated under reduced pressure. The crude material was purified by column chromatography (100-200 mesh silica gel; 5% MeOH-DCM) to afford 4-fluoro-3,10,10-trimethyl-7,8,9,10-tetrahydro-6H-1,2,3a,9-tetraazadicyclopenta(a,f) naphthalene (5.5 g, 84%) as a white solid.

Step 13: A stirred solution of 4-fluoro-3,10,10-trimethyl-7,8,9,10-tetrahydro-6H-1,2,3a,9-tetraazadicyclopenta(a,f) naphthalene (5.2 g, 19 mmol, 1 eq.) in DMF (50 mL) at −10° C. was treated portion wise over 10 min with solid N-bromosuccinimide (3.75 g, 21 mmol, 1.1 eq.), and the reaction mixture was allowed to warm to RT and stirred for 1 h. After completion (monitored by TLC), the reaction mixture was diluted with water (50 mL) and extracted with ethyl acetate (3×300 mL). The combined organic layers were washed with water (100 mL) and brine (100 mL), dried over anhydrous $Na_2SO_4$ and evaporated under reduced pressure. The crude residue was purified by column chromatography (100-200 mesh silica gel; 5% MeOH-DCM) to afford 6-bromo-5-fluoro-3,11,11-trimethyl-8,9,10,11-tetrahydro-7H-cyclopenta[f][1,2,4]triazolo[4,3-a]quinoxaline (4.0 g, 60%) as a brown solid.

Synthesis of 8-bromo-9-fluoro-1,4,4-trimethyl-6-(trifluoromethyl)-4,5-dihydro-[1,2,4]triazolo[4,3-a] quinoxaline (Intermediate B-62)

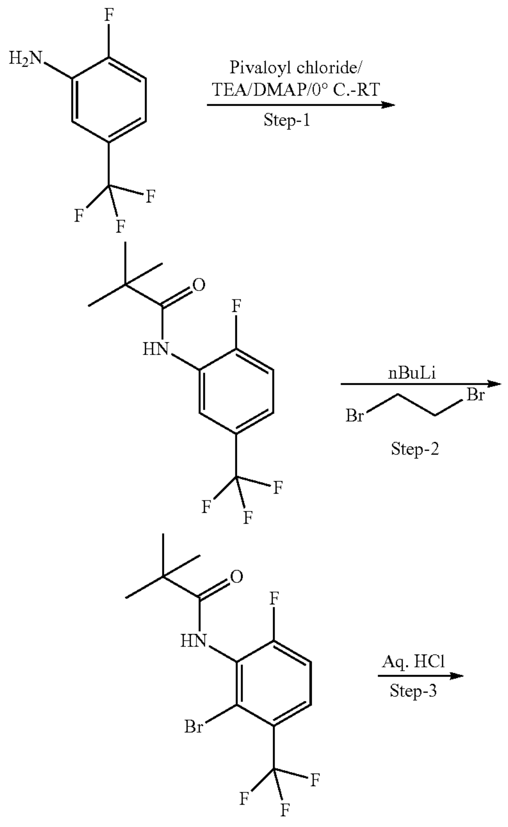

-continued

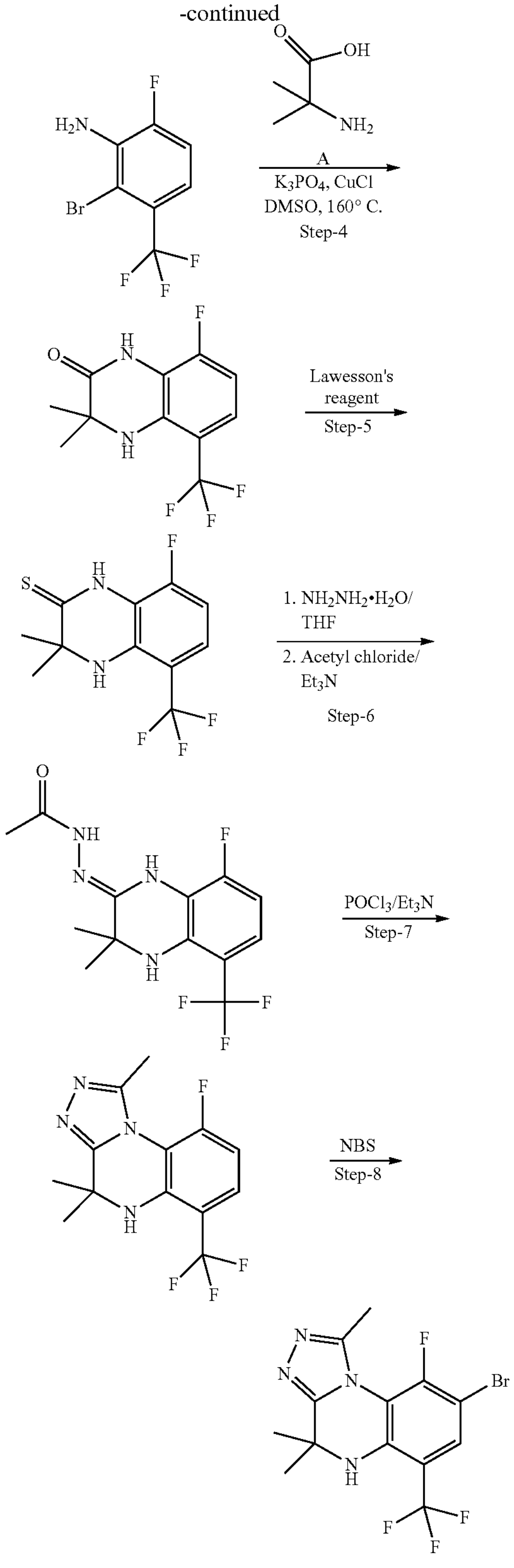

intermediate B-62

Step 1: To a stirred solution of 2-fluoro-5-trifluoromethyl-phenylamine (50 g, 0.729 mol) in DCM (2 L) was added pyridine (56.18 mL, 0.6975 mol) followed by DMAP (1.02 g, 0.01 mol), the resulting reaction mixture was cooled to 0°

C. and pivolyl chloride (58.9 g, 0.49 mol) was added dropwise at 0° C. The reaction mixture was then stirred for another 2 h at 0° C. and poured into ice-cooled 1N HCl solution. The two layers were separated and the aqueous layer was extracted with DCM (2×200 mL). The combined organic layers were washed with water (2×200 mL) and brine (750 mL), dried over anhydrous $Na_2SO_4$ and concentrated under reduced pressure. The crude residue was purified by column chromatography (silica 100-200 mesh; 5% ethyl acetate/hexane) to afford N-(2-Fluoro-5-trifluoromethyl-phenyl)-2,2-dimethyl-propionamide (70 g, 95%) as a white solid.

Step 2: To a stirred solution of N-(2-fluoro-5-trifluoromethyl-phenyl)-2,2-dimethyl-propionamide (23 g, 0.087 mol) in THF (250 mL) was added n-BuLi (1.8 M in Hexane) (120.8 mL, 0.217 mol) dropwise at 0° C. and the reaction mixture was stirred for 30 min at 0° C. The reaction mixture was cooled to −78° C. and 1,2-dibromo ethane (19.61 g, 0.104 mol) was added dropwise. The resulting reaction mixture was slowly warmed to room temperature and stirred for 16 h. The reaction mixture was then poured into ice-cooled 1N HCl (250 mL) solution. The organic layer was separated and the aqueous layer extracted with diethyl ether (2×500 mL). The combined organic layers were washed with water (2×500 mL) and brine (500 mL), dried over anhydrous $Na_2SO_4$ and concentrated under reduced pressure. The crude material was purified by trituration using MTBE to afford N-(2-bromo-6-fluoro-3-trifluoromethyl-phenyl)-2,2-dimethyl-propionamide (8 g, 26.7%) as a white solid.

Step 3: N-(2-Bromo-6-fluoro-3-trifluoromethyl-phenyl)-2,2-dimethyl-propionamide (12 g, 0.035 mol) was added to 70% $H_2SO_4$ (86 mL), and the resulting suspension was heated to 110° C. for 2 h. After completion (monitored by TLC), the reaction mixture was cooled to 0° C. and slowly poured into ice-cold water (250 mL). The resulting aqueous phase was then extracted with ethyl acetate (4×250 mL), and the combined organic layers were washed with water (2×150 mL) and brine (400 mL), dried over anhydrous $Na_2SO_4$ and concentrated under reduced pressure. The crude residue was purified by column chromatography (silica 100-200 mesh; 5% ethyl acetate/hexane) to afford 2-bromo-6-fluoro-3-trifluoromethyl-phenylamine (7.5 g, 83%) as a brown liquid.

Step 4: To a stirred suspension of 2-bromo-6-fluoro-3-trifluoromethyl-phenylamine (7.5 g, 0.029 mol) in dry DMSO (112.5 mL) was added 2-amino-2-methyl-propionic acid (5.97 g, 0.058 mol), followed by $K_3PO_4$ (12.31 g, 0.058 mol) at room temperature, and the resulting reaction mixture was degassed with nitrogen for 30 minutes. Then, CuCl (0.288 g, 0.0029 mol) was added and the reaction mixture was heated at 160° C. for 16 h. After completion (monitored by LCMS), the reaction mixture was cooled to room temperature and filtered through celite. The celite bed was washed with ethyl acetate (100 mL), and the resulting filtrate was poured into ice cold water. The aqueous fraction was extracted with MTBE (3×150 mL), and the combined organic layers were washed with water (2×150 mL) and brine (100 mL), dried over anhydrous $Na_2SO_4$ and evaporated under reduced pressure. The crude material was purified by column chromatography (100-200 mesh silica gel; 30% ethyl acetate/hexane) to afford 8-fluoro-3,3-dimethyl-5-trifluoromethyl-3,4-dihydro-1H-quinoxalin-2-one (1.8 g, 24%) as a brown solid.

Step 5: To a solution of 8-fluoro-3,3-dimethyl-5-trifluoromethyl-3,4-dihydro-1H-quinoxalin-2-one (950 mg, 3.62 mmol) in toluene (12 mL) was added Lawesson's reagent (2.2 g, 5.43 mmol) at RT and the reaction mixture was refluxed at 120° C. for 2 h. After completion (monitored by TLC), the reaction mixture was concentrated, and the solid residue was quenched with sat. $NaHCO_3$ solution (50 mL). The resulting aqueous phase was extracted with ethyl acetate (3×150 mL), and the combined organic layers were washed with water (100 mL) and brine (100 mL), dried over anhydrous $Na_2SO_4$ and evaporated under reduced pressure. The crude material was purified by column chromatography (100-200 mesh silica gel; 20% ethyl acetate/hexane) to afford 8-fluoro-3,3-dimethyl-5-trifluoromethyl-3,4-dihydro-1H-quinoxaline-2-thione (900 mg, 89%) as a yellow solid.

Step 6: To a stirring solution of 7-bromo-3,3,8-trimethyl-3,4-dihydro-1H-pyrido[2,3-b]pyrazine-2-thione (900 mg, 3.23 mmol) in tetrahydrofuran (25 mL) was dropwise added hydrazine hydrate (486 mg, 9.71 mmol) at 0° C., and the reaction mixture was stirred at room temperature for 16 h. Triethyl amine (2.72 mL, 16.17 mmol) and acetyl chloride (0.689 mL, 9.7028 mmol) were added dropwise at 0° C. and the reaction mixture was stirred for 2 h at room temperature. After completion (monitored by LCMS), the reaction mixture was diluted with water (25 mL) and extracted with 10% MeOH in DCM (5×50 mL). The combined organic layers were washed with brine (50 mL), dried over $Na_2SO_4$ and concentrated under reduced pressure to afford acetic acid (7-bromo-3,3,8-trimethyl-3,4-dihydro-1H-pyrido[2,3-b]pyrazin-2-ylidene)-hydrazide (1 g, crude) as a white solid.

Step 7: Acetic acid (7-bromo-3,3,8-trimethyl-3,4-dihydro-1H-pyrido[2,3-b]pyrazin-2-ylidene)-hydrazide (1 g, 3.14 mmol) was cooled to −10° C., and phosphoryl chloride (1.46 mL, 15.7 mmol) was added dropwise, followed by dropwise addition of triethyl amine (0.44 mL, 3.14 mmol). Then, the reaction mixture was stirred at −10° C. to RT for 20 min and then refluxed for 4 h. After completion (monitored by LCMS), the reaction mixture was cooled to 0° C. and quenched with crushed ice-water (25 mL). The aqueous phase was then basified by adding cold ammonium solution (25 mL) dropwise, and the resulting basic aqueous fraction was then extracted with ethyl acetate (3×50 mL). The combined organic layers were washed with brine (50 mL), dried over anhydrous $Na_2SO_4$ and concentrated under reduced pressure. The crude residue was purified by trituration using MTBE to afford 9-fluoro-1,4,4-trimethyl-6-trifluoromethyl-4,5-dihydro-[1,2,4]triazolo[4,3-a]quinoxaline (700 mg, 74%) as an off-white solid.

Step 8: To a solution of 9-fluoro-1,4,4-trimethyl-6-trifluoromethyl-4,5-dihydro-[1,2,4]triazolo[4,3-a]quinoxaline (1.65 g, 5.49 mmol) in DMF (30 mL) was added NBS (1.27 g, 7.137 mmol) portion wise at 0° C., and the resulting reaction mixture was stirred at room temperature for 16 h. After completion (monitored by LCMS), the reaction mixture was diluted with water (150 mL) and extracted with ethyl acetate (2×150 mL). The combined organic layers were washed with water (150 mL) and brine (100 mL), dried over anhydrous $Na_2SO_4$ and concentrated under reduced pressure. The crude residue was purified by column chromatography (230-400 mesh silica gel; 5% MeOH/DCM) to afford 8-bromo-9-fluoro-1,4,4-trimethyl-6-(trifluoromethyl)-4,5-dihydro-[1,2,4]triazolo[4,3-a]quinoxaline (1.3 g, 63%) as an off-white solid.

Synthesis of 8-bromo-1,4,4,9-tetramethyl-6-(methylthio)-4,5-dihydro-[1,2,4]triazolo[4,3-a]quinoxaline (Intermediate B-63)

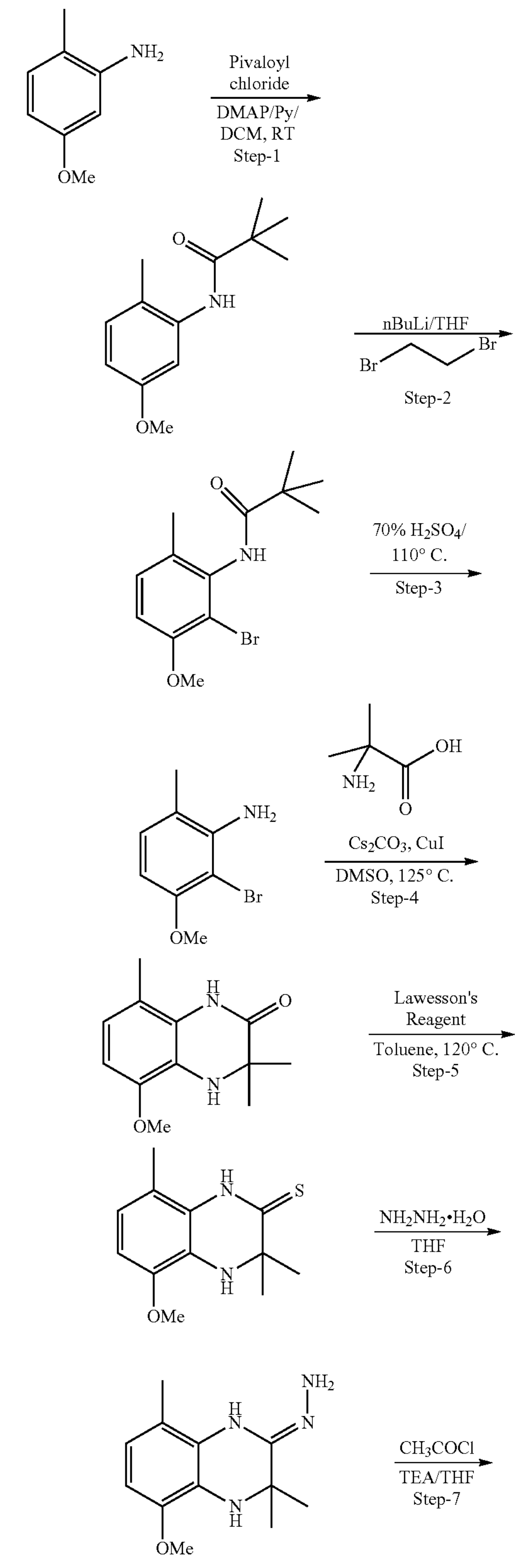

-continued

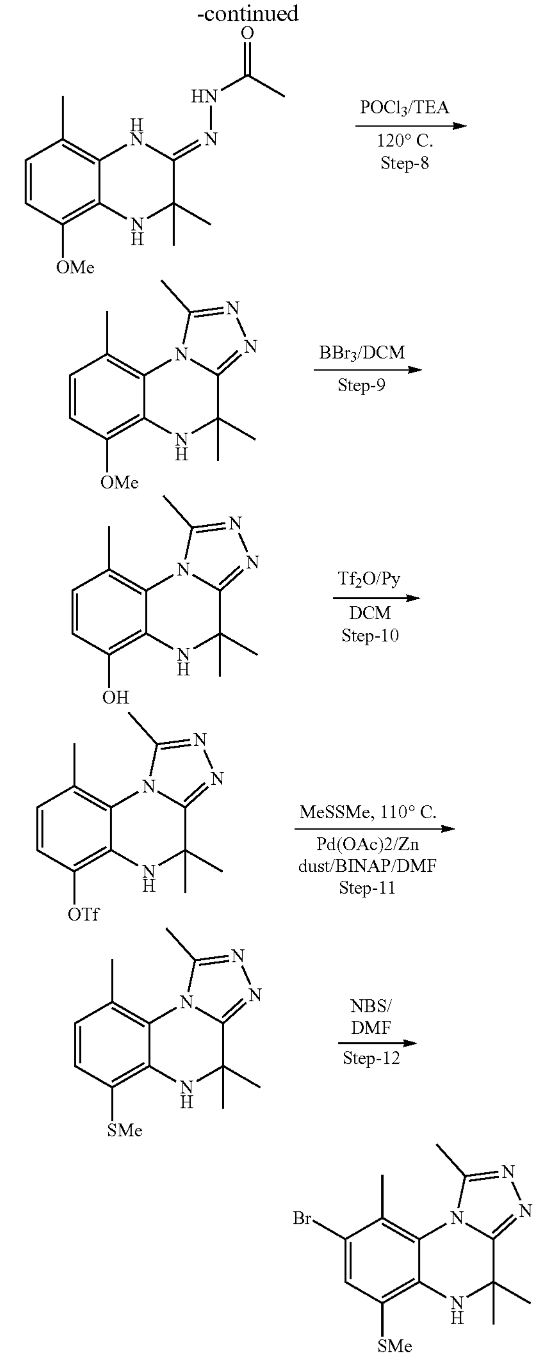

intermediate B-63

Step 1: To a stirring solution of 2-fluoro-5-methoxy aniline (7.5 g, 54.67 mmol, 1 eq), pyridine (28.83 mL, 364.68 mmol, 2 eq), and DMAP (0.22 g, 1.8224 mmol, 0.01 eq) in dichloromethane (315 mL) was added dropwise pivolyl chloride (24.17 g, 200.46 mmol, 1.1 eq) at 0° C., and the reaction mixture was stirred for another 1 h at 0° C. and then poured into an ice-cooled 1N HCl solution. The organic layer was separated and the aqueous layer extracted with diethyl ether (2×20 mL). The combined organic layers were washed with water (2×20 mL) and brine (20 mL), dried over anhydrous $Na_2SO_4$, and concentrated under reduced pressure. The crude material was purified by column chromatography (100-200 mesh silica gel; 5% ethyl acetate/hexane)

to afford compound N-(5-methoxy-2-methyl-phenyl)-2,2-dimethyl-propionamide (11.5 g, 95%) as a white solid.

Step 2: To a stirred solution of compound N-(5-Methoxy-2-methyl-phenyl)-2,2-dimethyl-propionamide (10.0 g, 45.24 mmol, 1 eq) in THF (100 mL) was added n-BuLi (2.2 M, 45.2 mL, 99.5 mmol, 2.1 eq) at 0° C., and the reaction mixture was stirred for 10 h at 0° C. Then, 1,2-dibromo ethane (3.8 mL, 54.28 mmol, 1.2 eq) was added dropwise at −78° C., and the reaction mixture was stirred for 12 h at room temperature. The reaction mixture was poured into ice-cooled 1N HCl solution, the organic layer was separated and the aqueous layer extracted with diethyl ether (2×100 mL). The combined organic layers were washed with water (2×50 mL) and brine (50 mL), dried over anhydrous $Na_2SO_4$, and concentrated under reduced pressure. The crude residue was purified by column chromatography (100-200 mesh silica gel; 20% ethyl acetate/hexane) to afford compound N-(2-bromo-3-methoxy-6-methyl-phenyl)-2,2-dimethyl-propionamide (3.8 g, 29.52%) as a white solid.

Step 3: 70% $H_2SO_4$ (10 mL) was added to N-(2-bromo-3-methoxy-6-methyl-phenyl)-2,2-dimethyl-propionamide (1.5 g, 5.0 mmol, 1 eq), and the reaction mixture was stirred at 110° C. for 2 h. The reaction mixture was then cooled to 0° C., water (50 mL) was slowly added and the mixture was stirred for 10 min. The aqueous phase was extracted with ethyl acetate (5×50 mL). The combined organic layers were washed with water (2×100 mL) and brine (100 mL), dried over anhydrous $Na_2SO_4$, and concentrated under reduced pressure. The crude material was purified by column chromatography (100-200 mesh silica gel; 5% ethyl acetate/hexane) to afford compound N-(2-Bromo-3-methoxy-6-methyl-phenyl)-2,2-dimethyl-propionamide (0.53 g, 49%) as a white solid.

Step 4: A suspension of compound N-(2-Bromo-3-methoxy-6-methyl-phenyl)-2,2-dimethyl-propionamide (0.7 5 g, 3.472 mmol, 1 eq), 2-aminoisobutyric acid (0.715 g, 6.944 mmol, 2 eq) and cesium carbonate (2.262 g, 9.09 mmol, 2 eq) in dimethyl acetamide (7.5 mL) in a sealed tube was deoxygenated with argon for 10 min, and cuprous iodide (0.066 g, 0.3472 mmol, 0.1 eq) was then added. After deoxygenating with argon for 10 mi once more, the reaction mixture was stirred at 160° C. for 3 h. The reaction mixture was then cooled to room temperature and filtered through a celite bed, which was washed by ethyl acetate (50 mL). The filtrate was washed with water (2×30 mL) and brine (30 mL), dried over anhydrous $Na_2SO_4$, and concentrated under reduced pressure. The crude residue was purified by column chromatography (230-400 mesh silica gel; 30% ethyl acetate/hexane) to afford compound 5-Methoxy-3,3,8-trimethyl-3,4-dihydro-1H-quinoxalin-2-one (0.35 g, 45.8%) as a light black solid.

Step 5: To a stirred solution of 5-methoxy-3,3,8-trimethyl-3,4-dihydro-1H-quinoxalin-2-one (0.16 g, 0.727 mmol, 1 eq) in toluene (6 mL) was added Lawesson's reagent (0.441 g, 1.090 mmol, 1.5 eq), and the reaction mixture was stirred at 120° C. for 30 min. The reaction mixture was then cooled to room temperature and saturated sodium bicarbonate solution (20 mL) was added. The organic layer was separated and the aqueous phase was extracted with ethyl acetate (2×20 mL). The combined organic layers were washed with water (2×20 mL) and brine (20 mL), dried over anhydrous $Na_2SO_4$, and concentrated under reduced pressure. The crude material was purified by column chromatography (230-400 mesh silica gel; 20% ethyl acetate/hexane) to afford 5-methoxy-3,3,8-trimethyl-3,4-dihydro-1H-quinoxaline-2-thione (0.15 g, 87.4%) as a yellowish white solid.

Step 6: To a stirring solution of 5-methoxy-3,3,8-trimethyl-3,4-dihydro-1H-quinoxaline-2-thione (1.0 g, 4.237 mmol, 1 eq) in tetrahydrofuran (6 mL) was added dropwise hydrazine hydrate (0.62 mL, 12.711 mmol, 3 eq) at 0° C., and the reaction mixture was stirred for 16 h at room temperature. Triethyl amine (2.88 mL, 21.185 mmol, 5 eq) was then added and the reaction mixture was stirred for another 10 min.

Step 7: Acetyl chloride (1.0 mL, 12.711 mmol, 3 eq) was then added very slowly at 0° C. and the mixture was stirred for 2 h at room temperature. Then, the reaction mixture was diluted with water (50 mL) and extracted with dichloromethane (5×50 mL). The combined organic layers were washed with brine (100 mL), dried over $Na_2SO_4$, and concentrated under reduced pressure. The crude material was washed with diethyl ether to afford acetic acid (5-methoxy-3,3,8-trimethyl-3,4-dihydro-1H-quinoxalin-2-ylidene)-hydrazide (1.075 g, 91.9%) as a white solid.

Step 8: Acetic acid (5-methoxy-3,3,8-trimethyl-3,4-dihydro-1H-quinoxalin-2-ylidene)-hydrazide was cooled to −10° C. and phosphorus oxychloride (1.41 mL, 25.815 mmol, 9.5 eq) was added dropwise, followed by dropwise addition of triethyl amine (0.37 mL, 2.217 mmol, 1 eq). The reaction mixture was stirred at −10° C. for 10 min, 10 min at room temperature and then for 4 h at reflux temperature. The reaction mixture was cooled to 0° C. and 25 g crushed ice was added. The aqueous phase was then slowly added to a cold ammonium solution (100 mL), and extracted with ethyl acetate (3×50 mL). The combined organic layers were washed with brine (100 mL), dried over anhydrous $Na_2SO_4$, and concentrated under reduced pressure. The crude residue was purified by column chromatography (230-400 mesh silica gel; 5% methanol/dichloromethane) to afford 6-methoxy-1,4,4,9-tetramethyl-4,5-dihydro-[1,2,4]triazolo[4,3-a]quinoxaline (0.25 g, 35.6%) as a yellow solid.

Step 9: To a cold stirring solution of 6-methoxy-1,4,4,9-tetramethyl-4,5-dihydro-[1,2,4]triazolo[4,3-a]quinoxaline (0.3 m, 1.162 mmol, 1 eq) in dichloromethane (10 mL) was added a $BBr_3$ solution (1 M in dichloromethane, 5.81 mL, 5.81 mmol, 5 eq) dropwise, and the reaction mixture was stirred for 16 h at room temperature. The reaction mixture was then cooled to 0° C. and methanol (6 mL) was added to the dropwise for quenching. After quenching, the reaction mixture was neutralized by stirring with a saturated solution of $NaHCO_3$. Following extraction with dichloromethane (2×30 mL), the combined organic layers were washed with brine (30 mL), dried over anhydrous $Na_2SO_4$, and concentrated under reduced pressure. The crude residue was purified by column chromatography (100-200 mesh silica gel; 5% methanol/dichloromethane) to afford 1,4,4,9-tetramethyl-4,5-dihydro-[1,2,4]triazolo[4,3-a]92uinoxaline-6-ol (0.2 g, 70.5%) as an off-white solid.

Step 10: To a cold stirring solution of 1,4,4,9-tetramethyl-4,5-dihydro-[1,2,4]triazolo[4,3-a]93uinoxaline-6-ol (0.2 g, 0.82 mmol, 1 eq) in dichloromethane (17 mL) was added triethyl amine (0.17 mL, 1.23 mmol, 1.5 eq) and DMAP (0.15 g, 1.23 mmol, 1.5 eq). The reaction mixture was then cooled to 0° C., trifluoromethanesulfonic anhydride (0.277 g, 0.9836 mmol, 1.2 eq) was added dropwise, and the reaction mixture was stirred for 2 h at 0° C. The reaction mixture was diluted with dichloromethane (20 mL) and washed with water (2×20 mL) and brine (20 mL). The organic layer was dried over anhydrous $Na_2SO_4$, and concentrated under reduced pressure. The crude residue was purified by column chromatography (230-400 mesh silica gel; 5% methanol/dichloromethane) to afford trifluoromethanesulfonic acid 1,4,4,9-tetramethyl-4,5-dihydro-[1,2,4]triazolo[4,3-a]93uinoxaline-6-yl ester (0.15 g, 48.6%) as an off-white solid.

Step 11: A suspension of trifluoro-methanesulfonic acid 1,4,4,9-tetramethyl-4,5-dihydro-[1,2,4]triazolo[4,3-a]93uinoxaline-6-yl ester (0.5 g. 1.329 mmol, 1 eq), dimethyl disulfide (0.075 g, 0.7978 mmol, 0.6 eq) and zinc dust (0.0867 g, 1.329 mmol, 1 eq) in dimethylformamide (6 mL) was deoxygenated well with argon gas for 10 min. Palladium acetate (0.009 g, 0.03987 mmol, 0.03 eq) and BINAP (0.027 g, 0.0431 mmol, 0.0325 eq) were then added to the reaction mixture, which was again deoxygenated with argon for 10 min. The reaction mixture was stirred for 16 h at 110° C., cooled to room temperature and filtered through a celite bed. The filtrate was diluted with ethyl acetate (50 mL) and washed with water (5×10 mL) and brine (10 mL). The organic layer was dried over anhydrous $Na_2SO_4$, and concentrated under reduced pressure. The crude material was purified by column chromatography (230-400 mesh silica gel; 5% methanol/dichloromethane) to afford 1,4,4,9-tetramethyl-6-methylsulfanyl-4,5-dihydro-[1,2,4]triazolo[4,3-a]quinoxaline (0.23 g, 63%) as an off-white solid.

Step 12: To a cold stirring solution of 1,4,4,9-tetramethyl-6-methylsulfanyl-4,5-dihydro-[1,2,4]triazolo[4,3-a]quinoxaline (0.15 g, 0.58 mmol, 1 eq) in dimethyl formamide (5 mL) was added N-bromosuccinimide (0.114 m, 0.64 mmol, 1 eq) portion wise, and the reaction mixture was stirred for 2 h at room temperature. The reaction mixture was then diluted with ethyl acetate (50 mL) and washed with water (5×10 mL) and brine (10 mL). The organic layer was dried over $Na_2SO_4$, and concentrated under reduced pressure. The crude residue was purified by column chromatography (230-400 mesh silica gel; 5% methanol/dichloromethane) to afford 8-bromo-1,4,4,9-tetramethyl-6-(methylthio)-4,5-dihydro-[1,2,4]triazolo[4,3-a]quinoxaline (0.25 g, 32%) as a yellow solid.

Synthesis of 8-bromo-6-methoxy-1,4,4,9-tetramethyl-4,5-dihydro-[1,2,4]triazolo[4,3-a]quinoxaline (Intermediate B-64)

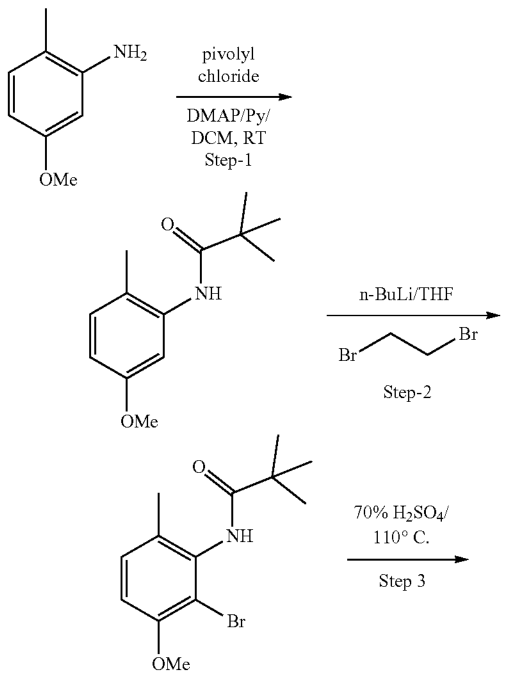

-continued

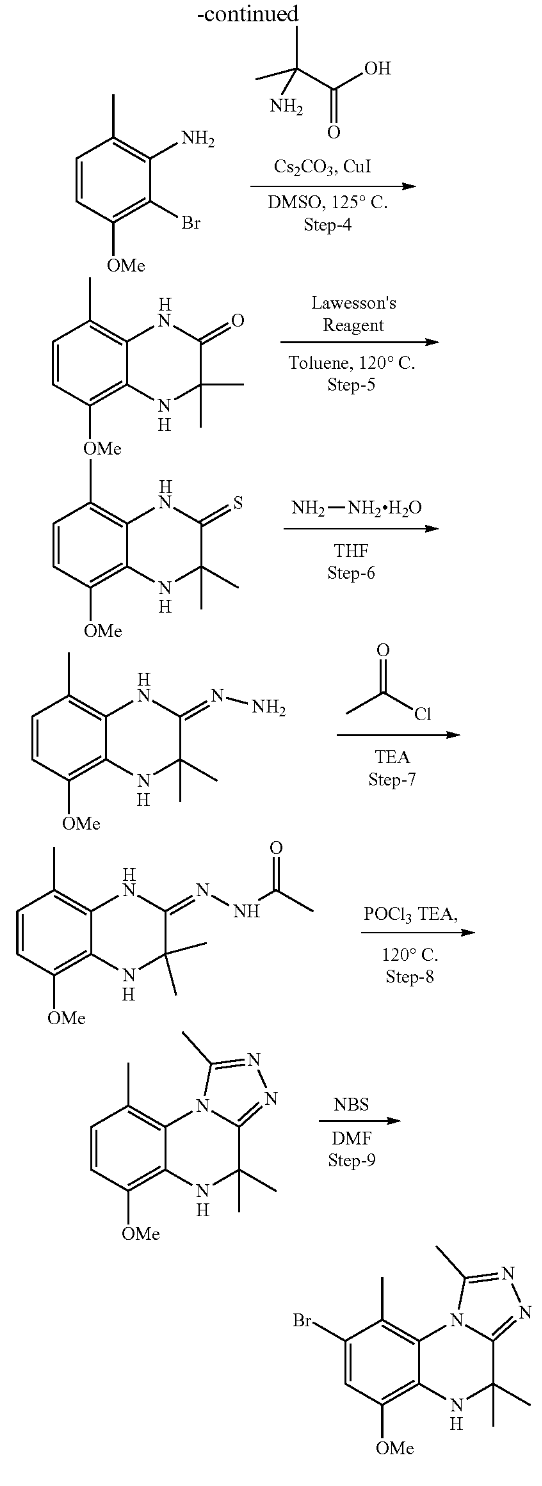

intermediate B-64

Step 1: To a stirring solution of 2-fluoro-5-methoxy aniline (7.5 g, 54.67 mmol, 1 eq), pyridine (28.83 mL, 364.68 mmol, 2 eq), and DMAP (0.22 g, 1.8224 mmol, 0.01 eq) in dichloromethane (315 mL) was added dropwise pivolyl chloride (24.17 g, 200.46 mmol, 1.1 eq) at 0° C., and the reaction mixture was stirred for another 1 h at 0° C. and then poured into an ice-cooled 1N HCl solution. The organic layer was separated and the aqueous layer extracted with diethyl ether (2×20 mL). The combined organic layers were washed with water (2×20 mL) and brine (20 mL), dried over anhydrous $Na_2SO_4$, and concentrated under reduced pressure. The crude material was purified by column chromatography (100-200 mesh silica gel; 5% ethyl acetate/hexane) to afford compound N-(5-methoxy-2-methyl-phenyl)-2,2-dimethyl-propionamide (11.5 g, 95%) as a white solid.

Step 2: To a stirred solution of compound N-(5-Methoxy-2-methyl-phenyl)-2,2-dimethyl-propionamide (10.0 g, 45.24 mmol, 1 eq) in THF (100 mL) was added n-BuLi (2.2 M, 45.2 mL, 99.5 mmol, 2.1 eq) at 0° C., and the reaction mixture was stirred for 10 h at 0° C. Then, 1,2-dibromo ethane (3.8 mL, 54.28 mmol, 1.2 eq) was added dropwise at −78° C., and the reaction mixture was stirred for 12 h at room temperature. The reaction mixture was poured into ice-cooled 1N HCl solution, the organic layer was separated and the aqueous layer extracted with diethyl ether (2×100 mL). The combined organic layers were washed with water (2×50 mL) and brine (50 mL), dried over anhydrous $Na_2SO_4$, and concentrated under reduced pressure. The crude residue was purified by column chromatography (100-200 mesh silica gel; 20% ethyl acetate/hexane) to afford compound N-(2-bromo-3-methoxy-6-methyl-phenyl)-2,2-dimethyl-propionamide (3.8 g, 29.52%) as a white solid.

Step 3: 70% $H_2SO_4$ (10 mL) was added to N-(2-bromo-3-methoxy-6-methyl-phenyl)-2,2-dimethyl-propionamide (1.5 g, 5.0 mmol, 1 eq), and the reaction mixture was stirred at 110° C. for 2 h. The reaction mixture was then cooled to 0° C., water (50 mL) was slowly added and the mixture was stirred for 10 min. The aqueous phase was extracted with ethyl acetate (5×50 mL). The combined organic layers were washed with water (2×100 mL) and brine (100 mL), dried over anhydrous $Na_2SO_4$, and concentrated under reduced pressure. The crude material was purified by column chromatography (100-200 mesh silica gel; 5% ethyl acetate/hexane) to afford compound N-(2-Bromo-3-methoxy-6-methyl-phenyl)-2,2-dimethyl-propionamide (0.53 g, 49%) as a white solid.

Step 4: A suspension of compound N-(2-Bromo-3-methoxy-6-methyl-phenyl)-2,2-dimethyl-propionamide (0.7 5 g, 3.472 mmol, 1 eq), 2-aminoisobutyric acid (0.715 g, 6.944 mmol, 2 eq) and cesium carbonate (2.262 g, 9.09 mmol, 2 eq) in dimethyl acetamide (7.5 mL) in a sealed tube was deoxygenated with argon for 10 min, and cuprous iodide (0.066 g, 0.3472 mmol, 0.1 eq) was then added. After deoxygenating with argon for 10 min once more, the reaction mixture was stirred at 160° C. for 3 h. The reaction mixture was then cooled to room temperature and filtered through a celite bed, which was washed by ethyl acetate (50 mL). The filtrate was washed with water (2×30 mL) and brine (30 mL), dried over anhydrous $Na_2SO_4$, and concentrated under reduced pressure. The crude residue was purified by column chromatography (230-400 mesh silica gel; 30% ethyl acetate/hexane) to afford compound 5-Methoxy-3,3,8-trimethyl-3,4-dihydro-1H-quinoxalin-2-one (0.35 g, 45.8%) as a light black solid.

Step 5: To a stirred solution of 5-methoxy-3,3,8-trimethyl-3,4-dihydro-1H-quinoxalin-2-one (0.16 g, 0.727 mmol, 1 eq) in toluene (6 mL) was added Lawesson's reagent (0.441 g, 1.090 mmol, 1.5 eq), and the reaction mixture was stirred at 120° C. for 30 min. The reaction mixture was then cooled to room temperature and saturated sodium bicarbonate solution (20 mL) was added. The organic layer was separated and the aqueous phase was extracted with ethyl acetate (2×20 mL). The combined organic layers were washed with water (2×20 mL) and brine (20 mL), dried over anhydrous $Na_2SO_4$, and concentrated under reduced pressure. The crude material was purified by column chromatography (230-400 mesh silica gel; 20% ethyl acetate/hexane) to afford 5-methoxy-3,3,8-trimethyl-3,4-dihydro-1H-quinoxaline-2-thione (0.15 g, 87.4%) as a yellowish white solid.

Step 6: To a stirring solution of 5-methoxy-3,3,8-trimethyl-3,4-dihydro-1H-quinoxaline-2-thione (1.0 g, 4.237 mmol, 1 eq) in tetrahydrofuran (6 mL) was added dropwise hydrazine hydrate (0.62 mL, 12.711 mmol, 3 eq) at 0° C., and the reaction mixture was stirred for 16 h at room temperature. Triethyl amine (2.88 mL, 21.185 mmol, 5 eq) was then added and the reaction mixture was stirred for another 10 min.

Step 7: Acetyl chloride (1.0 mL, 12.711 mmol, 3 eq) was then added very slowly at 0° C. and the mixture was stirred for 2 h at room temperature. Then, the reaction mixture was diluted with water (50 mL) and extracted with dichloromethane (5×50 mL). The combined organic layers were washed with brine (100 mL), dried over $Na_2SO_4$, and concentrated under reduced pressure. The crude material was washed with diethyl ether to afford acetic acid (5-methoxy-3,3,8-trimethyl-3,4-dihydro-1H-quinoxalin-2-ylidene)-hydrazide (1.075 g, 91.9%) as a white solid.

Step 8: Acetic acid (5-methoxy-3,3,8-trimethyl-3,4-dihydro-1H-quinoxalin-2-ylidene)-hydrazide was cooled to −10° C. and phosphorus oxychloride (1.41 mL, 25.815 mmol, 9.5 eq) was added dropwise, followed by dropwise addition of triethyl amine (0.37 mL, 2.217 mmol, 1 eq). The reaction mixture was stirred at −10° C. for 10 min, 10 min at room temperature and then for 4 h at reflux temperature. The reaction mixture was cooled to 0° C. and 25 g crushed ice was added. The aqueous phase was then slowly added to a cold ammonium solution (100 mL), and extracted with ethyl acetate (3×50 mL). The combined organic layers were washed with brine (100 mL), dried over anhydrous $Na_2SO_4$, and concentrated under reduced pressure. The crude residue was purified by column chromatography (230-400 mesh silica gel; 5% methanol/dichloromethane) to afford 6-methoxy-1,4,4,9-tetramethyl-4,5-dihydro-[1,2,4]triazolo[4,3-a]quinoxaline (0.25 g, 35.6%) as a yellow solid.

Step 9: To a cold stirring solution of 6-methoxy-1,4,4,9-tetramethyl-4,5-dihydro-[1,2,4]triazolo[4,3-a]quinoxaline (0.15 g, 0.58 mmol, 1 eq) in dimethyl formamide (5 mL) was added N-bromosuccinimide (0.114 g, 0.6395 mmol, 1 eq) portion wise, and the reaction mixture was stirred for 2 h at room temperature. The reaction mixture was then diluted with ethyl acetate (50 mL) and washed with water (5×10 mL) and brine (10 mL). The organic layer was dried over $Na_2SO_4$, and concentrated under reduced pressure. The crude material was purified by column chromatography (230-400 mesh silica gel; 5% methanol/dichloromethane) to afford 8-bromo-6-methoxy-1,4,4,9-tetramethyl-4,5-dihydro-[1,2,4]triazolo[4,3-a]quinoxaline (0.07 g, 36%) as a yellow solid.

Synthesis of 2-(8-bromo-9-fluoro-1,4,4-trimethyl-4,5-dihydro-[1,2,4]triazolo[4,3-a]95uinoxaline-6-yl) propan-2-ol (Intermediate B-65)

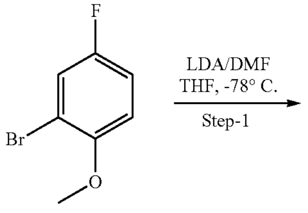

-continued

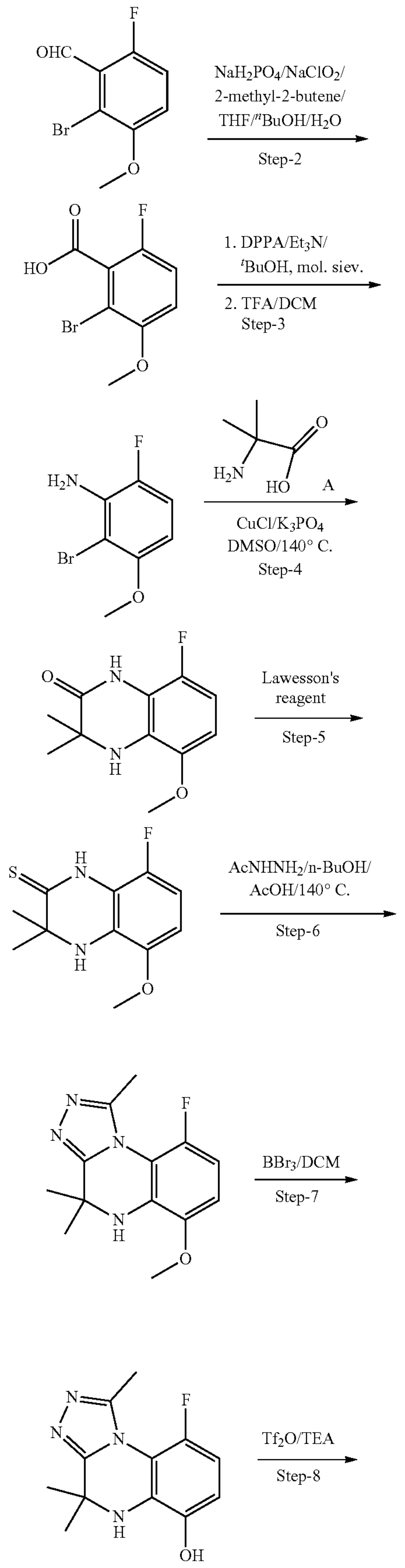

-continued

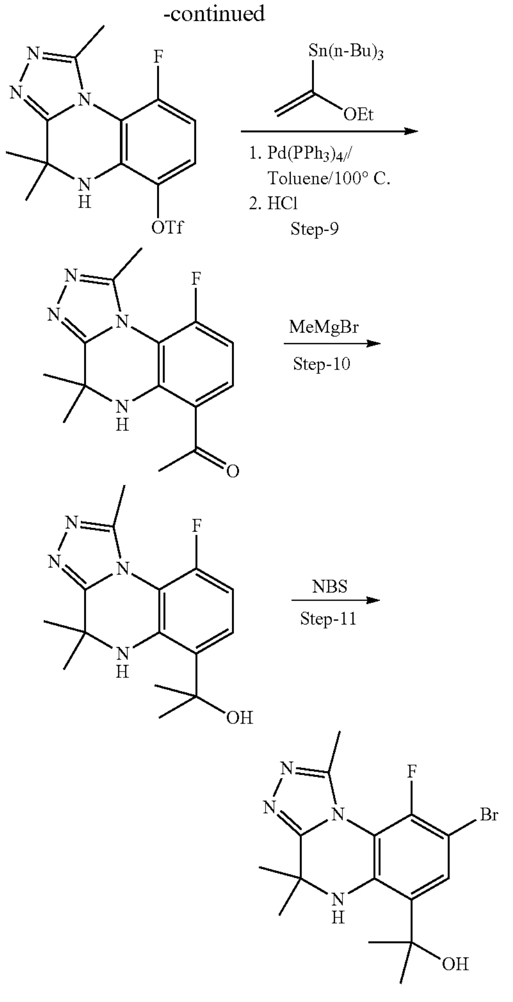

intermediate B-65

Step 1: To a stirred solution of 2-bromo-4-fluoro-1-methoxy-benzene (30.0 g, 0.15 mol) in THF (300 mL) was added LDA 2M in THF (77.0 mL, 0.16 mol) at −78° C. under $N_2$ atmosphere, and the resulting solution was stirred at −78° C. for 30 min, followed by addition of DMF (12.5 mL, 0.16 mol) at −78° C. and stirring for 30 min at the same temperature. After completion (monitored by TLC), the reaction was quenched with $H_2O$ (100 mL) at 0° C., and the resulting solution was extracted with EtOAc (2×250 mL). The combined organic layers were dried over anhydrous $Na_2SO_4$, filtered and evaporated under reduced pressure to afford 2-bromo-6-fluoro-3-methoxy-benzaldehyde (40 g, crude) as a pale yellow solid.

Step 2: To a stirred solution of 2-bromo-6-fluoro-3-methoxy-benzaldehyde (40.0 g, 0.18 mol) in a mixture of THF:n-butanol:water $H_2O$ (396 mL, 1:1:0.3) was added $NaH_2PO_4 \cdot 2H_2O$ (106.7 g, 0.69 mol), $NaClO_2$ (68.0 g, 0.75 mol) and 2-methyl-2-butene (66 mL, 0.62 mol) at 0° C., and the resulting reaction mixture was stirred for 16 h at room temperature. After completion (monitored by TLC), the reaction mixture was concentrated under reduced pressure and the obtained residue was diluted with water. The pH was adjusted to 7-8 using saturated $NaHCO_3$ solution, and the resulting basic aqueous layer was washed with EtOAc, and the organic phase was discarded. The aqueous layer was acidified to pH 2 with 3N HCl solution and extracted with EtOAc (twice). The combined organic layers were dried over $Na_2SO_4$ and concentrated under reduced pressure to afford 2-bromo-6-fluoro-3-methoxy-benzoic acid (26 g, 60%) as a white solid.

Step 3: To a stirred solution of 2-bromo-6-fluoro-3-methoxy-benzoic acid (26 g, 0.11 mol) in tert-butanol (170 mL) was added TEA (21.6 mL, 0.16 mol), 4 Å molecular sieves (20.5 g) and DPPA (34 mL, 0.16 mol) at room temperature under $N_2$ atmosphere, and the resulting reaction mixture was heated at reflux temperature for 16 h. After completion (monitored by TLC), the reaction mixture was concentrated under reduced pressure at 45° C. The crude residue was diluted with $H_2O$, and extracted with DCM (twice). The combined organic layers were dried over $Na_2SO_4$ and concentrated under reduced pressure. The crude material was diluted with DCM (550 mL) and to this was added slowly TFA (240 mL) at 0° C. Then, the resulting reaction mixture was stirred for 1 h at room temperature. After completion (monitored by TLC), the reaction mixture was concentrated under reduced pressure, the obtained crude residue was diluted with $H_2O$, and the pH adjusted to 7-8 with saturated $NaHCO_3$ solution at 0° C. The product was extracted with DCM (twice), and the combined organic layers were dried over $Na_2SO_4$ and concentrated under reduced pressure. The crude material was purified by column chromatography (100-200 mesh silica gel; 0-1% Ethyl acetate/hexane) to afford 2-bromo-6-fluoro-3-methoxy-phenylamine (18 g, 78%) as a pale yellow liquid.

Step 4: To a stirred solution of 2-bromo-6-fluoro-3-methoxy-phenylamine (18 g, 0.09 mol) in DMSO (180 mL) was added α-aminoisobutyric acid (16.9 g, 0.17 mol) and $K_3PO_4{\cdot}3H_2O$ (34.7 g, 0.17 mol) at room temperature under $N_2$ atmosphere. The resulting reaction mixture was degassed with $N_2$ for 10 min, copper(I) chloride (0.81 g, 0.008 mol) was added, and the resulting suspension was heated at 140° C. for 16 h. After completion (monitored by TLC), the reaction mixture was quenched into ice water and the product was extracted with EtOAc (twice). The combined organic layers were washed with water and brine, dried over $Na_2SO_4$ and concentrated under reduced pressure. The crude residue was triturated with hexane to afford 8-fluoro-5-methoxy-3,3-dimethyl-3,4-dihydro-1H-quinoxalin-2-one (14.0 g, 76%) as a brown solid.

Step 5: To a stirred solution of 8-fluoro-5-methoxy-3,3-dimethyl-3,4-dihydro-1H-quinoxalin-2-one (14.0 g, 0.06 mol) in Toluene (280 mL), was added Lawesson's reagent (37.9 g, 0.095 mol) and the resulting reaction mixture was maintained at reflux temperature for 1 h. After completion (monitored by TLC), the reaction mixture was quenched with saturated $NaHCO_3$ solution and the product was extracted with EtOAc (3 times). The combined organic layers were dried over $Na_2SO_4$ and concentrated under reduced pressure. The crude residue was purified by column chromatography (100-200 mesh silica gel; 0-7% ethyl acetate/hexane) to afford 8-fluoro-5-methoxy-3,3-dimethyl-3,4-dihydro-1H-quinoxaline-2-thione (14.0 g, 93%) as a yellow solid.

Step 6: To a stirred solution of 8-fluoro-5-methoxy-3,3-dimethyl-3,4-dihydro-1H-quinoxaline-2-thione (14.0 g, 0.05 mol) in n-butanol (700 mL), was added acetic hydrazide (14.3 g, 0.19 mol), and acetic acid (70 mL) at room temperature under $N_2$ atmosphere, and the resulting reaction mixture was maintained for at 140° C. for 16 h. After completion (monitored by TLC), the reaction mixture was concentrated under reduced pressure. The obtained crude residue was purified by column chromatography (100-200 mesh silica gel; 1-2% MeOH in DCM) to afford 9-fluoro-6-methoxy-1,4,4-trimethyl-4,5-dihydro-[1,2,4]triazolo[4,3-a]quinoxaline (11.0 g, 72%) as an off-white solid.

Step 7: To a stirred solution of 9-fluoro-6-methoxy-1,4,4-trimethyl-4,5-dihydro-[1,2,4]triazolo[4,3-a]quinoxaline (11.0 g, 0.04 mol) in DCM (110 mL), was added slowly $BBr_3$ (1.0 M solution in DCM 210.0 mL, 0.21 mol) at 0° C., and the resulting reaction mixture was maintained for 16 h at room temperature. After completion (monitored by TLC), the reaction mixture was cooled to 0° C. and methanol (100.0 mL) was slowly added at 0° C. After evaporation under reduced pressure, the obtained crude residue was diluted with $H_2O$ and the pH was adjusted to 7-8 with saturated $NaHCO_3$ solution. The product was then extracted with 10% MeOH in DCM (twice). The combined organic layers were dried over $Na_2SO_4$ and concentrated under reduced pressure. The obtained crude material was purified by trituration with hexane, filtered and dried to afford 9-fluoro-1,4,4-trimethyl-4,5-dihydro-[1,2,4]triazolo[4,3-a]97uinoxaline-6-ol (8.0 g, 77%) as a light brown solid.

Step 8: To a stirred solution of 9-fluoro-1,4,4-trimethyl-4,5-dihydro-[1,2,4]triazolo[4,3-a]97uinoxaline-6-ol (8.0 g, 0.03 mol) in DCM (240.0 mL), was added DMAP (6.0 g, 0.05 mol), TEA (7.0 mL, 0.05 mol) and triflic anhydride (6.5 mL, 0.05 mol) at 0° C., and the resulting reaction mixture was maintained for 16 h at room temperature. After completion (monitored by TLC), the reaction mixture was washed with water twice. The organic layer was dried over $Na_2SO_4$ and concentrated under reduced pressure. The obtained crude residue was purified by column chromatography (100-200 mesh silica gel; 1-4% MeOH in DCM) to afford trifluoromethanesulfonic acid 9-fluoro-1,4,4-trimethyl-4,5-dihydro-[1,2,4]triazolo[4,3-a]97uinoxaline-6-yl ester (10.0 g, 81%) as an off-white solid.

Step 9: To a stirred solution of trifluoromethanesulfonic acid 9-fluoro-1,4,4-trimethyl-4,5-dihydro-[1,2,4]triazolo[4,3-a]97uinoxaline-6-yl ester (6 g, 15.78 mmol) in Toluene (120 mL), tributyl-(1-ethoxy-vinyl)-stannane (7.99 mL, 23.664 mmol) was added at room temperature, and the reaction mixture was degassed with $N_2$ gas for 5 min. To this was added $Pd(PPh_3)_4$ (4.56 g, 3.94 mmol) and the reaction was heated for 18 h at 100° C. After completion (monitored by TLC), the reaction mixture was cooled to room temperature, 2N HCl (50 mL) was added and the mixture was stirred for 2 h. Then, the reaction mixture was partitioned between water and toluene, and the aqueous phase was quenched with saturated $NaHCO_3$ solution at ice-cooled temperature and extracted with ethyl acetate. The combined organic layers were dried over $Na_2SO_4$ and concentrated under reduced pressure. The obtained crude material was purified by column chromatography (100-200 mesh silicagel; 6% MeOH-DCM) to afford 1-(9-fluoro-1,4,4-trimethyl-4,5-dihydro-[1,2,4]triazolo[4,3-a]97uinoxaline-6-yl)-ethanone (1.8 g, 41.67%) of as an off-white solid.

Step 10: To a stirred solution of 1-(9-fluoro-1,4,4-trimethyl-4,5-dihydro-[1,2,4]triazolo[4,3-a]97uinoxaline-6-yl)-ethanone (1.7 g, 6.198 mmol) in THF (50 mL), MeMgBr (3 M in ether, 0.33 mL, 30.991 mmol) was added at ice-cooled temperature, and the reaction mixture was stirred at room temperature for 1 h. After completion (monitored by TLC), the reaction mixture was quenched with saturated $NH_4Cl$ solution and extracted with ethyl acetate. The combined organic layers were dried over $Na_2SO_4$ and concentrated under reduced pressure. The obtained crude material was purified over column chromatography (100-200 mesh silica gel; ethyl acetate) to afford 2-(9-fluoro-1,4,4-trimethyl-4,5-dihydro-[1,2,4]triazolo[4,3-a]97uinoxaline-6-yl)-propan-2-ol (11) (1.6 g, 89.38%) as an off-white solid.

Step 11: To a stirred solution of 2-(9-fluoro-1,4,4-trimethyl-4,5-dihydro-[1,2,4]triazolo[4,3-a]98uinoxaline-6-yl)-propan-2-ol (1.89 g, 6.51 mmol) in DMF (12 mL) was added NBS (1.159 g, 6.513 mmol) at ice cooled temperature, and the reaction mixture was stirred at room temperature for 1 h. After completion (monitored by TLC), the reaction mixture was quenched with water and extracted with ethyl acetate. The organic layer was dried over $Na_2SO_4$ and concentrated under reduced pressure. The obtained crude compound was purified over column chromatography (100-200 mesh silica gel; ethyl acetate) to afford 2-(8-bromo-9-fluoro-1,4,4-trimethyl-4,5-dihydro-[1,2,4]triazolo[4,3-a]98uinoxaline-6-yl)-propan-2-ol (1.87 g, 77.92%) as an off-white solid.

The intermediates in Table 3 were synthesized in analogy to the synthesis depicted in Reaction Scheme 1:

| Intermediate | Structure | NMR |
|---|---|---|
| Int-B-25 | 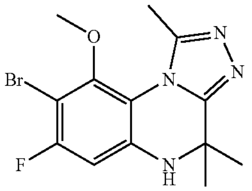 [SMILES: COc1c(Br)c(F)cc2c1-n1c(C)nnc1C(C)(C)N2] | $^1H$ NMR (DMSO-$d_6$) δ: 7.00 (s, 1H), 6.77 (d, 1H), 3.61 (s, 3H), 2.47 (s, 3H), 1.47 (s, 6H) |
| Int-B-37 | 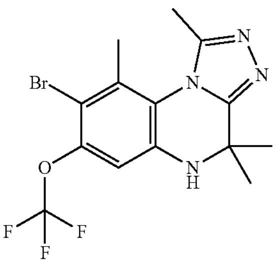 [SMILES: Cc1c(Br)c(OC(F)(F)F)cc2c1-n1c(C)nnc1C(C)(C)N2] | $^1H$ NMR (DMSO-$d_6$) δ: 7.01 (s, 1H), 6.95 (s, 1H), 2.40 (s, 6H), 1.43 (bs, 6H). |

Synthesis of 4-bromopyrazolo[1,5-a]pyridine (Intermediate C-75)

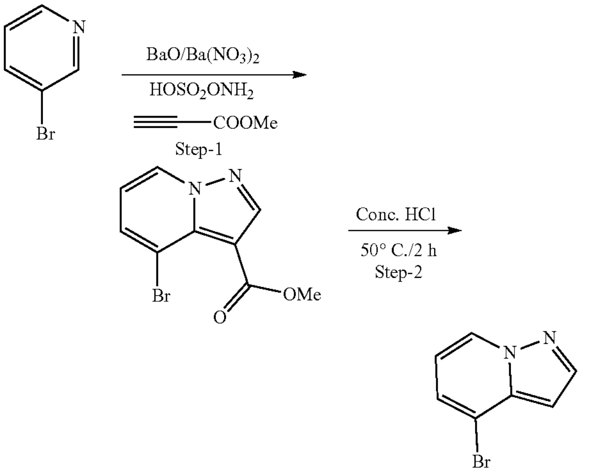

intermediate C-75

Step 1: To a solution of BaO (3.1 g, 20.253 mmol, 3.2 eq) in $H_2O$ (5 mL), 3-bromopyridine (1 g, 6.329 mmol, 1 eq) and Ba(NO3)2 (3.3 g, 12.658 mmol, 2 eq) were added slowly at RT. To this suspension, hydroxylamine-O-sulfonic acid (3.57 g, 31.645, 5 eq) dissolved in $H_2O$ (5 mL) was added and the reaction mixture was heated at 90° C. for 16 h. Then, the reaction mixture was filtered through and the filtrate was evaporated under reduced pressure. The crude residue was dissolved in DMF (10 mL), $K_2CO_3$ (0.87 g, 6.329 mmol, 1 eq) and methyl propiolate (0.53 g, 6.329 mmol, 1 eq) were added at RT and the reaction was stirred again at RT for another 16 h. After completion (monitored by TLC), the mixture was diluted with water and extracted with EtOAc. The organic layer was washed with brine, dried over $Na_2SO_4$, filtered and evaporated under reduced pressure. The crude material was purified by column chromatography to afford 4-bromopyrazolo[1,5-a]pyridine-3-carboxylate (0.15 g, 9%) as a brown solid.

Step 2: To 4-bromopyrazolo[1,5-a]pyridine-3-carboxylate (1.5 g, 5.88 mmol, 1 eq), conc HCl (10 mL) was added at RT. The reaction was then stirred at 50° C. for 2 h. After completion (monitored by TLC), the reaction mixture was quenched with ice and basified with $NaHCO_3$ solution. The aqueous layer was extracted with EtOAc The organic layer was washed with water and brine, dried over $Na_2SO_4$, filtered and evaporated under reduced pressure. The crude residue was purified by column chromatography to afford 4-bromopyrazolo[1,5-a]pyridine (0.7 g, 61%) as a brown liquid.

Synthesis of 4-bromo-6-fluoropyrazolo[1,5-a]pyridine (Intermediate C-76)

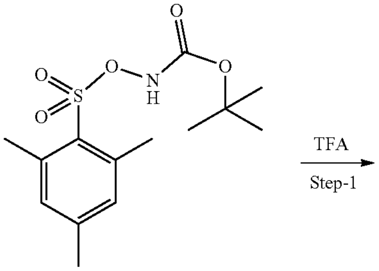

-continued

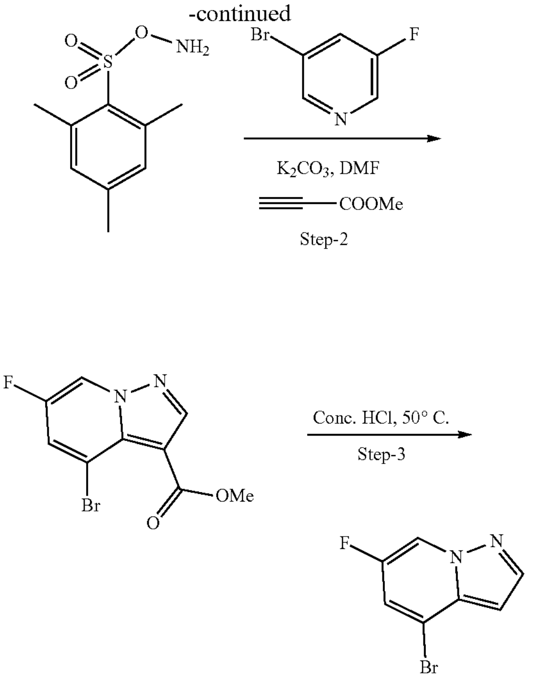

intermediate C-76

Step 1: To tert-butyl ((mesitylsulfonyl)oxy)carbamate (0.5 g, 1.587 mmol, 1 eq), TFA (2 mL) was added at 0° C., and the reaction mixture was stirred at RT for 2 h. After completion (monitored by TLC), the reaction mixture was quenched with ice and a white precipitate was formed. The solid was filtered off and dissolved in DCM. The DCM solution of the compound was used for the next step without further treatment.

Step 2: To a solution of O-(mesitylsulfonyl)hydroxylamine (from the previous step) in DCM, 3-bromo-5-fluoropyridine (0.3 g, 1.704 mmol, 1 eq) was added at 0° C. and the mixture was stirred at the same temperature for 3 h. The, the reaction mixture was evaporated under reduced pressure, and the crude residue was dissolved in DMF (10 mL). $K_2CO_3$ (0.47 g, 3.408 mmol, 2 eq) and methyl propiolate (0.172 g, 2.044 mmol, 1.2 eq) were added at RT, and the reaction was stirred at RT for 16 h. After completion (monitored by TLC), the reaction mixture was diluted with water and extracted with EtOAc. The combined organic layers were washed with water and brine, dried over $Na_2SO_4$, filtered and evaporated under reduced pressure. The crude material was purified by column chromatography to afford methyl 4-bromo-6-fluoropyrazolo[1,5-a]pyridine-3-carboxylate (0.2 g, 21.5%) as a brown solid (mixture of regio-isomers).

Step 3: To methyl 4-bromo-6-fluoropyrazolo[1,5-a]pyridine-3-carboxylate (0.25 g, 0.915 mmol, 1 eq), conc. HCl (5 mL) was added at RT, and the reaction mixture was heated at 50° C. for 3 h. After completion (monitored by TLC), the reaction mixture was quenched with $NaHCO_3$ solution and extracted with EtOAc. The organic layer was washed with water and brine, dried over $Na_2SO_4$, filtered and evaporated under reduced pressure. The crude residue was purified by SFC purification to afford the desired regio-isomer of compound 4-bromo-6-fluoropyrazolo[1,5-a]pyridine (0.02 g, 10%) as a brown gum.

Synthesis of 6-fluoro-1,4,4,9-tetramethyl-8-(tetramethyl-1,3,2-dioxaborolan-2-yl)-4H,5H[1,2,4]triazolo[4,3-a]quinoxaline (Intermediate D-7)

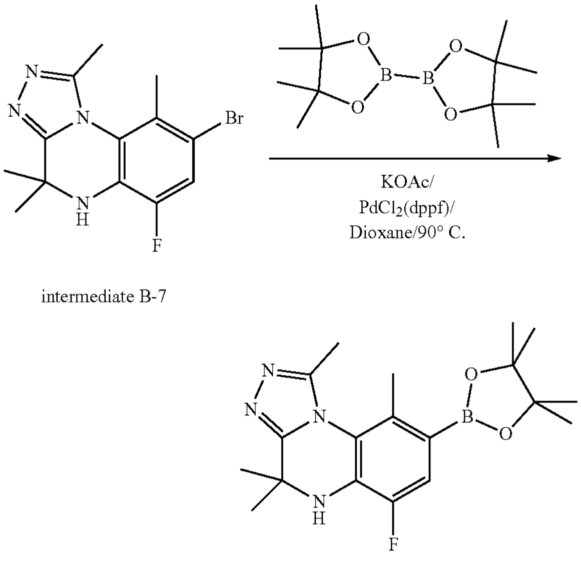

intermediate B-7 intermediate D-7

A stirred solution of intermediate B-7 (3.0 g, 9.23 mmol, 1 eq), bis-pinacolatodiborane (3.5 g, 13.85 mmol, 1.5 eq) and potassium acetate (2.7 g, 27.69 mmol, 3 eq) in 1,4-dioxane (100 mL) was deoxygenated with argon gas for 10 min. $PdCl_2$(dppf)·DCM (0.753 g, 0.923 mmol. 0.1 eq) was then added and the reaction mixture was refluxed for 16 h at 90° C. The reaction mixture was then cooled to room temperature and filtered through a celite bed. The filtrate was concentrated under reduced pressure to afford the crude material which was purified by column chromatography (230-400 mesh silica gel; 5% MeOH/DCM) to yield 6-fluoro-1,4,4,9-tetramethyl-8-(tetramethyl-1,3,2-dioxaborolan-2-yl)-4H,5H[1,2,4]triazolo[4,3-a]quinoxaline (2.0 g, 80%) as a light brown solid.

Synthesis of 9-ethyl-6-fluoro-1,4,4-trimethyl-8-(tetramethyl-1,3,2-dioxaborolan-2-yl)-4H,5H-[1,2,4]triazolo[4,3-a]quinoxaline (Intermediate D-9)

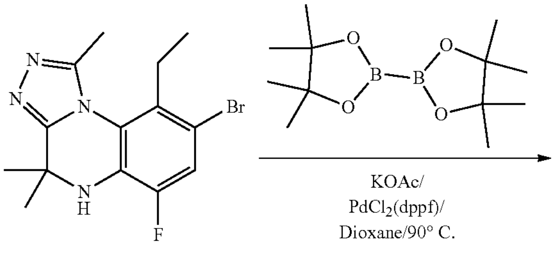

intermediate B-9

-continued

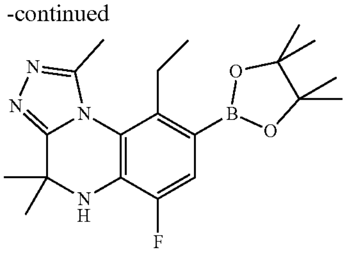

intermediate D-9

A stirred solution of intermediate B-9 (0.3 g, 0.884 mmol, 1 eq), bis-pinacolatodiborane (0.447 g, 1.769 mmol, 2 eq) and potassium acetate (0.26 g, 2.652 mmol, 3 eq) in 1,4-dioxane (10 mL) was deoxygenated with argon gas for 10 min. $PdCl_2$(dppf)·DCM (0.072 g, 0.088 mmol. 0.1 eq) was added to the reaction mixture, which was refluxed for 16 h at 90° C. The reaction mixture was then cooled to room temperature and filtered through a celite bed. The filtrate was concentrated under reduced pressure to afford the crude material which was purified by column chromatography (230-400 mesh silica gel; 5% MeOH/DCM) to yield 9-ethyl-6-fluoro-1,4,4-trimethyl-8-(tetramethyl-1,3,2-dioxaborolan-2-yl)-4H,5H-[1,2,4]triazolo[4,3-a]quinoxaline (0.32 g, 94%) as a light brown solid.

Synthesis of 6-fluoro-9-methoxy-1,4,4-trimethyl-8-(tetramethyl-1,3,2-dioxaborolan-2-yl)-4H,5H-[1,2,4]triazolo[4,3-a]quinoxaline (Intermediate D-10)

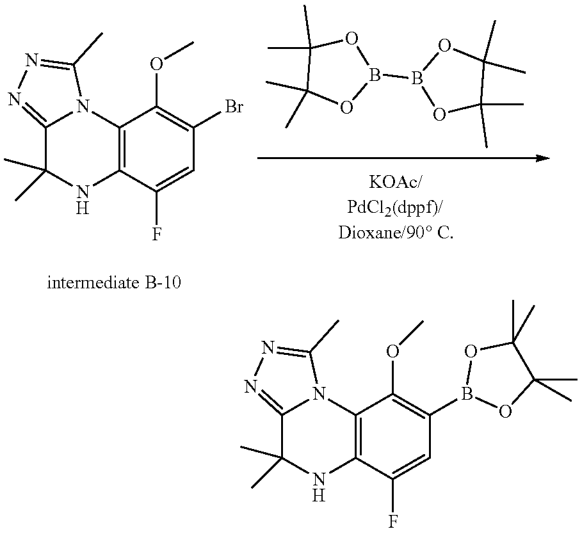

intermediate B-10 intermediate D-10

A stirred solution of intermediate B-10 (0.25 g, 0.733 mmol, 1 eq), bis-pinacolatodiborane (0.371 g, 1.466 mmol, 2 eq) and potassium acetate (0.215 g, 2.199 mmol, 3 eq) in 1,4-dioxane (10 mL) was deoxygenated with argon gas for 10 min. $PdCl_2$(dppf)·DCM (0.06 g, 0.073 mmol. 0.1 eq) was added to the reaction mixture, which was then refluxed for 16 h at 90° C. The reaction mixture was cooled to room temperature and filtered through a celite bed. The filtrate was concentrated under reduced pressure to afford the crude material which was purified by column chromatography (230-400 mesh silica gel; 5% MeOH/DCM) to yield 6-fluoro-9-methoxy-1,4,4-trimethyl-8-(tetramethyl-1,3,2-dioxaborolan-2-yl)-4H,5H-[1,2,4]triazolo[4,3-a]quinoxaline (0.2 g, 71%) as a light brown solid.

Synthesis of 1-cyclopropyl-6-fluoro-4,4,9-trimethyl-8-(tetramethyl-1,3,2-dioxaborolan-2-yl)-4H,5H-[1,2,4]triazolo[4,3-a]quinoxaline (Intermediate D-12)

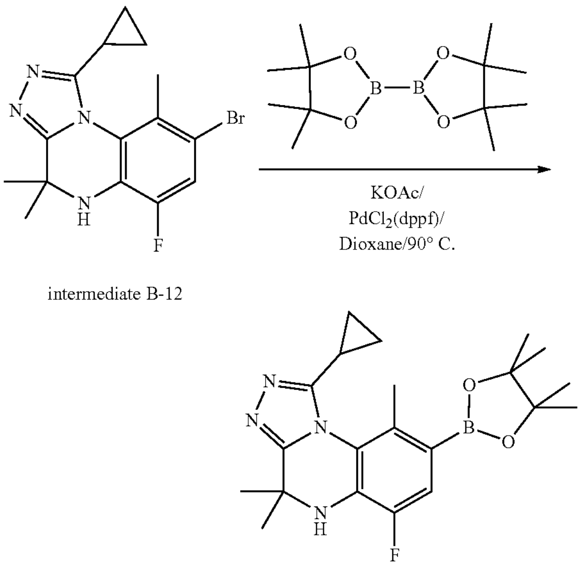

intermediate B-12 intermediate D-12

A stirred solution of intermediate B-12 (0.25 g, 0.712 mmol, 1 eq), bis-pinacolatodiborane (0.27 g, 1.068 mmol, 1.5 eq) and potassium acetate (0.209 g, 2.136 mmol, 3 eq) in 1,4-dioxane (10 mL) was deoxygenated with argon gas for 10 min. $PdCl_2$(dppf)·DCM (0.058 g, 0.071 mmol. 0.1 eq) was then added and the reaction mixture was refluxed for 16 h at 90° C. The reaction mixture was then cooled to room temperature and filtered through a celite bed. The filtrate was concentrated under reduced pressure and the crude material was purified by column chromatography (230-400 mesh silica gel; 5% MeOH/DCM) to afford 1-cyclopropyl-6-fluoro-4,4,9-trimethyl-8-(tetramethyl-1,3,2-dioxaborolan-2-yl)-4H,5H-[1,2,4]triazolo[4,3-a]quinoxaline (0.22 g, 77.7%) as a light brown solid.

Synthesis of 9-(difluoromethyl)-6-fluoro-1,4,4-trimethyl-8-(tetramethyl-1,3,2-dioxaborolan-2-yl)-4H,5H-[1,2,4]triazolo[4,3-a]quinoxaline (Intermediate D-43)

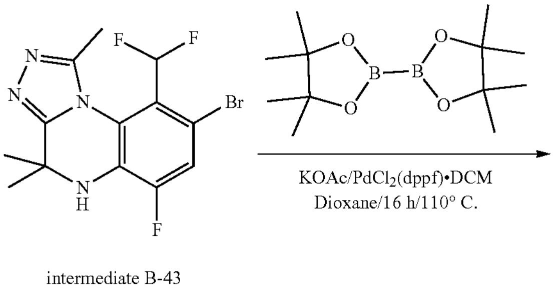

intermediate B-43

-continued

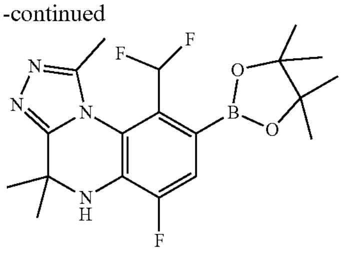

intermediate D-43

To a solution of intermediate B-43 (0.05 g, 0.138 mmol, 1 eq) in dioxane (10 mL) were added KOAc (0.041 g, 0.414 mmol, 3 eq) and bispincolatediborane (0.42 g, 0.166 mmol, 1.2 eq) The solution was degassed with argon for 20 min, followed by addition of $PdCl_2$(dppf)·DCM (0.011 g, 0.0138 mmol, 0.01 eq), and the reaction mixture was refluxed for 16 h. After completion (monitored by TLC), the reaction mixture was evaporated under reduced pressure to afford the crude material which was purified by column chromatography to yield 9-(difluoromethyl)-6-fluoro-1,4,4-trimethyl-8-(tetramethyl-1,3,2-dioxaborolan-2-yl)-4H,5H-[1,2,4]triazolo[4,3-a]quinoxaline (0.05 g, 89%), as a brown solid.

Synthesis of 9-fluoro-1,4,4,6-tetramethyl-8-(tetramethyl-1,3,2-dioxaborolan-2-yl)-4H,5H-[1,2,4]triazolo [4,3-a]quinoxaline (Intermediate D-60)

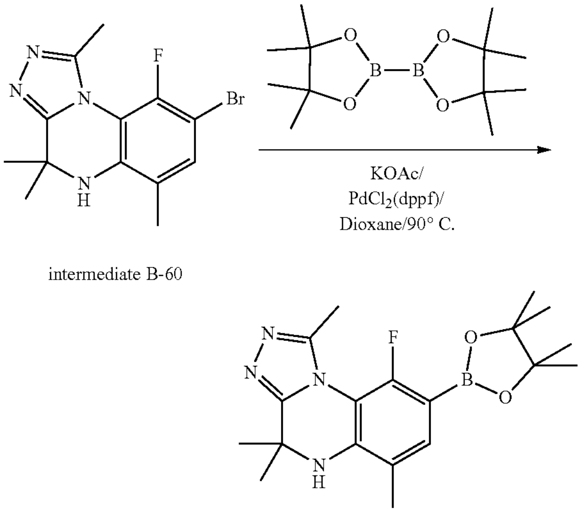

intermediate B-60 intermediate D-60

A stirred solution of intermediate B-60 (1.0 g, 3.076 mmol, 1 eq), bis-pinacolatodiborane (1.16 g, 4.615 mmol, 1.5 eq) and potassium acetate (0.904 g, 9.231 mmol, 3 eq) in 1,4-dioxane (50 mL) was deoxygenated with argon gas for 10 min. $PdCl_2$(dppf)·DCM (0.251 g, 0.307 mmol. 0.1 eq) was then added to the reaction mixture, which was refluxed for 16 h at 90° C. The reaction mixture was cooled to room temperature and then filtered through a celite bed. The filtrate was concentrated under reduced pressure to afford the crude material which was purified by column chromatography (230-400 mesh silica gel; 5% MeOH/DCM) to yield 9-fluoro-1,4,4,6-tetramethyl-8-(tetramethyl-1,3,2-dioxaborolan-2-yl)-4H,5H-[1,2,4]triazolo[4,3-a]quinoxaline (0.82 g, 73.3%) as a light brown solid.

Synthesis of 8-iodo-1,4,4,9-tetramethyl-4,5-dihydro-[1,2,4]triazolo[4,3-a]quinoxaline (Intermediate E-40)

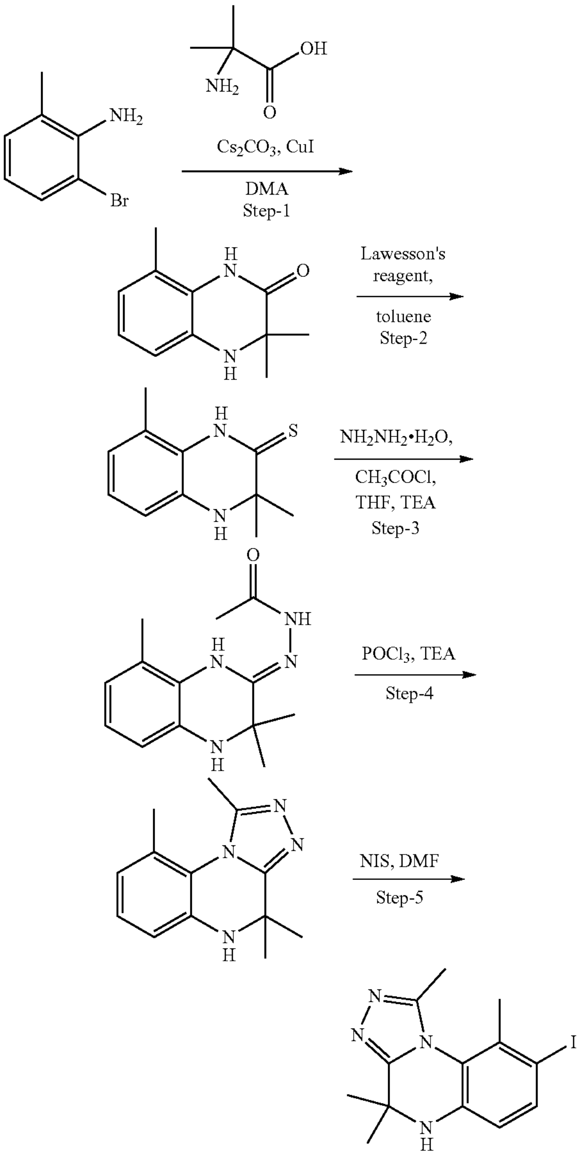

intermediate E-40

Step 1: A suspension of 2-bromo-6-methylaniline (1.0 g, 54.0 mmol, 1.0 eq) and 2-aminobutyric acid (1.1 g, 10.8 mmol, 2.0 eq) in DMSO (10 ml) in a sealed tube was deoxygenated with Ar for 20 minutes. $K_3PO_4$ (2.3 g, 10.8 mmol, 2.0 eq) and CuCl (53.0 mg, 5.4 mmol, 0.1 eq) were then added. The reaction mixture was then stirred at 140° C. for 16 h. After completion of the reaction, the reaction mixture was filtered through a celite bed and the celite bed was washed with EtOAc (100 ml). The filtrate was diluted with EtOAc (100 ml) and was washed with water (3×150 ml) and brine (200 ml), dried over anhydrous $Na_2SO_4$ and was then evaporated under reduced pressure to obtain the crude compound, which was purified by column chromatography (100-200 mesh silica gel; 30% EtOAc/hexane; $R_f$-value-0.4) to afford 3,3,8-trimethyl-3,4-dihydroquinoxalin-2(1H)-one (0.6 g, 60%).

Step 2: To a solution of 3,3,8-trimethyl-3,4-dihydroquinoxalin-2(1H)-one (7.0 g, 36.0 mmol, 1.0 eq) in toluene (75 ml) was added Lawesson's reagent (22.0 g, 55 mmol, 1.5 eq.) at ambient temperature and the reaction mixture was then refluxed at 120° C. for 40 minutes. After completion of the reaction (monitored by TLC), the reaction mixture was quenched with sat. $NaHCO_3$ solution (100 ml) followed by extraction with EtOAc (2×100 ml). The combined organic layers were washed with water (100 ml) and brine (100 ml), were dried over anhydrous $Na_2SO_4$ and evaporated under reduced pressure to obtain the crude compound which was purified by column chromatography (230-400 mesh silica gel; 20% EtOAc/hexane; $R_f$-value-0.4) to afford 3,3,8-trimethyl-3,4-dihydroquinoxaline-2(1H)-thione (5.0 g, 66%) as a yellow solid.

Step 3: To a stirring solution of compound 3,3,8-trimethyl-3,4-dihydroquinoxaline-2(1H)-thione (5.0 g, 62.4 mmol, 1 eq) in THF (30 ml) was added dropwise hydrazine hydrate (6.0 ml, 121.0 mmol, 5 eq) at 0° C. The reaction mixture was then stirred for 16 h at ambient temperature. TEA (16.5 ml, 122.7 mmol, 5 eq) was then added to the reaction mixture and the reaction mixture was stirred for another 10 minutes. Acetyl chloride (5.65 g, 73.65 mmol, 3 eq) was then added to the reaction mixture very slowly at 0° C. and the resulting reaction mixture was then stirred for 2 h at ambient temperature. The reaction mixture was then diluted with water (50 ml) and extracted with DCM (5×100 ml). The combined organic layers were washed with brine (100 ml), dried over $Na_2SO_4$ and concentrated under reduced pressure to obtain the crude material which was purified by washing with diethyl ether to afford N'-(3,3,8-trimethyl-3,4-dihydroquinoxalin-2(1H)-ylidene)acetohydrazide (2.0 g, 34%) as a white solid.

Step 4: N'-(3,3,8-trimethyl-3,4-dihydroquinoxalin-2(1H)-ylidene)acetohydrazide (6.0 g, 24 mmol, 1 eq) was taken up in a round bottom flask (50 ml) and was then cooled to −10° C. Phosphorus oxychloride (23.0 ml, 243 mmol, 10 eq) was then added dropwise to the compound followed by drop wise addition of TEA (3.5 ml, 24 mmol, 1 eq). After that the reaction mixture was stirred at −10° C. for 10 minutes and then 10 minutes at ambient temperature and finally at reflux for 4 h. The reaction mixture was then cooled to 0° C. and was then added dropwise into crushed ice in water under constant stirring. To this was then slowly added cold ammonia solution (100 ml). The aqueous part was then extract with DCM (2×100 mL). The combined organic layers were washed with brine (100 ml), dried over anhydrous $Na_2SO_4$ and concentrated under reduced pressure to obtain the crude compound, which was purified by column chromatography (230-400 mesh silica gel; 5% MeOH/DCM) to afford 1,4,4,9-tetramethyl-4,5-dihydro-[1,2,4]triazolo[4,3-a]quinoxaline (3.2 g, 58.6%) as a yellow solid.

Step 5: A stirred solution of 1,4,4,9-tetramethyl-4,5-dihydro-[1,2,4]triazolo[4,3-a]quinoxaline (3.0 g, 13 mmol, 1 eq) in DMF (40 mL) at −10° C. was treated portion wise over 10 min with solid N-iodosuccinimide (2.9 g, 13 mmol, 1.0 eq). The reaction mixture was allowed to warm to RT and stirred for 1.5 h. After completion (monitored by LCMS), the reaction mixture was diluted with ethyl acetate (300 mL) and organic layer was washed with water (5×50 mL) and brine (250 mL), dried over anhydrous $Na_2SO_4$ and evaporated under reduced pressure. The crude residue was purified by column chromatography (230-400 silica gel; 5% MeOH/DCM) to afford 8-iodo-1,4,4,9-tetramethyl-4,5-dihydro-[1,2,4]triazolo[4,3-a]quinoxaline (2 g, 43.43%) as an off-white solid.

Synthesis of 1-ethyl-7,9-difluoro-4,4-dimethyl-4,5-dihydro-[1,2,4]triazolo[4,3-a]quinoxaline-8-carboxylic acid (Intermediate F-1)

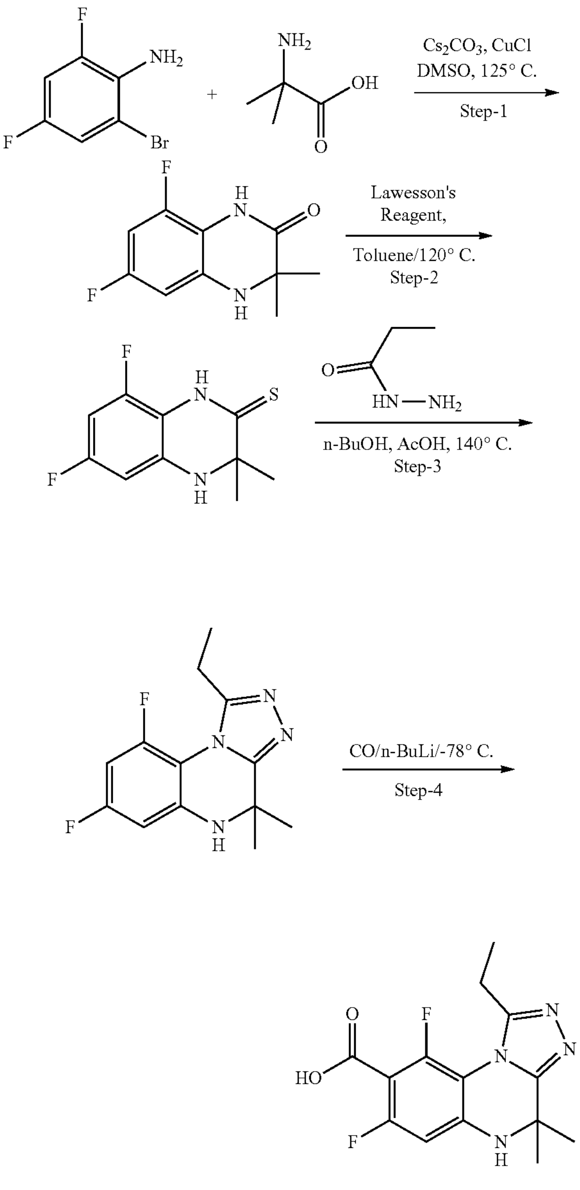

intermediate F-1

Step 1: A suspension of 2-bromo-4,6-difluoroaniline (25 g, 120.19 mmol, 1 eq.), 2-amino-2-methylpropanoic acid (24.75 g, 240.38 mmol, 2 eq.), $K_3PO_4$ (50.96 g, 240.38 mmol, 2 eq.) and CuI (2.29 g, 12.02 mmol, 0.1 eq.) in dry DMSO (375 mL) in a sealed tube were deoxygenated with Ar for 20 min. Reaction mixture was then stirred at 125° C. for 16 h. After completion of the reaction, it was filtered through celite bed and washed by EtOAc (100 mL). The filtrate was diluted with EtOAc (500 mL) and washed with water (3×150 mL), brine (200 mL), dried over anhydrous $Na_2SO_4$ and evaporated under reduced pressure. Crude product was purified by column chromatography to afford 6,8-difluoro-3,3-dimethyl-3,4-dihydroquinoxalin-2(1H)-one (34.0 g, 67%) as brown solid.

Step 2: To a solution of 6,8-difluoro-3,3-dimethyl-3,4-dihydroquinoxalin-2(1H)-one (34.0 g, 160 mmol, 1 eq.) in toluene (650 mL) was added Lawesson's reagent (97.3 g, 240 mmol, 1.5 eq.) at RT and the reaction mixture was refluxed at 120° C. for 40 min. After completion of reaction, the reaction mixture was quenched with sat. $NaHCO_3$ solution (250 mL) followed by extraction with EtOAc (3×150 mL). Combined organic layers was washed with water (300 mL), brine (200 mL), dried over anhydrous $Na_2SO_4$ and evaporated to get the crude product which was purified by column chromatography to afford 6,8-difluoro-3,3-dimethyl-3,4-dihydroquinoxaline-2(1H)-thione (26 g, 66%) as yellow solid.

Step 3: To a solution of 6,8-difluoro-3,3-dimethyl-3,4-dihydro-1H-quinoxaline-2-thione (20 g, 0.075 mol) inn-BuOH (362 mL) was added propanoic acid hydrazide (21 g, 0.249 mmol) followed by acetic acid (36.2 mL), and the resulting reaction mixture was stirred at 140° C. for 16 h. After completion (monitored by LC-MS), the reaction mixture was diluted with water (500 mL) and extracted with ethyl acetate (2×500 mL). The combined organic layers were washed with water (200 mL) and brine (200 mL), dried over anhydrous Na2SO4 and concentrated under reduced pressure. The crude residue was purified by trituration using MTBE and hexane to afford 1-Ethyl-7,9-difluoro-4,4-dimethyl-4,5-dihydro-[1,2,4]triazolo[4,3-a]quinoxaline (13 g, 56%) as a white solid.

Step 4: To a stirred solution of TMP (4 mL, 0.023 mol) in THF (50 mL) was added n-BuLi (12.26 mL, 0.033 mol) at −30° C., and the resulting solution was stirred at −30° C. for 15 min, followed by 0° C. for 30 min. Then, the mixture was cooled to −78° C. and a solution of [1-ethyl-7,9-difluoro-4,4-dimethyl-4,5-dihydro-[1,2,4]triazolo[4,3-a]quinoxaline] (2.5 g, 0.009 mol) in THF (50 mL) was added. The resulting reaction mixture was stirred at −78° C. for 2 h and dry ice was added. After completion (monitored by LCMS), the reaction mixture was quenched with cold water. The resulting aqueous phase was extracted with ethyl acetate and acidified to pH 4 using 1N HCl. The obtained solid was filtered and washed subsequently with water, ethyl acetate and MTBE, and dried under vacuum to afford [1-ethyl-7,9-difluoro-4,4-dimethyl-4,5-dihydro-[1,2,4]triazolo[4,3-a]quinoxaline-8-carboxylic acid] (1.27 g, 43%) as a light yellow solid.

Example 1: 3,5,11,11-tetramethyl-6-(1-(methylsulfonyl)-1H-indol-4-yl)-8,9,10,11-tetrahydrofuro[3,2-f][1,2,4]triazolo[4,3-a]quinoxaline

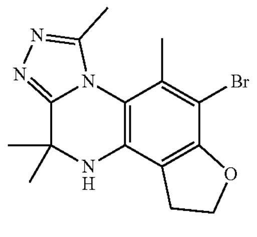

intermediate B-54

+

-continued

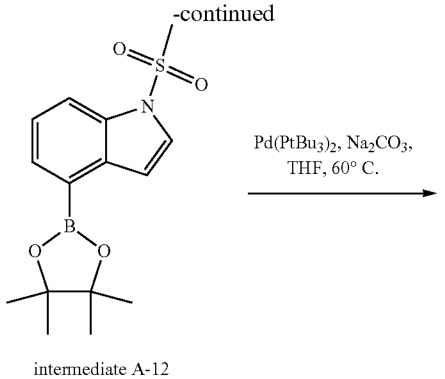

intermediate A-12

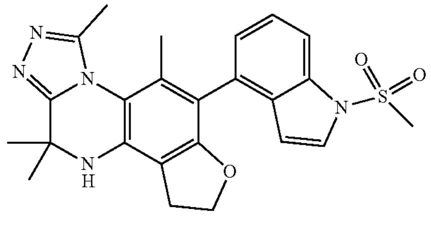

example 1

Intermediate B-54 (50 mg, 0.14 mmol, 1.0 eq.), intermediate A-12 (138 mg, 0.43 mmol, 3.0 eq.) and $Pd(PtBu_3)_2$ (3.7 mg, 0.0072 mmol, 0.05 eq.) were weighed out in a microwave vial, a stir bar was added, the vial was sealed and purged with nitrogen. Then, THF (0.9 mL) and 2M $Na_2CO_3$ solution (0.3 mL) were added, and the vial was slightly evacuated and backfilled/purged with nitrogen again. The reaction mixture was then heated at 60° C. overnight. Then, sat. $NaHCO_3$ solution and EtOAc were added, the layers were separated and the aqueous layer was extracted with EtOAc. The combined organic layers were then washed with brine, dried over $MgSO_4$ and the solvent was removed under reduced pressure. The obtained residue was purified reversed-phase HPLC to obtain 3,5,11,11-tetramethyl-6-(1-(methylsulfonyl)-1H-indol-4-yl)-8,9,10,11-tetrahydrofuro[3,2-f][1,2,4]triazolo[4,3-a]quinoxaline (19 mg, 29%).

$^1H$ NMR (600 MHz, DMSO-$d_6$) δ: 7.84 (dd, 1H), 7.58 (d, 1H), 7.44 (t, 1H), 7.25 (d, 1H), 6.46 (d, 1H), 6.08 (s, 1H), 4.53 (d, 1H), 4.46 (q, 1H), 3.49 (s, 3H), 3.21-3.13 (m, 2H), 2.42 (s, 3H), 1.94 (s, 3H), 1.66-1.40 (m, 6H).

The following examples were prepared in a similar manner (use of appropriate reagents and purification methods known to the person skilled in the art) as the synthesis described for example 1:

| Example Nr. | Structure | Inter-mediates | Yield % | Data |
|---|---|---|---|---|
| 2 | 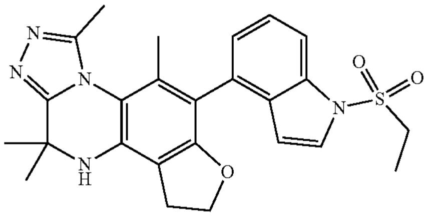 [SMILES: CCS(=O)(=O)n1ccc2c(-c3c(C)c4c(c5c3OCC5)NC(C)(C)c3nnc(C)n3-4)cccc21] | A-47, B-54 | 59 | $^{1}$H NMR (600 MHz, DMSO) δ = 7.84 (d, 1H), 7.59 (d, 1H), 7.42 (t, 1H), 7.24 (d, 1H), 6.46 (d, 1H), 6.08 (s, 1H), 4.53 (q, 1H), 4.46 (q, 1H), 3.66 (tt, 2H), 3.17 (p, 2H), 2.42 (s, 3H), 1.93 (s, 3H), 1.51 (d, 6H), 1.10 (t, 3H). |
| 3 | 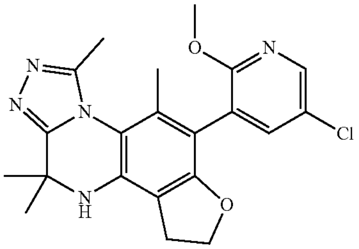 [SMILES: COc1ncc(Cl)cc1-c1c(C)c2c(c3c1OCC3)NC(C)(C)c1nnc(C)n1-2] | 5-chloro-2-methoxy-3-(4,4,5,5-tetramethyl-1,3,2-dioxaborolan-2-yl)pyridine, B-54 | 86 | 1H NMR (600 MHz, DMSO) δ = 8.23 (t, 1H), 7.77 (d, 1H), 6.11 (s, 1H), 4.57 (t, 1H), 4.49 (q, 1H), 3.85 (s, 3H), 3.13 (d, 2H), 2.38 (s, 3H), 1.98 (s, 3H), 1.49 (d, 6H). |
| 4 | 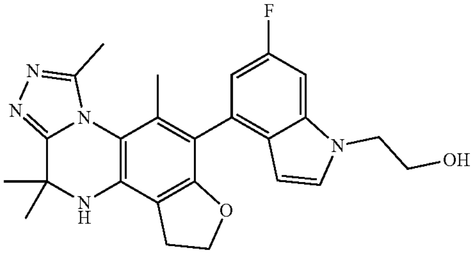 [SMILES: Cc1c(-c2cc(F)cc3c2ccn3CCO)c2c(c3c1-n1c(C)nnc1C(C)(C)N3)CCO2] | A-20, B-54 | 72 | 1H NMR (600 MHz, DMSO) δ = 7.35 (dd, 1H), 6.81 (d, 1H), 6.06 (d, 2H), 4.55 (q, 1H), 4.43 (q, 1H), 4.27-4.15 (m, 3H), 3.75 (q, 3H), 3.16 (qt, 2H), 2.41 (d, 3H), 1.96 (s, 3H), 1.51 (d, 6H). |
| 5 | 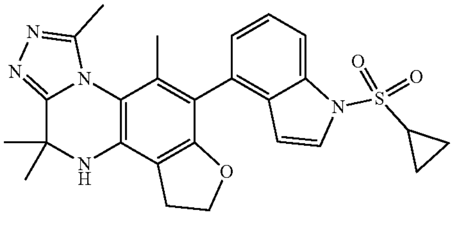 [SMILES: Cc1c(-c2cccc3c2ccn3S(=O)(=O)C2CC2)c2c(c3c1-n1c(C)nnc1C(C)(C)N3)CCO2] | A-48, B-54 | 74 | 1H NMR (600 MHz, DMSO) δ = 7.89 (d, 1H), 7.62-7.57 (m, 1H), 7.46-7.39 (m, 1H), 7.24 (d, 1H), 6.45 (d, 1H), 6.08 (s, 1H), 4.53 (q, 1H), 4.47 (d, 1H), 3.23-3.11 (m, 3H), 2.42 (s, 3H), 1.94 (s, 3H), 1.71-1.36 (m, 6H), 1.34-1.22 (m, 2H), 1.11 (dd, 2H). |
| 6 | 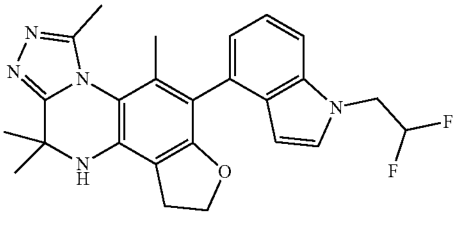 [SMILES: Cc1c(-c2cccc3c2ccn3CC(F)F)c2c(c3c1-n1c(C)nnc1C(C)(C)N3)CCO2] | A-42, B-54 | 51 | 1H NMR (600 MHz, DMSO) δ = 7.54 (d, 1H), 7.37 (d, 1H), 7.22 (t, 1H), 6.99 (d, 1H), 6.57-6.22 (m, 1H), 6.16 (d, 1H), 6.00 (s, 1H), 4.85-4.57 (m, 2H), 4.52 (d, 1H), 4.42 (q, 1H), 3.16 (dt, 2H), 2.41 (s, 3H), 1.93 (s, 3H), 1.51 (d, 6H). |
| 7 | 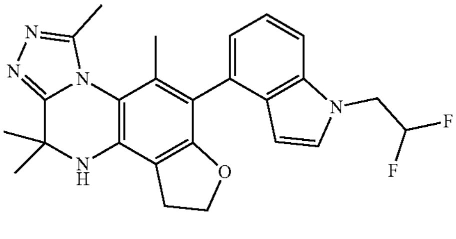 [SMILES: Cc1c(-c2cccc3c2ccn3CC(F)F)c2c(c3c1-n1c(C)nnc1C(C)(C)N3)CCO2] | A-30, B-54 | 91 | 1H NMR (600 MHz, DMSO) δ = 7.84 (d, 1H), 7.58 (d, 1H), 7.42 (t, 1H), 7.24 (d, 1H), 6.46 (d, 1H), 6.08 (s, 1H), 4.53 (q, 1H), 4.47 (d, 1H), 3.84 (p, 1H), 3.24-3.11 (m, 2H), 2.42 (s, 3H), 1.92 (s, 3H), 1.51 (d, 6H), 1.22 (dd, 6H). |

-continued

| Example Nr. | Structure | Inter-mediates | Yield % | Data |
|---|---|---|---|---|
| 8 | 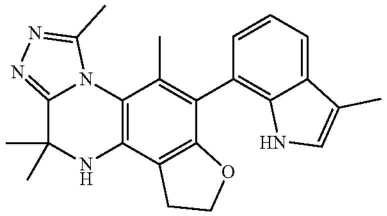 | 3-methyl-7-(4,4,5,5-tetramethyl-1,3,2-dioxaborolan-2-yl)-1H-indole, B-54 | 58 | 1H NMR (600 MHz, DMSO) δ = 10.29 (s, 1H), 7.46 (d, 1H), 7.08-7.00 (m, 2H), 6.95 (d, 1H), 5.99 (s, 1H), 4.48 (dq, 2H), 3.17 (ddp, 2H), 2.44 (s, 3H), 2.29 (s, 3H), 1.91 (s, 3H), 1.52 (d, 6H). |
| 9 | 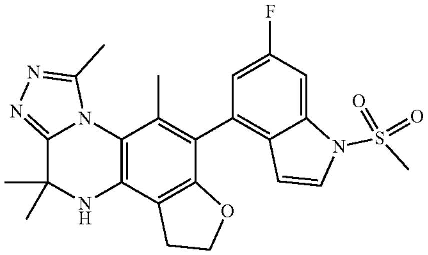 [SMILES: Cc1c(-c2cc(F)cc3c2ccn3S(C)(=O)=O)c2c(c3c1-n1c(C)nnc1C(C)(C)N3)CCO2] | A-2, B-54 | 30 | 1H NMR (600 MHz, DMSO) δ = 7.65-7.57 (m, 2H), 7.21-7.15 (m, 1H), 6.45 (d, 1H), 6.13 (s, 1H), 4.55 (q, 1H), 4.48 (q, 1H), 3.55 (s, 3H), 3.17 (t, 2H), 2.42 (s, 3H), 1.96 (s, 3H), 1.51 (d, 6H). |
| 10 | 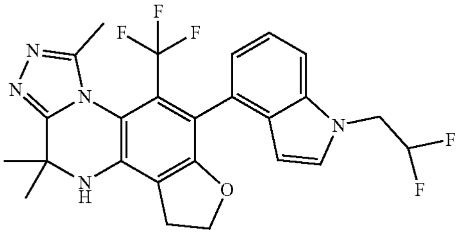 [SMILES: Cc1nnc2n1-c1c(c3c(c(-c4cccc5c4ccn5CC(F)F)c1C(F)(F)F)OCC3)NC2(C)C] | A-42, B-55 | 25 | 1H NMR (600 MHz, DMSO) δ = 7.56 (t, 1H), 7.33 (dd, 1H), 7.20 (ddd, 1H), 7.00 (dd, 1H), 6.61 (d, 1H), 6.41 (tdt, 1H), 6.16 (ddd, 1H), 4.80-4.62 (m, 2H), 4.62-4.51 (m, 1H), 4.52-4.28 (m, 1H), 3.26-3.03 (m, 1H), 2.46-2.35 (m, 3H), 1.79 (s, 3H), 1.32 (d, 3H). |
| 11 | 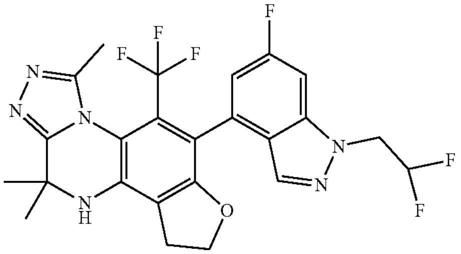 [SMILES: Cc1nnc2n1-c1c(c3c(c(-c4cc(F)cc5c4cnn5CC(F)F)c1C(F)(F)F)OCC3)NC2(C)C] | A-56, B-55 | 17 | 1H NMR (600 MHz, DMSO) δ = 7.92 (d, 1H), 7.77-7.58 (m, 1H), 7.24-6.92 (m, 1H), 6.75 (d, 1H), 6.48 (s, 1H), 5.08-4.74 (m, 2H), 4.76-4.56 (m, 1H), 4.47 (dt, 1H), 3.15 (ddd, 1H), 2.44 (d, 3H), 1.80 (s, 3H), 1.33 (d, 3H). |
| 12 | 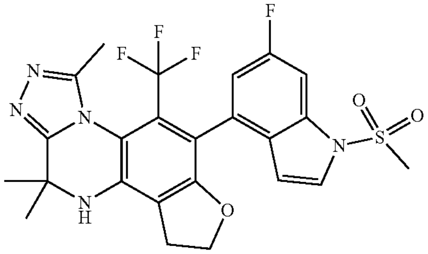 [SMILES: Cc1nnc2n1-c1c(c3c(c(-c4cc(F)cc5c4ccn5S(C)(=O)=O)c1C(F)(F)F)OCC3)NC2(C)C] | A-2, B-55 | 38 | 1H NMR (600 MHz, DMSO) δ = 7.67 (dd, 1H), 7.58 (td, 1H), 7.36-7.08 (m, 1H), 6.73 (s, 1H), 6.51 (dd, 1H), 4.74-4.54 (m, 1H), 4.46 (p, 1H), 3.58 (d, 3H), 3.47-3.30 (m, 1H), 3.16 (dp, 1H), 2.43 (d, 3H), 1.80 (s, 3H), 1.33 (d, 3H). |
| 13 | 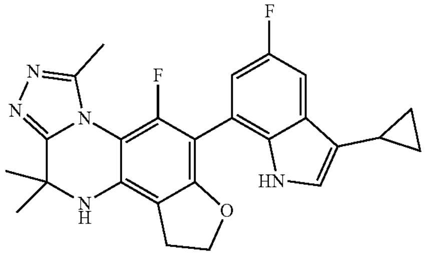 [SMILES: Cc1nnc2n1-c1c(F)c(-c3cc(F)cc4c(C5CC5)c[nH]c34)c3c(c1NC2(C)C)CCO3] | A-16, B-56 | 20 | 1H NMR (600 MHz, DMSO) δ = 10.55 (d, 1H), 7.07 (dd, 1H), 6.94 (dd, 1H), 6.41 (d, 1H), 4.62 (t, 2H), 3.17 (t, 1H), 2.46 (d, 3H), 1.95-1.87 (m, 1H), 1.57 (s, 6H), 0.90-0.81 (m, 2H), 0.65-0.55 (m, 2H). |

-continued
| Example Nr. | Structure | Inter-mediates | Yield % | Data |
|---|---|---|---|---|
| 18 | 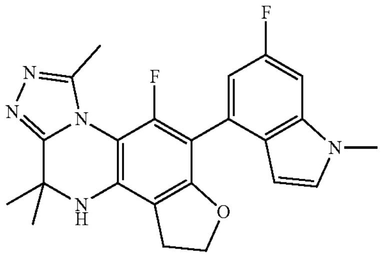 | A-73, B-56 | 26 | 1H NMR (600 MHz, DMSO) δ = 7.32 (q, 2H), 6.93 (dd, 1H), 6.43 (d, 1H), 6.25 (t, 1H), 4.61 (t, 2H), 3.78 (s, 3H), 3.17 (t, 2H), 2.46 (d, 3H), 1.55 (s, 6H). |
| 19 | 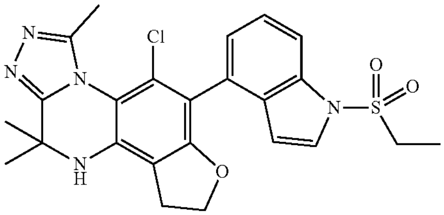 [SMILES: CCS(=O)(=O)n1ccc2c(-c3c(Cl)c4c(c5c3OCC5)NC(C)(C)c3nnc(C)n3-4)cccc21] | A-47, B-57 | 43 | 1H NMR (600 MHz, DMSO) δ = 7.87 (d, 1H), 7.60 (d, 1H), 7.44 (t, 1H), 7.28 (d, 1H), 6.52 (d, 1H), 6.46 (s, 1H), 4.60 (q, 1H), 4.54 (q, 1H), 3.67 (q, 2H), 3.21 (q, 1H), 2.54 (s, 3H), 1.54 (d, 6H), 1.11 (t, 3H). |
| 20 | 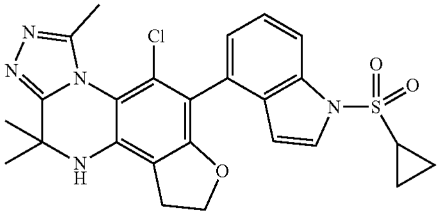 [SMILES: Cc1nnc2n1-c1c(Cl)c(-c3cccc4c3ccn4S(=O)(=O)C3CC3)c3c(c1NC2(C)C)CCO3] | A-48, B-57 | 37 | 1H NMR (600 MHz, DMSO) δ = 7.91 (d, 1H), 7.61 (d, 1H), 7.43 (t, 1H), 7.27 (d, 1H), 6.51 (d, 1H), 6.46 (s, 1H), 4.57 (dq, 2H), 3.25-3.12 (m, 1H), 2.54 (d, 3H), 1.59 (s, 3H), 1.48 (s, 3H), 1.34-1.20 (m, 3H), 1.17-1.07 (m, 2H). |
| 21 | 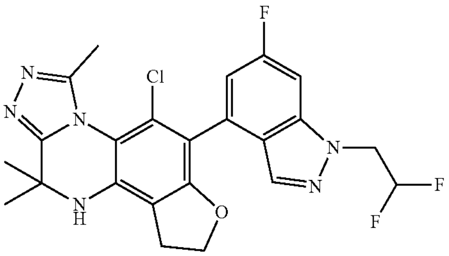 [SMILES: Cc1nnc2n1-c1c(Cl)c(-c3cc(F)cc4c3cnn4CC(F)F)c3c(c1NC2(C)C)CCO3] | A-56, B-57 | 24 | 1H NMR (600 MHz, DMSO) δ = 7.93 (d, 1H), 7.75-7.57 (m, 1H), 7.10 (dd, 1H), 6.54 (s, 1H), 6.46 (tt, 1H), 4.93 (tt, 2H), 4.60 (dq, 2H), 3.21 (td, 2H), 2.56 (s, 3H), 1.59 (s, 3H), 1.49 (s, 3H). |
| 23 | 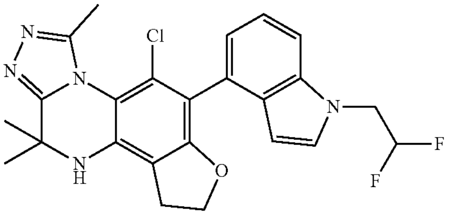 [SMILES: Cc1nnc2n1-c1c(Cl)c(-c3cccc4c3ccn4CC(F)F)c3c(c1NC2(C)C)CCO3] | A-42, B-57 | 69 | 1H NMR (600 MHz, DMSO) δ = 7.65-7.48 (m, 1H), 7.51-7.07 (m, 2H), 7.02 (dd, 1H), 6.38 (s, 2H), 6.20 (dd, 1H), 4.79-4.62 (m, 2H), 4.62-4.41 (m, 2H), 3.33-3.07 (m, 1H), 2.53 (s, 3H), 1.60 (s, 3H), 1.47 (s, 3H). |
| 24 | 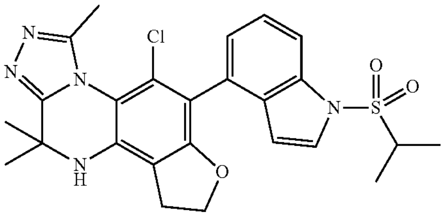 [SMILES: Cc1nnc2n1-c1c(Cl)c(-c3cccc4c3ccn4S(=O)(=O)C(C)C)c3c(c1NC2(C)C)CCO3] | A-30, B-57 | 17 | 1H NMR (600 MHz, DMSO) δ = 7.87 (d, 1H), 7.60 (d, 1H), 7.43 (t, 1H), 7.27 (d, 1H), 6.52 (d, 1H), 6.46 (s, 1H), 4.61 (q, 1H), 4.55 (t, 1H), 3.85 (hept, 1H), 3.25-3.16 (m, 1H), 2.54 (s, 3H), 1.59 (s, 3H), 1.48 (s, 3H), 1.23 (dd, 6H). |

-continued
| Example Nr. | Structure | Inter-mediates | Yield % | Data |
|---|---|---|---|---|
| 53 | 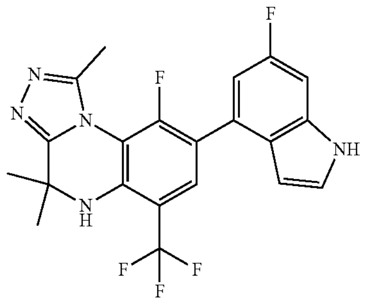 [SMILES: Cc1nnc2n1-c1c(F)c(-c3cc(F)cc4[nH]ccc34)cc(C(F)(F)F)c1NC2(C)C] | A-1, B-62 | 40 | 1H NMR (600 MHz, DMSO) δ = 11.37 (s, 1H), 7.69 (d, 1H), 7.44 (t, 1H), 7.29 (dd, 1H), 7.06 (dd, 1H), 6.41 (d, 1H), 6.28 (s, 1H), 2.56 (d, 3H), 1.62 (s, 6H). |
| 54 | 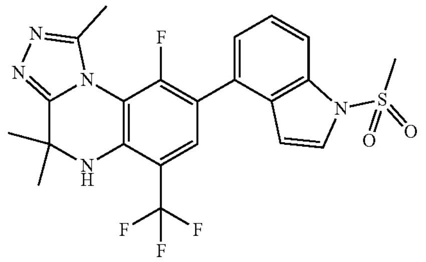 [SMILES: Cc1nnc2n1-c1c(F)c(-c3cccc4c3ccn4S(C)(=O)=O)cc(C(F)(F)F)c1NC2(C)C] | A-12, B-62 | 74 | 1H NMR (600 MHz, DMSO) δ = 7.96 (dd, 1H), 7.69 (d, 1H), 7.64 (d, 1H), 7.52 (dd, 1H), 7.49-7.39 (m, 1H), 6.83 (t, 1H), 6.30 (d, 1H), 3.51 (s, 3H), 2.55 (d, 3H), 1.63 (s, 6H). |
| 55 | 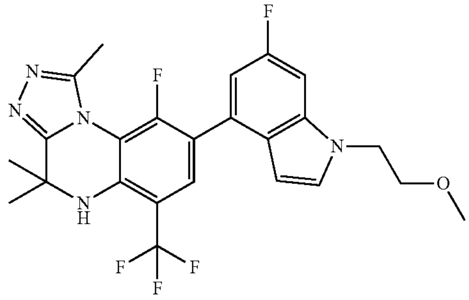 | A-24, B-62 | 53 | 1H NMR (600 MHz, DMSO) δ = 7.68 (d, 1H), 7.50 (dd, 1H), 7.44 (dd, 1H), 7.08 (dd, 1H), 6.41 (t, 1H), 6.30-6.26 (m, 1H), 4.36 (t, 2H), 3.68 (t, 2H), 3.25 (d, 3H), 2.55 (d, 3H), 1.62 (s, 6H). |
| 56 | 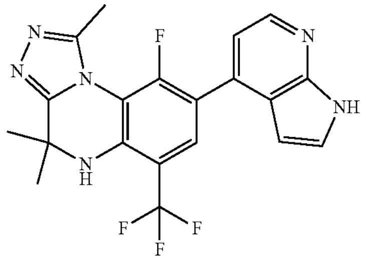 [SMILES: Cc1nnc2n1-c1c(F)c(-c3ccnc4[nH]ccc34)cc(C(F)(F)F)c1NC2(C)C] | 4-(4,4,5,5-tetramethyl-1,3,2-dioxaborolan-2-yl)-1H-pyrrolo[2,3-b]pyridine, B-62 | 25 | 1H NMR (600 MHz, DMSO) δ = 8.33 (d, 1H), 7.75 (d, 1H), 7.57 (dd, 1H), 7.23 (d, 1H), 6.51-6.46 (m, 1H), 6.38 (d, 1H), 2.57 (d, 3H), 1.62 (s, 7H). |
| 57 | 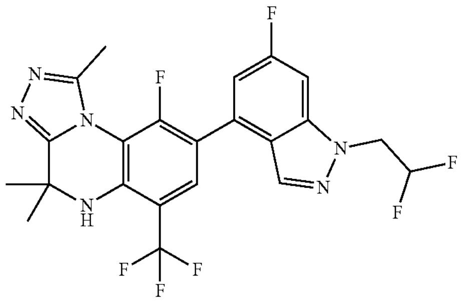 [SMILES: Cc1nnc2n1-c1c(F)c(-c3cc(F)cc4c3cnn4CC(F)F)cc(C(F)(F)F)c1NC2(C)C] | A-56, B-62 | 17 | 1H NMR (600 MHz, DMSO) δ = 8.29-8.13 (m, 1H), 7.87-7.66 (m, 2H), 7.30 (dd, 1H), 6.38 (d, 1H), 4.97 (td, 2H), 2.57 (d, 3H), 1.63 (s, 6H). |

-continued

| Example Nr. | Structure | Inter-mediates | Yield % | Data |
|---|---|---|---|---|
| 58 | 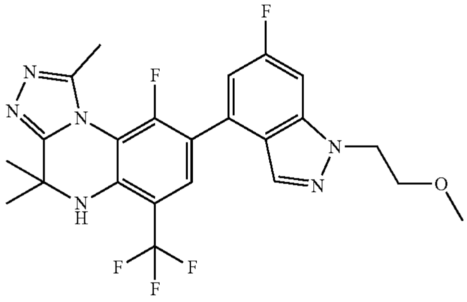 | A-58, B-62 | 100 | 1H NMR (600 MHz, DMSO) δ = 8.13-8.08 (m, 1H), 7.75 (d, 1H), 7.65 (ddd, 1H), 7.23 (dd, 1H), 6.37 (d, 1H), 4.58 (t, 2H), 3.78 (t, 2H), 3.22 (s, 3H), 2.57 (d, 3H), 1.63 (s, 6H). |
| 61 | 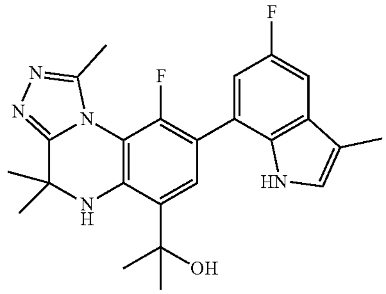 | A-15, B-65 | 51 | 1H NMR (600 MHz, DMSO) δ = 10.68 (d, 1H), 7.29 (dd, 1H), 7.28 (s, 1H), 7.23 (d, 1H), 7.19 (dd, 1H), 6.97 (dd, 1H), 5.88 (s, 1H), 2.52 (d, 3H), 2.26 (d, 3H), 1.58 (d, 12H). |
| 64 | 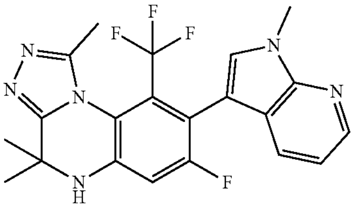 [SMILES: Cc1nnc2n1-c1c(cc(F)c(-c3cn(C)c4ncccc34)c1C(F)(F)F)NC2(C)C] | 1-methyl-3-(4,4,5,5-tetramethyl-1,3,2-dioxaborolan-2-yl)pyrrolo[2,3-b]pyridine, B-4 | 55 | 1H NMR (600 MHz, DMSO) δ = 8.34 (d, 1H), 7.76 (s, 1H), 7.38 (s, 1H), 7.20-7.12 (m, 3H), 3.91 (s, 3H), 1.76 (s, 3H), 1.31 (d, 6H). |
| 65 | 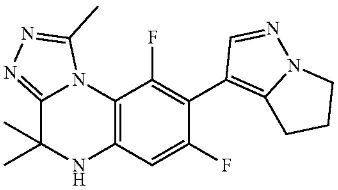 [SMILES: Cc1nnc2n1-c1c(cc(F)c(-c3cnn4c3CCC4)c1F)NC2(C)C] | 3-(4,4,5,5-tetramethyl-1,3,2-dioxaborolan-2-yl)-5,6-dihydro-4H-pyrrolo[1,2-b]pyrazole, B-1 | 57 | 1H NMR (600 MHz, DMSO) δ = 7.66 (s, 1H), 7.00 (d, 1H), 6.74 (dd, 1H), 4.15 (t, 2H), 2.93 (t, 2H), 2.62-2.55 (m, 2H), 2.53 (d, 3H), 1.49 (s, 6H). |
| 66 | 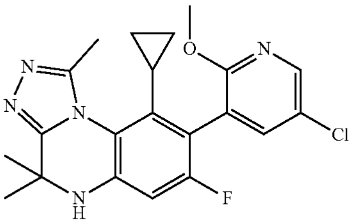 [SMILES: COc1ncc(Cl)cc1-c1c(F)cc2c(c1C1CC1)-n1c(C)nnc1C(C)(C)N2] | 5-chloro-2-methoxy-3-(4,4,5,5-tetramethyl-1,3,2-dioxaborolan-2-yl)pyridine, B-44 | 66 | 1H NMR (600 MHz, DMSO) δ = 8.30 (dd, 1H), 8.19-7.80 (m, 1H), 6.83 (d, 1H), 6.74 (dd, 1H), 3.88 (d, 3H), 2.07-1.93 (m, 1H), 1.70 (d, 3H), 1.15 (d, 3H), 0.78-0.57 (m, 1H), 0.53-0.23 (m, 1H), 0.05- −0.27 (m, 2H). |
| 75 | 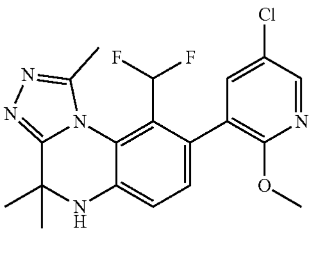 | 5-chloro-2-methoxy-3-(4,4,5,5-tetramethyl-1,3,2-dioxaborolan-2-yl)pyridine, B-52 | 61 | 1H NMR (600 MHz, DMSO) δ = 8.24 (d, 1H), 7.82 (d, 1H), 7.27-7.06 (m, 2H), 6.98 (s, 1H), 3.85 (s, 3H), 2.47 (s, 3H), 1.85-1.06 (m, 6H). |

-continued

| Example Nr. | Structure | Inter-mediates | Yield % | Data |
|---|---|---|---|---|
| 76 | 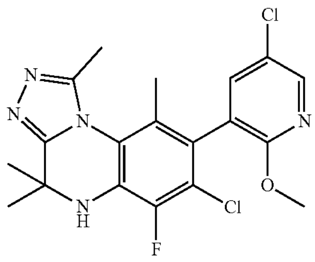 | 5-chloro-2-methoxy-3-(4,4,5,5-tetramethyl-1,3,2-dioxaborolan-2-yl)pyridine, B-53 | 26 | 1H NMR (600 MHz, DMSO) δ = 8.34 (d, 1H), 8.03 (d, 1H), 6.50 (s, 1H), 3.88 (s, 3H), 2.42 (s, 3H), 2.05 (s, 3H), 1.55 (s, 6H). |
| 79 | 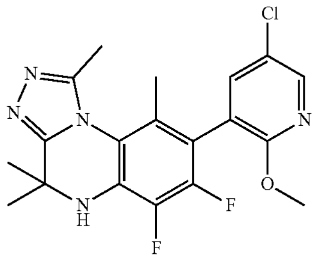 | 5-chloro-2-methoxy-3-(4,4,5,5-tetramethyl-1,3,2-dioxaborolan-2-yl)pyridine, B-38 | 14 | 1H NMR (600 MHz, DMSO) δ = 8.34 (d, 1H), 8.03 (d, 1H), 6.93-6.89 (m, 1H), 3.88 (s, 3H), 2.43 (s, 3H), 2.03 (s, 3H), 1.52 (d, 6H). |
| 82 | 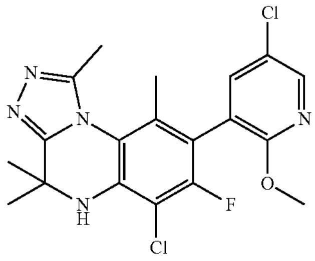 | 5-chloro-2-methoxy-3-(4,4,5,5-tetramethyl-1,3,2-dioxaborolan-2-yl)pyridine, B-51 | 41 | 1H NMR (600 MHz, DMSO) δ = 8.34 (d, 1H), 8.02 (d, 1H), 6.50 (s, 1H), 3.87 (s, 3H), 2.42 (s, 3H), 2.05 (s, 3H), 1.54 (s, 6H). |
| 84 | 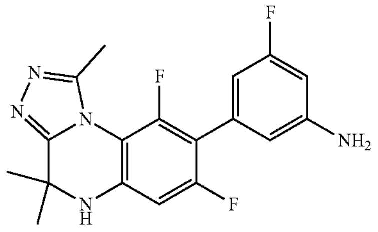 [SMILES: Cc1nnc2n1-c1c(cc(F)c(-c3cc(N)cc(F)c3)c1F)NC2(C)C] | (3-amino-5-fluoro-phenyl)boronic acid, B-1 | 72 | 1H NMR (600 MHz, DMSO) δ = 7.11 (d, 1H), 6.73 (dd, 1H), 6.46 (s, 1H), 6.42-6.35 (m, 2H), 5.53 (s, 2H), 2.52 (s, 3H), 1.51 (s, 6H). |
| 85 | 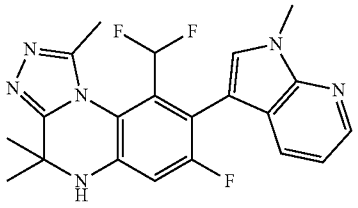 [SMILES: Cc1nnc2n1-c1c(cc(F)c(-c3cn(C)c4ncccc34)c1C(F)F)NC2(C)C] | 1-methyl-3-(4,4,5,5-tetramethyl-1,3,2-dioxaborolan-2-yl)pyrrolo[2,3-b]pyridine, B-28 | 15 | 1H NMR (600 MHz, DMSO) δ = 8.32 (dd, 1H), 7.74 (d, 1H), 7.66 (s, 1H), 7.22-6.76 (m, 4H), 3.91 (s, 3H), 1.67 (s, 3H), 1.35 (s, 3H). |
| 90 | 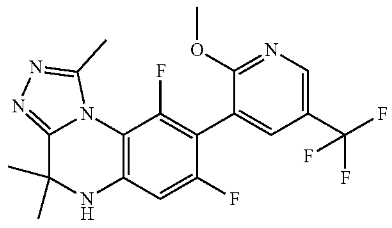 [SMILES: COc1ncc(C(F)(F)F)cc1-c1c(F)cc2c(c1F)-n1c(C)nnc1C(C)(C)N2] | 2-methoxy-3-(4, 4,5,5-tetramethyl-1,3,2-dioxaborolan-2-yl)-5-(trifluoromethyl)pyridine, B-1 | 26 | 1H NMR (600 MHz, DMSO) δ = 8.71-8.67 (m, 1H), 8.28-8.24 (m, 1H), 7.26 (d, 1H), 6.77 (dd, 1H), 3.98 (d, 3H), 2.50 (d, 3H), 1.55 (s, 3H), 1.48 (s, 3H). |

-continued

| Example Nr. | Structure | Inter-mediates | Yield % | Data |
|---|---|---|---|---|
| 92 | 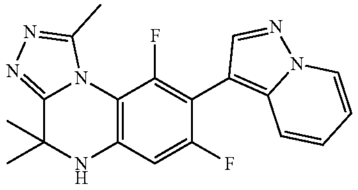 [SMILES: Cc1nnc2n1-c1c(cc(F)c(-c3cnn4ccccc34)c1F)NC2(C)C] | 3-(4,4,5,5-tetramethyl-1,3,2-dioxaborolan-2-yl)pyrazolo[1,5-a]pyridine, B-1 | 54 | 1H NMR (600 MHz, DMSO) δ = 8.76 (dd, 1H), 8.20 (s, 1H), 7.63 (d, 1H), 7.37-7.31 (m, 1H), 7.11 (d, 1H), 7.03-6.97 (m, 1H), 6.82 (dd, 1H), 2.56 (d, 3H), 1.53 (s, 6H). |
| 94 | 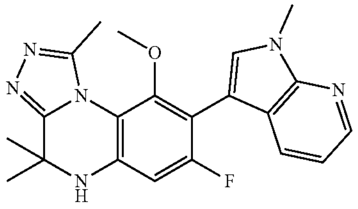 [SMILES: COc1c(-c2cn(C)c3ncccc23)c(F)cc2c1-n1c(C)nnc1C(C)(C)N2] | -methyl-3-(4,4,5,5-tetramethyl-1,3,2-dioxaborolan-2-yl)pyrrolo[2,3-b]pyridine, B-25 | 66 | 1H NMR (600 MHz, DMSO) δ = 8.33 (dd, 1H), 7.88 (dt, 1H), 7.73 (d, 1H), 7.16 (dd, 1H), 6.84 (s, 1H), 6.73 (d, 1H), 3.92 (s, 3H), 3.23 (s, 3H), 2.57 (s, 3H), 1.51 (s, 6H). |
| 99 | 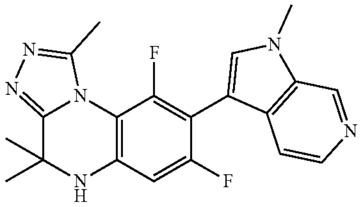 [SMILES: Cc1nnc2n1-c1c(cc(F)c(-c3cn(C)c4cnccc34)c1F)NC2(C)C] | 1-methyl-3-(4,4,5,5-tetramethyl-1,3,2-dioxaborolan-2-yl)pyrrolo[2,3-c]pyridine, B-1 | 29 | 1H NMR (600 MHz, DMSO) δ = 8.94 (s, 1H), 8.21 (d, 1H), 7.83 (s, 1H), 7.47 (d, 1H), 7.09 (d, 1H), 6.81 (dd, 1H), 4.01 (d, 3H), 2.56 (d, 3H), 1.53 (s, 6H). |
| 101 | 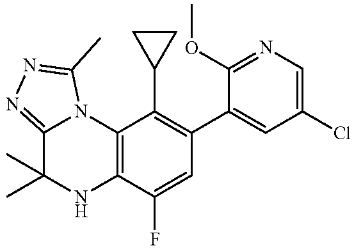 [SMILES: COc1ncc(Cl)cc1-c1cc(F)c2c(c1C1CC1)-n1c(C)nnc1C(C)(C)N2] | 5-chloro-2-methoxy-3-(4,4,5,5-tetramethyl-1,3,2-dioxaborolan-2-yl)pyridine, B-45 | 47 | 1H NMR (600 MHz, DMSO) δ = 8.27 (d, 1H), 7.94 (s, 1H), 7.16 (d, 1H), 6.53 (s, 1H), 3.90 (s, 3H), 2.56 (s, 3H), 2.12-2.03 (m, 3H), 1.77 (s, 3H), 1.15 (s, 3H), 0.53 (d, 2H). |
| 108 | 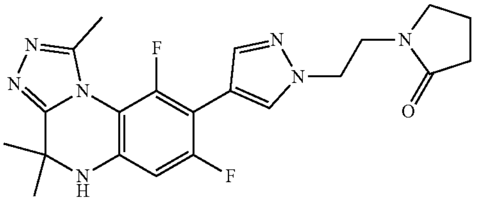 [SMILES: Cc1nnc2n1-c1c(cc(F)c(-c3cnn(CCN4CCCC4=O)c3)c1F)NC2(C)C] | 1-[2-[4-(4,4,5,5-tetramethyl-1,3,2-dioxaborolan-2-yl)pyrazol-1-yl]ethyl]pyrrolidin-2-one, B-1 | 18 | 1H NMR (600 MHz, DMSO) δ = 8.05 (d, 1H), 7.79 (dd, 1H), 7.01 (dd, 1H), 6.75 (dd, 1H), 4.32 (t, 2H), 3.63-3.54 (m,2H), 3.15 (t, 2H), 2.55 (d, 3H), 2.16 (t, 2H), 1.86 (p, 2H), 1.49 (s, 6H). |
| 113 | 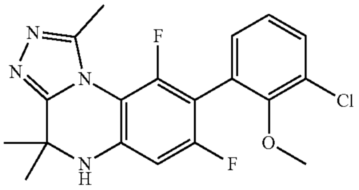 [SMILES: COc1c(Cl)cccc1-c1c(F)cc2c(c1F)-n1c(C)nnc1C(C)(C)N2] | (3-chloro-2-methoxyphenyl)boronic acid, B-1 | 71 | 1H NMR (600 MHz, DMSO) δ = 7.60 (dd, 1H), 7.40 (dd, 1H), 7.28 (t, 1H), 7.22 (d, 1H), 6.78 (dd, 1H), 3.55 (s, 3H), 2.49 (d, 3H), 1.52 (d, 6H). |
| 117 | 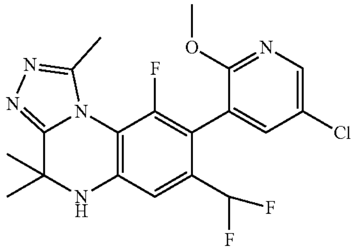 [SMILES: COc1ncc(Cl)cc1-c1c(C(F)F)cc2c(c1F)-n1c(C)nnc1C(C)(C)N2] | 5-chloro-2-methoxy-3-(4,4,5,5-tetramethyl-1,3,2-dioxaborolan-2-yl)pyridine, B-29 | 26 | 1H NMR (600 MHz, DMSO) δ = 8.35 (d, 1H), 7.92 (d, 1H), 7.26 (d, 1H), 7.15 (s, 1H), 6.76 (s, 1H), 3.86 (s, 3H), 2.49 (d, 3H), 1.54 (s, 3H), 1.51 (s, 3H). |

-continued

| Example Nr. | Structure | Intermediates | Yield % | Data |
|---|---|---|---|---|
| 118 | 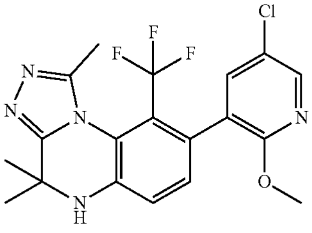 | 5-chloro-2-methoxy-3-(4,4,5,5-tetramethyl-1,3,2-dioxaborolan-2-yl)pyridine, B-48 | 60 | 1H NMR (600 MHz, DMSO) δ = 8.30 (dd, 1H), 7.92 (dd, 1H), 7.32-7.13 (m, 3H), 3.83 (d, 3H), 2.44 (d, 3H), 1.74 (s, 3H), 1.26 (s, 3H). |
| 119 | 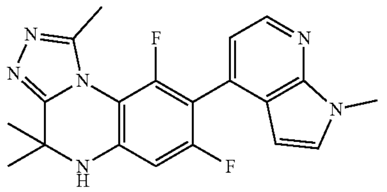 | 1-methyl-4-(4,4,5,5-tetramethyl-1,3,2-dioxaborolan-2-yl)pyrrolo[2,3-b]pyridine, B-1 | 61 | 1H NMR (600 MHz, DMSO) δ = 8.36 (d, 1H), 7.59 (d, 1H), 7.27 (s, 1H), 7.19 (d, 1H), 6.83 (dd, 1H), 6.41-6.37 (m, 1H), 3.88 (s, 3H), 2.52 (d, 3H), 1.55 (s, 6H). |
| 121 | 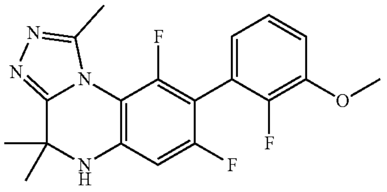 | (2-fluoro-3-methoxyphenyl)boronic acid, B-1 | 83 | 1H NMR (600 MHz, DMSO) δ = 7.26 (dtt, 3H), 7.05 (td, 1H), 6.79 (dd, 1H), 3.89 (s, 3H), 2.49 (d, 3H), 1.52 (d, 6H). |

Example 14: 5-fluoro-6-(5-fluoro-3-methyl-H-indol-7-yl)-3,11,11-trimethyl-8,9,10,11-tetrahydrofuro[3,2-f][1,2,4]triazolo[4,3-a]quinoxaline

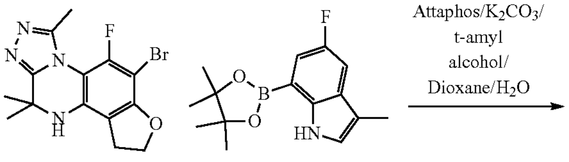

intermediate B-56 intermediate A-16

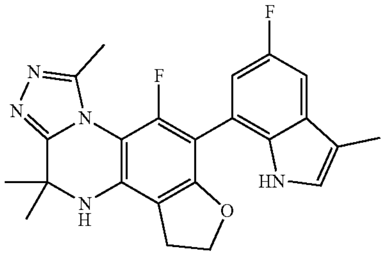

example 14

To a solution of intermediate B-56 (0.15 g, 0.42 mmol, 1 eq.) in a t-amyl alcohol:dioxane (2:1) mixture (7.5 mL) are added a 2M $K_2CO_3$ (1.0 mL) solution and intermediate A-15 (0.23 g, 0.849 mmol, 2.0 eq). The solution is degassed with argon for 20 mini, followed by addition of Attaphos (0.015 g, 0.021 mmol, 0.05 eq.), and the reaction mixture is refluxed at 90° C. for 16 h. After completion (monitored by TLC), the reaction mixture is filtered through a celite pad and washed with ethyl acetate. The combined organic layers are evaporated under reduced pressure to obtain a crude residue, which was purified by prep-HPLC to afford example 14 (0.09 g, 54%) as a white solid.

$^1$H NMR (400 MHz, $CDCl_3$): δ 7.87 (s, 11H), 7.26-7.30 (m, 11H), 7.04 (d, J=8.0 Hz, 2H), 4.73 (t, J=8.6 Hz, 2H), 3.82 (s, 11H), 3.16 (t, J=8.4 Hz, 2H), 2.57 (d, J=10.0 Hz, 3H), 2.31 (s, 3H), 1.69 (s, 6H).

The following examples were prepared in a similar manner (use of appropriate reagents and purification methods known to the person skilled in the art) as the synthesis described for example 14:

| Example Nr. | Structure | Inter-mediates | Yield % | Data |
|---|---|---|---|---|
| 15 | 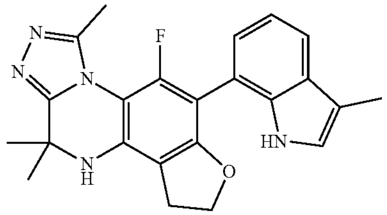 | 3-methyl-7-(4,4,5,5-tetramethyl-1,3,2-dioxaborolan-2-yl)-1H-indole, B-56 | 32 | 1H NMR (600 MHz, DMSO) δ = 10.41 (d, 1H), 7.50 (d, 1H), 7.11-7.01 (m, 3H), 6.38-6.32 (m, 1H), 4.64-4.56 (m, 2H), 3.18 (t, 2H), 2.49-2.42 (m, 3H), 2.29 (d, 3H), 1.60-1.55 (m, 6H). |
| 16 | 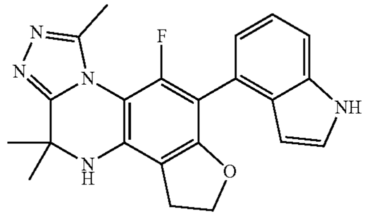 [SMILES: Cc1nnc2n1-c1c(F)c(-c3cccc4[nH]ccc34)c3c(c1NC2(C)C)CCO3] | indole-4-boronic acid, B-56 | 60 | 1H NMR (600 MHz, DMSO) δ = 11.15-11.09 (m, 1H), 7.41 (dd, 1H), 7.34 (t, 1H), 7.18-7.10 (m, 1H), 7.03 (d, 1H), 6.35 (d, 1H), 6.24 (q, 1H), 4.59 (t, 2H), 3.18 (t, 2H), 2.46 (d, 3H), 1.56 (s, 6H). |
| 17 | 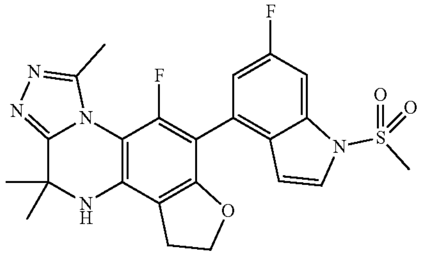 [SMILES: Cc1nnc2n1-c1c(F)c(-c3cc(F)cc4c3ccn4S(C)(=O)=O)c3c(c1NC2(C)C)CCO3] | A-2, B-56 | 58 | 1H NMR (600 MHz, DMSO) δ = 7.65 (ddd, 1H), 7.61 (d, 1H), 7.25 (dd, 1H), 6.66 (tt, 1H), 6.52 (d, 1H), 4.64 (t, 2H), 3.53 (s, 3H), 3.19 (t, 2H), 2.47 (d, 3H), 1.56 (s, 6H). |
| 26 | 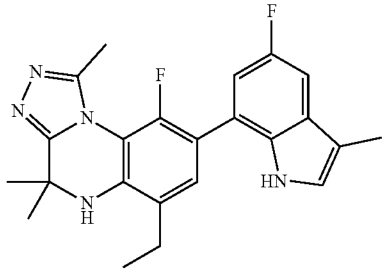 | A-15, B-58 | 47 | 1H NMR (600 MHz, DMSO) δ = 10.66 (s, 1H), 7.28 (dt, 1H), 7.20 (dd, 2H), 6.97 (dd, 1H), 6.01 (s, 1H), 2.72 (q, 2H), 2.52 (d, 3H), 2.27 (s, 3H), 1.58 (s, 5H), 1.18 (td, 3H). |
| 27 | 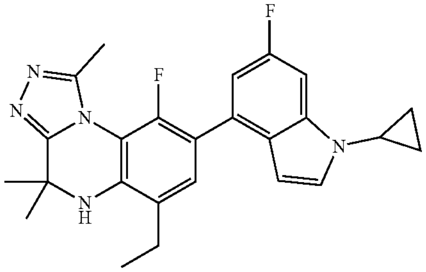 [SMILES: CCc1cc(-c2cc(F)cc3c2ccn3C2CC2)c(F)c2c1NC(C)(C)c1nnc(C)n1-2] | A-27, B-58 | 31 | 1H NMR (600 MHz, DMSO) δ = 7.41-7.36 (m, 2H), 7.24 (d, 1H), 7.03 (dd, 1H), 6.35 (s, 1H), 6.04 (d, 1H), 3.45 (tt, 1H), 2.71 (q, 2H), 2.52 (d, 3H), 1.56 (s, 6H), 1.18 (t, 3H), 1.12-1.04 (m, 2H), 0.98 (dd, 2H). |
| 28 | 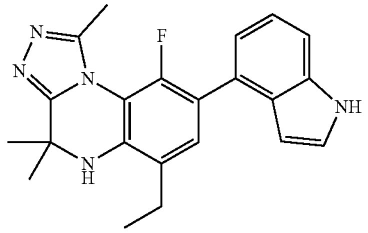 [SMILES: CCc1cc(-c2cccc3[nH]ccc23)c(F)c2c1NC(C)(C)c1nnc(C)n1-2] | 112ndole-4-boronic acid, B-58 | 67 | 1H NMR (600 MHz, DMSO) δ = 11.22 (s, 1H), 7.44 (d, 1H), 7.40 (t, 1H), 7.25 (d, 1H), 7.19 (t, 1H), 7.08 (d, 1H), 6.39 (d, 1H), 5.97 (s, 1H), 2.72 (q, 2H), 2.53 (t, 3H), 1.56 (s, 6H), 1.18 (t, 3H). |

-continued

| Example Nr. | Structure | Inter-mediates | Yield % | Data |
|---|---|---|---|---|
| 29 | 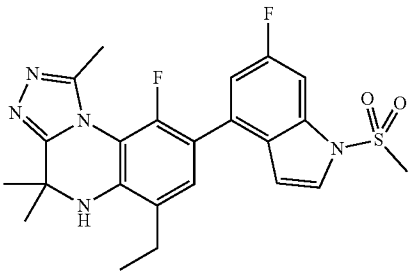 | A-2, B-58 | 34 | 1H NMR (600 MHz, DMSO) δ = 7.70-7.64 (m, 2H), 7.31 (dd, 1H), 7.24 (d, 1H), 6.77 (s, 1H), 6.12 (d, 1H), 3.54 (s, 3H), 2.72 (q, 2H), 2.53 (d, 3H), 1.56 (s, 6H), 1.18 (t, 3H). |
| 32 | 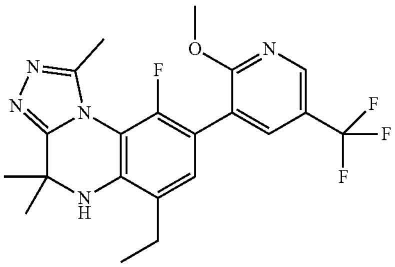 [SMILES: CCc1cc(-c2cc(C(F)(F)F)cnc2OC)c(F)c2c1NC(C)(C)c1nnc(C)n1-2] | 2-methoxy-3-(4,4,5,5-tetramethyl-1,3,2-dioxaborolan-2-yl)-5-(trifluoromethyl)pyridine, B-58 | 39 | 1H NMR (600 MHz, DMSO) δ = 8.63 (dt, 1H), 8.14 (d, 1H), 7.19 (d, 1H), 6.09 (d, 1H), 3.98 (s, 3H), 2.68 (q, 2H), 2.49 (s, 3H), 1.54 (s, 6H), 1.16 (t, 3H). |
| 36 | 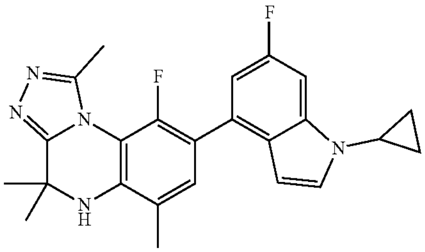 [SMILES: Cc1cc(-c2cc(F)cc3c2ccn3C2CC2)c(F)c2c1NC(C)(C)c1nnc(C)n1-2] | A-27, B-60 | 39 | 1H NMR (600 MHz, DMSO) δ = 7.39 (dd, 2H), 7.25 (d, 1H), 7.00 (dd, 1H), 6.34 (t, 1H), 5.99 (d, 1H), 3.46 (tt, 1H), 2.52 (d, 3H), 2.29 (s, 3H), 1.56 (s, 6H), 1.12-1.04 (m, 2H), 1.01-0.95 (m, 2H). |
| 37 | 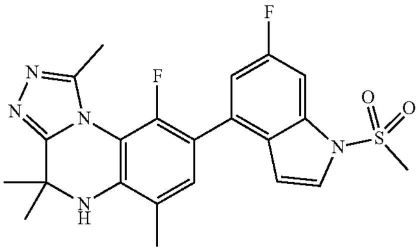 [SMILES: Cc1cc(-c2cc(F)cc3c2ccn3S(C)(=O)=O)c(F)c2c1NC(C)(C)c1nnc(C)n1-2] | A-2, B-60 | 39 | 1H NMR (600 MHz, DMSO) δ = 7.70-7.63 (m, 2H), 7.31-7.23 (m, 2H), 6.76 (t, 1H), 6.07 (d, 1H), 3.55 (s, 3H), 2.53 (d, 3H), 2.30 (s, 3H), 1.57 (s, 6H). |
| 38 | 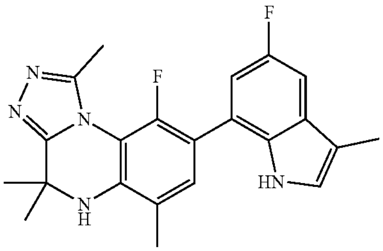 | A-15, B-60 | 41 | 1H NMR (600 MHz, DMSO) δ = 10.64 (d, 1H), 7.28 (dd, 1H), 7.22 (d, 1H), 7.21-7.16 (m, 1H), 6.95 (dd, 1H), 5.97 (d, 1H), 2.51 (d, 3H), 2.29 (s, 3H), 2.26 (s, 3H), 1.58 (s, 6H). |
| 39 | 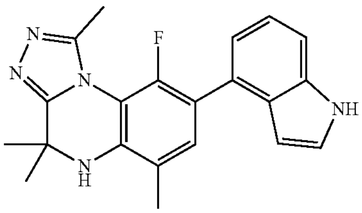 [SMILES: Cc1cc(-c2cccc3[nH]ccc23)c(F)c2c1NC(C)(C)c1nnc(C)n1-2] | indole-4-boronic acid, B-60 | 67 | 1H NMR (600 MHz, DMSO) δ = 11.21 (s, 1H), 7.44 (d, 1H), 7.39 (t, 1H), 7.24 (d, 1H), 7.18 (t, 1H), 7.05 (d, 1H), 6.37 (t, 1H), 5.92 (s, 1H), 2.53 (d, 3H), 2.29 (s, 3H), 1.57 (s, 6H). |

-continued

| Example Nr. | Structure | Inter-mediates | Yield % | Data |
|---|---|---|---|---|
| 44 | 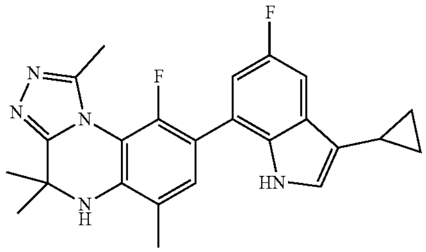 [SMILES: Cc1cc(-c2cc(F)cc3c(C4CC4)c[nH]c23)c(F)c2c1NC(C)(C)c1nnc(C)n1-2] | A-16, B-60 | 19 | 1H NMR (600 MHz, DMSO) δ = 10.67-10.64 (m, 1H), 7.37 (dd, 1H), 7.23-7.19 (m, 1H), 7.10 (d, 1H), 6.95 (dd, 1H), 5.97 (d, 1H), 2.52 (s, 1H), 2.29 (s, 3H), 2.08 (s, 2H), 1.96-1.87 (m, 1H), 1.58 (s, 6H), 0.89-0.82 (m, 2H), 0.65-0.58 (m, 2H). |
| 49 | 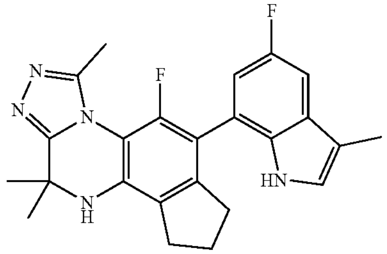 | A-15, B-61 | 42 | 1H NMR (600 MHz, DMSO) δ = 10.59 (d, 1H), 7.27 (dd, 1H), 7.15 (d, 1H), 6.93 (dd, 1H), 6.16-6.11 (m, 1H), 2.86 (dt, 3H), 2.47 (d, 4H), 2.26 (s, 3H), 2.15-1.94 (m, 2H), 1.59 (s, 3H), 1.56 (s, 3H). |
| 50 | 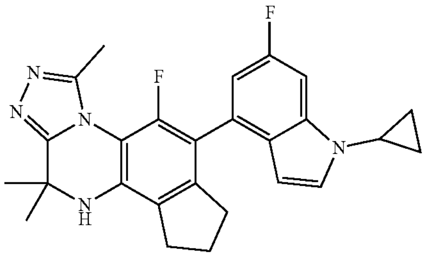 [SMILES: Cc1nnc2n1-c1c(F)c(-c3cc(F)cc4c3ccn4C3CC3)c3c(c1NC2(C)C)CCC3] | A-27, B-61 | 38 | 1H NMR (600 MHz, DMSO) δ = 7.38 (dd, 1H), 7.34 (d, 1H), 6.97 (dd, 1H), 6.19-6.13 (m, 2H), 3.45 (dt, 1H), 2.87 (q, 3H), 2.58-2.52 (m, 1H), 2.45 (d, 3H), 2.12-2.02 (m, 1H), 1.98 (dt, 1H), 1.61 (s, 3H), 1.49 (s, 3H), 1.08 (dd, 2H), 1.05-0.93 (m, 2H). |
| 51 | 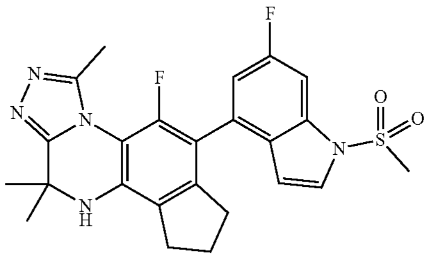 [SMILES: Cc1nnc2n1-c1c(F)c(-c3cc(F)cc4c3ccn4S(C)(=O)=O)c3c(c1NC2(C)C)CCC3] | A-2, B-61 | 45 | 1H NMR (600 MHz, DMSO) δ = 7.70-7.63 (m, 1H), 7.62 (d, 1H), 7.28 (dd, 1H), 6.62 (dd, 1H), 6.23 (d, 1H), 3.57 (s, 3H), 2.89 (dt, 3H), 2.58-2.50 (m, 1H), 2.47 (d, 3H), 2.07 (s, 1H), 2.05-1.95 (m, 1H), 1.56 (d, 6H). |
| 71 | 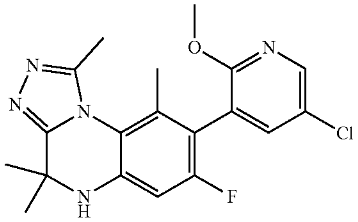 [SMILES: COc1ncc(Cl)cc1-c1c(F)cc2c(c1C)-n1c(C)nnc1C(C)(C)N2] | 5-chloro-2-methoxy-3-(4,4,5,5-tetramethyl-1,3,2-dioxaborolan-2-yl)pyridine, B-3 | 42 | 1H NMR (600 MHz, DMSO) δ = 8.31 (d, 1H), 7.96 (d, 1H), 6.81 (s, 1H), 6.73 (d, 1H), 3.87 (s, 3H), 2.43 (s, 3H), 2.05 (s, 3H), 1.47 (d, 6H). |
| 77 | 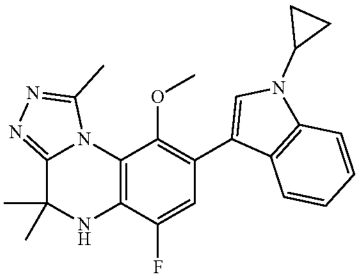 [SMILES: COc1c(-c2cn(C3CC3)c3ccccc23)cc(F)c2c1-n1c(C)nnc1C(C)(C)N2] | A-77, B-10 | 16 | 1H NMR (400 MHz, DMSO) δ = 7.72-7.58 (m, 3H), 7.32 (d, 1H), 7.24 (t, 1H), 7.14 (t, 1H), 6.52 (s, 1H), 3.53 (dd, 1H), 3.22 (s, 3H), 2.61 (s, 3H), 1.53 (s, 6H), 1.15-1.00 (m, 4H). |

-continued

| Example Nr. | Structure | Inter- mediates | Yield % | Data |
|---|---|---|---|---|
| 80 | 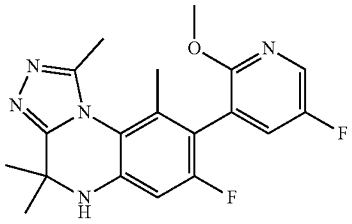 [SMILES: COc1ncc(F)cc1-c1c(F)cc2c(c1C)-n1c(C)nnc1C(C)(C)N2] | 5-fluoro-2-methoxy-3-(4,4,5,5-tetramethyl-1,3,2-dioxaborolan-2-yl)pyridine, B-3 | 35 | 1H NMR (600 MHz, DMSO) δ = 8.25 (dd, 1H), 7.86 (dd, 1H), 6.81 (s, 1H), 6.74 (d, 1H), 3.85 (d, 3H), 2.43 (s, 3H), 2.05 (s, 3H), 1.47 (s, 6H). |
| 86 | 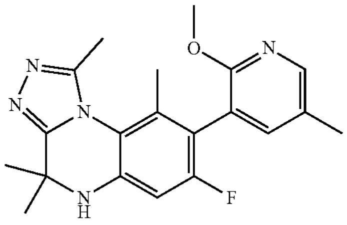 | 2-methoxy-5-methyl-3-(4,4,5,5-tetramethyl-1,3,2-dioxaborolan-2-yl)pyridine, B-3 | 35 | 1H NMR (600 MHz, DMSO) δ = 8.06 (dd, 1H), 7.57 (d, 1H), 6.72 (d, 2H), 3.83 (s, 3H), 2.41 (s, 3H), 2.28 (s, 3H), 2.02 (s, 3H), 1.46 (d, 6H). |
| 98 | 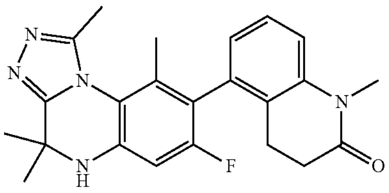 | A-79, B-3 | 40 | 1H NMR (600 MHz, DMSO) δ = 7.38 (t, 1H), 7.18 (dd, 1H), 7.03-6.98 (m, 1H), 6.79-6.71 (m, 2H), 3.31 (s, 3H), 2.57 (tdd, 2H), 2.52-2.42 (m, 2H), 2.41 (s, 3H), 1.98 (s, 3H), 1.47 (d, 6H). |
| 103 | 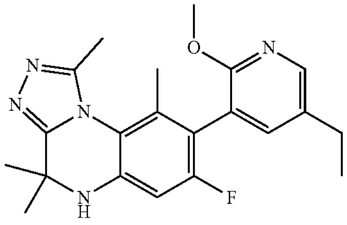 [SMILES: CCc1cnc(OC)c(-c2c(F)cc3c(c2C)-n2c(C)nnc2C(C)(C)N3)c1] | A-80, B-3 | 22 | 1H NMR (600 MHz, DMSO) δ = 8.08 (d, 1H), 7.61 (d, 1H), 6.73 (d, 2H), 3.83 (s, 3H), 2.61 (q, 2H), 2.42 (s, 3H), 2.02 (s, 3H), 1.48 (s, 3H), 1.45 (s, 3H), 1.21 (t, 3H). |
| 104 | 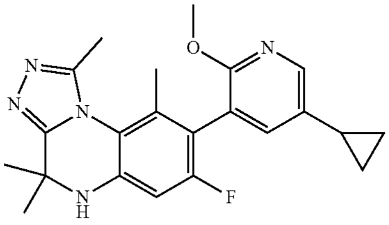 [SMILES: COc1ncc(C2CC2)cc1-c1c(F)cc2c(c1C)-n1c(C)nnc1C(C)(C)N2] | A-81, B-3 | 21 | 1H NMR (600 MHz, DMSO) δ = 8.05 (d, 1H), 7.39 (d, 1H), 6.72 (d, 2H), 3.82 (s, 3H), 2.42 (s, 3H), 2.00 (s, 3H), 1.95 (tt, 1H), 1.48 (s, 3H), 1.44 (s, 3H), 1.00-0.89 (m, 2H), 0.77-0.66 (m, 2H). |
| 106 | 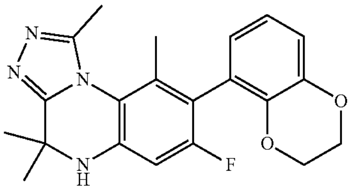 [SMILES: Cc1c(-c2cccc3c2OCCO3)c(F)cc2c1-n1c(C)nnc1C(C)(C)N2] | A-82, B-3 | 43 | 1H NMR (600 MHz, DMSO) δ = 6.95-6.88 (m, 2H), 6.80 (dd, 1H), 6.71 (d, 1H), 6.68 (s, 1H), 4.30-4.18 (m, 4H), 2.41 (s, 3H), 2.05 (s, 3H), 1.46 (d, 6H). |

-continued

| Example Nr. | Structure | Inter-mediates | Yield % | Data |
|---|---|---|---|---|
| 112 | 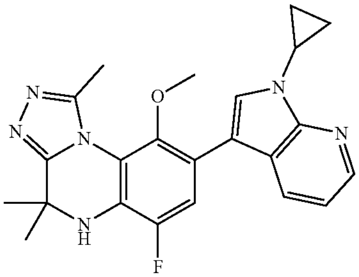 [SMILES: COc1c(-c2cn(C3CC3)c3ncccc23)cc(F)c2c1-n1c(C)nnc1C(C)(C)N2] | A-83, B-10 | 41 | 1H NMR (400 MHz, DMSO) δ = 8.34 (dd, 1H), 8.08 (dd, 1H), 7.78 (s, 1H), 7.38 (d, 1H), 7.20 (dd, 1H), 6.56 (s, 1H), 3.71 (q, 1H), 3.21 (s, 3H), 2.62 (s, 3H), 1.53 (s, 6H), 1.14-1.06 (m, 4H). |
| 115 | 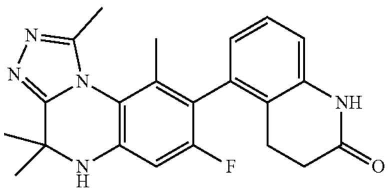 [SMILES: Cc1c(-c2cccc3c2CCC(=O)N3)c(F)cc2c1-n1c(C)nnc1C(C)(C)N2] | A-84, B-3 | 44 | 1H NMR (600 MHz, DMSO) δ = 10.17 (s, 1H), 7.25 (t, 1H), 6.94 (d, 1H), 6.89 (d, 1H), 6.78-6.70 (m, 2H), 2.57 (dt, 2H), 2.41 (s, 3H), 2.47-2.33 (m, 2H), 1.98 (s, 3H), 1.47 (d, 6H). |

Example 22: 5-chloro-6-(5-chloro-2-methoxypyridin-3-yl)-3,11,11-trimethyl-8,9,10,11-tetrahydrofuro[3,2-f][1,2,4]triazolo[4,3-a]quinoxaline

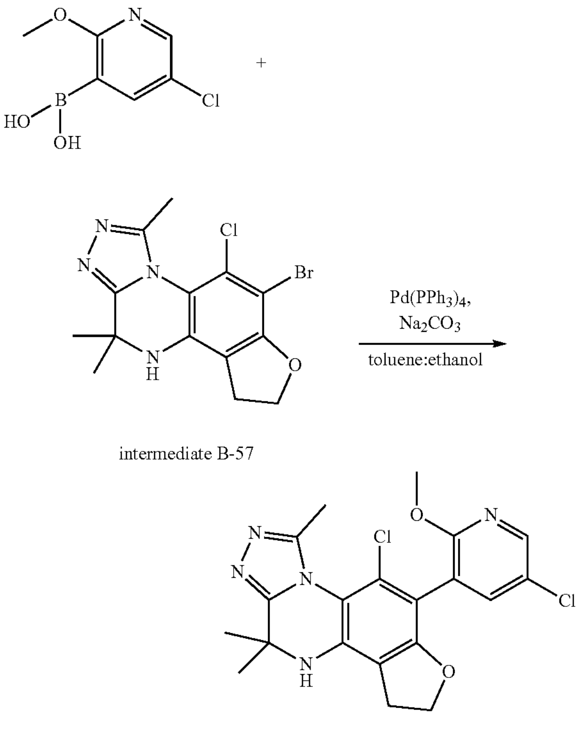

intermediate B-57 example 22

To a stirred solution of intermediate B-57 (80 mg, 0.22 mmol, 1 eq) and 5-chloro-2-methoxy-3-(4,4,5,5-tetramethyl-1,3,2-dioxaborolan-2-yl)pyridine (61 mg, 0.32 mmol, 1.5 eq) in a mixture of toluene (1.8 nil) and ethanol (0.3 mL) was added 2M $Na_2CO_3$ solution (0.43 mL, 4 eq). The reaction mixture was degassed with argon for 30 minutes. $Pd(PPh_3)_4$ (25 mg, 0.022 mmol, 0.1 eq) was added to the reaction mixture and the reaction mixture was heated at 90° C. for 16 h. The reaction mixture was filtered through a celite bed, which was afterwards washed with ethyl acetate. The filtrate was washed with water followed by brine. The organic layer was dried with anhydrous $Na_2SO_4$, filtered and concentrated. The obtained crude residue was purified by column chromatography to afford example 22 (63 mg, 67%) as an off-white solid.

1H NMR (600 MHz, DMSO-d6) δ 8.27 (d, J=2.8 Hz, 1H), 7.83 (d, J=2.8 Hz, 1H), 6.49 (d, J=3.5 Hz, 1H), 4.65 (q, J=8.8 Hz, 1H), 4.61-4.53 (m, 1H), 3.86 (d, J=2.7 Hz, 2H), 3.19 (s, 2H), 2.51 (h, J=2.0 Hz, 3H), 1.58 (s, 3H), 1.44 (s, 3H).

The following examples were prepared in a similar manner (use of appropriate reagents and purification methods known to the person skilled in the art) as the synthesis described for example 22:

| Example Nr. | Structure | Inter-mediates | Yield % | Data |
|---|---|---|---|---|
| 41 | 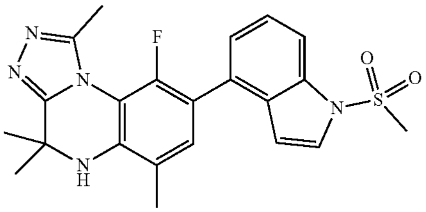 [SMILES: Cc1cc(-c2cccc3c2ccn3S(C)(=O)=O)c(F)c2c1NC(C)(C)c1nnc(C)n1-2] | A-12, B-60 | 44 | 1H NMR (600 MHz, DMSO) δ = 7.90 (dd, 1H), 7.64 (d, 1H), 7.48 (dd, 1H), 7.36 (d, 1H), 7.22 (d, 1H), 6.78-6.74 (m, 0H), 6.01 (d, 1H), 3.49 (s, 3H), 2.53 (s, 3H), 2.30 (s, 3H), 1.57 (s, 7H). |
| 59 | 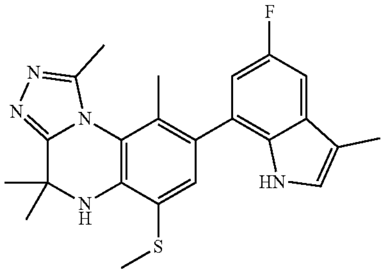 | A-15, B-63 | 45 | NA |
| 60 | 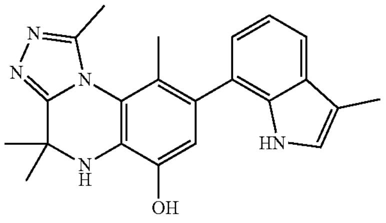 | 3-methyl-7-(4,4,5,5-tetramethyl-1,3,2-dioxaborolan-2-yl)-1H-indole, B-64 (followed by demethylation with $BBr_3$) | 5 | 1H NMR (600 MHz, DMSO) δ = 10.42 (d, 1H), 7.50 (dt, 1H), 7.11-7.03 (m, 3H), 6.96 (dd, 1H), 6.84 (s, 1H), 2.67 (s, 3H), 2.30 (d, 3H), 1.93 (s, 3H), 1.27 (s, 2H). |
| 63 | 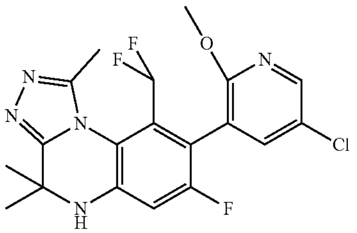 [SMILES: COc1ncc(Cl)cc1-c1c(F)cc2c(c1C(F)F)-n1c(C)nnc1C(C)(C)N2] | 5-chloro-2-methoxy-3-(4,4,5,5-tetramethyl-1,3,2-dioxaborolan-2-yl)pyridine, B-28 | 37 | 1H NMR (600 MHz, DMSO) δ = 8.30 (d, 1H), 7.93 (s, 1H), 7.25 (s, 1H), 7.09 (s, 1H), 7.01 (d, 1H), 3.84 (s, 3H), 2.46 (s, 3H), 1.58 (s, 6H). |
| 67 | 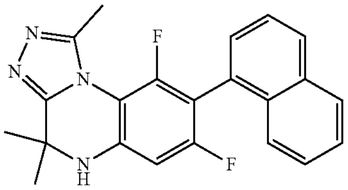 [SMILES: Cc1nnc2n1-c1c(cc(F)c(-c3cccc4ccccc34)c1F)NC2(C)C] | Naphthalene-1-boronic acid, B-1 | | 1H NMR (600 MHz, DMSO) δ = 8.08-8.01 (m, 2H), 7.68-7.61 (m, 2H), 7.62-7.51 (m, 3H), 7.22 (d, 1H), 6.86 (dd, 1H), 2.45 (d, 3H), 1.57 (d, 6H). |
| 68 | 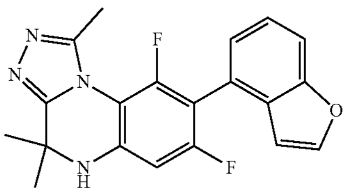 [SMILES: Cc1nnc2n1-c1c(cc(F)c(-c3cccc4occc34)c1F)NC2(C)C] | 4-Benzofuranyl-boronic acid, B-1 | | 1H NMR (600 MHz, DMSO) δ = 8.04 (d, 1H), 7.68 (dd, 1H), 7.44 (t, 1H), 7.35 (d, 1H), 7.20 (d, 1H), 6.87 (s, 1H), 6.82 (dd, 1H), 2.53 (s, 3H), 1.54 (s, 6H). |
| 69 | 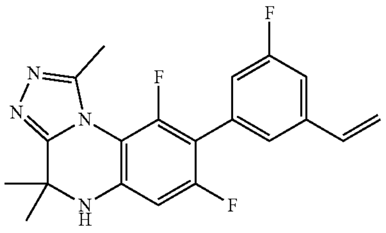 [SMILES: C=Cc1cc(F)cc(-c2c(F)cc3c(c2F)-n2c(C)nnc2C(C)(C)N3)c1] | (3-Fluoro-5-vinylphenyl)boronic acid, B-1 | | |

-continued

| Example Nr. | Structure | Inter-mediates | Yield % | Data |
|---|---|---|---|---|
| 70 | 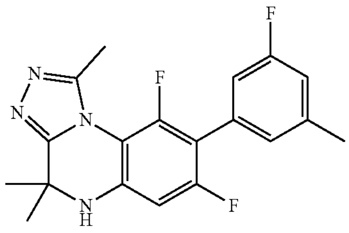 | (3-fluoro-5-methylphenyl)boronic acid, B-1 | | |
| 74 | 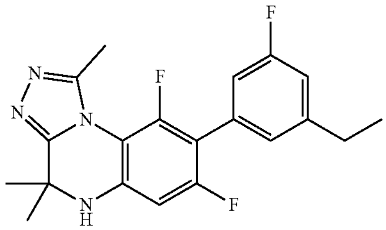 [SMILES: CCc1cc(F)cc(-c2c(F)cc3c(c2F)-n2c(C)nnc2C(C)(C)N3)c1] | (3-fluoro-5-ethylphenyl)boronic acid, B-1 | | |
| 78 | 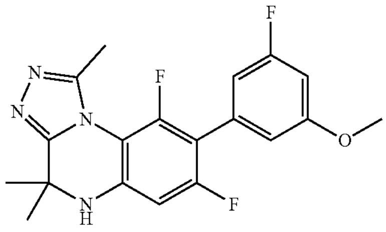 | (3-fluoro-5-methoxy-phenyl)boronic acid, B-2 | 47 | 1H NMR (600 MHz, DMSO) δ = 7.19 (d, 1H), 6.96-6.89 (m, 3H), 6.76 (dd, 1H), 3.82 (s, 3H), 2.54 (d, 3H), 1.51 (s, 6H). |
| 83 | 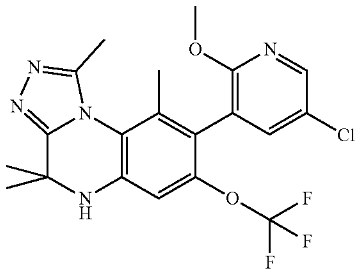 [SMILES: COc1ncc(Cl)cc1-c1c(OC(F)(F)F)cc2c(c1C)-n1c(C)nnc1C(C)(C)N2] | 5-chloro-2-methoxy-3-(4,4,5,5-tetramethyl-1,3,2-dioxaborolan-2-yl)pyridine, B-37 | 47 | 1H NMR (600 MHz, DMSO) δ = 8.32 (d, 1H), 7.92 (d, 1H), 6.94 (s, 1H), 3.85 (s, 3H), 2.44 (s, 3H), 2.04 (s, 3H), 1.48 (d, 6H). |
| 88 | 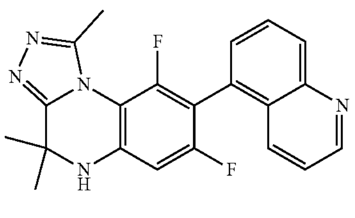 [SMILES: Cc1nnc2n1-c1c(cc(F)c(-c3cccc4ncccc34)c1F)NC2(C)C] | quinolin-5-ylboronic acid, B-1 | | 1H NMR (600 MHz, DMSO) δ = 8.97 (dd, 1H), 8.19-8.10 (m, 3H), 7.90 (dd, 2H), 7.72 (dd, 1H), 7.57 (dd, 2H), 6.86 (dd, 2H), 2.46 (d, 5H), 2.08 (s, 1H). |
| 102 | 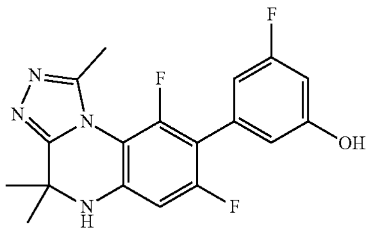 [SMILES: Cc1nnc2n1-c1c(cc(F)c(-c3cc(O)cc(F)c3)c1F)NC2(C)C] | (3-fluoro-5-hydroxy-phenyl)boronic acid, B-1 | 35 | 1H NMR (600 MHz, DMSO) δ = 7.17 (d, 1H), 6.78-6.70 (m, 3H), 6.63 (dt, 1H), 2.53 (s, 3H), 1.51 (s, 6H). |

-continued

| Example Nr. | Structure | Intermediates | Yield % | Data |
|---|---|---|---|---|
| 105 | 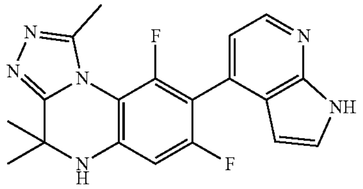 [SMILES: Cc1nnc2n1-c1c(cc(F)c(-c3ccnc4[nH]ccc34)c1F)NC2(C)C] | 1H-pyrrolo[2,3-b]pyridin-4-ylboronic acid, B-1 | 52 | 1H NMR (600 MHz, DMSO) δ = 8.31 (d, 1H), 7.54 (t, 1H), 7.26 (d, 1H), 7.15 (d, 1H), 6.83 (dd, 1H), 6.39-6.34 (m, 1H), 2.53 (s, 3H), 2.08 (s, 1H), 1.55 (s, 6H). |
| 111 | 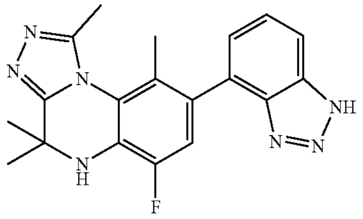 [SMILES: Cc1c(-c2cccc3[nH]nnc23)cc(F)c2c1-n1c(C)nnc1C(C)(C)N2] | 8-bromo-6-fluoro-1,4,4,9-tetramethyl-5H-[1,2,4]triazolo[4,3-a]quinoxaline, B-7 | | |
| 114 | 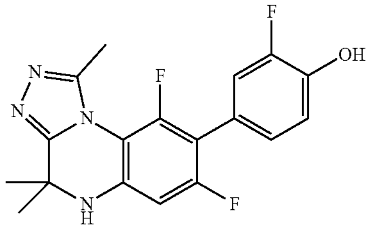 [SMILES: Cc1nnc2n1-c1c(cc(F)c(-c3ccc(O)c(F)c3)c1F)NC2(C)C] | (3-fluoro-4-methoxy-phenyl)boronic acid, B-1 (followed by demethylation with DL-methionin) | 100 | 1H NMR (600 MHz, DMSO) δ = 7.29 (dd, 1H), 7.16-7.09 (m, 2H), 7.05 (t, 1H), 6.77-6.71 (m, 1H), 2.53 (s, 3H), 1.50 (s, 6H). |

Example 25: 5-chloro-6-(4-fluoro-1H-indazol-6-yl)-3,11,11-trimethyl-8,9,10,11-tetrahydrofuro[3,2-f][1,2,4]triazolo[4,3-a]quinoxaline

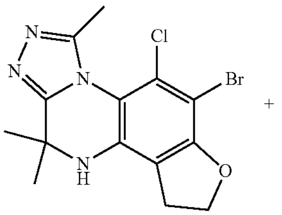

intermediate B-57

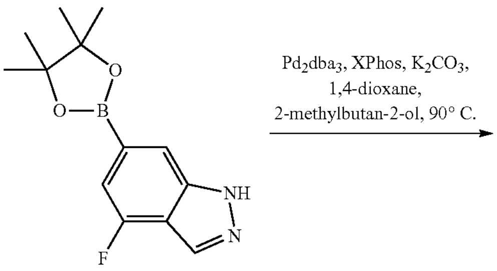

intermediate A-74

-continued

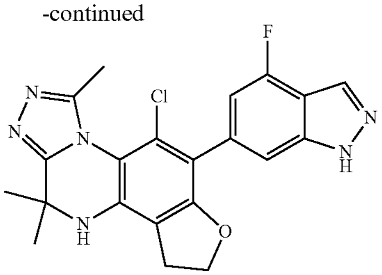

example 25

Intermediate B-57 (60 mg, 0.16 mmol, 1 eq.), intermediate A-74 (85 mg, 0.32 mmol, 2 eq.), $Pd_2dba_3$ (15 mg, 0.016 mmol, 0.1 eq.) and 2-dicyclohexylphosphino-2',4',6'-triisopropylbiphenyl (Xphos, 15.5 mg, 0.0325 mmol, 0.2 eq.) were weighed out into a microwave vial under nitrogen. A stirring bar was added and the vial was sealed. Then, 1,4-dioxane (1.2 mL), 2-methylbutan-2-ol (1.2 mL) and 2M $K_2CO_3$ solution (0.4 mL) were added, and nitrogen gas was bubbled through the reaction mixture for two minutes. The reaction mixture was then heated to 90° C. for 2 hours. Then, DCM and water were added, and the resulting mixture was filtered through a hydrophobic frit. The organic layer was evaporated and the residue was purified via silica gel chromatography to yield 5-chloro-6-(4-fluoro-1H-indazol-6-yl)-3,11,11-trimethyl-8,9,10,11-tetrahydrofuro[3,2-f][1,2,4]triazolo[4,3-a]quinoxaline (38 mg, 55%).

1H NMR (600 MHz, DMSO) δ=8.21 (t, 1H), 7.40 (d, 1H), 6.93 (dd, 1H), 6.46 (s, 1H), 4.61 (t, 2H), 3.20 (t, 2H), 2.55 (s, 3H), 1.52 (s, 6H).

Example 30: 6-Ethyl-9-fluoro-8-(5-fluoro-3-tetra-hydro-furan-3-yl-1H-indol-7-yl)-1,4,4-trimethyl-5H-[1,2,4]triazolo[4,3-a]quinoxaline

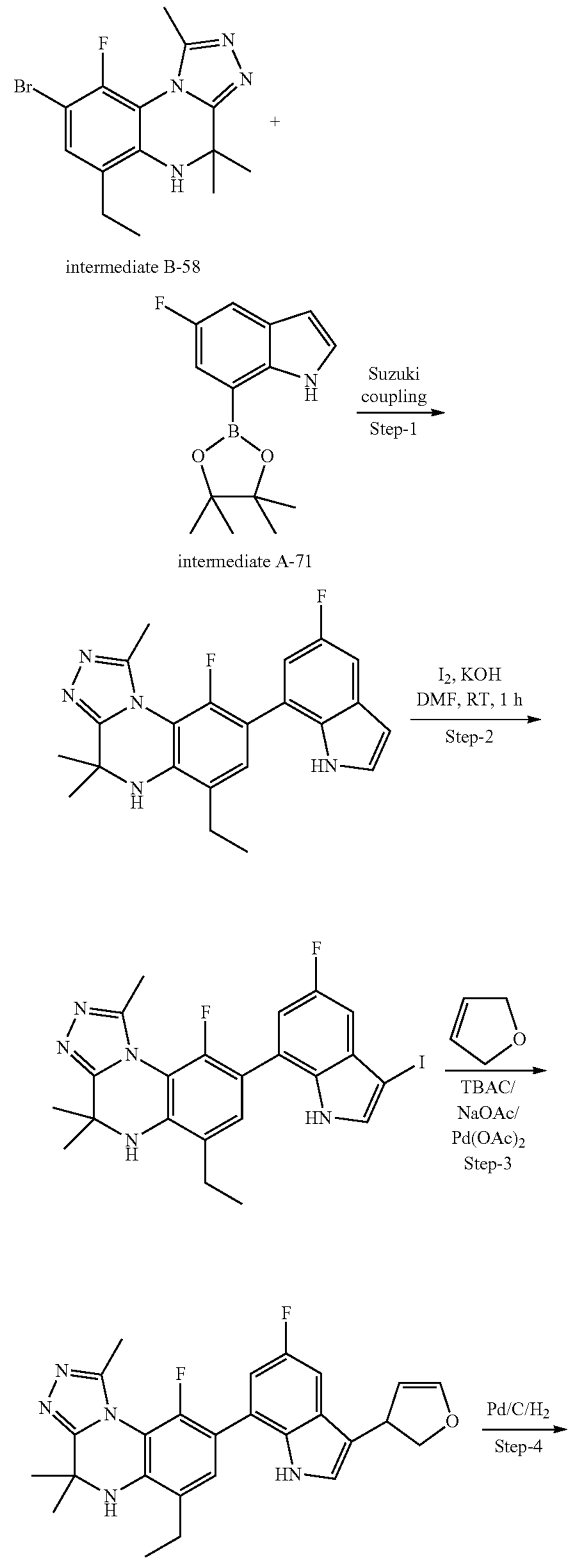

-continued

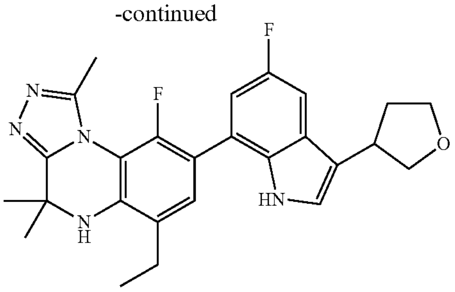

example 30

Step 1: To a solution of intermediate B-58 (0.81 g, 2.38 mmol, 1.0 eq.) in a t-amyl alcohol:1-4 dioxane (2:1) mixture (30 mL) were added aqueous $K_2CO_3$ solution (5 mL) and intermediate A-71 (1.2 g, 4.77 mmol, 2 eq). The solution was degassed with argon for 20 min followed by addition of Attaphos (0.085 g, 0.119 mmol, 0.05 eq.), and the reaction mixture was refluxed at 100° C. for 16 h. After completion (monitored by TLC), the reaction mixture was evaporated under reduced pressure. The crude residue was purified by flash column chromatography (230-400 mesh silica gel; 5% MeOH/DCM) to afford 6-ethyl-9-fluoro-8-(5-fluoro-1H-indol-7-yl)-1,4,4-trimethyl-4,5-dihydro-[1,2,4]triazolo[4,3-a]quinoxaline (0.7 g, 74.5%) as a white solid.

Step 2: To a stirred solution of 6-ethyl-9-fluoro-8-(5-fluoro-1H-indol-7-yl)-1,4,4-trimethyl-4,5-dihydro-[1,2,4]triazolo[4,3-a]quinoxaline (0.8 g, 2.03 mmol, 1 eq) in DMF (25 mL), KOH (0.285 g, 5.02 mmol, 2.5 eq) and iodine (0.517 g, 2.03 mmol, 1.0 eq) in DMF (20 mL) were added at 0° C. and the resulting reaction mixture was stirred for 1 h at 0° C. The reaction mixture was diluted with EtOAc (800 mL), washed with aq. sodium metabisulfite (2×300 mL), water (4×300 mL) and brine (300 mL), dried over $Na_2SO_4$, filtered and concentrated under reduced pressure to afforded 7-{6-ethyl-9-fluoro-1,4,4-trimethyl-4H,5H-[1,2,4]triazolo[4,3-a]quinoxalin-8-yl}-5-fluoro-3-iodo-1H-indole (0.65 g, 61%).

Step 3: A solution of 7-{6-ethyl-9-fluoro-1,4,4-trimethyl-4H,5H-[1,2,4]triazolo[4,3-a]quinoxalin-8-yl}-5-fluoro-3-iodo-1H-indole (0.2 g, 0.48 mmol, 1.0 eq.) in DMF (7 mL) was degassed with argon for 20 min, followed by addition of tetrabutyl ammonium chloride (0.134 g, 0.48 mmol, 1.0 eq.), NaOAc (0.118 g, 1.44 mmol, 3.0 eq.), $Pd(OAc)_2$ (10.8 mg, 0.048 mmol, 0.1 eq.) and 2,5-dihydrofuran (0.355 mL, 4.8 mmol, 10 eq.). The reaction mixture was stirred at 50° C. for 48 h. After completion (monitored by TLC), the reaction mixture was filtered through a celite bed and the filtrate was concentrated under reduced pressure. The crude residue was purified by prep. HPLC (10% MeOH/DCM) to afford (3-(2,3-dihydrofuran-3-yl)-7-{6-ethyl-9-fluoro-1,4,4-trimethyl-4H,5H-[1,2,4]triazolo[4,3-a]quinoxalin-8-yl}-5-fluoro-1H-indole (0.07 g, 31%) as a white solid.

Step 4: A solution of 3-(2,3-dihydrofuran-3-yl)-7-{6-ethyl-9-fluoro-1,4,4-trimethyl-4H,5H-[1,2,4]triazolo[4,3-a]quinoxalin-8-yl}-5-fluoro-1H-indole (0.07 g, 0.15 mmol, 1.0 eq.) in ethanol (5 mL) was degassed with argon for 10 min, followed by addition of Pd—C (10 mg, 10 wt % loading), and the reaction mixture was stirred at rt under hydrogen atmosphere. for 3 h. After completion (monitored by TLC), the reaction mixture was filtered through a celite bed and the filtrate was concentrated under reduced pressure to afford 6-Ethyl-9-fluoro-8-(5-fluoro-3-tetrahydro-furan-3-yl-1H-indol-7-yl)-1,4,4-trimethyl-5H-[1,2,4]triazolo[4,3-a]quinoxaline (0.06 g, 85%) as a white solid.

$^1$H NMR (400 MHz, DMSO-$d_6$): δ 10.8 (s, 1H), 7.38 (dd, J=2 HZ, J=9.6 Hz, 1H), 7.26 (d, J=2.4 Hz, 1H), 7.18 (d, J=8.0 Hz, 1H), 6.97 (dd, J=2.0 Hz, J=10 Hz, 1H), 6.03 (s, 1H) 4.12 (t, J=6.8 Hz, 1H), 3.91-3.95 (m, 1H), 3.82 (q, J=7.6 Hz, J=15.2 Hz, 1H), 3.56-3.64 (m, 2H), 2.71 (q, J=7.2 Hz, 14.4 Hz, 2H), 2.52 (s, 3H), 2.32-2.35 (m, 1H), 2.01-2.04 (m, 1H), 1.56 (s, 6H), 1.16 (t, J=6.8 Hz, 3H).

The following examples were prepared in a similar manner (use of appropriate reagents and purification methods known to the person skilled in the art) as the synthesis described for example 30:

-continued

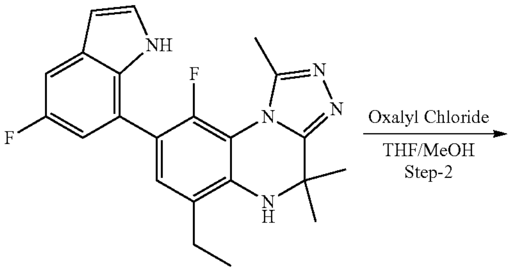

| Example Nr. | Structure | Inter-mediates | Yield % | Data |
|---|---|---|---|---|
| 52 | 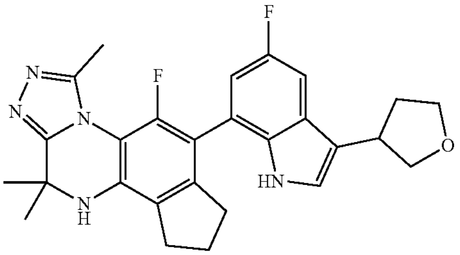 [SMILES: Cc1nnc2n1-c1c(F)c(-c3cc(F)cc4c(C5CCOC5)c[nH]c34)c3c(c1NC2(C)C)CCC3] | A-71, B-61 | 30 | 1H NMR (600 MHz, DMSO) δ = 10.74 (d, 1H), 7.38 (dt, 1H), 7.24 (d, 1H), 6.96 (dd, 1H), 6.14 (d, 1H), 4.13 (td, 1H), 3.95 (tdd, 1H), 3.84 (q, 1H), 3.65 (td, 1H), 3.62-3.54 (m, 1H), 2.87 (q, 3H), 2.47 (d, 4H), 2.42-2.30 (m, 1H), 2.14-1.93 (m, 3H), 1.60 (s, 3H), 1.55 (s, 3H). |

Example 31: 2-[7-(6-Ethyl-9-fluoro-1,4,4-trimethyl-5H-[1,2,4]triazolo[4,3-a]quinoxalin-8-yl)-5-fluoro-1H-indol-3-yl]-ethanol

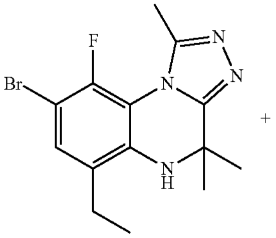

intermediate B-58

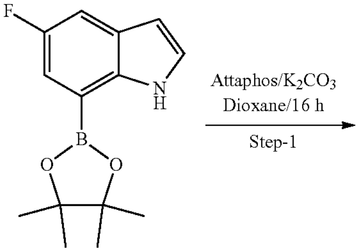

intermediate A-71

-continued

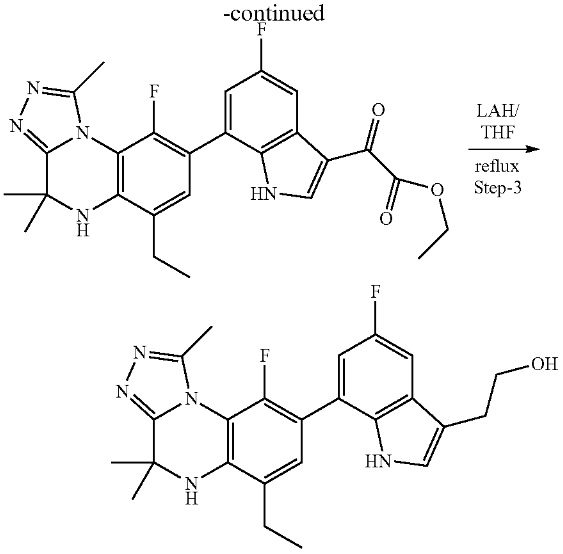

example 31

Step 1: To a solution of intermediate B-58 (0.81 g, 2.38 mmol, 1.0 eq.) in a t-amyl alcohol: 1-4 dioxane (2:1) mixture (30 mL) were added aqueous $K_2CO_3$ solution (5 mL) and intermediate A-71 (1.2 g, 4.77 mmol, 2 eq). The solution was degassed with argon for 20 min followed by addition of Attaphos (0.085 g, 0.119 mmol, 0.05 eq.), and the reaction mixture was refluxed at 100° C. for 16 h. After completion (monitored by TLC), the reaction mixture was evaporated under reduced pressure. The crude residue was purified by flash column chromatography (230-400 mesh silica gel; 5% MeOH/DCM) to afford 6-ethyl-9-fluoro-8-(5-fluoro-1H-indol-7-yl)-1,4,4-trimethyl-4,5-dihydro-[1,2,4]triazolo[4,3-a]quinoxaline (0.7 g, 74.5%) as a white solid.

Step 2: To a solution of 6-ethyl-9-fluoro-8-(5-fluoro-1H-indol-7-yl)-1,4,4-trimethyl-4,5-dihydro-[1,2,4]triazolo[4,3-a]quinoxaline (0.43 g, 1.092 mmol, 1 eq) in THF (20 mL), oxalyl chloride (0.2 mL, 2.404 mmol, 3 eq) was added at RT, and the reaction was stirred for 16 h. EtOH (10 mL) was added and stirring was continued for another 2 h. After completion (monitored by TLC), the reaction mixture was quenched with water and extracted with EtOAc. The combined organic layers were washed with brine, dried over $Na_2SO_4$, filtered and evaporated under reduced pressure to afford ethyl 2-(7-{6-ethyl-9-fluoro-1,4,4-trimethyl-4H,5H-[1,2,4]triazolo[4,3-a]quinoxalin-8-yl}-5-fluoro-1H-indol-3-yl)-2-oxoacetate (0.4 g, 74.3%) as a brown gum.

Step 3: To a solution of ethyl 2-(7-{6-ethyl-9-fluoro-1,4,4-trimethyl-4H,5H-[1,2,4]triazolo[4,3-a]quinoxalin-8-yl}-5-fluoro-1H-indol-3-yl)-2-oxoacetate (0.4 g, 0.81 mmol, 1 eq) in THF (40 mL), Lithium aluminium hydride (0.154 g, 4.052 mmol, 5 eq) was added at 0° C., and the reaction mixture was refluxed for 16 h. After completion (monitored by TLC), the reaction mixture was quenched with saturated $Na_2SO_4$ solution and extracted with EtOAc. The combined organic layers were washed with water and brine, dried over $Na_2SO_4$, filtered and evaporated under reduced pressure. The crude residue was purified by prep. HPLC to afford 2-[7-(6-ethyl-9-fluoro-1,4,4-trimethyl-5H-[1,2,4]triazolo[4,3-a]quinoxalin-8-yl)-5-fluoro-1H-indol-3-yl]-ethanol (0.04 g, 11.2%) as a white solid.

$^1$H NMR (400 MHz, DMSO-$d_6$): δ 10.72 (s, 1H), 7.32 (d, J=10.0 Hz, 1H), 7.17-7.21 (m, 2H), 6.95 (d, J=9.6 Hz, 1H), 6.02 (s, 1H), 4.61 (s, 1H), 3.65 (t, J=6.8 Hz, 2H), 2.83 (t, J=6.8 Hz, 2H), 2.67-2.72 (m, 2H), 1.56 (s, 6H), 1.16 (t, J=7.6 Hz, 3H).

The following examples were prepared in a similar manner (use of appropriate reagents and purification methods known to the person skilled in the art) as the synthesis described for example 31:

| Example Nr. | Structure | Inter-mediates | Yield % | Data |
|---|---|---|---|---|
| 46 | 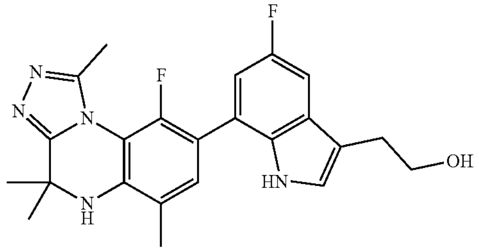 [SMILES: Cc1cc(-c2cc(F)cc3c(CCO)c[nH]c23)c(F)c2c1NC(C)(C)c1nnc(C)n1-2] | B-60, A-71 | 22 | 1H NMR (600 MHz, DMSO) δ = 10.69 (d, 1H), 7.32 (dd, 1H), 7.21 (dd, 2H), 6.93 (dd, 1H), 5.97 (d, 1H), 4.73-4.67 (m, 1H), 3.67 (td, 2H), 2.84 (t, 2H), 2.51 (d, 3H), 2.28 (s, 3H), 1.58 (s, 6H). |

Example 33: 8-(6-Fluoro-1-methylsulfonyl-1H-indol-4-yl)-1,4,4,6-tetramethyl-9-(trifluoromethyl)-5H-[1,2,4]triazolo[4,3-a]quinoxaline

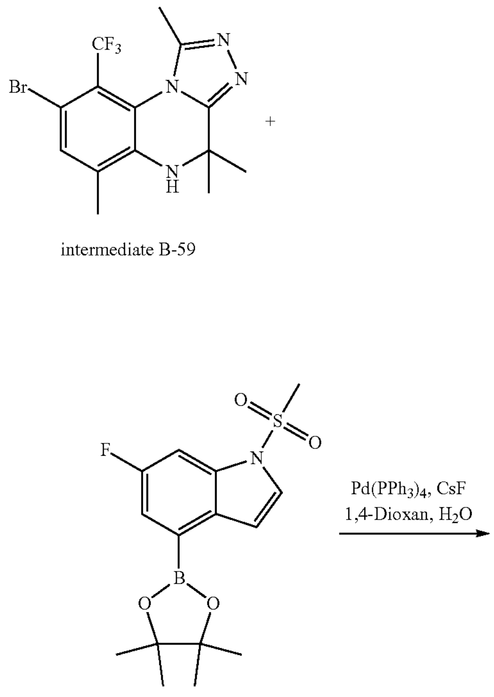

intermediate B-59 intermediate A-2

-continued

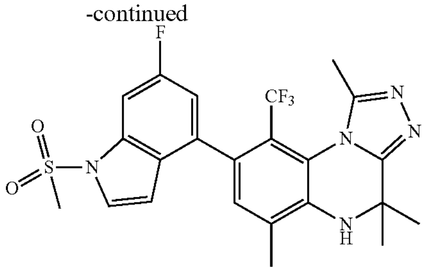

To a solution of intermediate B-59 (0.14 g, 0.373 mmol, 1 eq) in a dioxane:$H_2O$ mixture (15 ml) were added CsF (0.17 g, 1.119 mmol, 3 eq) and intermediate A-2 (0.252 g, 0.746 mmol, 2 eq) in a sealed tube. The solution was degassed with argon for 20 min, followed by addition of $Pd(PPh_3)_4$ (0.021 g, 0.018 mmol, 0.05 eq), and the reaction mixture was refluxed at 90° C. for 16 h. After completion (monitored by TLC), the reaction mixture was filtered through a celite bed. The filtrate was concentrated under reduced pressure to afford the crude material which was purified by column chromatography (5% MeOH/DCM), followed by prep. HPLC purification to afford 8-(6-Fluoro-1-methylsulfonyl-1H-indol-4-yl)-1,4,4,6-tetramethyl-9-(trifluoromethyl)-5H-[1,2,4]triazolo[4,3-a]quinoxaline (0.06 g, 31.7%) as an off-white solid.

1H NMR (400 MHz, dmso-d6, AT 100° C.): δ 7.67 (d, J=9.6 Hz, 1H), 7.57 (d, J=3.2 Hz, 1H), 7.16 (bs, 2H), 6.48 (bs, 1H), 6.04 (s, 1H), 3.47 (s, 3H), 2.46 (s, 3H), 2.35 (s, 3H), 1.86 (bs, 3H), 1.31 (bs, 3H).

The following examples were prepared in a similar manner (use of appropriate reagents and purification methods known to the person skilled in the art) as the synthesis described for example 33:

| Example Nr. | Structure | Inter-mediates | Yield % | Data |
|---|---|---|---|---|
| 35 | 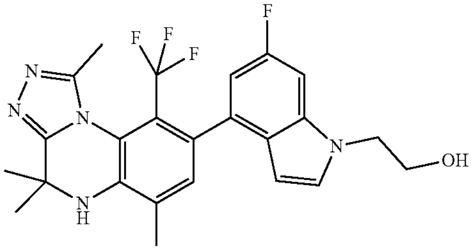 [SMILES: Cc1cc(-c2cc(F)cc3c2ccn3CCO)c(C(F)(F)F)c2c1NC(C)(C)c1nnc(C)n1-2] | A-20, B-59 | 29 | 1H NMR (600 MHz, DMSO) δ = 7.44-7.32 (m, 2H), 7.17 (d, 1H), 7.00-6.76 (m, 1H), 6.23 (d, 1H), 6.12 (dd, 1H), 4.95 (q, 1H), 4.22 (tdd, 2H), 3.75 (p, 2H), 2.46 (d, 3H), 2.32 (d, 3H), 1.84 (s, 3H), 1.28 (s, 3H). |
| 47 | 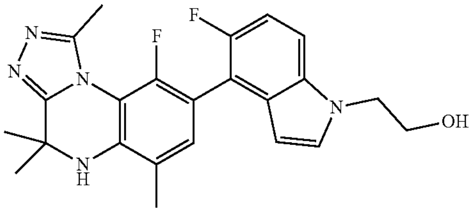 [SMILES: Cc1cc(-c2c(F)ccc3c2ccn3CCO)c(F)c2c1NC(C)(C)c1nnc(C)n1-2] | A-76, B-60 | 31 | 1H NMR (600 MHz, DMSO) δ = 7.55 (dd, 1H), 7.47 (d, 1H), 7.21 (d, 1H), 7.09 (t, 1H), 6.29 (d, 1H), 6.01 (d, 1H), 4.91 (t, 1H), 4.26 (t, 2H), 3.74 (q, 2H), 2.48 (d, 3H), 2.29 (s, 3H), 1.57 (d, 6H). |

Example 34: 8-(6-Fluoro-1-methylsulfonyl-1H-indol-4-yl)-1,4,4,6-tetramethyl-9-(trifluoromethyl)-5H-[1,2,4]triazolo[4,3-a]quinoxaline

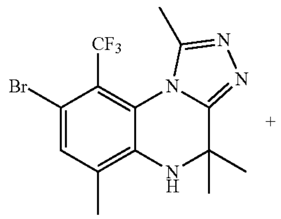

intermediate B-59

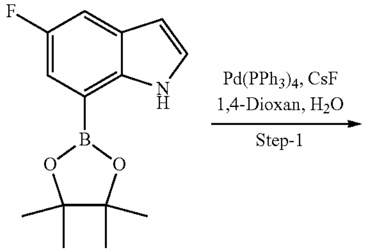

intermediate A-71

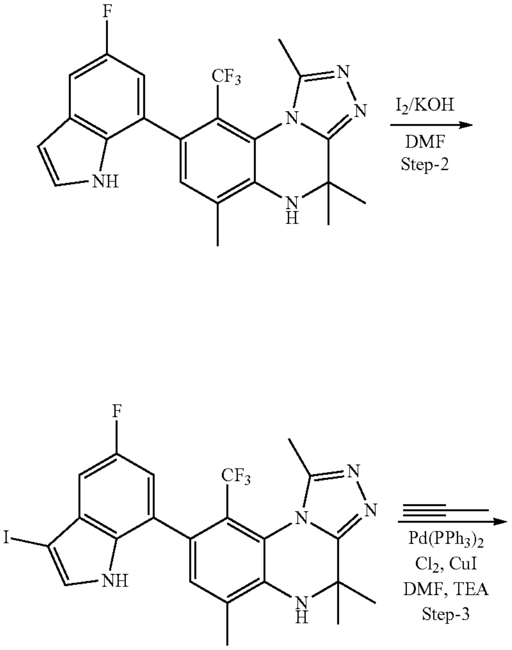

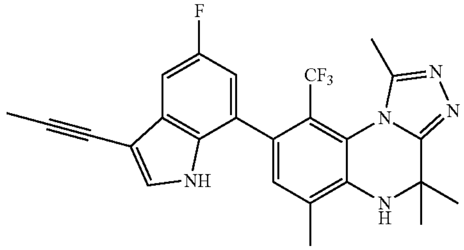

example 34

Step 1: To a solution of intermediate B-59 (0.2 g, 0.533 mmol, 1 eq) in a dioxane-water mixture (15 mL) were added CsF (0.248 g, 1.599 mmol, 3 eq) and intermediate A-71 (0.278 g, 1.066 mmol, 2 eq) in a sealed tube. The solution was degassed with argon for 20 min, followed by addition of $Pd(PPh_3)_4$ (0.03 g, 0.026 mmol, 0.05 eq), and the reaction mixture was refluxed at 90° C. for 16 h. After completion (monitored by TLC), the reaction mixture was filtered through a celite bed. The filtrate was concentrated under reduced pressure to afford the crude material which was purified by column chromatography (5% MeOH/DCM) to yield compound 5-fluoro-7-[1,4,4,6-tetramethyl-9-(trifluoromethyl)-4H,5H-[1,2,4]triazolo[4,3-a]quinoxalin-8-yl]-1H-indole (0.19 g, 83.3%) as an off-white solid.

Step 2: To a stirred solution of 5-fluoro-7-[1,4,4,6-tetramethyl-9-(trifluoromethyl)-4H,5H-[1,2,4]triazolo[4,3-a]quinoxalin-8-yl]-1H-indole (0.19 g, 0.443 mmol, 1 eq) in dimethylformamide (6 mL) was added potassium hydroxide powder (0.037 g, 0.664 mmol, 1.5 eq), and the reaction mixture was stirred for 30 min at room temperature. Iodine (0.123 g, 0.487 mmol, 1.1 eq) was added to the reaction mixture and stirring was continued for 2 h. The reaction mixture was then diluted with ethyl acetate (50 mL), washed with water (5×20 mL) and brine (20 ml), dried over anhydrous $Na_2SO_4$, and concentrated under reduced pressure. The crude residue was purified by silica gel (230-400 silica; 5% MeOH/DCM) to afford 5-fluoro-3-iodo-7-[1,4,4,6-tetramethyl-9-(trifluoromethyl)-4H,5H-[1,2,4]triazolo[4,3-a]quinoxalin-8-yl]-1H-indole (0.23 g, 93%) as a light brown solid.

Step 3: A solution of 5-fluoro-3-iodo-7-[1,4,4,6-tetramethyl-9-(trifluoromethyl)-4H,5H-[1,2,4]triazolo[4,3-a]quinoxalin-8-yl]-1H-indole (0.23 g, 0.414 mmol, 1 eq) in dimethylformamide (3 mL) and TEA (4 ml) was deoxygenated with argon gas for 10 min in a sealed tube. $Pd(PPh_3)_2Cl_2$ (0.015 g, 0.0207 mmol, 0.05 eq) and CuI (0.002 g, 0.015 mmol, 0.025 eq) were then added to the reaction mixture, which was again deoxygenated with argon gas for 10 min at −78° C. In a test tube, propyne gas was condensed in TEA (4 mL) at −78° C. The volume rose to 5 mL. The condensed propyne gas was then instantly poured into the reaction mixture at −78° C. The reaction mixture was then stirred for 2 h at −78° C. and 14 h at room temperature. The reaction mixture was diluted with ethyl acetate (50 mL). The organic layer was washed with water (5×20 mL) and brine (20 mL), dried over anhydrous $Na_2SO_4$, and concentrated under reduced pressure. The crude residue was purified by column chromatography (silica gel; 5% MeOH/DCM) to afford 8-(6-Fluoro-1-methylsulfonyl-1H-indol-4-yl)-1,4,4,6-tetramethyl-9-(trifluoromethyl)-5H-[1,2,4]triazolo[4,3-a]quinoxaline (0.042 g, 21.7%) as an off-white solid.

1H NMR (400 MHz, dmso-d6, AT 100°): δ 10.83 (s, 1H), 7.48 (s, 1H), 7.27 (d, 1H, J=9.08 Hz), 7.16 (s, 1H), 6.96 (bs, 1H), 5.98 (s, 1H), 2.47 (s, 3H), 2.34 (s, 3H), 2.1 (s, 3H), 1.86 (bs, 3H), 1.32 (bs, 3H).

The following examples were prepared in a similar manner (use of appropriate reagents and purification methods known to the person skilled in the art) as the synthesis described for example 34:

| Example Nr. | Structure | Intermediates | Yield % | Data |
|---|---|---|---|---|
| 42 | 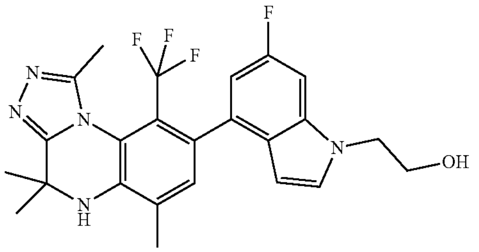 [SMILES: Cc1cc(-c2cc(F)cc3c2ccn3CCO)c(C(F)(F)F)c2c1NC(C)(C)c1nnc(C)n1-2] | B-60, A-71 | 39 | 1H NMR (600 MHz, DMSO) δ = 11.23 (d, 1H), 7.62 (d, 1H), 7.28 (dd, 1H), 7.23 (d, 1H), 7.05 (dd, 1H), 6.00 (d, 1H), 2.52 (s, 3H), 2.29 (s, 3H), 2.10 (s, 3H), 1.58 (s, 6H). |

Example 40: 4-[5-Fluoro-7-(9-fluoro-1,4,4,6-tetramethyl-5H-[1,2,4]triazolo[4,3-a]quinoxalin-8-yl)-1H-indol-3-yl]-but-3-yn-2-ol

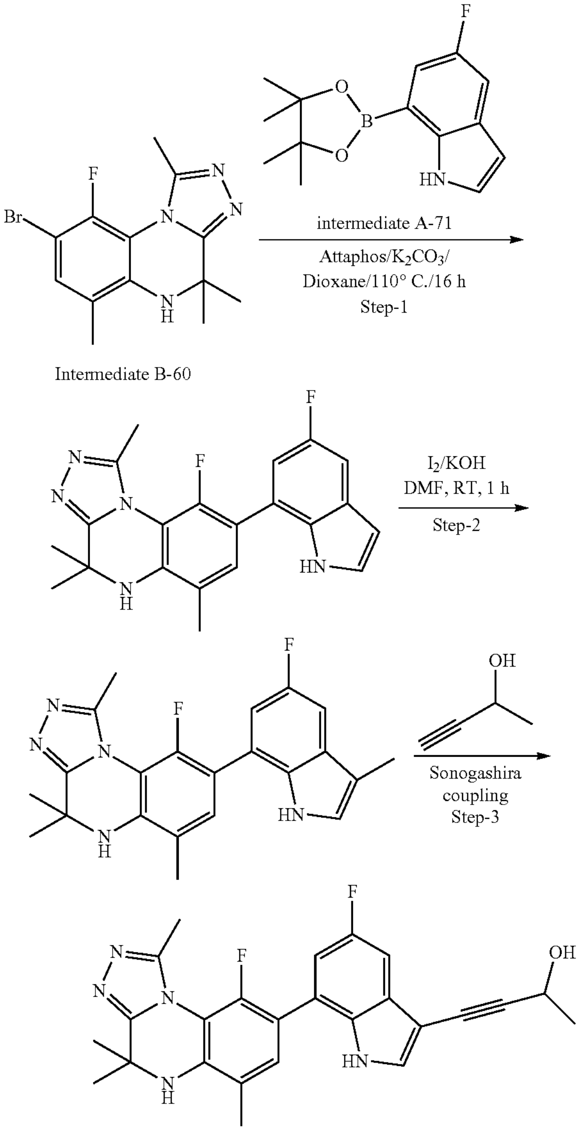

example 40

Step 1: To a solution of intermediate B-60 (2.4 g, 9.191 mmol, 1 eq) in dioxane (50 mL) were added aqueous $K_2CO_3$ (3.81 g, 27.57 mmol, 3 eq) and intermediate A-71 (2.98 g, 9.191 mmol, 1 eq) at RT. The solution was degassed with argon for 20 min, followed by addition of Attaphos (0.325 g, 0.459 mmol, 0.05 eq), and the reaction mixture was refluxed at 110° C. for 16 h. After completion (monitored by TLC), the reaction mixture was evaporated under reduced pressure. The crude residue was purified by flash column chromatography (230-400 mesh silica gel; 5% MeOH/DCM) to afford 5-fluoro-7-{9-fluoro-1,4,4,6-tetramethyl-4H,5H-[1,2,4]triazolo[4,3-a]quinoxalin-8-yl}-1H-indole (2.2 g, 63.2%) as a white solid.

Step 2: To a stirred solution of compound 5-fluoro-7-{9-fluoro-1,4,4,6-tetramethyl-4H,5H-[1,2,4]triazolo[4,3-a]quinoxalin-8-yl}-1H-indole (1 g, 2.638 mmol, 1 eq) in DMF (10 mL), KOH (0.26 g, 6.596 mmol, 2.5 eq) and iodine (0.47 g, 2.638 mmol, 1 eq) in DMF (10 mL) were added at 0° C. and the resulting reaction mixture was stirred for 1 h at 0° C. The reaction mixture was diluted with EtOAc (100 mL), washed with aq. sodium metabisulfite (2×200 mL), water (4×200 mL) and brine (200 mL), dried over $Na_2SO_4$, filtered and concentrated under reduced pressure to afforded 5-fluoro-7-{9-fluoro-1,4,4,6-tetramethyl-4H,5H-[1,2,4]triazolo[4,3-a]quinoxalin-8-yl}-3-iodo-1H-indole (1.3 g, 98%) as a brown solid.

Step 3: A solution of 5-fluoro-7-{9-fluoro-1,4,4,6-tetramethyl-4H,5H-[1,2,4]triazolo[4,3-a]quinoxalin-8-yl}-3-iodo-1H-indole (0.4 g, 0.791 mmol, 1 eq) in DMF (6 mL) and TEA (6 mL) was degassed with argon for 20 min, followed by addition of CuI (0.003 g, 0.019 mmol, 0.025 eq.), $PdCl_2(PPh)_3$ (0.027 g, 0.039 mmol, 0.05 eq) and but-3-yn-2-ol (0.083 g, 1.187 mmol, 1.5 eq). The reaction mixture was stirred at rt for 16 h. After completion (monitored by TLC), the reaction mixture was filtered through a celite bed and the filtrate was concentrated under reduced pressure. The crude material was purified by prep. HPLC to afford 4-[5-Fluoro-7-(9-fluoro-1,4,4,6-tetramethyl-5H-[1,2,4]triazolo[4,3-a]quinoxalin-8-yl)-1H-indol-3-yl]-but-3-yn-2-ol (0.1 g, 28%) as a white solid.

$^1$H NMR (400 MHz, DMSO-$d_6$): δ 11.34 (s, 1H), 7.67 (d, J=2.4 Hz, 1H), 7.28 (d, J=11.2 Hz, 1H), 7.23 (d, J=7.6 Hz, 1H), 7.06 (d, J=12.4 Hz, 1H), 6.01 (s, 1H), 5.38 (s, 1H), 4.64 (t, J=6.0 Hz, 1H), 2.28 (s, 3H), 1.57 (s, 6H), 1.42 (s, 3H).

Example 43: 4-[5-Fluoro-7-(9-fluoro-1,4,4,6-tetramethyl-5H-[1,2,4]triazolo[4,3-a]quinoxalin-8-yl)-1H-indol-3-yl]-2-methyl-but-3-yn-2-ol

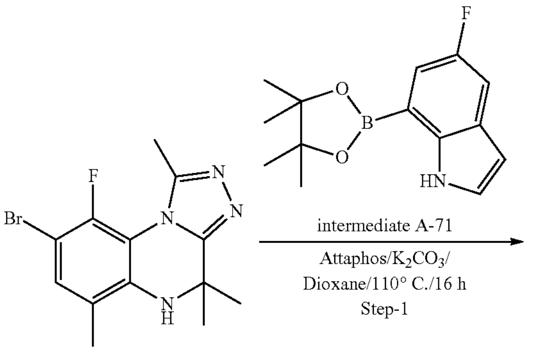

Intermediate B-60

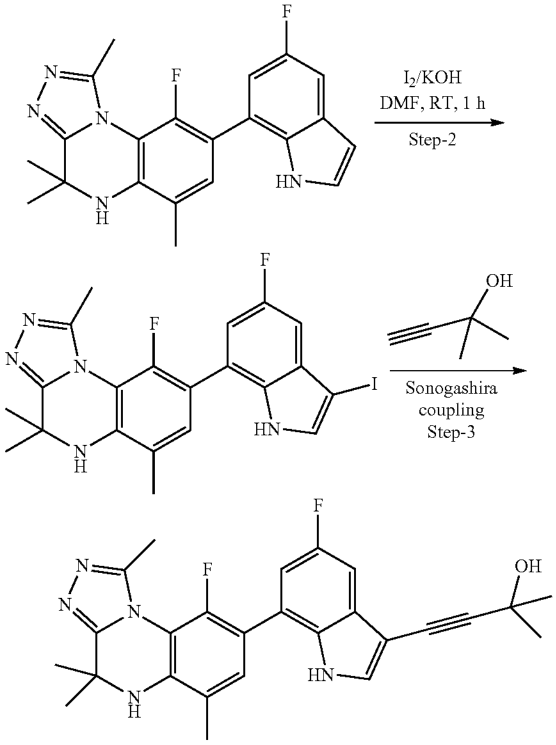

example 43

Step 1: To a solution of intermediate B-60 (2.4 g, 9.191 mmol, 1 eq) in dioxane (50 mL) were added aqueous $K_2CO_3$ (3.81 g, 27.57 mmol, 3 eq) and intermediate A-71 (2.98 g, 9.191 mmol, 1 eq) at RT. The solution was degassed with argon for 20 min, followed by addition of Attaphos (0.325 g, 0.459 mmol, 0.05 eq), and the reaction mixture was refluxed at 110° C. for 16 h. After completion (monitored by TLC), the reaction mixture was evaporated under reduced pressure. The crude residue was purified by flash column chromatography (230-400 mesh silica gel; 5% MeOH/DCM) to afford 5-fluoro-7-{9-fluoro-1,4,4,6-tetramethyl-4H,5H-[1,2,4]triazolo[4,3-a]quinoxalin-8-yl}-1H-indole (2.2 g, 63.2%) as a white solid.

Step 2: To a stirred solution of compound 5-fluoro-7-{9-fluoro-1,4,4,6-tetramethyl-4H,5H-[1,2,4]triazolo[4,3-a]quinoxalin-8-yl}-1H-indole (1 g, 2.638 mmol, 1 eq) in DMF (10 mL), KOH (0.26 g, 6.596 mmol, 2.5 eq) and iodine (0.47 g, 2.638 mmol, 1 eq) in DMF (10 mL) were added at 0° C. and the resulting reaction mixture was stirred for 1 h at 0° C. The reaction mixture was diluted with EtOAc (100 mL), washed with aq. sodium metabisulfite (2×200 mL), water (4×200 mL) and brine (200 mL), dried over $Na_2SO_4$, filtered and concentrated under reduced pressure to afford 5-fluoro-7-{9-fluoro-1,4,4,6-tetramethyl-4H,5H-[1,2,4]triazolo[4,3-a]quinoxalin-8-yl}-3-iodo-1H-indole (1.3 g, 98%) as a brown solid.

Step 3: A solution of 5-fluoro-7-{9-fluoro-1,4,4,6-tetramethyl-4H,5H-[1,2,4]triazolo[4,3-a]quinoxalin-8-yl}-3-iodo-1H-indole (0.4 g, 0.791 mmol, 1 eq) in DMF (6 mL) and TEA (6 mL) was degassed with argon for 20 min, followed by addition of CuI (0.003 g, 0.019 mmol, 0.025 eq.), $PdCl_2(PPh)_3$ (0.027 g, 0.039 mmol, 0.05 eq) and 2-methyl-but-3-yn-2-ol (0.1 g, 1.187 mmol, 1.5 eq). The reaction mixture was stirred at rt for 16 h. After completion (monitored by TLC), the reaction mixture was filtered through a celite bed and the filtrate was concentrated under reduced pressure. The crude material was purified by prep. HPLC to afford 4-[5-fluoro-7-(9-fluoro-1,4,4,6-tetramethyl-5H-[1,2,4]triazolo[4,3-a]quinoxalin-8-yl)-1H-indol-3-yl]-2-methyl-but-3-yn-2-ol (0.18 g, 49.4%) as a white solid.

$^1H$ NMR (400 MHz, DMSO-$d_6$): δ 11.31 (s, 1H), 7.65 (d, J=2.8 Hz, 1H), 7.28 (d, J=11.2 Hz, 1H), 7.23 (d, J=7.6 Hz, 1H), 7.06 (d, J=10.0 Hz, 1H), 6.00 (s, 1H), 5.38 (s, 1H), 2.28 (s, 3H), 1.57 (s, 6H), 1.51 (s, 6H).

Example 45: 9-Fluoro-1,4,4,6-tetramethyl-8-pyrazolo[1,5-a]pyridin-4-yl-5H-[1,2,4]triazolo[4,3-a]quinoxaline

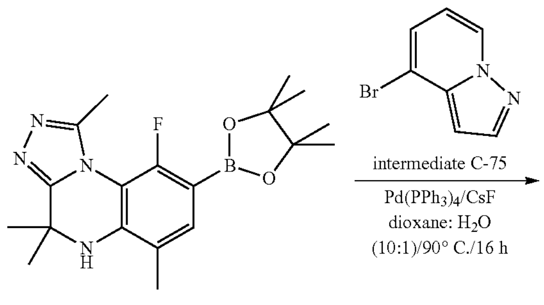

intermediate D-60

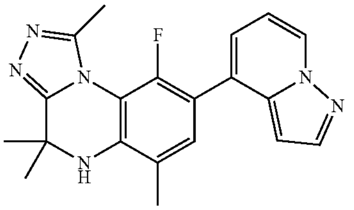

example 45

To a stirred solution of intermediate D-60 (0.48 g, 1.29 mmol, 1.2 eq.) in a dioxane:$H_2O$ (10:1) mixture (20 mL) were added CsF (0.49 g, 3.214 mmol, 3 eq.) and intermediate C-75 (0.21 g, 1.07 mmol, 1 eq.) in a sealed tube. The solution was degassed with argon for 20 min, followed by addition of $Pd(PPh_3)_4$ (0.062 g, 0.05 mmol, 0.05 eq.), and the reaction mixture was refluxed at 90° C. for 16 h. After completion (monitored by TLC), the reaction mixture was filtered through a celite bed. The filtrate was concentrated under reduced pressure to afford the crude material which was purified by column chromatography (5% MeOH/DCM), followed by prep. HPLC to afford compound 9-fluoro-1,4,4,6-tetramethyl-8-pyrazolo[1,5-a]pyridin-4-yl-5H-[1,2,4]triazolo[4,3-a]quinoxaline (0.17 g, 44%) as an off-white solid.

$^1$H NMR (400 MHz, DMSO-$d_6$): δ 8.72 (d, J=6.9 Hz, 1H), 8.04 (s, 1H), 7.29 (t, J=8.2 Hz, J=9.2 Hz, 2H), 6.99 (t, J=6.9 Hz, 1H), 6.56 (s, 1H), 6.6 (s, 1H), 2.53 (s, 3H), 2.29 (s, 3H), 1.56 (s, 6H).

The following examples were prepared in a similar manner (use of appropriate reagents and purification methods known to the person skilled in the art) as the synthesis described for example 45:

| Example Nr. | Structure | Intermediates | Yield % | Data |
|---|---|---|---|---|
| 48 | 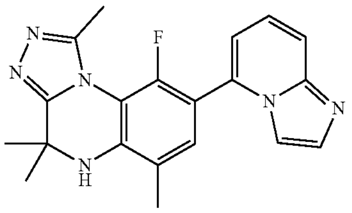 [SMILES: Cc1cc(-c2cccc3nccn23)c(F)c2c1NC(C)(C)c1nnc(C)n1-2] | 5-bromoimidazo[1,2-a]pyridine, D-60 | 41 | 1H NMR (600 MHz, DMSO) δ = 7.77 (d, 1H), 7.68-7.60 (m, 2H), 7.38-7.31 (m, 2H), 6.98 (d, 1H), 6.23 (d, 1H), 2.51 (d, 3H), 2.30 (s, 3H), 1.59 (s, 6H). |
| 62 | 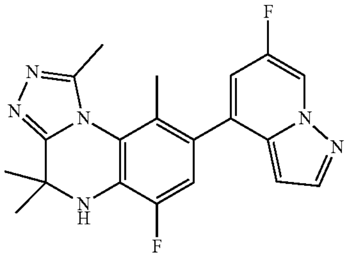 [SMILES: Cc1c(-c2cc(F)cn3nccc23)cc(F)c2c1-n1c(C)nnc1C(C)(C)N2] | C-76, D-7 | 33 | 1H NMR (400 MHz, DMSO) δ = 9.06 (dd, 1H), 8.06 (d, 1H), 7.53-7.45 (m, 1H), 7.31 (d, 1H), 6.65 (s, 1H), 6.46 (d, 1H), 2.08 (d, 3H), 1.52 (s, 6H). |
| 72 | 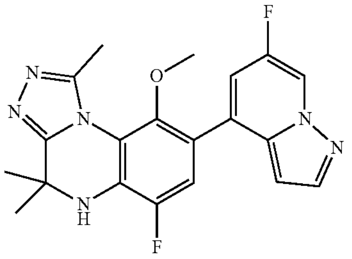 [SMILES: COc1c(-c2cc(F)cn3nccc23)cc(F)c2c1-n1c(C)nnc1C(C)(C)N2] | C-76, D-10 | 52 | 1H NMR (400 MHz, DMSO) δ = 9.09-9.01 (m, 1H), 8.05 (d, 1H), 7.49 (dd, 1H), 7.39 (d, 1H), 6.85 (s, 1H), 6.58 (d, 1H), 3.25 (s, 3H), 2.56 (s, 3H), 1.55 (s, 6H). |
| 91 | 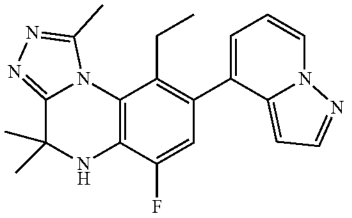 [SMILES: CCc1c(-c2cccn3nccc23)cc(F)c2c1-n1c(C)nnc1C(C)(C)N2] | C-75, D-9 | 94 | 1H NMR (400 MHz, DMSO) δ = 8.74 (d, 1H), 8.05 (d, 1H), 7.31 (d, 1H), 7.23 (d, 1H), 7.00 (t, 1H), 6.67 (s, 1H), 6.42 (s, 1H), 1.54 (s, 6H), 0.53 (t, 3H). |
| 116 | 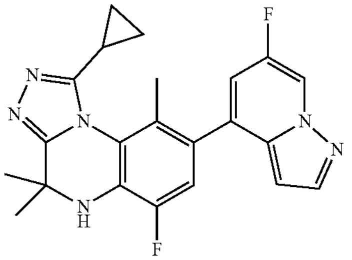 [SMILES: Cc1c(-c2cc(F)cn3nccc23)cc(F)c2c1-n1c(C3CC3)nnc1C(C)(C)N2] | C-76 | 44 | 1H NMR (400 MHz, DMSO) δ = 9.06 (dd, 1H), 8.04 (d, 1H), 7.52 (d, 1H), 7.32 (d, 1H), 6.64 (d, 1H), 6.45 (d, 1H), 2.24 (s, 3H), 1.95 (s, 1H), 1.51 (s, 6H), 1.11 (s, 4H). |

Example 73: 8-(5-fluoro-1H-indol-1-yl)-1,4,4,9-tetramethyl-5H-[1,2,4]triazolo[4,3-a]quinoxaline

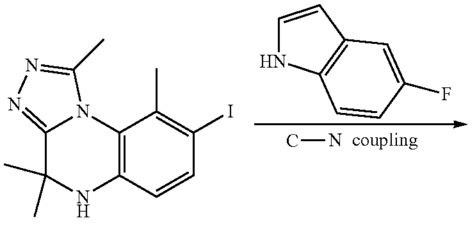

intermediate E-40

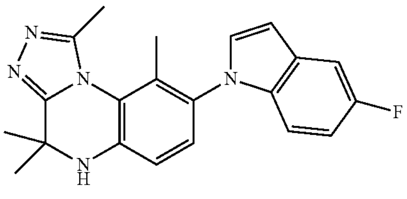

example 73

A stirred solution of intermediate E-40 (0.40 g, 1.129 mmol, 1.0 eq), 5-fluoro-1H-indole (0.158 g, 1.355 mmol, 1.2 eq), $K_3PO_4$ (0.467 g, 3.387 mmol, 3.0 eq) in 1,4 dioxane (20 mL) was degassed with argon for 30 mii. N,N'-Dimethylethylenediamine (0.080 g, 0.564 mmol, 0.5 eq) and CuI (0.107 g, 0.564 mmol, 0.5 eq) were added and the reaction was stirred for 16 h at 90° C. in a sealed tube. After completion (monitored by TLC), the reaction mixture was filtered through a celite bed and washed 3 times with dioxane. The combined organic layers were concentrated to afford the crude product which was purified by column chromatography (230-400 mesh silica gel; 0 to 2% MeOH in DCM) and again purified by prep. HPLC to yield 8-(5-Fluoro-1H-indol-1-yl)-1,4,4,9-tetramethyl-5H-[1,2,4]triazolo[4,3-a]quinoxaline (0.0298 g, 7%).

1H NMR (400 MHz, dmso-d6): δ 7.61 (s, 11H), 7.41-7.44 (m, 11H), 7.24 (d, J=8.4 Hz, 11H), 7.00-7.07 (m, 3H), 6.66-6.72 (m, 2H), 1.89 (s, 3H), 1.45-1.49 (in, 6H).

The following examples were prepared in a similar manner (use of appropriate reagents and purification methods known to the person skilled in the art) as the synthesis described for example 73:

| Example Nr. | Structure | Intermediates | Yield % | Data |
|---|---|---|---|---|
| 89 | 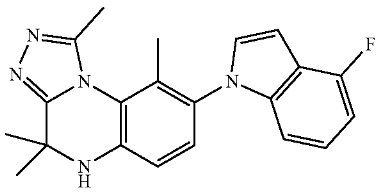 [SMILES: Cc1c(-n2ccc3c(F)cccc32)ccc2c1-n1c(C)nnc1C(C)(C)N2] | 4-fluoro-1H-indole, E-40 | 6 | 1H NMR (400 MHz, DMSO) δ = 7.59 (s, 1H), 7.25 (d, 1H), 7.15 (d, 1H), 7.02 (d, 1H), 6.97-6.84 (m, 2H), 6.78-6.70 (m, 2H), 2.47 (s, 3H), 1.89 (s, 3H), 1.50 (s, 3H), 1.45 (s, 3H). |
| 93 | 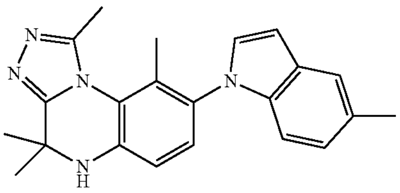 | 5-methyl-1H-indole, E-40 | 6 | 1H NMR (400 MHz, DMSO) δ = 7.49-7.40 (m, 2H), 7.21 (d, 1H), 7.05-6.93 (m, 3H), 6.69 (s, 1H), 6.56 (d, 1H), 2.47 (s, 3H), 2.40 (s, 3H), 1.89 (s, 3H), 1.48 (d, 6H). |
| 95 | 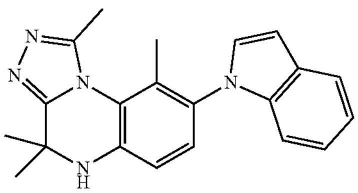 [SMILES: Cc1c(-n2ccc3ccccc32)ccc2c1-n1c(C)nnc1C(C)(C)N2] | indole, E-40 | 5 | 1H NMR (400 MHz, DMSO) δ = 7.66 (d, 1H), 7.52 (d, 1H), 7.23 (d, 1H), 7.21-7.12 (m, 1H), 7.15-7.04 (m, 2H), 7.02 (d, 1H), 6.71 (s, 1H), 6.67 (d, 1H), 2.47 (s, 3H), 1.90 (s, 3H), 1.48 (d, 6H). |
| 120 | 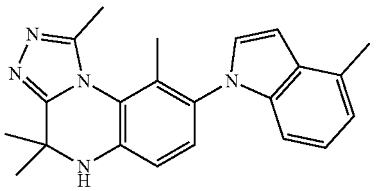 | 4-methyl-1H-indole, E-40 | 7 | 1H NMR (400 MHz, DMSO) δ = 7.49 (d, 1H), 7.21 (d, 1H), 7.11-6.97 (m, 2H), 6.94-6.86 (m, 2H), 6.73-6.65 (m, 2H), 2.53 (s, 3H), 2.47 (s, 3H), 1.90 (s, 3H), 1.48 (d, 6H). |

Example 81: 9-(Difluoro-methyl)-6-fluoro-1,4,4-trimethyl-8-pyrazolo[1,5-a]pyridin-4-yl-5H-[1,2,4]triazolo[4,3-a]quinoxaline

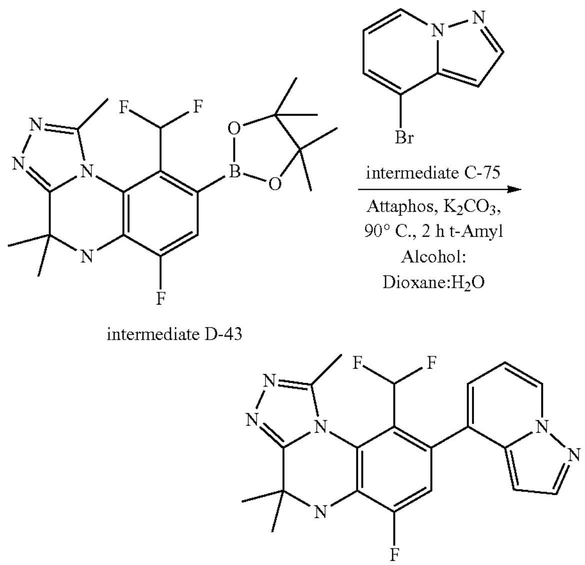

intermediate D-43 example 81

To a solution of intermediate C-75 (0.1 g, 0.510 mmol, 1.0 eq) in a t-amyl alcohol:dioxane:$H_2O$ (3:2:1) mixture (30 mL), $K_2CO_3$ (0.211 g, 1.53 mmol, 3 eq) was added at RT. The solution was degassed with argon for 20 min, followed by addition of intermediate D-43 (0.249 g, 0.612 mmol, 1.2 eq) and Attaphos (0.020 g, 0.0277 mmol, 0.05 eq). The reaction mixture was then heated at 90° C. for 2 h. After completion (monitored by TLC & LCMS), the reaction mixture was diluted with water and extracted with EtOAc. The organic layer was washed with brine, dried over $Na_2SO_4$, filtered and evaporated under reduced pressure. The crude residue was purified by column chromatography (MeOH-DCM), followed by a second column chromatography (acetone-hexane). The product was then washed with ether to afford 9-(difluoro-methyl)-6-fluoro-1,4,4-trimethyl-8-pyrazolo[1,5-a]pyridin-4-yl-5H-[1,2,4]triazolo[4,3-a]quinoxaline (0.09 g, 40%) as a white solid.

1H NMR (400 MHz, dmso-d6): δ 8.72 (d, J=6.8 Hz, 1H), 7.99-7.98 (m, 1H), 7.39-7.36 (m, 1H), 7.24-7.22 (m, 1H), 7.08-6.95 (m, 3H), 6.34 (s, 1H), 1.54-1.52 (m, 6H Example 87: 1-Ethyl-7,9-difluoro-4,4-dimethyl-8-[(3-pyridin-3-yl-pyrrolidin-1-yl)-methyl]-5H-[1,2,4]triazolo[4,3-a]quinoxaline

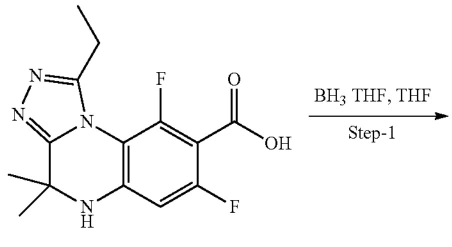

intermediate F-1

-continued

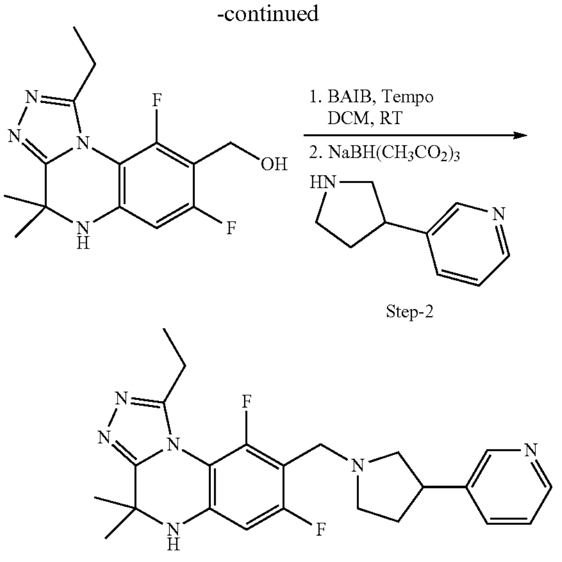

example 87

Step 1: A suspension of 1-ethyl-7,9-difluoro-4,4-dimethyl-5H-[1,2,4]triazolo[4,3-a]quinoxaline-8-carboxylic acid (2.5 g, 8.1 mmol, 1 eq) in THF (2.2 mL) is cooled to 0° C. and stirred under nitrogen atmosphere. Borane THF (25 mL, 24.8956 mmol, 3 eq) is slowly added dropwise at 0° C., and the reaction is allowed to slowly warm to ambient temperature and stirred at RT. After completion, the reaction is cooled to 0° C. and ethanol is added. After evaporation, the reaction mixture is extracted with DCM. The organic layer is washed with brine, dried over magnesium sulfate and evaporated under reduced pressure. The crude residue is purified by column chromatography to afford (1-ethyl-7,9-difluoro-4,4-dimethyl-5H-[1,2,4]triazolo[4,3-a]quinoxalin-8-yl)methanol (1.2 g, 50%).

Step 2: To a solution of (1-ethyl-7,9-difluoro-4,4-dimethyl-5H-[1,2,4]triazolo[4,3-a]quinoxalin-8-yl)methanol (65 mg, 0.2209 mmol, 1 eq) in dichloromethane (0.9 mL) were added [bis[acetoxy)-iodo]benzene (82 mg, 0.254 mmol, 1.15 eq) and Tempo (7 mg, 0.0442 mmol, 0.2 eq), and the solution was stirred at RT for 5 h. More BAIB (1.5 eq) was added, and the reaction was stirred at ambient temperature overnight. Then, 3-pyrrolidin-3-ylpyridine (65.5 mg, 0.4417 mmol, 2 eq) and natriumtriacetoxyborohydride (94 mg, 0.4417 mmol, 2 eq) were added and the reaction was stirred at RT overnight After completion (followed by LCMS), 10 mL of a 1M NaOH solution was added and the compound was extracted with EtOAc (2×). The combined organic layers were washed with brine, dried over magnesium sulfate, and evaporated under reduced pressure. The crude residue was purified by prep. HPLC to afford 1-ethyl-7,9-difluoro-4,4-dimethyl-8-[(3-pyridin-3-yl-pyrrolidin-1-yl)-methyl]-5H-[1,2,4]triazolo[4,3-a]quinoxaline (9 mg, 10%).

1H NMR (600 MHz, DMSO) δ=8.48 (d, 1H), 8.39 (dd, 1H), 7.69 (dt, 1H), 7.30 (dd, 1H), 7.01 (s, 1H), 6.67 (d, 1H), 3.74 (s, 2H), 3.34 (d, 1H), 2.97 (t, 1H), 2.89 (td, 2H), 2.74 (dd, 2H), 2.53 (s, 1H), 2.28 (dddd, 1H), 1.75 (ddt, 1H), 1.47 (d, 6H), 1.22 (t, 3H).

Example 97: 9-(Difluoro-methyl)-7-fluoro-8-(7-fluoro-1H-indol-3-yl)-1,4,4-trimethyl-5H-[1,2,4]triazolo[4,3-a]quinoxaline

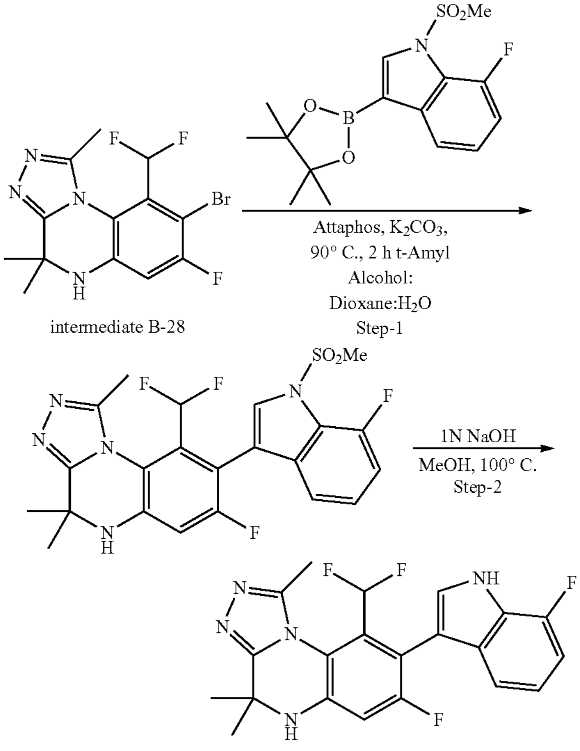

intermediate B-28 example 97

Step 1: To a solution of intermediate B-29 (0.3 g, 0.833 mmol, 1.0 eq) in a t-amyl alcohol:dioxane:$H_2O$ (3:2:1) mixture (30 mL), $K_2CO_3$ (0.345 g, 2.49 mmol, 3 eq) was added at RT. The solution was degassed with argon for 20 min, followed by addition of intermediate A-78 (0.423 g, 1.24 mmol, 1.5 eq) and Attaphos (0.030 g, 0.0416 mmol, 0.05 eq). The reaction mixture was then heated at 90° C. for 2 h. After (monitored by TLC & LCMS), the reaction mixture was diluted with water (100 mL) and extracted with ethyl acetate (2×250 mL). The organic layer was washed with brine (75 mL), dried over $Na_2SO_4$, filtered and evaporated under reduced pressure. The crude residue was purified by column chromatography (MeOH-DCM) to afford 3-[9-(difluoromethyl)-7-fluoro-1,4,4-trimethyl-4H,5H-[1,2,4]triazolo[4,3-a]quinoxalin-8-yl]-7-fluoro-1-methanesulfonyl-1H-indole (0.3 g, 72.98%) as a white solid.

Step 2: To a stirred solution of 3-[9-(difluoromethyl)-7-fluoro-1,4,4-trimethyl-4H,5H-[1,2,4]triazolo[4,3-a]quinoxalin-8-yl]-7-fluoro-1-methanesulfonyl-1H-indole (0.3 g, 0.608 mmol, 1.0 eq) in MeOH (20 mL) was added 1 N NaOH solution (10 mL) and the reaction mixture was stirred at 100° C. for. After completion (monitored by TLC), the reaction mixture was concentrated and acidified with 2N HCl solution to get a solid, filtered and washed with diethyl ether to get the crude product which was purified by prep. HPLC to afford 4-{6,7-difluoro-1,4,4,9-tetramethyl-4H,5H-[1,2,4]triazolo[4,3-a]quinoxalin-8-yl}-1-(ethanesulfonyl)-6-fluoro-1H-indole (0.03 g, 11.95%)

1H NMR (400 MHz, dmso-d6, 100° C.): δ 11.62 (s, 1H), 7.45 (s, 1H), 7.05-7.08 (m, 2H), 6.91-6.99 (m, 2H), 6.81-6.86 (m, 1H), 6.67 (s, 1H), 1.53 (s, 6H).

The following examples were prepared in a similar manner (use of appropriate reagents and purification methods known to the person skilled in the art) as the synthesis described for example 97:

| Example Nr. | Structure | Inter-mediates | Yield % | Data |
|---|---|---|---|---|
| 96 | 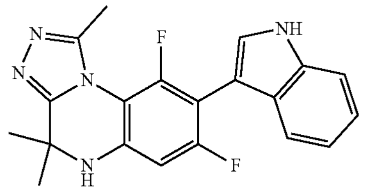 [SMILES: Cc1nnc2n1-c1c(cc(F)c(-c3c[nH]c4ccccc34)c1F)NC2(C)C] | 1-(methylsulfonyl)-3-(4,4,5,5-tetramethyl-1,3,2-dioxaborolan-2-yl)-1H-indole, B-1 | | 1H NMR (600 MHz, DMSO) δ = 7.56 (d, 1H), 7.53-7.41 (m, 2H), 7.17 (ddd, 1H), 7.07 (ddd, 1H), 6.81 (dd, 1H), 2.56 (d, 3H), 1.53 (s, 6H). |
| 107 | 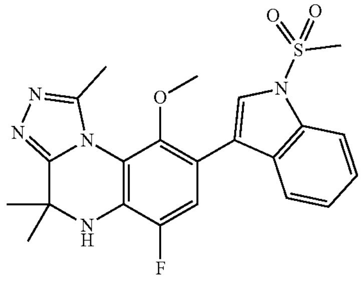 [SMILES: COc1c(-c2cn(S(C)(=O)=O)c3ccccc23)cc(F)c2c1-n1c(C)nnc1C(C)(C)N2] | 1-(methylsulfonyl)-3-(4,4,5,5-tetramethyl-1,3,2-dioxaborolan-2-yl)-1H-indole, B-10 | 30 | 1H NMR (400 MHz, DMSO) δ = 7.93 (d, 1H), 7.80 (s, 1H), 7.73 (d, 1H), 7.50-7.33 (m, 3H), 6.71 (s, 1H), 3.49 (s, 3H), 3.28 (s, 3H), 2.61 (s, 3H), 1.55 (s, 6H). |

Example 100: 7,9-Difluoro-8-(5-fluoro-spiro[1,2-dihydro-indole-3,1'-cyclopropane]-7-yl)-1,4,4-trimethyl-5H-[1,2,4]triazolo[4,3-a]quinoxaline

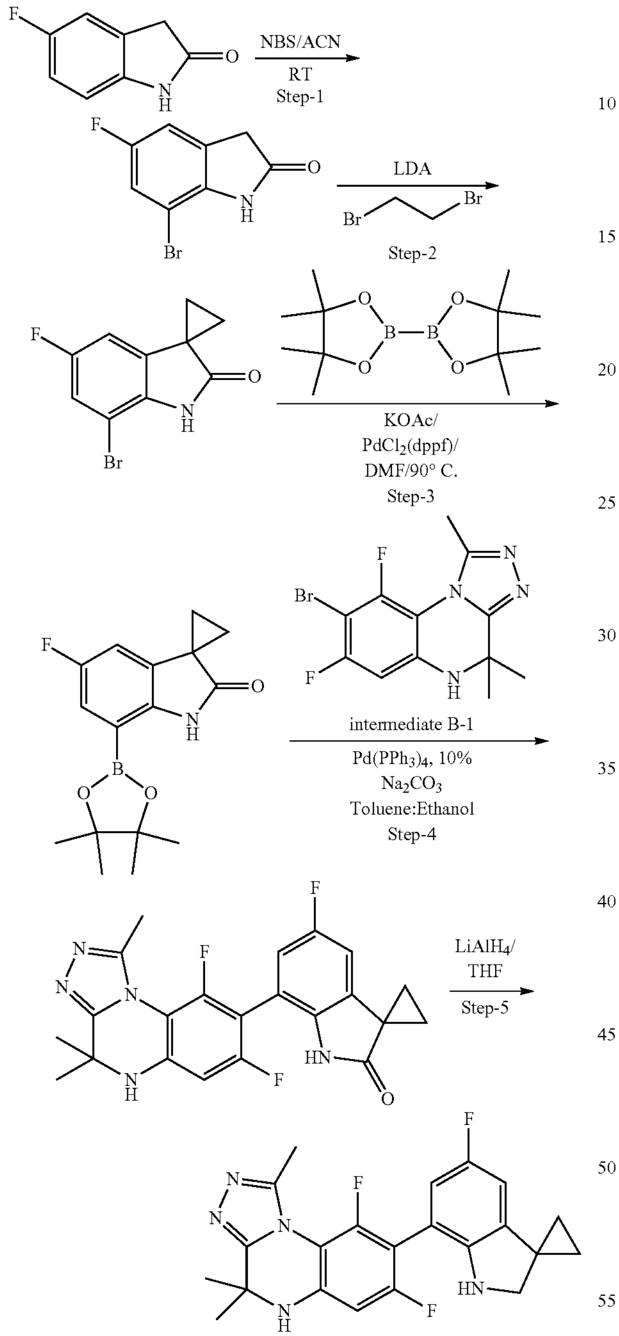

example 100

Step 1: To a stirred solution of 5-fluoroindolin-2-one (5.0 g, 33.11 mmol, 1 eq) in acetonitrile was added N-bromosuccinimide (5.8 g, 33.11 mmol, 1 eq) and the reaction mixture was stirred at RT for 48 h. After completion (monitored by TLC), the white precipitate was filtered to get the crude material, which was washed with pentane to afford 7-bromo-5-fluoro-2,3-dihydro-1H-indol-2-one (4.7 g, 67%) as a white solid.

Step 2: To a solution of DIPA (1.94 mL, 13.91 mmol, 3.2 eq) in THF (20 mL) was slowly added n-BuLi (7.0 mL, 13.91 mmol, 3.2 eq) at −78° C. and the reaction mixture was stirred for 30 min. 7-Bromo-5-fluoro-2,3-dihydro-1H-indol-2-one (1.0 g, 4.35 mmol, 1 eq) in THF (10 mL) was added at −78° C., the reaction mixture was stirred at −78° C. for 1 h and subsequently at room temperature. Then the reaction was again cooled to −78° C. and 1,2-dibromoethane (0.376 mL, 4.35 mmol, 1 eq) was added. The reaction mixture was allowed to warm to RT over 2 h and stirred at RT for 16 h. After completion (monitored by TLC), the reaction mixture was quenched with $NH_4Cl$ (50 mL) and extracted with ethyl acetate (3×50 mL). The combined organic layers were washed with water (50 mL) and brine (50 mL), dried over anhydrous $Na_2SO_4$ and evaporated under reduced pressure. The crude residue was purified by column chromatography (100-200 mesh silica gel; 30% EtOAc-Hex) to afford 7'-bromo-5'-fluoro-1',2'-dihydrospiro[cyclopropane-1,3'-indole]-2'-one (0.320 g, 29%) as an off-white solid.

Step 3: To a solution of 7'-bromo-5'-fluoro-1',2'-dihydrospiro[cyclopropane-1,3'-indole]-2'-one (0.2 g, 0.649 mmol, 1 eq) in dioxane were added KOAc (0.127 g, 1.298 mmol, 2 eq) and Bispincolatediborane (0.328 g, 1.298 mmol, 2 eq). The solution was degassed with argon for 20 min, followed by addition of $PdCl_2$(dppf)·DCM (0.026 g, 0.032 mmol, 0.05 eq) The reaction mixture was refluxed for 16 h. After completion (monitored by TLC), the reaction mixture was diluted with water (50 mL) and extracted with ethyl acetate (3×50 mL). The combined organic layers were washed with water (50 mL) and brine (50 mL), dried over anhydrous $Na_2SO_4$ and evaporated under reduced pressure. The crude residue was purified by column chromatography (100-200 mesh silica gel; 20% EtOAc-Hex) to afford 5'-fluoro-7'-(tetramethyl-1,3,2-dioxaborolan-2-yl)-1',2'-dihydrospiro[cyclopropane-1,3'-indole]-2'-one (0.085 g, 36%) as a brown solid.

Step 4: To a solution of 5'-fluoro-7'-(tetramethyl-1,3,2-dioxaborolan-2-yl)-1',2'-dihydrospiro[cyclopropane-1,3'-indole]-2'-one (0.085 g, 0.280 mmol, 1 eq) in a toluene:ethanol (2:1) mixture (10 mL), intermediate B-1 (0.116 g, 0.42 mmol, 1.5 eq) and 10% $Na_2CO_3$ (0.2 mL) were added at RT. After degassing the reaction mixture with argon, Pd $(PPh_3)_4$ (0.016 g, 0.014 mmol, 0.05 eq) was added and the reaction mixture heated at 110° C. for 16 h. After completion (monitored by TLC), the reaction mixture was filtered through a pad of celite and evaporated. The crude residue was purified by column chromatography (230-400 mesh silica gel; 6% MeOH:DCM) to afford 7'-{7,9-difluoro-1,4,4-trimethyl-4H,5H-[1,2,4]triazolo[4,3-a]quinoxalin-8-yl}-5'-fluoro-1',2'-dihydrospiro[cyclopropane-1,3'-indole]-2'-one (0.070 g, 59%) as a white solid.

Step 5: To a THF (20 mL) solution of $LiAlH_4$ (0.55 g, 14.62 mmol, 12.5 eq) was added a solution of 7'-{7,9-difluoro-1,4,4-trimethyl-4H,5H-[1,2,4]triazolo[4,3-a]quinoxalin-8-yl}-5'-fluoro-1',2'-dihydrospiro[cyclopropane-1,3'-indole]-2'-one (0.5 g, 1.17 mmol, 1 eq) in THF (4 mlL at 0° C. Then, the reaction mixture was stirred for 4 h at 90° C. After completion (monitored by TLC), the reaction mixture was cooled to RT and quenched with aq $Na_2SO_4$ (10 mL) and extracted with ethyl acetate (3×50 mL). The combined organic layers were washed with water (50 mL) and brine (50 mL), dried over anhydrous $Na_2SO_4$ and evaporated under reduced pressure. The crude residue was purified by column chromatography (230-400 mesh silica gel; 3% MeOH:DCM) and further by prep. HPLC to obtain 7,9-Difluoro-8-(5-fluoro-spiro[1,2-dihydro-indole-3,1'-cyclopropane]-7-yl)-1,4,4-trimethyl-5H-[1,2,4]triazolo[4,3-a]quinoxaline (0.2 g, 41%) as an off-white solid.

$^1$H NMR (400 MHz, DMSO-$d_6$): δ 7.10 (s, 1H), 6.71 (s, 2H), 6.56 (s, 1H), 3.48 (s, 2H), 1.65 (s, 3H), 1.51 (s, 6H), 0.98 (d, J=12.0 Hz, 4H).

The following examples were prepared in a similar manner (use of appropriate reagents and purification methods known to the person skilled in the art) as the synthesis described for example 100:

| Example Nr. | Structure | Inter-mediates | Yield % | Data |
|---|---|---|---|---|
| 109 | 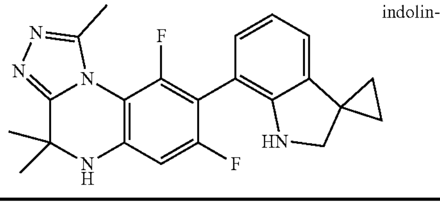 | indolin-2-one, B-1 | 45 | 1H NMR (600 MHz, DMSO) δ = 7.05 (d, 1H), 6.85 (d, 1H), 6.77-6.71 (m, 1H), 6.60 (dd, 1H), 6.56 (t, 1H), 5.48 (s, 1H), 3.49 (t, 2H), 2.56-2.44 (m, 3H), 1.59-1.45 (m, 6H), 1.03-0.87 (m, 4H). |

Example 110: 4-(7,9-Difluoro-1,4,4-trimethyl-5H-[1,2,4]triazolo[4,3-a]quinoxalin-8-yl)-6-fluoro-benzothiazole

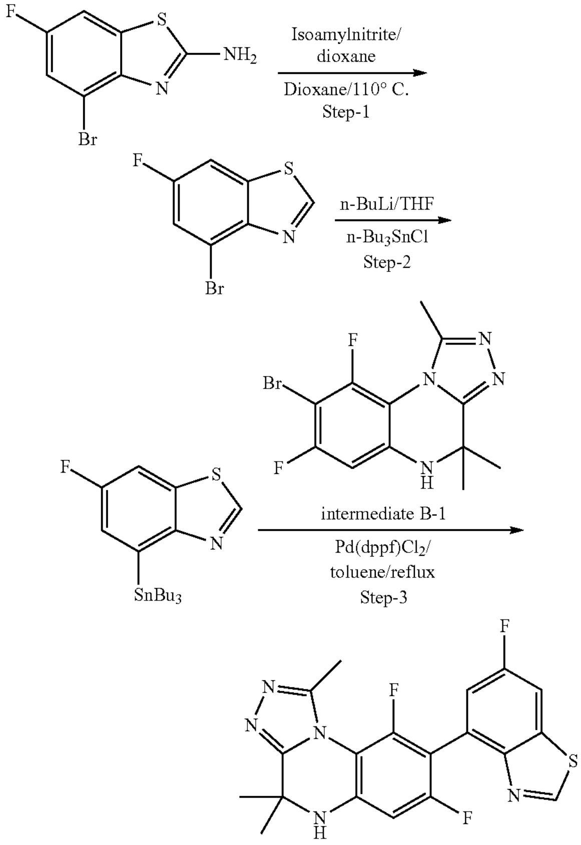

example 110

Step 1: To a solution of 4-bromo-6-fluorobenzo[d]thiazol-2-amine (1 g, 4.046 mmol, 1 eq) in dioxane (30 mL), isoamyl nitrite (1.63 mL, 12.14 mmol, 3 eq) was added at RT, and the reaction mixture was refluxed for 2 h. After completion (monitored by TLC), the reaction mixture was evaporated under reduced pressure and the crude was purified by column chromatography to afford 4-bromo-6-fluoro-1,3-benzothiazole (0.6 g) as a brown gum.

Step 2: To a solution of 4-bromo-6-fluoro-1,3-benzothiazole (0.4 g, 1.724 mmol, 1 eq) in THF (10 mL), n-BuLi (1.9 M, 1.08 ml, 2.06 mmol, 1.2 eq) was added at −78° C. dropwise. After stirring the reaction mixture at the same temperature, n-$Bu_3SnCl$ (0.56 ml, 2.06 mmol, 1.2 eq) was added and the mixture was allowed to slowly come to RT. After completion (monitored by TLC), the reaction mixture was quenched with $NH_4Cl$ solution and extracted with EtOAc. The organic layer was washed with water and brine, dried over $Na_2SO_4$, filtered and evaporated under reduced pressure to get crude 6-fluoro-4-(tributylstannyl)-1,3-benzothiazole (0.15 g, 78.7%) which was used for the next step without further purification.

Step 3: To a solution of intermediate B-1 (0.5 g, 1.519 mmol, 1 eq) in DMF (10 mL) were added LiCl (0.193 g, 4.557 mmol, 3 eq) and 6-fluoro-4-(tributylstannyl)-1,3-benzothiazole (0.806 g, 1.823 mmol, 1.2 eq) in a sealed tube. The solution was degassed with argon for 20 min, followed by addition of $Pd(PPh_3)_4$ (0.175 g, 0.151 mmol, 0.1 eq) The reaction mixture was stirred at 110° C. for 16 h. After completion (monitored by LCMS), reaction mixture was evaporated to dryness and the residue was diluted with ethyl acetate (50 mL). The organic layer was washed with water (2×30 mL) and brine (30 mL), dried over anhydrous $Na_2SO_4$ and evaporated under reduced pressure. The crude residue was purified by column chromatography (230-400 silica gel; 5% MeOH/DCM) to afford 4-(7,9-Difluoro-1,4,4-trimethyl-5H-[1,2,4]triazolo[4,3-a]quinoxalin-8-yl)-6-fluoro-benzothiazole (0.04 g, 6.5%) as an off-white solid.

$^1$H NMR (400 MHz, DMSO-$d_6$): δ 9.37 (s, 1H), 8.21 (d, J=10.4 Hz, 1H), 7.62 (d, J=8.8 Hz, 1H), 7.27 (s, 1H), 6.80 (d, J=11.2 Hz, 1H), 1.51-1.54 (m, 6H).

Example 122: 7,9-Difluoro-N-[(3-methoxyphenyl)-methyl]-1,4,4-trimethyl-5H-[1,2,4]triazolo[4,3-a]quinoxaline-8-carboxylic acid amide

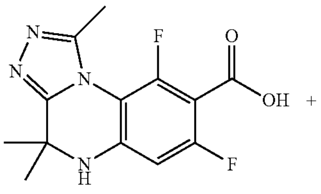

-continued

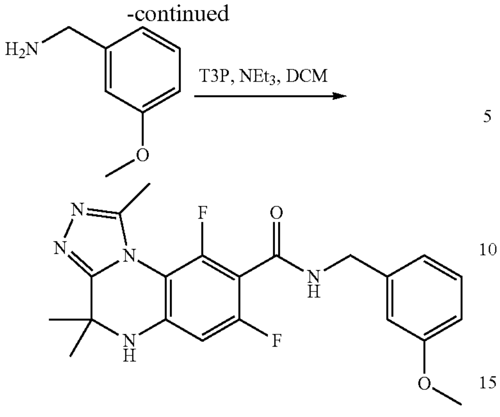

example 122

To a solution of 7,9-difluoro-1,4,4-trimethyl-4,5-dihydro-[1,2,4]triazolo[4,3-a]quinoxaline-8-carboxylic acid (40 mg, 0.136 mmol, 1 eq), 3-methoxybenzylamine (0.052 mL, 0.408 mmol, 3 eq) and triethylamine (0.094 mL, 0.68 mmol, 5 eq) in DCM (2.75 mL) was added T3P (50% in EtOAc, 0.16 mL, 0.272 mmol, 2 eq) and the reaction mixture was stirred at RT overnight. After completion, 1M Na2CO3 solution (40 mL) was added and the reaction was stirred for 1 h at RT. The aqueous phase was then extracted with DCM (3×) and the combined organic layers were dried over sodium sulfate and evaporated under reduced pressure. The crude material was purified by column chromatography to yield 7,9-Difluoro-N-[(3-methoxyphenyl)-methyl]-1,4,4-trimethyl-5H-[1,2,4]triazolo[4,3-a]quinoxaline-8-carboxylic acid amide.

1H NMR (600 MHz, DMSO) δ=9.13 (s, 1H), 7.30-7.22 (m, 2H), 6.91 (dd, 2H), 6.83 (dt, 1H), 6.70 (dd, 1H), 4.46 (d, 2H), 3.75 (s, 3H), 2.54 (d, 3H), 1.49 (s, 6H).

Biological Assays

Agonistic Mode of Action on the Glucocorticoid Receptor

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of ligand-induced activation of the GR and therefore for the identification of compounds with agonistic properties. The GAL4/UAS reporter was premixed with a vector that constitutively expressed *Renilla* luciferase, which served as an internal positive control for transfection efficiency.

The complete culture medium for the assay was:

DMEM F-12 (1:1) MIXTURE (LONZA cat. No: BE04-687F/U1) 500 mL 5 mL of 100 mM Sodium Pyruvate (LONZA cat. No: BE12-115E)

25 mL of 7.5% Sodium Bicarbonate (LONZA cat. No BE17-613E)

6.5 mL of 1 M Hepes (LONZA cat. No: BE17-737E)

5 mL of 100× Penicillin/Streptomycin (LONZA cat. No DE17-602E)

50 mL of Fetal Bovine Serum (Euroclone cat. No ECS 0180L)

0.25 mL of 10 mg/mL Puromycin (InvivoGen cat.: ant-pr-1)

0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 30 µl Opti-MEM (GIBCO, cat. #31985062) as assay buffer. To test the compounds an 8-point half-log compound dilution curve was generated in 100% DMSO starting from a 2 mM stock and compounds were then diluted 1:50 in Opti-MEM. 10 µl of compounds were then added to the wells containing 30 µl Opti-MEM resulting in a final assay concentration range from 10 µM to 0.003 µM in 0.5% DMSO. Compounds were tested at 8 concentrations in quadruplicate data points. Cells were incubated for 6 hour with compounds and beclometasone (Sigma, cat. #Y0000351) as control compound at 37° C., 5% $CO_2$ and 95% humidity in a total volume of 40 µl. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the agonist beclometasone:

$$\%\ \text{effect}=((\text{compound}-\text{min})/(\text{max}-\text{min}))\times 100$$

[min=Opti-MEM only, max=beclometasone]

To calculate $EC_{50}$, max, min and slope factor for each compound a concentration response curve was fitted by plotting % effect versus compound concentration using a 4 parameter logistic equation:

$$y=A+(B-A)/(1+((10C)/x)D)$$

[A=min y, B=max y, C=log $EC_{50}$, D=slope]

Antagonistic Mode of Action on the Glucocorticoid Receptor

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of antagonistic properties of compounds by measuring the ligand-induced inhibition of beclometasone-activated GR. The GAL4/UAS reporter was premixed with a vector that constitutively expressed *Renilla* luciferase, which served as an internal positive control for transfection efficiency.

The complete culture medium for the assay was:

DMEM F-12 (1:1) MIXTURE (LONZA cat. No: BE04-687F/U1) 500 mL 5 mL of 100 mM Sodium Pyruvate (LONZA cat. No: BE12-115E)

25 mL of 7.5% Sodium Bicarbonate (LONZA cat. No BE17-613E)

6.5 mL of 1 M Hepes (LONZA cat. No: BE17-737E)

5 mL of 100× Penicillin/Streptomycin (LONZA cat. No DE17-602E)

50 mL of Fetal Bovine Serum (Euroclone cat. No ECS 0180L)

0.25 mL of 10 mg/mL Puromycin (InvivoGen cat.: ant-pr-1)

0.5 mL of 100 mg/mL Zeocin (InvivoGen cat.: ant-zn-1)

Cryo-preserved CHO-Gal4/GR cells were suspended in complete medium and 5000 cells/25 μl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 20 μl Opti-MEM (GIBCO, cat. #31985062) as assay buffer. For testing compounds an 8-point half-log compound dilution curve was generated in 100% DMSO starting from a 2 mM stock and compounds were then diluted 1:50 in Opti-MEM. To test the compounds in the antagonist mode 10 μl of compounds were then added to the wells containing 20 μl Opti-MEM and incubated for 10 min. After this pre-incubation 10 μl of the reference agonist beclometasone (Sigma, cat. #Y0000351) at an EC50 of 2.5 nM were added resulting in a final assay concentration range from 10 μM to 0.003 μM in 0.5% DMSO in a total volume of 40 μl. Compounds were tested at 8 concentrations in quadruplicate data points. Cells were incubated for 6 hour with compounds and mifepristone as control compound (Sigma, cat. #M8046) at 37° C., 5% $CO_2$ and 95% humidity. Finally, cells were lysed with 20 μl of Triton/Luciferin solution and the signal of the emitted luminescence was recorded at the FLIPR$^{TETRA}$ for 2 minutes.

The relative efficacy of a compound (% effect) was calculated based on the full effect of the antagonist mifepristone:

$$\%\ \text{effect}=((\text{compound}-\text{min})/(\text{max}-\text{min}))\times-100$$

[min=Opti-MEM only, max=mifepristone]

To calculate $IC_{50}$, max, min and slope factor for each compound a concentration response curve was fitted by plotting % effect versus compound concentration using a 4 parameter logistic equation:

$$y=A+(B-A)/(1+((10C)/x)D)$$

[A=min y, B=max y, C=log $IC_{50}$, D=slope]

In Table 4 below, the IC50 or EC50 ranges of the Examples are summarized which were observed in the agonistic assay or the antagonistic assay described above.

TABLE 4

(A < 100 nM, B = 100 nM-1 μM, C = 1 μM-15μM):

| Ex.# | $IC_{50}$ or $EC_{50}$ |
|---|---|
| 1 | A |
| 2 | A |
| 3 | A |
| 4 | B |
| 5 | B |
| 6 | B |
| 7 | C |
| 8 | B |
| 9 | B |
| 10 | A |
| 11 | B |

TABLE 4-continued (A < 100 nM, B = 100 nM-1 μM, C = 1 μM-15μM):

| Ex.# | $IC_{50}$ or $EC_{50}$ |
|---|---|
| 12 | B |
| 13 | A |
| 14 | A |
| 15 | A |
| 16 | B |
| 17 | B |
| 18 | B |
| 19 | A |
| 20 | A |
| 21 | A |
| 22 | B |
| 23 | B |
| 24 | B |
| 25 | C |
| 26 | B |
| 27 | A |
| 28 | A |
| 29 | B |
| 30 | B |
| 31 | C |
| 32 | C |
| 33 | A |
| 34 | A |
| 35 | A |
| 36 | A |
| 37 | A |
| 38 | A |
| 39 | A |
| 40 | B |
| 41 | B |
| 42 | B |
| 43 | B |
| 44 | B |
| 45 | B |
| 46 | B |
| 47 | B |
| 48 | C |
| 49 | A |
| 50 | A |
| 51 | B |
| 52 | B |
| 53 | A |
| 54 | B |
| 55 | B |
| 56 | C |
| 57 | C |
| 58 | C |
| 59 | B |
| 60 | B |
| 61 | C |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | B |
| 78 | B |
| 79 | B |
| 80 | B |
| 81 | B |
| 82 | B |
| 83 | B |
| 84 | B |
| 85 | B |
| 86 | B |
| 87 | B |

TABLE 4-continued

| (A < 100 nM, B = 100 nM-1 μM, C = 1 μM-15μM): | |
|---|---|
| Ex.# | $IC_{50}$ or $EC_{50}$ |
| 88 | B |
| 89 | B |
| 90 | B |
| 91 | B |
| 92 | B |
| 93 | B |
| 94 | B |
| 95 | B |
| 96 | B |
| 97 | B |
| 98 | B |
| 99 | C |
| 100 | C |
| 101 | C |
| 102 | C |
| 103 | C |
| 104 | C |
| 105 | C |
| 106 | C |
| 107 | C |
| 108 | C |
| 109 | C |
| 110 | C |
| 111 | C |
| 112 | C |
| 113 | C |
| 114 | C |
| 115 | C |
| 116 | C |
| 117 | C |
| 118 | C |
| 119 | C |
| 120 | C |
| 121 | B |
| 122 | B |

The invention claimed is:

1. A compound according to the following formula:

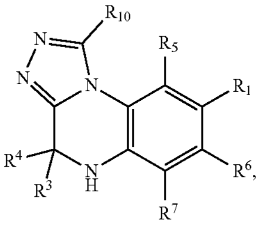

or a physiologically acceptable salt or stereoisomer thereof, wherein:

$R^1$ is C(O)NH—$C_{1-6}$ alkylene-aryl, $C_{3-10}$ cycloalkyl, 3- to 7-membered heterocycloalkyl, aryl, or 5- to 10-membered heteroaryl, wherein the $C_{1-6}$ alkylene is linear or branched and is saturated or unsaturated;

$R^3$ is H or $C_{1-10}$ alkyl, wherein the $C_{1-10}$ alkyl is linear or branched and is saturated or unsaturated;

$R^4$ is H or $C_{1-10}$ alkyl, wherein the $C_{1-10}$ alkyl is linear or branched and is saturated or unsaturated;

$R^5$ is F, Cl, Br, I, $C_{1-10}$ alkyl, $OC_{1-10}$ alkyl, or $C_{3-10}$ cycloalkyl, wherein each $C_{1-10}$ alkyl is independently linear or branched and is independently saturated or unsaturated;

$R^6$ is H, F, Cl, Br, I, $C_{1-10}$ alkyl, $OC_{1-10}$ alkyl, or $C_{3-10}$ cycloalkyl, wherein each $C_{1-10}$ alkyl is independently linear or branched and is independently saturated or unsaturated;

$R^7$ is H, F, Cl, Br, I, OH, $C_{1-10}$ alkyl, $SC_{1-10}$ alkyl, or $C_{3-10}$ cycloalkyl, wherein each $C_{1-10}$ alkyl is independently linear or branched and is independently saturated or unsaturated;

or $R^6$ and $R^7$, taken together with the carbon atoms to which they are attached, form a $C_{3-10}$ cycloalkyl or 3- to 7-membered heterocycloalkyl; and $R^{10}$ is $C_{1-10}$ alkyl or $C_{3-10}$ cycloalkyl, wherein the $C_{1-10}$ alkyl is linear or branched and is saturated or unsaturated;

wherein each $C_{1-10}$ alkyl, $C_{1-6}$ alkylene, $C_{3-10}$ cycloalkyl, and 3- to 7-membered heterocycloalkyl is optionally and independently substituted with one or more substituents independently selected from the group consisting of F, Cl, Br, I, CN, $C_{1-6}$ alkyl, $CF_3$, $CF_2H$, $CFH_2$, $CF_2Cl$, $CFCl_2$, C(O)$C_{1-6}$ alkyl, C(O)OH, C(O)O$C_{1-6}$ alkyl, C(O)$NH_2$, C(O)NH$C_{1-6}$ alkyl, C(O)N($C_{1-6}$ alkyl)$_2$, OH, =O, $OCF_3$, $OCF_2H$, $OCFH_2$, $OCF_2Cl$, $OCFCl_2$, O$C_{1-6}$ alkyl, OC(O)$C_{1-6}$ alkyl, OC(O)O$C_{1-6}$ alkyl, OC(O)NH$C_{1-6}$ alkyl, OC(O)N($C_{1-6}$ alkyl)$_2$, OS(O)$_2$$NH_2$, OS(O)$_2$NH$C_{1-6}$ alkyl, OS(O)$_2$N($C_{1-6}$ alkyl)$_2$, $NH_2$, NH$C_{1-6}$ alkyl, N($C_{1-6}$ alkyl)$_2$, NHC(O)$C_{1-6}$ alkyl, NHC(O)O$C_{1-6}$ alkyl, NHC(O)$NH_2$, NHC(O)NH$C_{1-6}$ alkyl, NHC(O)N($C_{1-6}$ alkyl)$_2$, N($C_{1-6}$ alkyl)-C(O)$C_{1-6}$ alkyl, N($C_{1-6}$ alkyl)-C(O)O$C_{1-6}$ alkyl, N($C_{1-6}$ alkyl)-C(O)$NH_2$, N($C_{1-6}$ alkyl)-C(O)NH$C_{1-6}$ alkyl, N($C_{1-6}$ alkyl)-C(O)N($C_{1-6}$ alkyl)$_2$, NHS(O)$_2$OH, NHS(O)$_2$$C_{1-6}$ alkyl, NHS(O)$_2$O$C_{1-6}$ alkyl, NHS(O)$_2$$NH_2$, NHS(O)$_2$NH$C_{1-6}$ alkyl, NHS(O)$_2$N($C_{1-6}$ alkyl)$_2$, N($C_{1-6}$ alkyl)-S(O)$_2$OH, N($C_{1-6}$ alkyl)-S(O)$_2$$C_{1-6}$ alkyl, N($C_{1-6}$ alkyl)-S(O)$_2$O$C_{1-6}$ alkyl, N($C_{1-6}$ alkyl)-S(O)$_2$$NH_2$, N($C_{1-6}$ alkyl)-S(O)$_2$NH$C_{1-6}$ alkyl, N($C_{1-6}$ alkyl)-S(O)$_2$N($C_{1-6}$ alkyl)$_2$, $SCF_3$, $SCF_2H$, $SCFH_2$, S$C_{1-6}$ alkyl, S(O)$C_{1-6}$ alkyl, S(O)$_2$$C_{1-6}$ alkyl, S(O)$_2$OH, S(O)$_2$O$C_{1-6}$ alkyl, S(O)$_2$$NH_2$, S(O)$_2$NH$C_{1-6}$ alkyl, S(O)$_2$N($C_{1-6}$ alkyl)$_2$, $C_{3-6}$ cycloalkyl, 3- to 7-membered heterocycloalkyl, phenyl, 5- or 6-membered heteroaryl, O$C_{3-6}$ cycloalkyl, O(3- to 7-membered heterocycloalkyl), Ophenyl, O(5- or 6-membered heteroaryl), C(O)$C_{3-6}$ cycloalkyl, C(O)(3- to 7-membered heterocycloalkyl), C(O) phenyl, C(O)(5- or 6-membered heteroaryl), S(O)$_2$$C_{3-6}$ cycloalkyl, S(O)$_2$(3- to 7-membered heterocycloalkyl), S(O)$_2$phenyl, and S(O)$_2$(5- or 6-membered heteroaryl), wherein each $C_{1-6}$ alkyl is independently linear or branched and is independently saturated or unsaturated;

wherein each aryl and 5- to 10-membered heteroaryl is optionally and independently substituted with one or more substituents independently selected from the group consisting of F, Cl, Br, I, CN, $C_{1-6}$ alkyl, $C_{2-6}$ alkenyl, $C_{2-6}$ alkynyl, $C_{2-6}$ alkynylene-CH(OH)$CH_3$, $C_{2-6}$ alkynylene-C($CH_3$)$_2$OH, $CF_3$, $CF_2H$, $CFH_2$, $CF_2C_1$, $CFCl_2$, $C_{1-6}$ alkylene-$CF_3$, $C_{1-6}$ alkylene-$CF_2H$, $C_{1-6}$ alkylene-$CFH_2$, $C_{1-6}$ alkylene-OH, $C_{1-6}$ alkylene-O$C_{1-6}$ alkyl, C(O)$C_{1-6}$ alkyl, C(O)OH, C(O)O$C_{1-6}$ alkyl, C(O)NHOH, C(O)$NH_2$, C(O)NH$C_{1-6}$ alkyl, C(O)N($C_{1-6}$ alkyl)$_2$, OH, =O, $OCF_3$, $OCF_2H$, $OCFH_2$, $OCF_2Cl$, $OCFCl_2$, $OC_{1-6}$ alkyl, $OC_{3-6}$ cycloalkyl, O(3- to 7-membered heterocycloalkyl), $NH_2$, $NHC_{1-6}$ alkyl, $N(C_{1-6}$ alkyl$)_2$, $NHC(O)C_{1-6}$ alkyl, $N(C_{1-6}$ alkyl)-$C(O)C_{1-6}$ alkyl, $NHC(O)NH_2$, $NHC(O)NHC_{1-6}$ alkyl, $NHC(O)N(C_{1-6}$ alkyl$)_2$, $N(C_{1-6}$ alkyl)-$C(O)NHC_{1-6}$ alkyl, $N(C_{1-6}$ alkyl)-$C(O)N(C_{1-6}$ alkyl$)_2$, $NHS(O)_2C_{1-6}$ alkyl, $SCF_3$, $SC_{1-6}$ alkyl, $S(O)C_{1-6}$ alkyl, $S(O)_2C_{1-6}$ alkyl, $S(O)_2C_{3-6}$ cycloalkyl, $S(O)_2$—$C_{1-6}$ alkylene-$C_{3-6}$ cycloalkyl, $S(O)_2NH_2$, $S(O)_2NHC_{1-6}$ alkyl, $S(O)_2N(C_{1-6}$ alkyl$)_2$, $C_{3-6}$ cycloalkyl, $C_{1-6}$ alkylene-$C_{3-6}$ cycloalkyl, 3- to 7-membered heterocycloalkyl; $C_{1-6}$ alkylene-(3- to 7-membered heterocycloalkyl), phenyl; and 5- or 6-membered heteroaryl, wherein each $C_{1-6}$ alkylene and $C_{1-6}$ alkyl is independently linear or branched and is independently saturated or unsaturated;

with the proviso that if $R^1$ is indolyl or indazolyl and $R^7$ is H, F or Cl, then the indolyl or indazolyl of $R^1$ is bound via its 5-membered ring to the remainder of the compound.

2. The compound according to claim 1, or a physiologically acceptable salt or stereoisomer thereof, wherein:

each $C_{1-10}$ alkyl, $C_{1-6}$ alkylene, $C_{3-10}$ cycloalkyl, and 3- to 7-membered heterocycloalkyl is optionally and independently substituted with one or more substituents independently selected from the group consisting of F, Cl, Br, I, CN, $C_{1-6}$ alkyl, $CF_3$, $CF_2H$, $CFH_2$, $CF_2Cl$, $CFCl_2$, OH, =O, $OCF_3$, $OCF_2H$, $OCFH_2$, $OCF_2Cl$, $OCFCl_2$, $OC_{1-6}$ alkyl, $C_{3-6}$ cycloalkyl, pyridinyl, and 3- to 7-membered heterocycloalkyl, wherein each $C_{1-6}$ alkyl is independently linear or branched and is independently saturated or unsaturated; or each aryl and 5- to 10-membered heteroaryl is optionally and independently substituted with one or more substituents independently selected from the group consisting of F, Cl, Br, I, CN, $C_{1-6}$ alkyl, $C_{2-6}$ alkenyl, $C_{2-6}$ alkynyl, $CF_3$, $CF_2H$, $CFH_2$, $CF_2Cl$, $CFCl_2$, $C_{1-6}$ alkylene-$CF_3$, $C_{1-6}$ alkylene-$CF_2H$, $C_{1-6}$ alkylene-$CFH_2$, $C(O)C_{1-6}$ alkyl, C(O)OH, $C(O)OC_{1-6}$ alkyl, $NH_2$, OH, =O, $C_{1-6}$ alkylene-OH, $C_{1-6}$ alkylene-$OC_{1-6}$ alkyl, $OCF_3$, $OCF_2H$, $OCFH_2$, $OCF_2Cl$, $OCFCl_2$, $OC_{1-6}$ alkyl, $OC_{3-6}$ cycloalkyl, O(3- to 7-membered heterocycloalkyl), $SCF_3$, $SC_{1-6}$ alkyl, $S(O)C_{1-6}$ alkyl, $S(O)_2C_{1-6}$ alkyl, $S(O)_2C_{3-6}$ cycloalkyl, $S(O)_2$—$C_{1-6}$ alkylene-$C_{3-6}$ cycloalkyl, $S(O)_2NH_2$, $S(O)_2NHC_{1-6}$ alkyl, $S(O)_2N(C_{1-6}$ alkyl$)_2$, $C_{3-6}$ cycloalkyl, $C_{1-6}$ alkylene-$C_{3-6}$ cycloalkyl, 3- to 7-membered heterocycloalkyl, $C_{1-6}$ alkylene-(3- to 7-membered heterocycloalkyl), phenyl, and 5- or 6-membered heteroaryl, wherein each $C_{1-6}$ alkylene and $C_{1-6}$ alkyl is independently linear or branched.

3. The compound according to claim 1, or a physiologically acceptable salt or stereoisomer thereof, wherein:

$R^1$ is aryl, 5- to 10-membered heteroaryl, $CH_2$-(3- to 7-membered heterocycloalkyl), or C(O)NH—$CH_2$-aryl; or $R^3$ is $C_{1-6}$-alkyl and $R^4$ is $C_{1-6}$-alkyl, wherein each $C_{1-6}$ alkyl is independently linear or branched and is independently saturated or unsaturated.

4. The compound according to claim 1, or a physiologically acceptable salt or stereoisomer thereof, wherein $R^3$ is $CH_3$ and $R^4$ is $CH_3$; or $R^5$ is F, Cl, $CF_3$, $CHF_2$, $CH_2CH_2CH_3$, $CH_2CH_3$, $CH_3$, $OCH_2CH_2CH_3$, $OCH_2CH_3$, $OCH_3$, or cyclopropyl.

5. The compound according to claim 1, or a physiologically acceptable salt or stereoisomer thereof, wherein $R^6$ and $R^7$, taken together with the carbon atoms to which they are attached, form:

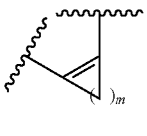 , 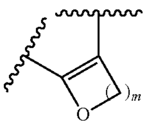 , or 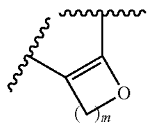 , wherein m is 1, 2, 3, or 4.

6. The compound according to claim 1, or a physiologically acceptable salt or stereoisomer thereof, wherein $R^6$ and $R^7$, taken together with the carbon atoms to which they are attached, form:

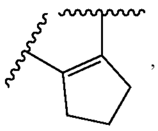 , 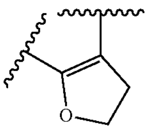 , or 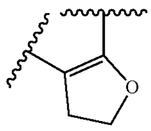 .

7. The compound according to claim 1, or a physiologically acceptable salt or stereoisomer thereof, wherein;

$R^3$ is $C_{1-3}$ alkyl and $R^4$ is $C_{1-3}$ alkyl, wherein each $C_{1-3}$ alkyl is independently linear or branched and is independently saturated or unsaturated;

$R^5$ is F, Cl, $CF_3$, $CHF_2$, $CH_2CH_2CH_3$, $CH_2CH_3$, $CH_3$, $OCH_2CH_2CH_3$, $OCH_2CH_3$, $OCH_3$, or $C_{3-10}$ cycloalkyl;

$R^6$ is H, F, Cl, $OCF_3$, or $CHF_2$; or $R^7$ is H, F, Cl, $CH_2CH_3$, $CH_3$, $CF_3$, $SCH_3$, OH, or $C(CH_3)_2OH$.

8. The compound according to claim 1, or a physiologically acceptable salt or stereoisomer thereof, wherein $R^{10}$ is $CH_3$.

9. A pharmaceutical dosage form comprising a compound according to claim 1, or a physiologically acceptable salt or stereoisomer thereof.

10. A method for the treatment and/or prophylaxis of pain and/or inflammation in a subject in need thereof, said method comprising administering to the subject an effective amount therefor of the compound according to claim 1 or a physiologically acceptable salt or stereoisomer thereof.

11. A method for the treatment and/or prophylaxis of inflammatory pain in a subject in need thereof, said method comprising administering to the subject an effective amount therefor of the compound according to claim 1 or a physiologically acceptable salt or stereoisomer thereof.

12. A compound according to the following formula:

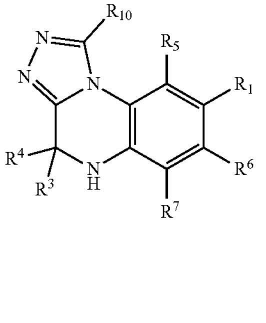

or a physiologically acceptable salt or stereoisomer thereof, wherein:

$R^1$ is:

(i) imidazopyridinyl, pyrrolopyridinyl, pyrazolopyridinyl, dihydropyrrolopyrazolyl, pyrimidinyl, pyridazinyl, pyrazinyl, pyrrolyl, $CH_2$-pyrrolidinyl, imidazolyl, pyrazolyl, oxazolyl, isoxazolyl, thiazolyl, isothiazolyl, furanyl, thienyl, triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, dihydrobenzodioxinyl, benzothiadiazolyl, benzothiazolyl, benzotriazolyl, benzooxazolyl, benzooxadiazolyl, quinazolinyl, quinoxalinyl, carbazolyl, quinolinyl, dihydroquinolinonyl, dibenzofuranyl, dibenzothienyl, imidazothiazolyl, indazolyl, indolizinyl, indolyl, indolinyl, isoquinolinyl, naphthyridinyl, oxazolyl, oxadiazolyl, phenazinyl, phenothiazinyl, phthalazinyl, purinyl, phenazinyl, tetrazolyl, triazinyl, or $C(O)NHCH_2$-phenyl; or (ii) phenyl or naphthalenyl, wherein the phenyl or naphthalenyl is optionally substituted with one or more substituents independently selected from the group consisting of F, Cl, Br, I, $CH_3$, $CH_2CH_3$, $OCH_3$, $CF_3$, $C_{3-10}$ cycloalkyl, $CH_2C_{3-10}$ cycloalkyl, $S(O)_2C_{3-10}$ cycloalkyl, $S(O)_2CH_2C_{3-10}$ cycloalkyl, $S(O)_2CH_3$, $S(O)_2CH_2CH_3$, $CH_2CH_2OCH_3$, $OCH_3$, $C{\equiv}CCH_3$, $CH_2CH_2C(O)NH_2$, $CH_2CH_2C(O)N(CH_3)_2$, $C(O)CH_3$, $CH{=}CH_2$, $NH_2$, and $CH_2CH_2O$; or (iii) pyridinyl, wherein the pyridinyl is optionally substituted with one or more substituents independently selected from the group consisting of F, Cl, Br, I, $CH_3$, $CH_2CH_3$, $OCH_3$, $CF_3$, $C_{3-10}$ cycloalkyl, $CH_2C_{3-10}$ cycloalkyl, $S(O)_2C_{3-10}$ cycloalkyl, $S(O)_2CH_2C_{3-10}$ cycloalkyl, $S(O)_2CH_3$, $S(O)_2CH_2CH_3$, $CH_2CH_2OCH_3$, $OCH_2CH_2OH$, $C{\equiv}CCH_3$, $CH_2CH_2C(O)NH_2$, $C(O)CH_3$, $CH{=}CH_2$, $NH_2$, and $CH_2CH_2OH$; or (iv) any of the following structures (II), (III), (IV), (V) or (VI):

(II)

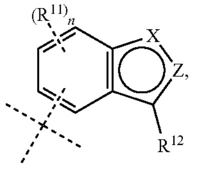

(III)

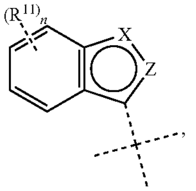

(IV)

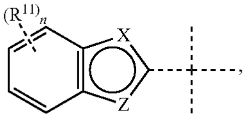

-continued (V)

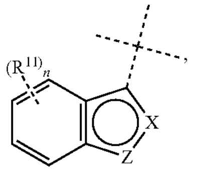

or (VI)

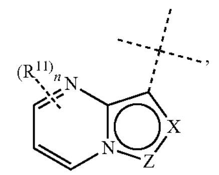

wherein

X is S, O, N, $NR^{13}$, or $CR^{13}$;

Z is S, O, N, $NR^{13}$, or $CR^{13}$;

each $R^{11}$, $R^{12}$ and $R^{13}$ is independently H, F, Cl, Br, I, CN, $CF_3$, $CH_2CHF_2$, $C_{1-10}$ alkyl, $C_{3-10}$ cycloalkyl, $CH_2C_{3-10}$ cycloalkyl, 3- to 7-membered heterocycloalkyl, $S(O)C_{1-10}$ alkyl, $S(O)C_{3-10}$ cycloalkyl, S(O)(3- to 7-membered heterocycloalkyl), $S(O)_2C_{1-10}$ alkyl, $S(O)_2C_{3-10}$ cycloalkyl, $S(O)_2CH_2C_{3-10}$ cycloalkyl, $S(O)_2$(3- to 7-membered heterocycloalkyl), $P(O)(C_{1-10}$ alkyl$)_2$, $P(O)(C_{1-10}$ alkyl$)(C_{3-10}$ cycloalkyl), $P(O)(C_{1-10}$ alkyl)(3- to 7-membered heterocycloalkyl), $P(O)(OC_{1-10}$ alkyl$)_2$, $P(O)(OC_{1-10}$ alkyl$)(OC_{3-10}$ cycloalkyl), $P(O)(OC_{1-10}$ alkyl)(O(3- to 7-membered heterocycloalkyl)), $OC_{1-10}$ alkyl, $SC_{1-10}$ alkyl, $NHC_{1-10}$ alkyl, $N(C_{1-10}$ alkyl$)_2$, $C(O)C_{1-10}$ alkyl, $C(O)OC_{1-10}$ alkyl, $C(O)NH_2$, $C(O)NHC_{1-10}$ alkyl, $C(O)N(C_{1-10}$ alkyl$)_2$, $OC_{3-10}$ cycloalkyl, $NHC_{3-10}$ cycloalkyl, $N(C_{1-10}$ alkyl$)(C_{3-10}$ cycloalkyl), $C(O)C_{3-10}$ cycloalkyl, $C(O)OC_{3-10}$ cycloalkyl, $C(O)NHC_{3-10}$ cycloalkyl; $C(O)N(C_{1-10}$ alkyl$)(C_{3-10}$ cycloalkyl), O(3- to 7-membered heterocycloalkyl), NH(3- to 7-membered heterocycloalkyl), $N(C_{1-10}$ alkyl)(3- to 7-membered heterocycloalkyl), C(O)(3- to 7-membered heterocycloalkyl), C(O)O(3- to 7-membered heterocycloalkyl), C(O)N(H)(3- to 7-membered heterocycloalkyl), $C(O)N(C_{1-10}$ alkyl)(3- to 7-membered heterocycloalkyl), $-CH_2CH_2OCH_2-$, $CH_2CH_2OCH_3$, $C{\equiv}CCH(OH)CH_3$, $C{\equiv}CC(OH)(CH_3)_2$, or $CH_2CH_2OH$, wherein each $C_{1-10}$ alkyl is independently linear or branched and is independently saturated or unsaturated; and n is 0, 1, 2 or 3; or (v) any of the following structures (1), (2), (3), (4), (5), (6), (7), (8), (9), (10), (11), (12), (13), (14), (15), (16), or (17):

(1)

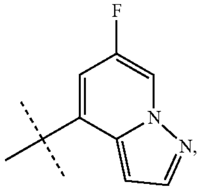

-continued (2)

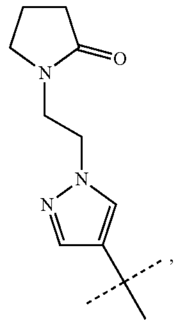

(3)

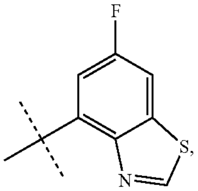

(4)

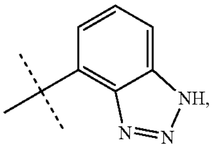

(5)

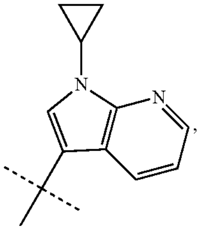

(6)

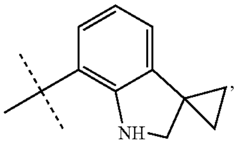

(7)

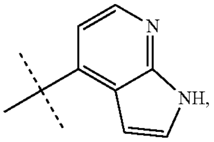

(8)

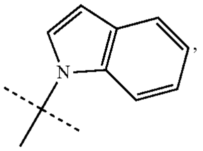

(9)

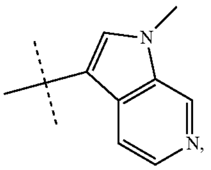

-continued (10)

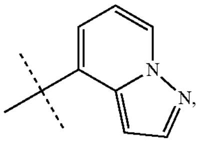

(11)

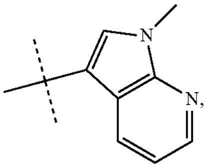

(12)

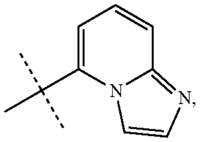

(13)

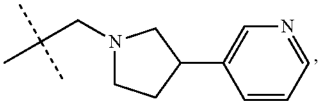

(14)

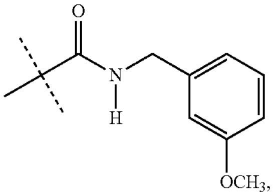

(15)

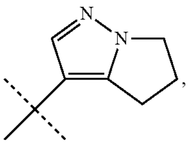

(16)

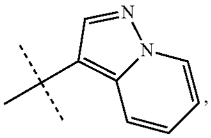

or (17)

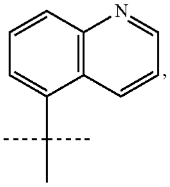

wherein each of (6), (7), (8), or (16) is optionally substituted with one substituent selected from the group consisting of F and $CH_3$;

$R^3$ is H or $C_{1-10}$ alkyl, wherein the $C_{1-10}$ alkyl is linear or branched and is saturated or unsaturated;

$R^4$ is H or $C_{1-10}$ alkyl, wherein the $C_{1-10}$ alkyl is linear or branched and is saturated or unsaturated;

$R^5$ is F, Cl, Br, I, $C_{1-10}$ alkyl, $OC_{1-10}$ alkyl, or $C_{3-10}$ cycloalkyl, wherein each $C_{1-10}$ alkyl is independently linear or branched and is independently saturated or unsaturated;

$R^6$ is H, F, Cl, Br, I, $C_{1-10}$ alkyl, $OC_{1-10}$ alkyl, or $C_{3-10}$ cycloalkyl, wherein each $C_{1-10}$ alkyl is independently linear or branched and is independently saturated or unsaturated;

$R^7$ is H, F, Cl, Br, I, OH, $C_{1-10}$ alkyl, $SC_{1-10}$-alkyl, or $C_{3-10}$ cycloalkyl, wherein each $C_{1-10}$ alkyl is independently linear or branched and is independently saturated or unsaturated;

or $R^6$ and $R^7$, taken together with the carbon atoms to which they are attached, form a $C_{3-10}$ cycloalkyl or 3- to 7-membered heterocycloalkyl; and $R^{10}$ is $C_{1-10}$ alkyl or $C_{3-10}$ cycloalkyl, wherein the $C_{1-10}$ alkyl is linear or branched and is saturated or unsaturated;

wherein each $C_{1-10}$ alkyl, $C_{1-6}$ alkylene, $C_{3-10}$ cycloalkyl and 3- to 7-membered heterocycloalkyl is optionally and independently substituted with one or more substituents independently selected from the group consisting of F, Cl, Br, I, CN, $C_{1-6}$ alkyl, $CF_3$, $CF_2H$, $CFH_2$, $CF_2Cl$, $CFCl_2$, $C(O)C_{1-6}$ alkyl, C(O)OH, $C(O)OC_{1-6}$ alkyl, $C(O)NH_2$, $C(O)NHC_{1-6}$ alkyl, $CON(C_{1-6}$ alkyl$)_2$, OH, =O, $OCF_3$, $OCF_2H$, $OCFH_2$, $OCF_2Cl$, $OCFCl_2$, O—$C_{1-6}$ alkyl, OC(O) $C_{1-6}$ alkyl, $OC(O)OC_{1-6}$ alkyl, $OC(O)NHC_{1-6}$-alkyl, $OC(O)N(C_{1-6}$ alkyl$)_2$; $OS(O)_2NH_2$, $OS(O)_2NHC_{1-6}$ alkyl, $OS(O)_2N(C_{1-6}$ alkyl$)_2$, $NH_2$, $NHC_{1-6}$ alkyl, $N(C_{1-6}$ alkyl$)_2$, $NHC(O)C_{1-6}$ alkyl, $NHC(O)OC_{1-6}$ alkyl, $NHC(O)NH_2$, $NHC(O)NHC_{1-6}$ alkyl, NHC(O) $N(C_{1-6}$ alkyl$)_2$, $N(C_{1-6}$ alkyl$)$-$C(O)C_{1-6}$ alkyl, $N(C_{1-6}$ alkyl$)$-$C(O)OC_{1-6}$ alkyl, $N(C_{1-6}$ alkyl$)$-$C(O)NH_2$, $N(C_{1-6}$ alkyl$)$-$C(O)NHC_{1-6}$ alkyl, $N(C_{1-6}$ alkyl$)$-C (O)$N(C_{1-6}$ alkyl$)_2$, $NHS(O)_2OH$, $NHS(O)_2C_{1-6}$ alkyl, $NHS(O)_2OC_{1-6}$ alkyl, $NHS(O)_2NH_2$, $NHS(O)_2NHC_{1-6}$ alkyl, $NHS(O)_2N(C_{1-6}$ alkyl$)_2$, $N(C_{1-6}$ alkyl$)$-$S(O)_2OH$, $N(C_{1-6}$ alkyl$)$-$S(O)_2C_{1-6}$ alkyl, $N(C_{1-6}$ alkyl$)$-$S(O)_2OC_{1-6}$ alkyl, $N(C_{1-6}$ alkyl$)$-$S(O)_2NH_2$, $N(C_{1-6}$ alkyl$)$-$S(O)_2NHC_{1-6}$ alkyl, $N(C_{1-6}$ alkyl$)$-$S(O)_2N(C_{1-6}$ alkyl$)_2$, $SCF_3$, $SCF_2H$, $SCFH_2$, $SC_{1-6}$ alkyl, $S(O)C_{1-6}$ alkyl, $S(O)_2C_{1-6}$ alkyl, $S(O)_2OH$, $S(O)_2OC_{1-6}$ alkyl, $S(O)_2NH_2$, $S(O)_2NHC_{1-6}$ alkyl, $S(O)_2N(C_{1-6}$ alkyl$)_2$, $C_{3-6}$ cycloalkyl, 3- to 7-membered heterocycloalkyl, phenyl, 5- or 6-membered heteroaryl, $OC_{3-6}$ cycloalkyl, O(3- to 7-membered heterocycloalkyl), Ophenyl; O(5- or 6-membered heteroaryl), $C(O)C_{3-6}$ cycloalkyl, C(O)(3- to 7-membered heterocycloalkyl), C(O) phenyl, C(O)(5- or 6-membered heteroaryl), $S(O)_2C_{3-6}$ cycloalkyl, $S(O)_2$(3- to 7-membered heterocycloalkyl, $S(O)_2$phenyl, and $S(O)_2$(5- or 6-membered heteroaryl), wherein each $C_{1-6}$ alkyl is independently linear or branched and is independently saturated or unsaturated; and with the proviso that if $R^1$ is indolyl or indazolyl and $R^7$ is H, F or Cl, then the indolyl or indazolyl of $R^1$ is bound via its 5-membered ring to the remainder of the compound.

13. The compound according to claim 12, or a physiologically acceptable salt or stereoisomer thereof, wherein:

$R^1$ is phenyl, naphthalenyl, pyridinyl, imidazopyridinyl, pyrrolopyridinyl, pyrazolopyridinyl, dihydropyrrolopyrazolyl, pyrimidinyl, pyridazinyl, pyrazinyl, pyrrolyl, $CH_2$-pyrrolidinyl, imidazolyl, pyrazolyl, oxazolyl, isoxazolyl, thiazolyl, isothiazolyl, furanyl, thienyl, triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dihydroquinolinonyl, dihydrobenzodioxinyl, dibenzofuranyl, dibenzothienyl, imidazothiazolyl, indazolyl, indolizinyl, indolyl, indolinyl, isoquinolinyl, naphthyridinyl, oxazolyl, oxadiazolyl, phenazinyl, phenothiazinyl, phthalazinyl, purinyl, phenazinyl, tetrazolyl, triazinyl, $C(O)NHCH_2$-phenyl, or (6)

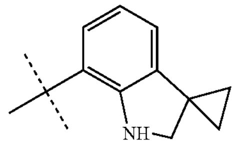

wherein (6) is optionally substituted with one substituent selected from the group consisting of F and $CH_3$;

$R^3$ is $C_{1-6}$ alkyl and $R^4$ is $C_{1-6}$ alkyl, wherein each $C_{1-6}$ alkyl is independently linear or branched and is independently saturated or unsaturated;

$R^5$ is F, Cl, $C_{1-6}$ alkyl, $OC_{1-6}$ alkyl, or $C_{3-10}$ cycloalkyl, wherein each $C_{1-6}$ alkyl is independently linear or branched and is independently saturated or unsaturated;

$R^6$ is H, F, Cl, $C_{1-6}$ alkyl, $OC_{1-6}$ alkyl, or $C_{3-10}$ cycloalkyl, wherein each $C_{1-6}$ alkyl is independently linear or branched and is independently saturated or unsaturated;

$R^7$ is H, F, Cl, OH, $C_{1-6}$ alkyl; $SC_{1-6}$ alkyl, or $C_{3-10}$ cycloalkyl, wherein each $C_{1-6}$ alkyl is independently linear or branched and is independently saturated or unsaturated; or $R^{10}$ is $C_{1-6}$ alkyl or $C_{3-10}$ cycloalkyl, wherein the $C_{1-6}$ alkyl is linear or branched and is saturated or unsaturated.

14. A pharmaceutical dosage form comprising a compound according to claim 12, or a physiologically acceptable salt or stereoisomer thereof.

15. A method for the treatment and/or prophylaxis of pain and/or inflammation in a subject in need thereof, said method comprising administering to the subject an effective amount therefor of the compound according to claim 12 or a physiologically acceptable salt or stereoisomer thereof.

16. A method for the treatment and/or prophylaxis of inflammatory pain in a subject in need thereof, said method comprising administering to the subject an effective amount therefor of the compound according to claim 12 or a physiologically acceptable salt or stereoisomer thereof.

17. A compound selected from the group consisting of:

1 3,5,11,11-tetramethyl-6-(1-(methylsulfonyl)-1H-indol-4-yl)-8,9,10,11-tetrahydrofuro[3,2-f][1,2,4]triazolo[4,3-a]quinoxaline;

2 6-(1-(ethylsulfonyl)-1H-indol-4-yl)-3,5,11,11-tetramethyl-8,9,10,11-tetrahydrofuro[3,2-f][1,2,4]triazolo[4,3-a]quinoxaline;

3 6-(5-chloro-2-methoxypyridin-3-yl)-3,5,11,11-tetramethyl-8,9,10,11-tetrahydrofuro[3,2-f][1,2,4]triazolo[4,3-a]quinoxaline;

4 2-(6-fluoro-4-(3,5,11,11-tetramethyl-8,9,10,11-tetrahydrofuro[3,2-f][1,2,4]triazolo[4,3-a]quinoxalin-6-yl)-1H-indol-1-yl) ethan-1-ol;

5 6-(1-(cyclopropylsulfonyl)-1H-indol-4-yl)-3,5,11,11-tetramethyl-8,9,10,11-tetrahydrofuro[3,2-f][1,2,4]triazolo[4,3-a]quinoxaline;

6 6-(1-(2,2-difluoroethyl)-1H-indol-4-yl)-3,5,11,11-tetramethyl-8,9,10,11-tetrahydrofuro[3,2-f][1,2,4]triazolo[4,3-a]quinoxaline;

7 6-(1-(isopropylsulfonyl)-1H-indol-4-yl)-3,5,11,11-tetramethyl-8,9,10,11-tetrahydrofuro[3,2-f][1,2,4]triazolo[4,3-a]quinoxaline;

8 3,5,11,11-tetramethyl-6-(3-methyl-1H-indol-7-yl)-8,9,10,11-tetrahydrofuro[3,2-f][1,2,4]triazolo[4,3-a]quinoxaline;

9 6-(6-fluoro-1-(methylsulfonyl)-1H-indol-4-yl)-3,5,11,11-tetramethyl-8,9,10,11-tetrahydrofuro[3,2-f][1,2,4]triazolo[4,3-a]quinoxaline;

10 6-(1-(2,2-difluoroethyl)-1H-indol-4-yl)-3,11,11-trimethyl-5-(trifluoromethyl)-8,9,10,11-tetrahydrofuro[3,2-f][1,2,4]triazolo[4,3-a]quinoxaline;

11 6-(1-(2,2-difluoroethyl)-6-fluoro-1H-indazol-4-yl)-3,11,11-trimethyl-5-(trifluoromethyl)-8,9,10,11-tetrahydrofuro[3,2-f][1,2,4]triazolo[4,3-a]quinoxaline;

12 6-(6-fluoro-1-(methylsulfonyl)-1H-indol-4-yl)-3,11,11-trimethyl-5-(trifluoromethyl)-8,9,10,11-tetrahydrofuro[3,2-f][1,2,4]triazolo[4,3-a]quinoxaline;

13 6-(3-cyclopropyl-5-fluoro-1H-indol-7-yl)-5-fluoro-3,11,11-trimethyl-8,9,10,11-tetrahydrofuro[3,2-f][1,2,4]triazolo[4,3-a]quinoxaline;

14 5-fluoro-6-(5-fluoro-3-methyl-1H-indol-7-yl)-3,11,11-trimethyl-8,9,10,11-tetrahydrofuro[3,2-f][1,2,4]triazolo[4,3-a]quinoxaline;

15 5-fluoro-3,11,11-trimethyl-6-(3-methyl-1H-indol-7-yl)-8,9,10,11-tetrahydrofuro[3,2-f][1,2,4]triazolo[4,3-a]quinoxaline;

16 5-fluoro-6-(1H-indol-4-yl)-3,11,11-trimethyl-8,9,10,11-tetrahydrofuro[3,2-f][1,2,4]triazolo[4,3-a]quinoxaline;

17 5-fluoro-6-(6-fluoro-1-(methylsulfonyl)-1H-indol-4-yl)-3,11,11-trimethyl-8,9,10,11-tetrahydrofuro[3,2-f][1,2,4]triazolo[4,3-a]quinoxaline;

18 5-fluoro-6-(6-fluoro-1-methyl-1H-indol-4-yl)-3,11,11-trimethyl-8,9,10,11-tetrahydrofuro[3,2-f][1,2,4]triazolo[4,3-a]quinoxaline;

19 5-chloro-6-(1-(ethylsulfonyl)-1H-indol-4-yl)-3,11,11-trimethyl-8,9,10,11-tetrahydrofuro[3,2-f][1,2,4]triazolo[4,3-a]quinoxaline;

20 5-chloro-6-(1-(cyclopropylsulfonyl)-1H-indol-4-yl)-3,11,11-trimethyl-8,9,10,11-tetrahydrofuro[3,2-f][1,2,4]triazolo[4,3-a]quinoxaline;

21 5-chloro-6-(1-(2,2-difluoroethyl)-6-fluoro-1H-indazol-4-yl)-3,11,11-trimethyl-8,9,10,11-tetrahydrofuro[3,2-f][1,2,4]triazolo[4,3-a]quinoxaline;

22 5-chloro-6-(5-chloro-2-methoxypyridin-3-yl)-3,11,11-trimethyl-8,9,10,11-tetrahydrofuro[3,2-f][1,2,4]triazolo[4,3-a]quinoxaline;

23 5-chloro-6-(1-(2,2-difluoroethyl)-1H-indol-4-yl)-3,11,11-trimethyl-8,9,10,11-tetrahydrofuro[3,2-f][1,2,4]triazolo[4,3-a]quinoxaline;

24 5-chloro-6-(1-(isopropylsulfonyl)-1H-indol-4-yl)-3,11,11-trimethyl-8,9,10,11-tetrahydrofuro[3,2-f][1,2,4]triazolo[4,3-a]quinoxaline;

25 5-chloro-6-(4-fluoro-1H-indazol-6-yl)-3,11,11-trimethyl-8,9,10,11-tetrahydrofuro[3,2-f][1,2,4]triazolo[4,3-a]quinoxaline;

26 6-Ethyl-9-fluoro-8-(5-fluoro-3-methyl-1H-indol-7-yl)-1,4,4-trimethyl-5H-[1,2,4]triazolo[4,3-a]quinoxaline;

27 8-(1-Cyclopropyl-6-fluoro-1H-indol-4-yl)-6-ethyl-9-fluoro-1,4,4-trimethyl-5H-[1,2,4]triazolo[4,3-a]quinoxaline;

28 6-Ethyl-9-fluoro-8-(1H-indol-4-yl)-1,4,4-trimethyl-5H-[1,2,4]triazolo[4,3-a]quinoxaline;

29 6-Ethyl-9-fluoro-8-(6-fluoro-1-methylsulfonyl-1H-indol-4-yl)-1,4,4-trimethyl-5H-[1,2,4]triazolo[4,3-a]quinoxaline;

30 6-Ethyl-9-fluoro-8-(5-fluoro-3-tetrahydro-furan-3-yl-1H-indol-7-yl)-1,4,4-trimethyl-5H-[1,2,4]triazolo[4,3-a]quinoxaline;

31 2-[7-(6-Ethyl-9-fluoro-1,4,4-trimethyl-5H-[1,2,4]triazolo[4,3-a]quinoxalin-8-yl)-5-fluoro-1H-indol-3-yl]-ethanol;

32 6-Ethyl-9-fluoro-8-[2-methoxy-5-(trifluoromethyl)-pyridin-3-yl]-1,4,4-trimethyl-5H-[1,2,4]triazolo[4,3-a]quinoxaline;

33 8-(6-Fluoro-1-methylsulfonyl-1H-indol-4-yl)-1,4,4,6-tetramethyl-9-(trifluoromethyl)-5H-[1,2,4]triazolo[4,3-a]quinoxaline;

34 8-(5-Fluoro-3-prop-1-ynyl-1H-indol-7-yl)-1,4,4,6-tetramethyl-9-(trifluoromethyl)-5H-[1,2,4]triazolo[4,3-a]quinoxaline;

35 2-[6-Fluoro-4-[1,4,4,6-tetramethyl-9-(trifluoromethyl)-5H-[1,2,4]triazolo[4,3-a]quinoxalin-8-yl]-1H-indol-1-yl]-ethanol;

36 8-(1-Cyclopropyl-6-fluoro-1H-indol-4-yl)-9-fluoro-1,4,4,6-tetramethyl-5H-[1,2,4]triazolo[4,3-a]quinoxaline;

37 9-Fluoro-8-(6-fluoro-1-methylsulfonyl-1H-indol-4-yl)-1,4,4,6-tetramethyl-5H-[1,2,4]triazolo[4,3-a]quinoxaline;

38 9-Fluoro-8-(5-fluoro-3-methyl-1H-indol-7-yl)-1,4,4,6-tetramethyl-5H-[1,2,4]triazolo[4,3-a]quinoxaline;

39 9-Fluoro-8-(1H-indol-4-yl)-1,4,4,6-tetramethyl-5H-[1,2,4]triazolo[4,3-a]quinoxaline;

40 4-[5-Fluoro-7-(9-fluoro-1,4,4,6-tetramethyl-5H-[1,2,4]triazolo[4,3-a]quinoxalin-8-yl)-1H-indol-3-yl]-but-3-yn-2-ol;

41 9-Fluoro-1,4,4,6-tetramethyl-8-(1-methylsulfonyl-1H-indol-4-yl)-5H-[1,2,4]triazolo[4,3-a]quinoxaline;

42 9-Fluoro-8-(5-fluoro-3-prop-1-ynyl-1H-indol-7-yl)-1,4,4,6-tetramethyl-5H-[1,2,4]triazolo[4,3-a]quinoxaline;

43 4-[5-Fluoro-7-(9-fluoro-1,4,4,6-tetramethyl-5H-[1,2,4]triazolo[4,3-a]quinoxalin-8-yl)-1H-indol-3-yl]-2-methyl-but-3-yn-2-ol;

44 8-(3-Cyclopropyl-5-fluoro-1H-indol-7-yl)-9-fluoro-1,4,4,6-tetramethyl-5H-[1,2,4]triazolo[4,3-a]quinoxaline;

45 9-Fluoro-1,4,4,6-tetramethyl-8-pyrazolo[1,5-a]pyridin-4-yl-5H-[1,2,4]triazolo[4,3-a]quinoxaline;

46 2-[5-Fluoro-7-(9-fluoro-1,4,4,6-tetramethyl-5H-[1,2,4]triazolo[4,3-a]quinoxalin-8-yl)-1H-indol-3-yl]-ethanol;

47 2-[5-Fluoro-4-(9-fluoro-1,4,4,6-tetramethyl-5H-[1,2,4]triazolo[4,3-a]quinoxalin-8-yl)-1H-indol-1-yl]-ethanol;

48 9-Fluoro-8-imidazo[1,2-a]pyridin-5-yl-1,4,4,6-tetramethyl-5H-[1,2,4]triazolo[4,3-a]quinoxaline;

49 5-fluoro-6-(5-fluoro-3-methyl-1H-indol-7-yl)-3,11,11-trimethyl-8,9,10,11-tetrahydro-7H-cyclopenta[f][1,2,4]triazolo[4,3-a]quinoxaline;

50 6-(1-cyclopropyl-6-fluoro-1H-indol-4-yl)-5-fluoro-3,11,11-trimethyl-8,9,10,11-tetrahydro-7H-cyclopenta[f][1,2,4]triazolo[4,3-a]quinoxaline;

51 5-fluoro-6-(6-fluoro-1-(methylsulfonyl)-1H-indol-4-yl)-3,11,11-trimethyl-8,9,10,11-tetrahydro-7H-cyclopenta[f][1,2,4]triazolo[4,3-a]quinoxaline;

52 5-fluoro-6-(5-fluoro-3-(tetrahydrofuran-3-yl)-1H-indol-7-yl)-3,11,11-trimethyl-8,9,10,11-tetrahydro-7H-cyclopenta[f][1,2,4]triazolo[4,3-a]quinoxaline;

53 9-Fluoro-8-(6-fluoro-1H-indol-4-yl)-1,4,4-trimethyl-6-(trifluoromethyl)-5H-[1,2,4]triazolo[4,3-a]quinoxaline;

54 9-Fluoro-1,4,4-trimethyl-8-(1-methylsulfonyl-1H-indol-4-yl)-6-(trifluoromethyl)-5H-[1,2,4]triazolo[4,3-a]quinoxaline;

55 9-Fluoro-8-[6-fluoro-1-(2-methoxy-ethyl)-1H-indol-4-yl]-1,4,4-trimethyl-6-(trifluoromethyl)-5H-[1,2,4]triazolo[4,3-a]quinoxaline;

56 9-Fluoro-1,4,4-trimethyl-8-(1H-pyrrolo[2,3-b]pyridin-4-yl)-6-(trifluoromethyl)-5H-[1,2,4]triazolo[4,3-a]quinoxaline;

57 8-[1-(2,2-Difluoro-ethyl)-6-fluoro-1H-indazol-4-yl]-9-fluoro-1,4,4-trimethyl-6-(trifluoromethyl)-5H-[1,2,4]triazolo[4,3-a]quinoxaline;

58 9-Fluoro-8-[6-fluoro-1-(2-methoxy-ethyl)-1H-indazol-4-yl]-1,4,4-trimethyl-6-(trifluoromethyl)-5H-[1,2,4]triazolo[4,3-a]quinoxaline;

59 8-(5-Fluoro-3-methyl-1H-indol-7-yl)-1,4,4,9-tetramethyl-6-methylsulfanyl-5H-[1,2,4]triazolo[4,3-a]quinoxaline;

60 1,4,4,9-Tetramethyl-8-(3-methyl-1H-indol-7-yl)-5H-[1,2,4]triazolo[4,3-a]quinoxalin-6-ol;

61 2-[9-Fluoro-8-(5-fluoro-3-methyl-1H-indol-7-yl)-1,4,4-trimethyl-5H-[1,2,4]triazolo[4,3-a]quinoxalin-6-yl]-propan-2-ol;

62 6-Fluoro-8-(6-fluoro-pyrazolo[1,5-a]pyridin-4-yl)-1,4,4,9-tetramethyl-5H-[1,2,4]triazolo[4,3-a]quinoxaline;

63 8-(5-Chloro-2-methoxy-pyridin-3-yl)-9-(difluoro-methyl)-7-fluoro-1,4,4-trimethyl-5H-[1,2,4]triazolo[4,3-a]quinoxaline;

64 7-Fluoro-1,4,4-trimethyl-8-(1-methyl-1H-pyrrolo[2,3-b]pyridin-3-yl)-9-(trifluoromethyl)-5H-[1,2,4]triazolo[4,3-a]quinoxaline;

65 8-(5,6-Dihydro-4H-pyrrolo[1,2-b]pyrazol-3-yl)-7,9-difluoro-1,4,4-trimethyl-5H-[1,2,4]triazolo[4,3-a]quinoxaline;

66 8-(5-Chloro-2-methoxy-pyridin-3-yl)-9-cyclopropyl-7-fluoro-1,4,4-trimethyl-5H-[1,2,4]triazolo[4,3-a]quinoxaline;

67 7,9-Difluoro-1,4,4-trimethyl-8-naphthalen-1-yl-5H-[1,2,4]triazolo[4,3-a]quinoxaline;

68 8-(Benzofuran-4-yl)-7,9-difluoro-1,4,4-trimethyl-5H-[1,2,4]triazolo[4,3-a]quinoxaline;

69 7,9-Difluoro-8-(3-fluoro-5-vinyl-phenyl)-1,4,4-trimethyl-5H-[1,2,4]triazolo[4,3-a]quinoxaline;

70 7,9-Difluoro-8-(3-fluoro-5-methyl-phenyl)-1,4,4-trimethyl-5H-[1,2,4]triazolo[4,3-a]quinoxaline;

71 8-(5-Chloro-2-methoxy-pyridin-3-yl)-7-fluoro-1,4,4,9-tetramethyl-5H-[1,2,4]triazolo[4,3-a]quinoxaline;

72 6-Fluoro-8-(6-fluoro-pyrazolo[1,5-a]pyridin-4-yl)-9-methoxy-1,4,4-trimethyl-5H-[1,2,4]triazolo[4,3-a]quinoxaline;

73 8-(5-Fluoro-1H-indol-1-yl)-1,4,4,9-tetramethyl-5H-[1,2,4]triazolo[4,3-a]quinoxaline;

74 8-(3-Ethyl-5-fluoro-phenyl)-7,9-difluoro-1,4,4-trimethyl-5H-[1,2,4]triazolo[4,3-a]quinoxaline;

75 8-(5-Chloro-2-methoxy-pyridin-3-yl)-9-(difluoro-methyl)-1,4,4-trimethyl-5H-[1,2,4]triazolo[4,3-a]quinoxaline;

76 7-Chloro-8-(5-chloro-2-methoxy-pyridin-3-yl)-6-fluoro-1,4,4,9-tetramethyl-5H-[1,2,4]triazolo[4,3-a]quinoxaline;

77 8-(1-Cyclopropyl-1H-indol-3-yl)-6-fluoro-9-methoxy-1,4,4-trimethyl-5H-[1,2,4]triazolo[4,3-a]quinoxaline;

78 7,9-Difluoro-8-(3-fluoro-5-methoxy-phenyl)-1,4,4-trimethyl-5H-[1,2,4]triazolo[4,3-a]quinoxaline;

79 8-(5-Chloro-2-methoxy-pyridin-3-yl)-6,7-difluoro-1,4,4,9-tetramethyl-5H-[1,2,4]triazolo[4,3-a]quinoxaline;

80 7-Fluoro-8-(5-fluoro-2-methoxy-pyridin-3-yl)-1,4,4,9-tetramethyl-5H-[1,2,4]triazolo[4,3-a]quinoxaline;

81 9-(Difluoro-methyl)-6-fluoro-1,4,4-trimethyl-8-pyrazolo[1,5-a]pyridin-4-yl-5H-[1,2,4]triazolo[4,3-a]quinoxaline;

82 6-Chloro-8-(5-chloro-2-methoxy-pyridin-3-yl)-7-fluoro-1,4,4,9-tetramethyl-5H-[1,2,4]triazolo[4,3-a]quinoxaline;

83 8-(5-Chloro-2-methoxy-pyridin-3-yl)-1,4,4,9-tetramethyl-7-(trifluoromethyloxy)-5H-[1,2,4]triazolo[4,3-a]quinoxaline;

84 [3-(7,9-Difluoro-1,4,4-trimethyl-5H-[1,2,4]triazolo[4,3-a]quinoxalin-8-yl)-5-fluoro-phenyl]-amine;

85 9-(Difluoro-methyl)-7-fluoro-1,4,4-trimethyl-8-(1-methyl-1H-pyrrolo[2,3-b]pyridin-3-yl)-5H-[1,2,4]triazolo[4,3-a]quinoxaline;

86 7-Fluoro-8-(2-methoxy-5-methyl-pyridin-3-yl)-1,4,4,9-tetramethyl-5H-[1,2,4]triazolo[4,3-a]quinoxaline;

87 1-Ethyl-7,9-difluoro-4,4-dimethyl-8-[(3-pyridin-3-yl-pyrrolidin-1-yl)-methyl]-5H-[1,2,4]triazolo[4,3-a]quinoxaline;

88 7,9-Difluoro-1,4,4-trimethyl-8-quinolin-5-yl-5H-[1,2,4]triazolo[4,3-a]quinoxaline;

89 8-(4-Fluoro-1H-indol-1-yl)-1,4,4,9-tetramethyl-5H-[1,2,4]triazolo[4,3-a]quinoxaline;

90 7,9-Difluoro-8-[2-methoxy-5-(trifluoromethyl)-pyridin-3-yl]-1,4,4-trimethyl-5H-[1,2,4]triazolo[4,3-a]quinoxaline;

91 9-Ethyl-6-fluoro-1,4,4-trimethyl-8-pyrazolo[1,5-a]pyridin-4-yl-5H-[1,2,4]triazolo[4,3-a]quinoxaline;

92 7,9-Difluoro-1,4,4-trimethyl-8-pyrazolo[1,5-a]pyridin-3-yl-5H-[1,2,4]triazolo[4,3-a]quinoxaline;

93 1,4,4,9-Tetramethyl-8-(5-methyl-1H-indol-1-yl)-5H-[1,2,4]triazolo[4,3-a]quinoxaline;

94 7-Fluoro-9-methoxy-1,4,4-trimethyl-8-(1-methyl-1H-pyrrolo[2,3-b]pyridin-3-yl)-5H-[1,2,4]triazolo[4,3-a]quinoxaline;

95 8-(1H-Indol-1-yl)-1,4,4,9-tetramethyl-5H-[1,2,4]triazolo[4,3-a]quinoxaline;

96 7,9-Difluoro-8-(1H-indol-3-yl)-1,4,4-trimethyl-5H-[1,2,4]triazolo[4,3-a]quinoxaline;

97 9-(Difluoro-methyl)-7-fluoro-8-(7-fluoro-1H-indol-3-yl)-1,4,4-trimethyl-5H-[1,2,4]triazolo[4,3-a]quinoxaline;

98 5-(7-Fluoro-1,4,4,9-tetramethyl-5H-[1,2,4]triazolo[4,3-a]quinoxalin-8-yl)-1-methyl-3,4-dihydro-1H-quinolin-2-one;

99 7,9-Difluoro-1,4,4-trimethyl-8-(1-methyl-1H-pyrrolo[2,3-c]pyridin-3-yl)-5H-[1,2,4]triazolo[4,3-a]quinoxaline;

100 7,9-Difluoro-8-(5-fluoro-spiro[1,2-dihydro-indole-3,1'-cyclopropane]-7-yl)-1,4,4-trimethyl-5H-[1,2,4]triazolo[4,3-a]quinoxaline;

101 8-(5-Chloro-2-methoxy-pyridin-3-yl)-9-cyclopropyl-6-fluoro-1,4,4-trimethyl-5H-[1,2,4]triazolo[4,3-a]quinoxaline;

102 3-(7,9-Difluoro-1,4,4-trimethyl-5H-[1,2,4]triazolo[4,3-a]quinoxalin-8-yl)-5-fluoro-phenol;

103 8-(5-Ethyl-2-methoxy-pyridin-3-yl)-7-fluoro-1,4,4,9-tetramethyl-5H-[1,2,4]triazolo[4,3-a]quinoxaline;

104 8-(5-Cyclopropyl-2-methoxy-pyridin-3-yl)-7-fluoro-1,4,4,9-tetramethyl-5H-[1,2,4]triazolo[4,3-a]quinoxaline;

105 7,9-Difluoro-1,4,4-trimethyl-8-(1H-pyrrolo[2,3-b]pyridin-4-yl)-5H-[1,2,4]triazolo[4,3-a]quinoxaline;

106 8-(2,3-Dihydro-[1,4] benzodioxin-5-yl)-7-fluoro-1,4,4,9-tetramethyl-5H-[1,2,4]triazolo[4,3-a]quinoxaline;

107 6-Fluoro-9-methoxy-1,4,4-trimethyl-8-(1-methylsulfonyl-1H-indol-3-yl)-5H-[1,2,4]triazolo[4,3-a]quinoxaline;

108 1-[2-[4-(7,9-Difluoro-1,4,4-trimethyl-5H-[1,2,4]triazolo[4,3-a]quinoxalin-8-yl)-1H-pyrazol-1-yl]-ethyl]-pyrrolidin-2-one;

109 7,9-Difluoro-1,4,4-trimethyl-8-spiro[1,2-dihydro-indole-3,1'-cyclopropane]-7-yl-5H-[1,2,4]triazolo[4,3-a]quinoxaline;

110 4-(7,9-Difluoro-1,4,4-trimethyl-5H-[1,2,4]triazolo[4,3-a]quinoxalin-8-yl)-6-fluoro-benzothiazole;

111 8-(1H-Benzotriazol-4-yl)-6-fluoro-1,4,4,9-tetramethyl-5H-[1,2,4]triazolo[4,3-a]quinoxaline;

112 8-(1-Cyclopropyl-1H-pyrrolo[2,3-b]pyridin-3-yl)-6-fluoro-9-methoxy-1,4,4-trimethyl-5H-[1,2,4]triazolo[4,3-a]quinoxaline;

113 8-(3-Chloro-2-methoxy-phenyl)-7,9-difluoro-1,4,4-trimethyl-5H-[1,2,4]triazolo[4,3-a]quinoxaline;

114 4-(7,9-Difluoro-1,4,4-trimethyl-5H-[1,2,4]triazolo[4,3-a]quinoxalin-8-yl)-2-fluoro-phenol;

115 5-(7-Fluoro-1,4,4,9-tetramethyl-5H-[1,2,4]triazolo[4,3-a]quinoxalin-8-yl)-3,4-dihydro-1H-quinolin-2-one;

116 1-Cyclopropyl-6-fluoro-8-(6-fluoro-pyrazolo[1,5-a]pyridin-4-yl)-4,4,9-trimethyl-5H-[1,2,4]triazolo[4,3-a]quinoxaline;

117 8-(5-Chloro-2-methoxy-pyridin-3-yl)-7-(difluoromethyl)-9-fluoro-1,4,4-trimethyl-5H-[1,2,4]triazolo[4,3-a]quinoxaline;

118 8-(5-Chloro-2-methoxy-pyridin-3-yl)-1,4,4-trimethyl-9-(trifluoromethyl)-5H-[1,2,4]triazolo[4,3-a]quinoxaline;

119 7,9-Difluoro-1,4,4-trimethyl-8-(1-methyl-1H-pyrrolo[2,3-b]pyridin-4-yl)-5H-[1,2,4]triazolo[4,3-a]quinoxaline;

120 1,4,4,9-Tetramethyl-8-(4-methyl-1H-indol-1-yl)-5H-[1,2,4]triazolo[4,3-a]quinoxaline;

121 7,9-Difluoro-8-(2-fluoro-3-methoxy-phenyl)-1,4,4-trimethyl-5H-[1,2,4]triazolo[4,3-a]quinoxaline; and 122 7,9-Difluoro-N-[(3-methoxyphenyl)-methyl]-1,4,4-trimethyl-5H-[1,2,4]triazolo[4,3-a]quinoxaline-8-carboxylic acid amide;

or a physiologically acceptable salt or stereoisomer thereof.

18. A pharmaceutical dosage form comprising a compound according to claim 17, or a physiologically acceptable salt or stereoisomer thereof.

19. A method for the treatment and/or prophylaxis of pain and/or inflammation in a subject in need thereof, said method comprising administering to the subject an effective amount therefor of the compound according to claim 17 or a physiologically acceptable salt or stereoisomer thereof.

20. A method for the treatment and/or prophylaxis of inflammatory pain in a subject in need thereof, said method comprising administering to the subject an effective amount therefor of the compound according to claim 17 or a physiologically acceptable salt or stereoisomer thereof.

* * * * *